US011401510B2

(12) United States Patent
Hawkins et al.

(10) Patent No.: US 11,401,510 B2
(45) Date of Patent: Aug. 2, 2022

(54) GENERATION OF AIRWAY BASAL STEM CELLS FROM HUMAN PLURIPOTENT STEM CELLS

(71) Applicants: TRUSTEES OF BOSTON UNIVERSITY, Boston, MA (US); THE BOARD OF REGENTS OF THE UNIVERSITY OF TEXAS SYSTEM, Austin, TX (US)

(72) Inventors: Finn Joseph Hawkins, Boston, MA (US); Darrell N. Kotton, Newton, MA (US); Shingo Suzuki, Austin, TX (US); Brian R. Davis, Austin, TX (US); Cristina Barillà, Houston, TX (US)

(73) Assignees: TRUSTEES OF BOSTON UNIVERSITY, Boston, MA (US); THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 17/180,011

(22) Filed: Feb. 19, 2021

(65) Prior Publication Data

US 2021/0254016 A1 Aug. 19, 2021

Related U.S. Application Data

(60) Provisional application No. 62/978,514, filed on Feb. 19, 2020.

(51) Int. Cl.

| | |
|---|---|
| ***A61P 11/00*** | (2006.01) |
| ***A61P 11/06*** | (2006.01) |
| ***A61K 35/42*** | (2015.01) |
| ***C12N 5/00*** | (2006.01) |
| ***C12N 5/071*** | (2010.01) |

(52) U.S. Cl.

CPC ............ *C12N 5/0689* (2013.01); *A61K 35/42* (2013.01); *A61P 11/00* (2018.01); *A61P 11/06* (2018.01); *C12N 5/0062* (2013.01); *C12N 2500/90* (2013.01); *C12N 2501/115* (2013.01); *C12N 2501/119* (2013.01); *C12N 2501/15* (2013.01); *C12N 2501/155* (2013.01); *C12N 2501/39* (2013.01); *C12N 2501/405* (2013.01); *C12N 2501/415* (2013.01); *C12N 2501/999* (2013.01); *C12N 2506/45* (2013.01); *C12N 2513/00* (2013.01)

(58) Field of Classification Search

CPC ....... A61K 35/42; A61P 11/00; C12N 5/0062; C12N 2500/90; C12N 2501/115; C12N 2501/119; C12N 2501/15; C12N 2501/155; C12N 2501/39; C12N 2501/405; C12N 2501/415; C12N 2501/999; C12N 2506/45; C12N 2513/00

See application file for complete search history.

(56) References Cited

U.S. PATENT DOCUMENTS

| | | | | |
|---|---|---|---|---|
| 2014/0329318 | A1 | 11/2014 | Rajagopal et al. | |
| 2015/0175972 | A1 | 6/2015 | Jabbari | |
| 2015/0247124 | A1 | 9/2015 | Snoeck et al. | |
| 2017/0275592 | A1 | 9/2017 | Sachs et al. | |
| 2018/0208903 | A1* | 7/2018 | Kotton | C07K 14/4702 |

OTHER PUBLICATIONS

Longmire et al. Efficient Derivation of Purified Lung and Thyroid Progenitors from Embryonic Stem Cells 2012. Cell Stem Cell 10:398-411 (Year: 2012).*

Gowers et al. Optimized isolation and expansion of human airway epithelial basal cells from endobronchial biopsy samples 2018. J Tissue Eng Regen Med. 12:e313-e317 (Year: 2018).*

Tadoroko et al. BMP signaling and cellular dynamics during regeneration of airway epithelium from basal progenitors Development (2016) 143, 764-773 (Year: 2016).*

Horani et al. Rho-Associated Protein Kinase Inhibition Enhances Airway Epithelial Basal-Cell Proliferation and Lentivirus Transduction American Journal of Respiratory Cell and Molecular Biology vol. 49 Iss. 3, pp. 341-347 (Year: 2013).*

Miller et al. Basal stem cell fate specification is mediated by SMAD signaling in the developing human lung 2018, bioRxiv 461103 (Year: 2018).*

Chen et al. "A three-dimensional model of human lung development and disease from pluripotent stem cells." Nature Cell Biology 19(5): 542-549 (2017).

Dye et al. "In vitro generation of human pluripotent stem cell derived lung organoids." elife 4: e05098 pp. 1-25 (2015).

Fulcher et al. "Well-differentiated human airway epithelial cell cultures." In J. Picot (ed.) Methods in Molecular Medicine, vol. 107: Human Cell Culture Protocols, Second Edition. Chapter 13: 183-206 (2005).

Hawkins et al. "Prospective isolation of NKX2-1-expressing human lung progenitors derived from pluripotent stem cells." The Journal of Clinical Investigation 127(6): 2277-2294 (2017).

Konishi et al. "Directed induction of functional multi-ciliated cells in proximal airway epithelial spheroids from human pluripotent stem cells." Stem Cell Reports 6(1): 18-25 (2016).

McCauley et al. "Derivation of Epithelial-Only Airway Organoids from Human Pluripotent Stem Cells." Current Protocols in Stem Cell Biology 45(1): e51 pp. 1-27 (2018).

(Continued)

*Primary Examiner* — Taeyoon Kim
*Assistant Examiner* — Alexandra F Connors
(74) *Attorney, Agent, or Firm* — Nixon Peabody LLP; Ronald I. Eisenstein; Nicole D. Kling

(57) ABSTRACT

Described herein is a method of generating in-vitro differentiated airway basal cells and compositions thereof. Also described herein is a method of treating a pulmonary disease comprising administering the in-vitro differentiated airway basal cells and compositions thereof. In another aspect, described herein is a disease model comprising patient-derived or genetically modified in-vitro differentiated airway basal cells and compositions thereof.

26 Claims, 72 Drawing Sheets

Specification includes a Sequence Listing.

(56) References Cited

OTHER PUBLICATIONS

McCauley et al. “Efficient derivation of functional human airway epithelium from pluripotent stem cells via temporal regulation of Wnt signaling ” Cell Stem Cell 20(6): 844-857.e1-e6 (2017).
McCauley et al. “Single-cell transcriptomic profiling of pluripotent stem cell-derived SCGB3A2+ airway epithelium.” Stem Cell Reports 10(5): 1579-1595 (2018).
Montoro et al. “A revised airway epithelial hierarchy includes CFTR-expressing ionocytes.” Nature 560(7718):319-324 (2018).
Mou et al. “Dual SMAD signaling inhibition enables long-term expansion of diverse epithelial basal cells.” Cell Stem Cell 19(2): 217-231 (2016).
Nikolic et al. “Human embryonic lung epithelial tips are multipotent progenitors that can be expanded in vitro as long-term self-renewing organoids” Elife 6: e26575 pp. 1-33 (2017).
Ornitz et al. “The fibroblast growth factor signaling pathway.” Wiley Interdisciplinary Reviews: Developmental Biology 4(3): 215-266 (2015).
Plasschaert et al. “A single-cell atlas of the airway epithelium reveals the CFTR-rich pulmonary ionocyte.” Nature 560(7718): 377-381 (2018).
Rock et al. “Basal cells as stem cells of the mouse trachea and human airway epithelium.” Proceedings of the National Academy of Sciences 106(31): 12771-12775 (2009).
Suprynowicz et al. “Conditional cell reprogramming involves non-canonical β-catenin activation and mTOR-mediated inactivation of Akt.” PloS One 12(7): e0180897 pp. 1-23 (2017).
Volckaert et al. “Localized Fgf10 expression is not required for lung branching morphogenesis but prevents differentiation of epithelial progenitors.” Development 140(18): 3731-3742 (2013).
Yang et al. “Spatial-temporal lineage restrictions of embryonic p63+ progenitors establish distinct stem cell pools in adult airways.” Developmental Cell 44(6): 752-761 (2018).
Zhang et al. “Long-term in vitro expansion of epithelial stem cells enabled by pharmacological inhibition of PAK1-ROCK-Myosin II and TGF-β signaling.” Cell Reports 25(3): 598-610 (2018).
Fulcher et al. “Human nasal and tracheo-bronchial respiratory epithelial cell culture.” In S. Randal, M. Fulcher (eds.) Epithelial Cell Culture Protocols: Second Edition, Methods in Molecular Biology, vol. 945. Chapter 8: 109-21 (2012).
Miller et al. “In vitro and in vivo development of the human airway at single-cell resolution.” Developmental Cell 53(1): 117-128 (2010).

* cited by examiner

DEGs per cluster 1 2 3 4 5 6

RPS18
RPS2
RPL5
RPL12
RPS3
RPL10
ZFA51
RP812
KRT19 — KRT19
SELENOP
KRT13 — KRT13
LMO4
KRT15 — KRT15
S100A14
DLK1
APOE
AQP3
AC004233.2
IGFBP5
KRT4
XBP1 — XBP1
CP
HLA-A
CXCL17
KIAA1324
S100P
KLK11
CEACAM6
TFF3
KLK10
SCGB3A2 — SCGB3A2
SFTPA2
LCN2
SPINK1
MUC5B — MUC5B
C3
GSTA1
SCGB1A1 — SCGB1A1
BPIFB1
CXCL1
CCNO
CDC20B
BTG3
PTGES3

Extended passage of iBCs

BU3 NGPT 9 passages after GFP+/TOM+ sort

BU3 NGPT Karyotype

| | Basal | Secretory | Multiciliated | Ionocyte |
|---|---|---|---|---|
| 1 | *UPP1* | *SCGB3A1* | *TPPP3* | *TMEM61* |
| 2 | *MT2A* | *WFDC2* | *C20orf85* | *CRYM* |
| 3 | *LGALS1* | *MSMB* | *CAPS* | *MUC20* |
| 4 | *S100A2* | *BPIFB1* | *RSPH1* | *ANXA4* |
| 5 | *AREG* | *SERPINB3* | *TUBB4B* | *CFTR* |
| 6 | *ZFAS1* | *VMO1* | *TUBA1A* | *FAM43A* |
| 7 | *G0S2* | *SLPI* | *C9orf116* | *TMPRSS11E* |
| 8 | *S100A14* | *BPIFA1* | *PIFO* | *ITPR2* |
| 9 | *S100A10* | *CD74* | *MORN2* | *CEL* |
| 10 | *KRT17* | *CXCL17* | *C5orf49* | *NREP* |
| 11 | *KRT6A* | *PIGR* | *PSENEN* | *MUC20-OT1* |
| 12 | *HMGA1* | *SCGB1A1* | *CFAP126* | *ATP6V0A4* |
| 13 | *PHLDA1* | *CXCL1* | *FAM183A* | *AKR1B1* |
| 14 | *TMSB10* | *PSCA* | *FOXJ1* | *HES6* |
| 15 | *TIMP1* | *AGR2* | *AGR3* | *TIMP3* |
| 16 | *ADIRF* | *HLA-DRA* | *FAM229B* | *LRMP* |
| 17 | *TINAGL1* | *TNFSF10* | *KIF9* | *PLCG2* |
| 18 | *S100A16* | *CYP2F1* | *DNALI1* | *GADD45G* |
| 19 | *IGFBP6* | *GLUL* | *LRRIQ1* | *KIT* |
| 20 | *SH3BGRL3* | *XBP1* | *DYNLL1* | *AZGP1* |
| 21 | *C16orf74* | *STATH* | *IFT57* | *ATP6V0B* |
| 22 | *SNHG8* | *LYPD2* | *ODF3B* | *HEPACAM2* |
| 23 | *RPS21* | *S100A9* | *IFT22* | *ASCL2* |
| 24 | *RPL37A* | *GSN* | *NUDC* | *MGLL* |
| 25 | *RPL37* | *HLA-DRB5* | *CETN2* | *SDC2* |
| 26 | *IER3* | *ALDH1A1* | *UFC1* | *SIRT2* |
| 27 | *LAMC2* | *C3* | *TCTEX1D2* | *FOXI1* |
| 28 | *ITGB1* | *RARRES1* | *CFAP298* | *MYO6* |
| 29 | *EIF4EBP1* | *LY6E* | *DPCD* | *IQGAP2* |
| 30 | *RPL36* | *RARRES3* | *WDR54* | *DMRT2* |

*FIG. 15*

SEQUENCE LISTING

<160> NUMBER OF SEQ ID NOS: 63

<210> SEQ ID NO 1
<211> LENGTH: 2791
<212> TYPE: DNA
<213> ORGANISM: Mus musculus

<400> SEQUENCE: 1

```
agagggccca gcgccactgc agccgcgcca cctcccaggg ccgggccagc ccaggcgtcc     60
gcgctctcgg ggtggactcc ccccgctgcg cgctcaagcc ggcgatggct cctctcggat    120
acctcttagt gctctgcagc ctgaagcagg ctctgggcag ctacccgatc tggtggtcct    180
tggctgtggg accccagtac tcctctctga gcactcagcc cattctctgt gccagcatcc    240
caggcctggt accgaagcag ctgcgcttct gcaggaacta cgtggagatc atgcccagcg    300
tggctgaggg tgtcaaagcg ggcatccagg agtgccagca ccagttccga ggccggcgtt    360
ggaactgcac caccgtcagc aacagcctgg ccatctttgg ccctgttctg gacaaagcca    420
cccgggagtc agcctttgtc catgccatcg cctccgctgg agtagctttc gcagtgacac    480
gctcctgtgc agagggatca gctgctatct gtgggtgcag cagccgcctc cagggctccc    540
caggcgaggg ctggaagtgg ggcggctgta gtgaggacat tgaatttgga ggaatggtct    600
ctcgggagtt tgccgatgcc agggagaacc ggccggatgc ccgctctgcc atgaaccgtc    660
acaacaatga ggctgggcgc caggccatcg ccagtcacat gcacctcaag tgcaaatgcc    720
acgggctatc tggcagctgt gaagtgaaga cctgctggtg gtcgcagccg gacttccgca    780
ccatcgggga tttcctcaag gacaagtatg acagtgcctc ggagatggtg gtagagaaac    840
accgagagtc tcgtggctgg gtggagaccc tgaggccacg ttacacgtac ttcaaggtgc    900
cgacagaacg cgacctggtc tactacgagg cctcacccaa cttctgcgaa cctaaccccg    960
aaaccggctc cttcgggacg cgtgaccgca cctgcaatgt gagctcgcat ggcatagatg   1020
ggtgcgacct gttgtgctgc gggcgcgggc ataacgcgcg cactgagcga cggagggaga   1080
aatgccactg tgttttccat tggtgctgct acgtcagctg ccaggagtgc acacgtgtct   1140
atgacgtgca cacctgcaag taggagagct cctaacacgg gagcagggtt cattccgagg   1200
ggcaaggttc ctacctgggg gcggggttcc tacttggagg ggtctcttac ttggggactc   1260
ggttcttact tgagggcgga gatcctacct gtgagggtct catacctaag gacccggttt   1320
ctgccttcag cctgggctcc tatttgggat ctgggttcct ttttagggga gaagctcctg   1380
tctgggatac gggtttctgc ccgagggtgg ggctccactt ggggatggaa ttccaatttg   1440
ggccggaagt cctacctcaa tggcttggac tcctctcttg acccgacagg gctcaaatgg   1500
agacaggtaa gctactccct caactaggtg gggttcgtgc ggatgggtgg gaggggagag   1560
attagggtcc ctcctcccag aggcactgct ctatctagat acatgagagg gtgcttcagg   1620
gtgggcccta tttgggcttg aggatcccgt gggggcgggg cttcaccccg actgggtgga   1680
acttttggag accccccttcc actggggcaa ggcttcactg aagactcatg ggatggagct   1740
ccacggaagg aggagttcct gagcgagcct gggctctgag caggccatcc agctcccatc   1800
tggccccttt ccagtcctgg tgtaaggttc aacctgcaag cctcatctgc gcagagcagg   1860
atctcctggc agaatgaggc atggagaaga actcaggggt gataccaaga cctaacaaac   1920
cccgtgcctg ggtacctctt ttaaagctct gcaccccttc ttcaagggct ttcctagtct   1980
ccttggcaga gctttcctga ggaagatttg cagtccccca gagttcaagt gaacacccat   2040
agaacagaac agactctatc ctgagtagag agggttctct aggaatctct atggggactg   2100
```

```
ctaggaagga tcctgggcat gacagcctcg tatgatagcc tgcatccgct ctgacactta   2160

atactcagat ctcccgggaa acccagctca tccggtccgt gatgtccatg ccccaaatgc   2220

ctcagagatg ttgcctcact ttgagttgta tgaacttcgg agacatgggg acacagtcaa   2280

gccgcagagc cagggttgtt tcaggaccca tctgattccc cagagcctgc tgttgaggca   2340

atggtcacca gatccgttgg ccaccaccct gtcccgagct tctctagtgt ctgtctggcc   2400

tggaagtgag gtgctacata cagcccatct gccacaagag cttcctgatt ggtaccactg   2460

tgaaccgtcc ctccccccctc cagacagggg aggggatgtg gccatacagg agtgtgcctg   2520

gagagcgcgg aaagaggaag agaggctgca cacgcgtggt gactgactgt cttctgcctg   2580

gaactttgcg ttcgcgcttg taactttatt ttcaatgctg ctatatccac ccaccactgg   2640

atttagacaa aagtgatttt cttttttttt ttttcttttc tttctatgaa agaaattatt   2700

ttagtttata gtatgtttgt ttcaaataat ggggaaagta aaaagagaga aaaaaaaaaa   2760

aaaaaaaaaa aaaaaaaaaa aaaaaaaaaa a                                  2791
```

```
<210> SEQ ID NO 2
<211> LENGTH: 3287
<212> TYPE: DNA
<213> ORGANISM: Homo sapiens

<400> SEQUENCE: 2

atttccaatc tcaagtggac tttgttccaa ctattggggg cgtcgctccc cctcttcatg     60

gtcgcgggca aacttcctcc tcggcgcctc ttctaatgga gccccacctg ctcgggctgc    120

tcctcggcct cctgctcggt ggcaccaggg tcctcgctgg ctacccaatt tggtggtccc    180

tggccctggg ccagcagtac acatctctgg gctcacagcc cctgctctgc ggctccatcc    240

caggcctggt ccccaagcaa ctgcgcttct gccgcaatta catcgagatc atgcccagcg    300

tggccgaggg cgtgaagctg ggcatccagg agtgccagca ccagttccgg ggccgccgct    360

ggaactgcac caccatagat gacagcctgg ccatctttgg gcccgtcctc gacaaagcca    420

cccgcgagtc ggccttcgtt cacgccatcg cctcggccgg cgtggccttc gccgtcaccc    480

gctcctgcgc cgagggcacc tccaccattt gcggctgtga ctcgcatcat aaggggccgc    540

ctggcgaagg ctggaagtgg ggcggctgca gcgaggacgc tgacttcggc gtgttagtgt    600

ccagggagtt cgcggatgcg cgcgagaaca ggccggacgc gcgctcggcc atgaacaagc    660

acaacaacga ggcgggccgc acgactatcc tggaccacat gcacctcaaa tgcaagtgcc    720

acgggctgtc gggcagctgt gaggtgaaga cctgctggtg ggcgcagcct gacttccgtg    780

ccatcggtga cttcctcaag gacaagtatg acagcgcctc ggagatggta gtagagaagc    840

accgtgagtc ccgaggctgg gtggagaccc tccgggccaa gtactcgctc ttcaagccac    900

ccacggagag ggacctggtc tactacgaga actcccccaa cttttgtgag cccaacccag    960

agacgggttc ctttggcaca agggaccgga cttgcaatgt cacctcccac ggcatcgatg   1020

gctgcgatct gctctgctgt ggccggggcc acaacacgag gacggagaag cggaaggaaa   1080

aatgccactg catcttccac tggtgctgct acgtcagctg ccaggagtgt attcgcatct   1140

acgacgtgca cacctgcaag tagggcacca gggcgctggg aaggggtgaa gtgtgtggct   1200

gggcggattc agcgaagtct catgggaagc aggacctaga gccgggcaca gccctcagcg   1260

tcagacagca aggaactgtc accagccgca cgcgtggtaa atgacccaga cccaactcgc   1320

ctgtggacgg ggaggctctc cctctctctc atcttacatt tctcacccta ctctggatgg   1380
```

-continued tgtgtggttt ttaaagaagg gggctttctt tttagttctc tagggtctga taggaacaga 1440
cctgaggctt atctttgcac atgttaaaga aaataaaaat gaaaaaaaat ttgactccaa 1500
cagaacaggc tgggctaatg tgagctctca gcctggcagt caagacatca gcatgggcaa 1560
ggttctgttt ccaaactgct gcttctggtg acattccaag acgcctggag ggtgggagtc 1620
aggaagtagg acacacccct gcagtctcct tttcttggtc cactcccatt caaatttgag 1680
ctaatttctc attctgataa aagccatagg tttagctagg atgaagtggt aggaaggtcc 1740
gtggcagttg ttagagtagg atttggagtt tggaagaact ggcagctcag ggtggcctgg 1800
tcagccgttt gaagagcagc catgtgttct tctcagtctc attttctcta taaccctgtt 1860
ctgcacgagg ggcagtcaga tctcaaaatc tttttctacc attctgcagt ttccaccgtc 1920
aatgcagttt ttttttgtt tttttgtttt tttttttttt tggtggtagt ggaccttgta 1980
aataggctat gtaagggggc aagtcttctc tagctcaaat ggcttcctaa ataaataagc 2040
ggtatcttca gaaggggcca ttcagtcctt cccagccctg ctcacctgca gattctctgt 2100
acaaataact ccaggtagag cagttggact ccaggtcacc ttagtataag ttagacaaag 2160
ggtccgtgag ggagtagcca tcaattcctg aaattccaac tttgtgacta gcagatgggg 2220
aggatgaaaa ccatcccttt gcttcctctc caatacggac ccatcttact gtgtcctttc 2280
ctctctgggg ccaatgtgag taaacacaga cacagagttc tttcccccag ctcttcctcc 2340
ctcacctgca tgctgagata gcttccatcc atgcagttcc caaggatctg gattagaagt 2400
tcaaagggga accagcagtc acctactccc ttaggtgaag catctcacgg ctgagttctc 2460
cctgaggcat actggtccag ctgagcgtcc tagagaaagc tagcaaaagg gaggcacatg 2520
gatttcacag tatgaattgg ttcaacaact gtcttaggga gaatcagaaa gaagagatgc 2580
agcaggggaa tgagcagaac aaagattttt ctttctcccc cttctctctg gggtctacct 2640
aaccctgacc taaaatacca gggcagcgat ctcccagctg gtgcaggtgg gcttgccaag 2700
atggtcgtcc aggagcccgc cttcacttct aaatctgctg gccacaagcc ctgctaaaga 2760
tacacatctc accccctccg ccaagtctga aatgcccctc cccatctcac cttagactga 2820
aaagttttaa atcatgtcaa ctggataata cttgctttat gtgagaatac ttcagcagaa 2880
tggatacgaa ttttcaaaac aatcttttca tatctatgta ttctatatta aaagtgataa 2940
agtcatgttt ctggggcgta ttcaagtagc tgacaagtaa ttatttaata atagtacatg 3000
agtgcattgt aatgattctc gccgtagtca ggtaatagta tccaaccgaa atttcctacc 3060
aacctgctgt atccaaagtt ttgtaaaaag ttgtagaagt tgttgatctt tttgatttta 3120
tattcaaaaa gtctcttttt ataaatatta tttattatac aatgtatata cctttgagtt 3180
aactaagatt atatattata taaatatata tatatttgga gaaaatatat ttcatcatgc 3240 agttttttttc tgttaagtca ttaaagagaa ggtaaacaaa cctaaaa 3287

<210> SEQ ID NO 3
<211> LENGTH: 2996
<212> TYPE: DNA
<213> ORGANISM: Homo sapiens

<400> SEQUENCE: 3
gcgcacaccc gcgcacccgc ggccgcagga gggcccagcg acgccgccgc gccagctccc 60
agggcccggc cccccccggc gctcacgctc tcggggcgga ctcccggccc tccgcgccct 120
ctcgcgcggc gatggcccca ctcggatact tcttactcct ctgcagcctg aagcaggctc 180
tgggcagcta cccgatctgg tggtcgctgg ctgttgggcc acagtattcc tccctgggct 240

```
cgcagcccat cctgtgtgcc agcatcccgg gcctggtccc caagcagctc cgcttctgca    300
ggaactacgt ggagatcatg cccagcgtgg ccgagggcat caagattggc atccaggagt    360
gccagcacca gttccgcggc cgccggtgga actgcaccac cgtccacgac agcctggcca    420
tcttcgggcc cgtgctggac aaagctacca gggagtcggc ctttgtccac gccattgcct    480
cagccggtgt ggcctttgca gtgacacgct catgtgcaga aggcacggcc gccatctgtg    540
gctgcagcag ccgccaccag ggctcaccag gcaagggctg gaagtggggt ggctgtagcg    600
aggacatcga gtttggtggg atggtgtctc gggagttcgc cgacgcccgg gagaaccggc    660
cagatgcccg ctcagccatg aaccgccaca acaacgaggc tgggcgccag gccatcgcca    720
gccacatgca cctcaagtgc aagtgccacg ggctgtcggg cagctgcgag gtgaagacat    780
gctggtggtc gcaacccgac ttccgcgcca tcggtgactt cctcaaggac aagtacgaca    840
gcgcctcgga gatggtggtg gagaagcacc gggagtcccg cggctgggtg gagaccctgc    900
ggccgcgcta cacctacttc aaggtgccca cggagcgcga cctggtctac tacgaggcct    960
cgcccaactt ctgcgagccc aaccctgaga cgggctcctt cggcacgcgc gaccgcacct   1020
gcaacgtcag ctcgcacggc atcgacggct gcgacctgct gtgctgcggc cgcggccaca   1080
acgcgcgagc ggagcggcgc cgggagaagt gccgctgcgt gttccactgg tgctgctacg   1140
tcagctgcca ggagtgcacg cgcgtctacg acgtgcacac ctgcaagtag gcaccggccg   1200
cggctccccc tggacggggc gggccctgcc tgagggtggg cttttccctg ggtggagcag   1260
gactcccacc taaacggggc agtactcctc cctgggggcg ggactcctcc ctgggggtgg   1320
ggctcctacc tgggggcaga actcctacct gaaggcaggg ctcctccctg gagctagtgt   1380
ctcctctctg gtggctgggc tgctcctgaa tgaggcggag ctccaggatg gggaggggct   1440
ctgcgttggc ttctccctgg ggacggggct cccctggaca gaggcggggc tacagattgg   1500
gcggggcttc tcttgggtgg gacagggctt ctcctgcggg ggcgaggccc ctcccagtaa   1560
gggcgtggct ctgggtgggc ggggcactag gtaggcttct acctgcaggc ggggctcctc   1620
ctgaaggagg cggggctcta ggatggggca cggctctggg gtaggctgct ccctgagggc   1680
ggagcgcctc cttaggagtg gggttttatg gtggatgagg cttcttcctg gatggggcag   1740
agcttctcct gaccagggca aggccccttc cacgggggct gtggctctgg gtgggcgtgg   1800
cctgcatagg ctccttcctg tgggtggggc ttctctggga ccaggctcca atggggcggg   1860
gcttctctcc gcgggtggga ctcttccctg ggaaccgccc tcctgattaa ggcgtggctt   1920
ctgcaggaat cccggctcca gagcaggaaa ttcagcccac cagccacctc atccccaacc   1980
ccctgtaagg ttccatccac ccctgcgtcg agctgggaag gttccatgaa gcgagtcggg   2040
tccccaaccc gtgcccctgg gatccgaggg cccctctcca agcgcctggc tttggaatgc   2100
tccaggcgcg ccgacgcctg tgccacccct tcctcagcct ggggtttgac cacccacctg   2160
accaggggcc ctacctgggg aaagcctgaa gggcctccca gcccccaacc ccaagaccaa   2220
gcttagtcct gggagaggac agggacttcg cagaggcaag cgaccgaggc cctcccaaag   2280
aggcccgccc tgcccgggct cccacaccgt caggtactcc tgccagggaa ctggcctgct   2340
gcgccccagg ccccgcccgt ctctgctctg ctcagctgcg ccccccttctt tgcagctgcc  2400
cagcccctcc tccctgccct cgggtctccc cacctgcact ccatccagct acaggagaga   2460
tagaagcctc tcgtcccgtc cctccctttc ctccgcctgt ccacagcccc ttaagggaaa   2520
ggtaggaaga gaggtccagc cccccaggct gcccagagct gctggtctca tttgggggcg   2580
```

```
ttcgggaggt ttggggggca tcaacccccc gactgtgctg ctcgcgaagg tcccacagcc   2640

ctgagatggg ccggcccccct tcctggcccc tcatggcggg actggagaaa tggtccgctt   2700

tcctggagcc aatggcccgg cccctcctga ctcatccgcc tggcccggga atgaatgggg   2760

aggccgctga acccacccgg cccatatccc tggttgcctc atggccagcg cccctcagcc   2820

tctgccactg tgaaccggct cccaccctca aggtgcgggg agaagaagcg gccaggcggg   2880

gcgccccaag agcccaaaag agggcacacc gccatcctct gcctcaaatt ctgcgttttt   2940

ggttttaatg ttatatctga tgctgctata tccactgtcc aacggagtta gacgaa       2996
```

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

gttagcggat gctagggcaa atg                                          23


<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

gtggcttcag cggctaata                                               19


<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

agtgagaggg aagcagaaat gaa                                          23


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

ccggtggatg tggaatgtgt                                              20


<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

tccgagacaa tcgcgaacat                                              20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
accgtattgg caagtagccc 20

<210> SEQ ID NO 10
<211> LENGTH: 730
<212> TYPE: PRT
<213> ORGANISM: Homo sapiens

<400> SEQUENCE: 10

```
Met Pro Gly Val Ala Arg Leu Pro Leu Leu Leu Gly Leu Leu Leu Leu
1               5                   10                  15

Pro Arg Pro Gly Arg Pro Leu Asp Leu Ala Asp Tyr Thr Tyr Asp Leu
            20                  25                  30

Ala Glu Glu Asp Asp Ser Glu Pro Leu Asn Tyr Lys Asp Pro Cys Lys
        35                  40                  45

Ala Ala Ala Phe Leu Gly Asp Ile Ala Leu Asp Glu Glu Asp Leu Arg
    50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Arg Ala Ala Thr Ser Arg Pro Glu Arg
        115                 120                 125

Val Trp Pro Asp Gly Val Ile Pro Phe Val Ile Gly Gly Asn Phe Thr
    130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
        275                 280                 285

Lys Tyr Glu Val Asn Gly Val Lys Pro Pro Ile Gly Gln Arg Thr Arg
    290                 295                 300

Leu Ser Lys Gly Asp Ile Ala Gln Ala Arg Lys Leu Tyr Lys Cys Pro
```

-continued

```
305                 310                 315                 320

Ala Cys Gly Glu Thr Leu Gln Asp Ser Thr Gly Asn Phe Ser Ser Pro
                325                 330                 335

Glu Tyr Pro Asn Gly Tyr Ser Ala His Met His Cys Val Trp Arg Ile
            340                 345                 350

Ser Val Thr Pro Gly Glu Lys Ile Ile Leu Asn Phe Thr Ser Leu Asp
        355                 360                 365

Leu Tyr Arg Ser Arg Leu Cys Trp Tyr Asp Tyr Val Glu Val Arg Asp
    370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
                405                 410                 415

Arg Ser Ser Ser Asn Trp Val Gly Lys Gly Phe Phe Ala Val Tyr Glu
            420                 425                 430

Ala Ile Cys Gly Gly Asp Val Lys Lys Asp Tyr Gly His Ile Gln Ser
        435                 440                 445

Pro Asn Tyr Pro Asp Asp Tyr Arg Pro Ser Lys Val Cys Ile Trp Arg
    450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
                485                 490                 495

Asp Gly His Ser Glu Ser Ser Thr Leu Ile Gly Arg Tyr Cys Gly Tyr
            500                 505                 510

Glu Lys Pro Asp Asp Ile Lys Ser Thr Ser Ser Arg Leu Trp Leu Lys
        515                 520                 525

Phe Val Ser Asp Gly Ser Ile Asn Lys Ala Gly Phe Ala Val Asn Phe
    530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
                565                 570                 575

Gly Tyr Glu Leu Ala Pro Asp Lys Arg Arg Cys Glu Ala Ala Cys Gly
            580                 585                 590

Gly Phe Leu Thr Lys Leu Asn Gly Ser Ile Thr Ser Pro Gly Trp Pro
        595                 600                 605

Lys Glu Tyr Pro Pro Asn Lys Asn Cys Ile Trp Gln Leu Val Ala Pro
    610                 615                 620

Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr
                645                 650                 655

Ala Asp Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Phe Ser Glu Lys
    690                 695                 700

Arg Pro Ala Leu Gln Pro Pro Arg Gly Arg Pro His Gln Leu Lys Phe
705                 710                 715                 720

Arg Val Gln Lys Arg Asn Arg Thr Pro Gln
                725                 730
```

<210> SEQ ID NO 11
<211> LENGTH: 396
<212> TYPE: PRT
<213> ORGANISM: Homo sapiens

<400> SEQUENCE: 11

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
```

```
    370                 375                 380

Tyr Gln Asp Met Val Val Glu Gly Cys Gly Cys Arg
385                 390                 395


<210> SEQ ID NO 12
<211> LENGTH: 472
<212> TYPE: PRT
<213> ORGANISM: Homo sapiens

<400> SEQUENCE: 12

Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45

Glu Leu Gln Pro Gln Asp Lys Val Ser Glu His Met Leu Arg Leu Tyr
    50                  55                  60

Asp Arg Tyr Ser Thr Val Gln Ala Ala Arg Thr Pro Gly Ser Leu Glu
65                  70                  75                  80

Gly Gly Ser Gln Pro Trp Arg Pro Arg Leu Leu Arg Glu Gly Asn Thr
                85                  90                  95

Val Arg Ser Phe Arg Ala Ala Ala Ala Glu Thr Leu Glu Arg Lys Gly
            100                 105                 110

Leu Tyr Ile Phe Asn Leu Thr Ser Leu Thr Lys Ser Glu Asn Ile Leu
        115                 120                 125

Ser Ala Thr Leu Tyr Phe Cys Ile Gly Glu Leu Gly Asn Ile Ser Leu
    130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Leu Leu Arg Lys
        195                 200                 205

Ala Lys Glu Asn Glu Glu Phe Leu Ile Gly Phe Asn Ile Thr Ser Lys
    210                 215                 220

Gly Arg Gln Leu Pro Lys Arg Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285

Arg Ser Thr Gly Val Leu Leu Pro Leu Gln Asn Asn Glu Leu Pro Gly
    290                 295                 300

Ala Glu Tyr Gln Tyr Lys Lys Asp Glu Val Trp Glu Glu Arg Lys Pro
305                 310                 315                 320

Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
            340                 345                 350
```

-continued

```
Glu Gln Thr Leu Lys Lys Ala Arg Arg Lys Gln Trp Ile Glu Pro Arg
        355                 360                 365

Asn Cys Ala Arg Arg Tyr Leu Lys Val Asp Phe Ala Asp Ile Gly Trp
    370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
            420                 425                 430

Pro Glu Pro Cys Cys Val Pro Glu Lys Met Ser Ser Leu Ser Ile Leu
        435                 440                 445

Phe Phe Asp Glu Asn Lys Asn Val Val Leu Lys Val Tyr Pro Asn Met
    450                 455                 460

Thr Val Glu Ser Cys Ala Cys Arg
465                 470


<210> SEQ ID NO 13
<211> LENGTH: 408
<212> TYPE: PRT
<213> ORGANISM: Homo sapiens

<400> SEQUENCE: 13

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255
```

```
Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405


<210> SEQ ID NO 14
<211> LENGTH: 417
<212> TYPE: PRT
<213> ORGANISM: Homo sapiens

<400> SEQUENCE: 14

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
        35                  40                  45

Arg Glu Ile Gln Arg Glu Ile Leu Ser Ile Leu Gly Leu Pro His Arg
    50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
```

```
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Val His Leu Met Phe Pro Asp His Val Pro Lys Pro Cys Cys Ala Pro
    370                 375                 380

Thr Lys Leu Asn Ala Ile Ser Val Leu Tyr Phe Asp Asp Ser Ser Asn
385                 390                 395                 400

Val Ile Leu Lys Lys Tyr Arg Asn Met Val Val Arg Ser Cys Gly Cys
                405                 410                 415

His


<210> SEQ ID NO 15
<211> LENGTH: 513
<212> TYPE: PRT
<213> ORGANISM: Homo sapiens

<400> SEQUENCE: 15

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30

Ala Ala Ala Ala Ala Ala Ala Gly Gly Gln Leu Leu Gly Asp Gly Gly
        35                  40                  45

Ser Pro Gly Arg Thr Glu Gln Pro Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
```

-continued

```
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Phe Lys Val Ser Glu Val
        355                 360                 365

His Val Arg Thr Thr Arg Ser Ala Ser Ser Arg Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
        435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His


<210> SEQ ID NO 16
<211> LENGTH: 431
<212> TYPE: PRT
<213> ORGANISM: Homo sapiens

<400> SEQUENCE: 16

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
```

-continued

```
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

<210> SEQ ID NO 17

<211> LENGTH: 698
<212> TYPE: PRT
<213> ORGANISM: Homo sapiens

<400> SEQUENCE: 17

```
Met Asn Pro Phe Gln Lys Asn Glu Ser Lys Glu Thr Leu Phe Ser Pro
1               5                   10                  15

Val Ser Ile Glu Glu Val Pro Pro Arg Pro Pro Ser Pro Pro Lys Lys
            20                  25                  30

Pro Ser Pro Thr Ile Cys Gly Ser Asn Tyr Pro Leu Ser Ile Ala Phe
        35                  40                  45

Ile Val Val Asn Glu Phe Cys Glu Arg Phe Ser Tyr Tyr Gly Met Lys
    50                  55                  60

Ala Val Leu Ile Leu Tyr Phe Leu Tyr Phe Leu His Trp Asn Glu Asp
65                  70                  75                  80

Thr Ser Thr Ser Ile Tyr His Ala Phe Ser Ser Leu Cys Tyr Phe Thr
                85                  90                  95

Pro Ile Leu Gly Ala Ala Ile Ala Asp Ser Trp Leu Gly Lys Phe Lys
            100                 105                 110

Val Leu Ser Leu Ile Gly Leu Ser Leu Ile Ala Leu Gly Thr Gly Gly
        115                 120                 125

Ile Lys Pro Cys Val Ala Ala Phe Gly Gly Asp Gln Phe Glu Glu Lys
    130                 135                 140

His Ala Glu Glu Arg Thr Arg Tyr Phe Ser Val Phe Tyr Leu Ser Ile
145                 150                 155                 160

Asn Ala Gly Ser Leu Ile Ser Thr Phe Ile Thr Pro Met Leu Arg Gly
                165                 170                 175

Asp Val Gln Cys Phe Gly Glu Asp Cys Tyr Ala Leu Ala Phe Gly Val
            180                 185                 190

Pro Gly Leu Leu Met Val Ile Ala Leu Val Val Phe Ala Met Gly Ser
        195                 200                 205

Lys Ile Tyr Asn Lys Pro Pro Pro Glu Gly Asn Ile Val Ala Gln Val
    210                 215                 220

Phe Lys Cys Ile Trp Phe Ala Ile Ser Asn Arg Phe Lys Asn Arg Ser
225                 230                 235                 240

Gly Asp Ile Pro Lys Arg Gln His Trp Leu Asp Trp Ala Ala Glu Lys
                245                 250                 255

Tyr Pro Lys Gln Leu Ile Met Asp Val Lys Ala Leu Thr Arg Val Leu
            260                 265                 270

Phe Leu Tyr Ile Pro Leu Pro Met Phe Trp Ala Leu Leu Asp Gln Gln
        275                 280                 285

Gly Ser Arg Trp Thr Leu Gln Ala Ile Arg Met Asn Arg Asn Leu Gly
    290                 295                 300

Phe Phe Val Leu Gln Pro Asp Gln Met Gln Val Leu Asn Pro Leu Leu
305                 310                 315                 320

Val Leu Ile Phe Ile Pro Leu Phe Asp Phe Val Ile Tyr Arg Leu Val
                325                 330                 335

Ser Lys Cys Gly Ile Asn Phe Ser Ser Leu Arg Lys Met Ala Val Gly
            340                 345                 350

Met Ile Leu Ala Cys Leu Ala Phe Ala Val Ala Ala Ala Val Glu Ile
        355                 360                 365

Lys Ile Asn Glu Met Ala Pro Ala Gln Pro Gly Pro Gln Glu Val Phe
    370                 375                 380

Leu Gln Val Leu Asn Leu Ala Asp Asp Glu Val Lys Val Thr Val Val
```

385 390 395 400

Gly Asn Glu Asn Asn Ser Leu Leu Ile Glu Ser Ile Lys Ser Phe Gln
405 410 415

Lys Thr Pro His Tyr Ser Lys Leu His Leu Lys Thr Lys Ser Gln Asp
420 425 430

Phe His Phe His Leu Lys Tyr His Asn Leu Ser Leu Tyr Thr Glu His
435 440 445

Ser Val Gln Glu Lys Asn Trp Tyr Ser Leu Val Ile Arg Glu Asp Gly
450 455 460

Asn Ser Ile Ser Ser Met Met Val Lys Asp Thr Glu Ser Arg Thr Thr
465 470 475 480

Asn Gly Met Thr Thr Val Arg Phe Val Asn Thr Leu His Lys Asp Val
485 490 495

Asn Ile Ser Leu Ser Thr Asp Thr Ser Leu Asn Val Gly Glu Asp Tyr
500 505 510

Gly Val Ser Ala Tyr Arg Thr Val Gln Arg Gly Glu Tyr Pro Ala Val
515 520 525

His Cys Arg Thr Glu Asp Lys Asn Phe Ser Leu Asn Leu Gly Leu Leu
530 535 540

Asp Phe Gly Ala Ala Tyr Leu Phe Val Ile Thr Asn Asn Thr Asn Gln
545 550 555 560

Gly Leu Gln Ala Trp Lys Ile Glu Asp Ile Pro Ala Asn Lys Met Ser
565 570 575

Ile Ala Trp Gln Leu Pro Gln Tyr Ala Leu Val Thr Ala Gly Glu Val
580 585 590

Met Phe Ser Val Thr Gly Leu Glu Phe Ser Tyr Ser Gln Ala Pro Ser
595 600 605

Ser Met Lys Ser Val Leu Gln Ala Ala Trp Leu Leu Thr Ile Ala Val
610 615 620

Gly Asn Ile Ile Val Leu Val Val Ala Gln Phe Ser Gly Leu Val Gln
625 630 635 640

Trp Ala Glu Phe Ile Leu Phe Ser Cys Leu Leu Leu Val Ile Cys Leu
645 650 655

Ile Phe Ser Ile Met Gly Tyr Tyr Tyr Val Pro Val Lys Thr Glu Asp
660 665 670

Met Arg Gly Pro Ala Asp Lys His Ile Pro His Ile Gln Gly Asn Met
675 680 685

Ile Lys Leu Glu Thr Lys Lys Thr Lys Leu
690 695

<210> SEQ ID NO 18
<211> LENGTH: 564
<212> TYPE: PRT
<213> ORGANISM: Homo sapiens

<400> SEQUENCE: 18

Met Lys Glu His Gly Gly Thr Phe Ser Ser Thr Gly Ile Ser Gly Gly
1 5 10 15

Ser Gly Asp Ser Ala Met Asp Ser Leu Gln Pro Leu Gln Pro Asn Tyr
20 25 30

Met Pro Val Cys Leu Phe Ala Glu Glu Ser Tyr Gln Lys Leu Ala Met
35 40 45

Glu Thr Leu Glu Glu Leu Asp Trp Cys Leu Asp Gln Leu Glu Thr Ile
50 55 60

-continued

```
Gln Thr Tyr Arg Ser Val Ser Glu Met Ala Ser Asn Lys Phe Lys Arg
65                  70                  75                  80

Met Leu Asn Arg Glu Leu Thr His Leu Ser Glu Met Ser Arg Ser Gly
                85                  90                  95

Asn Gln Val Ser Glu Tyr Ile Ser Asn Thr Phe Leu Asp Lys Gln Asn
            100                 105                 110

Asp Val Glu Ile Pro Ser Pro Thr Gln Lys Asp Arg Glu Lys Lys Lys
        115                 120                 125

Lys Gln Gln Leu Met Thr Gln Ile Ser Gly Val Lys Lys Leu Met His
    130                 135                 140

Ser Ser Ser Leu Asn Asn Thr Ser Ile Ser Arg Phe Gly Val Asn Thr
145                 150                 155                 160

Glu Asn Glu Asp His Leu Ala Lys Glu Leu Glu Asp Leu Asn Lys Trp
                165                 170                 175

Gly Leu Asn Ile Phe Asn Val Ala Gly Tyr Ser His Asn Arg Pro Leu
            180                 185                 190

Thr Cys Ile Met Tyr Ala Ile Phe Gln Glu Arg Asp Leu Leu Lys Thr
        195                 200                 205

Phe Arg Ile Ser Ser Asp Thr Phe Ile Thr Tyr Met Met Thr Leu Glu
    210                 215                 220

Asp His Tyr His Ser Asp Val Ala Tyr His Asn Ser Leu His Ala Ala
225                 230                 235                 240

Asp Val Ala Gln Ser Thr His Val Leu Leu Ser Thr Pro Ala Leu Asp
                245                 250                 255

Ala Val Phe Thr Asp Leu Glu Ile Leu Ala Ala Ile Phe Ala Ala Ala
            260                 265                 270

Ile His Asp Val Asp His Pro Gly Val Ser Asn Gln Phe Leu Ile Asn
        275                 280                 285

Thr Asn Ser Glu Leu Ala Leu Met Tyr Asn Asp Glu Ser Val Leu Glu
    290                 295                 300

Asn His His Leu Ala Val Gly Phe Lys Leu Leu Gln Glu Glu His Cys
305                 310                 315                 320

Asp Ile Phe Met Asn Leu Thr Lys Lys Gln Arg Gln Thr Leu Arg Lys
                325                 330                 335

Met Val Ile Asp Met Val Leu Ala Thr Asp Met Ser Lys His Met Ser
            340                 345                 350

Leu Leu Ala Asp Leu Lys Thr Met Val Glu Thr Lys Lys Val Thr Ser
        355                 360                 365

Ser Gly Val Leu Leu Leu Asp Asn Tyr Thr Asp Arg Ile Gln Val Leu
    370                 375                 380

Arg Asn Met Val His Cys Ala Asp Leu Ser Asn Pro Thr Lys Ser Leu
385                 390                 395                 400

Glu Leu Tyr Arg Gln Trp Thr Asp Arg Ile Met Glu Glu Phe Phe Gln
                405                 410                 415

Gln Gly Asp Lys Glu Arg Glu Arg Gly Met Glu Ile Ser Pro Met Cys
            420                 425                 430

Asp Lys His Thr Ala Ser Val Glu Lys Ser Gln Val Gly Phe Ile Asp
        435                 440                 445

Tyr Ile Val His Pro Leu Trp Glu Thr Trp Ala Asp Leu Val Gln Pro
    450                 455                 460

Asp Ala Gln Asp Ile Leu Asp Thr Leu Glu Asp Asn Arg Asn Trp Tyr
465                 470                 475                 480

Gln Ser Met Ile Pro Gln Ser Pro Ser Pro Pro Leu Asp Glu Gln Asn
```

-continued

```
                485                 490                 495

Arg Asp Cys Gln Gly Leu Met Glu Lys Phe Gln Phe Glu Leu Thr Leu
            500                 505                 510

Asp Glu Glu Asp Ser Glu Gly Pro Glu Lys Glu Gly Glu Gly His Ser
        515                 520                 525

Tyr Phe Ser Ser Thr Lys Thr Leu Cys Val Ile Asp Pro Glu Asn Arg
    530                 535                 540

Asp Ser Leu Gly Glu Thr Asp Ile Asp Ile Ala Thr Glu Asp Lys Ser
545                 550                 555                 560

Pro Val Asp Thr


<210> SEQ ID NO 19
<211> LENGTH: 424
<212> TYPE: PRT
<213> ORGANISM: Homo sapiens

<400> SEQUENCE: 19

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly
        35                  40                  45

Val Asp Phe Asn Thr Leu Leu Gln Ser Met Lys Asp Glu Phe Leu Lys
    50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
```

-continued

```
    290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
    370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420


<210> SEQ ID NO 20
<211> LENGTH: 155
<212> TYPE: PRT
<213> ORGANISM: Homo sapiens

<400> SEQUENCE: 20

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155


<210> SEQ ID NO 21
<211> LENGTH: 154
<212> TYPE: PRT
<213> ORGANISM: Mus musculus

<400> SEQUENCE: 21

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
```

```
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150


<210> SEQ ID NO 22
<211> LENGTH: 154
<212> TYPE: PRT
<213> ORGANISM: Rattus norvegicus

<400> SEQUENCE: 22

Met Ala Ala Gly Ser Ile Thr Ser Leu Pro Ala Leu Pro Glu Asp Gly
1               5                   10                  15

Gly Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150


<210> SEQ ID NO 23
<211> LENGTH: 155
<212> TYPE: PRT
<213> ORGANISM: Bos taurus

<400> SEQUENCE: 23

Met Ala Ala Gly Ser Ile Thr Thr Leu Pro Ser Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
```

```
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155


<210> SEQ ID NO 24
<211> LENGTH: 158
<212> TYPE: PRT
<213> ORGANISM: Gallus gallus

<400> SEQUENCE: 24

Met Ala Ala Gly Ala Ala Gly Ser Ile Thr Thr Leu Pro Ala Leu Pro
1               5                   10                  15

Asp Asp Gly Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
        35                  40                  45

Asp Gly Arg Val Asp Gly Val Arg Glu Lys Ser Asp Pro His Ile Lys
    50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
        115                 120                 125

Ala Leu Lys Arg Thr Gly Gln Tyr Lys Pro Gly Pro Lys Thr Gly Pro
    130                 135                 140

Gly Gln Lys Ala Ile Leu Phe Leu Pro Met Ser Ala Lys Ser
145                 150                 155


<210> SEQ ID NO 25
<211> LENGTH: 398
<212> TYPE: PRT
<213> ORGANISM: Sus scrofa

<400> SEQUENCE: 25

Met Ser Phe Gly Trp Arg Gly Val Gly Leu Gly Arg Leu Leu Gly Asn
1               5                   10                  15

Arg Arg Gly Arg Gly Leu Trp Ser Cys Gly Gly Leu Gly Phe Gly Leu
            20                  25                  30

Leu Pro Arg Pro Arg Ile Ser Pro Ala Arg Asp Cys Leu Pro Thr Pro
        35                  40                  45

Phe Gly Cys Arg Ala Leu Ala Gly Arg Arg Ala Gly Arg Glu Glu Gly
    50                  55                  60

Arg Gly Arg Gly Gly Trp Trp Ala Phe Gly Gly Gly Asp Val Glu Asp
```

-continued

```
65                  70                  75                  80

Val Thr Pro Arg Gly Ser Ala Gly Ala Arg Pro Ala Asp Ser Glu Pro
                85                  90                  95

Ala Val Ala Ser Arg Ser Arg Ala Leu Gln Phe Gly Glu Ala Ala Leu
            100                 105                 110

Pro Arg Val Ala Ala Ala Glu Lys Pro Ser Pro Asn Pro Gln Leu Gln
        115                 120                 125

Gly Arg Arg Arg Ala Lys Arg Pro Asn Ser Thr Arg Leu Gly Ala Arg
    130                 135                 140

Gly Arg Gly Arg Val Pro Arg Gly Gly Arg Leu Gly Gly Arg Gly Arg
145                 150                 155                 160

Gly Arg Ala Pro Glu Arg Val Gly Gly Arg Gly Arg Gly Ser Ala Ala
                165                 170                 175

Ala Ala Ala Ala Ala Pro Arg Ala Ala Pro Gly Ala Arg Gly Pro Arg
            180                 185                 190

Gln Ser Pro Gly Gly Ala Met Ala Ala Gly Ser Ile Thr Thr Leu Pro
        195                 200                 205

Ala Leu Pro Glu Asp Gly Gly Ser Gly Ala Phe Pro Pro Gly His Phe
    210                 215                 220

Lys Asp Pro Lys Arg Leu Tyr Cys Lys Asn Gly Gly Phe Phe Leu Arg
225                 230                 235                 240

Ile His Pro Asp Gly Arg Val Asp Gly Val Arg Glu Lys Ser Asp Pro
                245                 250                 255

His Ile Lys Leu Gln Leu Gln Ala Glu Glu Arg Gly Val Val Ser Ile
            260                 265                 270

Lys Gly Val Cys Ala Asn Arg Tyr Leu Ala Met Lys Glu Asp Gly Arg
        275                 280                 285

Leu Leu Ala Ser Ile Leu Cys Phe Ile His Thr Gly Leu Leu Ser Ala
    290                 295                 300

Leu His Thr Leu Trp Pro Asp Pro Val Val Ala Tyr Pro Pro Phe Ala
305                 310                 315                 320

Trp Lys Leu Phe Ser Glu Ile Trp Thr Val Asn Ser Phe Thr Ser Phe
                325                 330                 335

Glu Lys Cys Val Thr Asp Glu Cys Phe Phe Phe Glu Arg Leu Glu Ser
            340                 345                 350

Asn Asn Tyr Asn Thr Tyr Arg Ser Arg Lys Tyr Ser Ser Trp Tyr Val
        355                 360                 365

Ala Leu Lys Arg Thr Gly Gln Tyr Lys Leu Gly Pro Lys Thr Gly Pro
    370                 375                 380

Gly Gln Lys Ala Ile Leu Phe Leu Pro Met Ser Ala Lys Ser
385                 390                 395
```

<210> SEQ ID NO 26
<211> LENGTH: 261
<212> TYPE: PRT
<213> ORGANISM: Canis lupus familiaris

<400> SEQUENCE: 26

```
Met Met His Arg Phe Glu Cys Tyr Phe Leu Thr Ala Leu Ile Cys Gly
1               5                   10                  15

Thr Ser Ala Pro Arg Ala Arg Ala Arg Ala Arg Ala Arg Ala Gln His
            20                  25                  30

Pro Gly Pro Arg Ala Ala Pro Gln Gly Ser Arg Arg Gly Glu Arg Pro
        35                  40                  45
```

```
Gly Gly Ala Arg Leu Gly Ala Arg Gly Arg Gly Arg Ala Leu Pro Gly
    50                  55                  60

Gly Arg Leu Gly Gly Arg Gly Arg Gly Arg Ala Pro Asp Arg Val Gly
65                  70                  75                  80

Gly Arg Gly Arg Gly Ala Ala Ala Ala Pro Arg Ala Ala Pro Gly Ala
                85                  90                  95

Arg Thr Pro Arg Gln Ser Pro Gly Gly Ala Met Ala Ala Gly Ser Ile
            100                 105                 110

Thr Thr Leu Pro Ala Leu Pro Glu Asp Gly Gly Ser Gly Ala Phe Pro
        115                 120                 125

Pro Gly His Phe Lys Asp Pro Lys Arg Leu Tyr Cys Lys Asn Gly Gly
    130                 135                 140

Phe Phe Leu Arg Ile His Pro Asp Gly Arg Val Asp Gly Val Arg Glu
145                 150                 155                 160

Lys Ser Asp Pro His Val Lys Leu Gln Leu Gln Ala Glu Glu Arg Gly
                165                 170                 175

Val Val Ser Ile Lys Gly Val Cys Ala Asn Arg Tyr Leu Ala Met Lys
            180                 185                 190

Glu Asp Gly Arg Leu Leu Ala Ser Lys Cys Val Thr Asp Glu Cys Phe
        195                 200                 205

Phe Phe Glu Arg Leu Glu Ser Asn Asn Tyr Asn Thr Tyr Arg Ser Arg
    210                 215                 220

Lys Tyr Ser Ser Trp Tyr Val Ala Leu Lys Arg Thr Gly Gln Tyr Lys
225                 230                 235                 240

Leu Gly Pro Lys Thr Gly Pro Gly Gln Lys Ala Ile Leu Phe Leu Pro
                245                 250                 255

Met Ser Ala Lys Ser
            260


<210> SEQ ID NO 27
<211> LENGTH: 155
<212> TYPE: PRT
<213> ORGANISM: Ovis aries

<400> SEQUENCE: 27

Met Ala Ala Gly Ser Ile Thr Thr Leu Pro Ala Leu Pro Glu Asp Gly
1               5                   10                  15

Gly Ser Ser Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155
```

<210> SEQ ID NO 28
<211> LENGTH: 155
<212> TYPE: PRT
<213> ORGANISM: Oryctolagus cuniculus

<400> SEQUENCE: 28

```
Met Ala Ala Glu Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 29
<211> LENGTH: 155
<212> TYPE: PRT
<213> ORGANISM: Xenopus laevis

<400> SEQUENCE: 29

```
Met Ala Ala Gly Ser Ile Thr Thr Leu Pro Thr Glu Ser Glu Asp Gly
1               5                   10                  15

Gly Asn Thr Pro Phe Ser Pro Gly Ser Phe Lys Asp Pro Lys Arg Leu
            20                  25                  30

Tyr Cys Lys Asn Gly Gly Phe Phe Leu Arg Ile Asn Ser Asp Gly Arg
        35                  40                  45

Val Asp Gly Ser Arg Asp Lys Ser Asp Ser His Ile Lys Leu Gln Leu
    50                  55                  60

Gln Ala Val Glu Arg Gly Val Val Ser Ile Lys Gly Ile Thr Ala Asn
65                  70                  75                  80

Arg Tyr Leu Ala Met Lys Glu Asp Gly Arg Leu Thr Ser Leu Arg Cys
                85                  90                  95

Ile Thr Asp Glu Cys Phe Phe Phe Glu Arg Leu Glu Ala Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Asn Gly Ser Ser Thr Gly Pro Gly Gln Lys
    130                 135                 140

Ala Ile Leu Phe Leu Pro Met Ser Ala Lys Ser
145                 150                 155
```

<210> SEQ ID NO 30

<211> LENGTH: 208
<212> TYPE: PRT
<213> ORGANISM: Homo sapiens

<400> SEQUENCE: 30

Met Trp Lys Trp Ile Leu Thr His Cys Ala Ser Ala Phe Pro His Leu
1 5 10 15

Pro Gly Cys Cys Cys Cys Cys Phe Leu Leu Leu Phe Leu Val Ser Ser
20 25 30

Val Pro Val Thr Cys Gln Ala Leu Gly Gln Asp Met Val Ser Pro Glu
35 40 45

Ala Thr Asn Ser Ser Ser Ser Ser Phe Ser Ser Pro Ser Ser Ala Gly
50 55 60

Arg His Val Arg Ser Tyr Asn His Leu Gln Gly Asp Val Arg Trp Arg
65 70 75 80

Lys Leu Phe Ser Phe Thr Lys Tyr Phe Leu Lys Ile Glu Lys Asn Gly
85 90 95

Lys Val Ser Gly Thr Lys Lys Glu Asn Cys Pro Tyr Ser Ile Leu Glu
100 105 110

Ile Thr Ser Val Glu Ile Gly Val Val Ala Val Lys Ala Ile Asn Ser
115 120 125

Asn Tyr Tyr Leu Ala Met Asn Lys Lys Gly Lys Leu Tyr Gly Ser Lys
130 135 140

Glu Phe Asn Asn Asp Cys Lys Leu Lys Glu Arg Ile Glu Glu Asn Gly
145 150 155 160

Tyr Asn Thr Tyr Ala Ser Phe Asn Trp Gln His Asn Gly Arg Gln Met
165 170 175

Tyr Val Ala Leu Asn Gly Lys Gly Ala Pro Arg Arg Gly Gln Lys Thr
180 185 190

Arg Arg Lys Asn Thr Ser Ala His Phe Leu Pro Met Val Val His Ser
195 200 205

<210> SEQ ID NO 31
<211> LENGTH: 209
<212> TYPE: PRT
<213> ORGANISM: Mus musculus

<400> SEQUENCE: 31

Met Trp Lys Trp Ile Leu Thr His Cys Ala Ser Ala Phe Pro His Leu
1 5 10 15

Pro Gly Cys Cys Cys Cys Phe Leu Leu Leu Phe Leu Val Ser Ser Phe
20 25 30

Pro Val Thr Cys Gln Ala Leu Gly Gln Asp Met Val Ser Gln Glu Ala
35 40 45

Thr Asn Cys Ser Ser Ser Ser Ser Ser Phe Ser Ser Pro Ser Ser Ala
50 55 60

Gly Arg His Val Arg Ser Tyr Asn His Leu Gln Gly Asp Val Arg Trp
65 70 75 80

Arg Arg Leu Phe Ser Phe Thr Lys Tyr Phe Leu Thr Ile Glu Lys Asn
85 90 95

Gly Lys Val Ser Gly Thr Lys Asn Glu Asp Cys Pro Tyr Ser Val Leu
100 105 110

Glu Ile Thr Ser Val Glu Ile Gly Val Val Ala Val Lys Ala Ile Asn
115 120 125

Ser Asn Tyr Tyr Leu Ala Met Asn Lys Lys Gly Lys Leu Tyr Gly Ser
130 135 140

```
Lys Glu Phe Asn Asn Asp Cys Lys Leu Lys Glu Arg Ile Glu Glu Asn
145                 150                 155                 160

Gly Tyr Asn Thr Tyr Ala Ser Phe Asn Trp Gln His Asn Gly Arg Gln
                165                 170                 175

Met Tyr Val Ala Leu Asn Gly Lys Gly Ala Pro Arg Arg Gly Gln Lys
            180                 185                 190

Thr Arg Arg Lys Asn Thr Ser Ala His Phe Leu Pro Met Thr Ile Gln
        195                 200                 205

Thr


<210> SEQ ID NO 32
<211> LENGTH: 215
<212> TYPE: PRT
<213> ORGANISM: Rattus norvegicus

<400> SEQUENCE: 32

Met Trp Lys Trp Ile Leu Thr His Cys Ala Ser Ala Phe Pro His Leu
1               5                   10                  15

Pro Gly Cys Cys Cys Cys Phe Leu Leu Leu Phe Leu Val Ser Ser Val
            20                  25                  30

Pro Val Thr Cys Gln Ala Leu Gly Gln Asp Met Val Ser Pro Glu Ala
        35                  40                  45

Thr Asn Ser Ser Ser Ser Ser Ser Ser Ser Ser Ser Ser Ser Ser Phe
    50                  55                  60

Ser Ser Pro Ser Ser Ala Gly Arg His Val Arg Ser Tyr Asn His Leu
65                  70                  75                  80

Gln Gly Asp Val Arg Trp Arg Lys Leu Phe Ser Phe Thr Lys Tyr Phe
                85                  90                  95

Leu Lys Ile Glu Lys Asn Gly Lys Val Ser Gly Thr Lys Lys Glu Asn
            100                 105                 110

Cys Pro Tyr Ser Ile Leu Glu Ile Thr Ser Val Glu Ile Gly Val Val
        115                 120                 125

Ala Val Lys Ala Ile Asn Ser Asn Tyr Tyr Leu Ala Met Asn Lys Lys
    130                 135                 140

Gly Lys Leu Tyr Gly Ser Lys Glu Phe Asn Asn Asp Cys Lys Leu Lys
145                 150                 155                 160

Glu Arg Ile Glu Glu Asn Gly Tyr Asn Thr Tyr Ala Ser Phe Asn Trp
                165                 170                 175

Gln His Asn Gly Arg Gln Met Tyr Val Ala Leu Asn Gly Lys Gly Ala
            180                 185                 190

Pro Arg Arg Gly Gln Lys Thr Arg Arg Lys Asn Thr Ser Ala His Phe
        195                 200                 205

Leu Pro Met Val Val His Ser
    210                 215


<210> SEQ ID NO 33
<211> LENGTH: 201
<212> TYPE: PRT
<213> ORGANISM: Danio rerio

<400> SEQUENCE: 33

Met Cys Lys Trp Lys Val Thr Lys Gly Ala Ser Ala Trp Phe Arg Leu
1               5                   10                  15

Ser Cys Leu Ser Leu Pro Leu Leu Leu Leu Phe Leu Cys Ser Ala Leu
            20                  25                  30
```

-continued

```
Pro Val Ala Cys His Asp Thr His Arg Ala Ile Arg Ala Pro Arg Gly
        35                  40                  45

Thr Asn Ser Ser Ser Ser Ala Val Val Gly Arg His Val Arg Ser Tyr
    50                  55                  60

Asn His Leu Thr Gly Asp Val Arg Arg Arg Lys Leu Phe Ser Tyr Gln
65                  70                  75                  80

Lys Phe Phe Leu Arg Ile Asp Lys Asn Gly Lys Val Asn Gly Thr Lys
                85                  90                  95

Ser Lys Asp Asp Pro Tyr Ser Thr Leu Glu Ile Lys Ser Val Asp Val
            100                 105                 110

Gly Ile Val Ala Ile Lys Gly Ile Gln Ser Asn Tyr Tyr Leu Ala Ile
        115                 120                 125

Asn Lys Lys Gly Val Val Tyr Gly Ala Arg Asp Phe Gly Ile Asp Cys
    130                 135                 140

Lys Leu Ile Glu Arg Ile Glu Glu Asn Arg Tyr Asn Thr Tyr Ala Ser
145                 150                 155                 160

Ala Glu Trp Met Asn Lys Lys Lys His Met Phe Val Gly Leu Ser Ala
                165                 170                 175

Asn Gly Arg Pro Met Arg Ala Lys Lys Thr Arg Arg Lys Asn Thr Ala
            180                 185                 190

Thr His Phe Leu Pro Ile Pro Ile Val
        195                 200


<210> SEQ ID NO 34
<211> LENGTH: 212
<212> TYPE: PRT
<213> ORGANISM: Gallus gallus

<400> SEQUENCE: 34

Met Cys Lys Trp Ile Leu Thr Asn Gly Ala Ser Ala Phe Ser His Leu
1               5                   10                  15

Pro Cys Cys Cys Leu Leu Leu Leu Phe Leu Val Ser Ser Val Pro Val
            20                  25                  30

Thr Cys His Asp Leu Gly Gln Asp Met Leu Ser Pro Glu Ala Thr Asn
        35                  40                  45

Ser Ser Ser Ser Ser Ser Ser Ser Phe Pro Ser Ser Phe Ser Ser Pro
    50                  55                  60

Ser Ser Ala Gly Arg His Val Arg Ser Tyr Asn His Leu Gln Gly Asp
65                  70                  75                  80

Val Arg Lys Arg Lys Leu Tyr Ser Tyr Asn Lys Tyr Phe Leu Lys Ile
                85                  90                  95

Glu Lys Asn Gly Lys Val Ser Gly Thr Lys Lys Glu Asn Cys Pro Phe
            100                 105                 110

Ser Ile Leu Glu Ile Thr Ser Val Glu Ile Gly Val Val Ala Val Lys
        115                 120                 125

Ser Ile Lys Ser Asn Tyr Tyr Leu Ala Met Asn Lys Lys Gly Lys Val
    130                 135                 140

Tyr Gly Ser Lys Glu Phe Asn Ser Asp Cys Lys Leu Lys Glu Arg Ile
145                 150                 155                 160

Glu Glu Asn Gly Tyr Asn Thr Tyr Ala Ser Leu Asn Trp Lys His Asn
                165                 170                 175

Gly Arg Gln Met Phe Val Ala Leu Asn Gly Arg Gly Ala Thr Lys Arg
            180                 185                 190

Gly Gln Lys Thr Arg Arg Lys Asn Thr Ser Ala His Phe Leu Pro Met
        195                 200                 205
```

Val Val Met Ser
    210

<210> SEQ ID NO 35
<211> LENGTH: 213
<212> TYPE: PRT
<213> ORGANISM: Bos taurus

<400> SEQUENCE: 35

Met Trp Lys Trp Ile Leu Thr His Cys Ala Ser Ala Phe Pro His Leu
1               5                   10                  15

Ser Gly Cys Cys Cys Cys Phe Leu Leu Leu Phe Leu Val Ser Ser Val
            20                  25                  30

Pro Val Thr Cys Gln Ala Leu Asp Gln Asp Met Val Ser Pro Gly Ala
        35                  40                  45

Thr Asn Ser Ser Ser Ser Ser Ser Ser Ser Ser Ser Ser Ser Val Ser
    50                  55                  60

Leu Pro Ser Ser Ala Gly Arg His Val Arg Ser Tyr Asn His Leu Gln
65                  70                  75                  80

Gly Asp Val Arg Trp Arg Lys Leu Phe Ser Phe Thr Lys Tyr Phe Leu
                85                  90                  95

Lys Ile Glu Asn Gly Lys Val Ser Gly Thr Lys Lys Glu Asn Cys Pro
            100                 105                 110

Tyr Ser Ile Leu Glu Ile Thr Ser Val Glu Ile Gly Val Val Ala Val
        115                 120                 125

Lys Ala Ile Asn Ser Asn Tyr Tyr Leu Ala Met Asn Lys Lys Gly Lys
    130                 135                 140

Leu Tyr Gly Ser Lys Glu Phe Asn Asn Asp Cys Lys Leu Lys Glu Arg
145                 150                 155                 160

Ile Glu Glu Asn Gly Tyr Asn Thr Tyr Ala Ser Phe Asn Trp Gln His
                165                 170                 175

Asn Gly Arg Gln Met Tyr Val Ala Leu Asn Gly Lys Gly Ala Pro Arg
            180                 185                 190

Arg Gly Gln Lys Thr Arg Arg Lys Asn Thr Ser Ala His Phe Leu Pro
        195                 200                 205

Met Val Val His Ser
    210

<210> SEQ ID NO 36
<211> LENGTH: 2506
<212> TYPE: DNA
<213> ORGANISM: Homo sapiens

<400> SEQUENCE: 36
agtgcgccgc ttccctcgcc gccgccccgc cagcatgccc ggcgtggccc gcctgccgct      60
gctgctcggg ctgctgctgc tcccgcgtcc cggccggccg ctggacttgg ccgactacac     120
ctatgacctg gcggaggagg acgactcgga gcccctcaac tacaaagacc cctgcaaggc     180
ggctgccttt cttggggaca ttgccctgga cgaagaggac ctgagggcct tccaggtaca     240
gcaggctgtg gatctcagac ggcacacagc tcgtaagtcc tccatcaaag ctgcagttcc     300
aggaaacact tctacccccca gctgccagag caccaacggg cagcctcaga ggggagcctg     360
tgggagatgg agaggtagat cccgtagccg gcgggcggcg acgtcccgac cagagcgtgt     420
gtggcccgat ggggtcatcc cctttgtcat tgggggaaac ttcactggta gccagagggc     480
agtcttccgg caggccatga ggcactggga gaagcacacc tgtgtcacct tcctggagcg     540

```
cactgacgag gacagctata ttgtgttcac ctatcgacct tgcgggtgct gctcctacgt    600

gggtcgccgc ggcgggggcc cccaggccat ctccatcggc aagaactgtg acaagttcgg    660

cattgtggtc cacgagctgg gccacgtcgt cggcttctgg cacgaacaca ctcggccaga    720

ccgggaccgc cacgtttcca tcgttcgtga gaacatccag ccagggcagg agtataactt    780

cctgaagatg gagcctcagg aggtggagtc cctgggggag acctatgact tcgacagcat    840

catgcattac gctcggaaca cattctccag gggcatcttc ctggatacca ttgtccccaa    900

gtatgaggtg aacggggtga aacctcccat tggccaaagg acacggctca gcaaggggga    960

cattgcccaa gcccgcaagc tttacaagtg cccagcctgt ggagagaccc tgcaagacag   1020

cacaggcaac ttctcctccc ctgaataccc caatggctac tctgctcaca tgcactgcgt   1080

gtggcgcatc tctgtcacac ccggggagaa gatcatcctg aacttcacgt ccctggacct   1140

gtaccgcagc cgcctgtgct ggtacgacta tgtggaggtc cgagatggct tctggaggaa   1200

ggcgcccctc cgaggccgct tctgcgggtc caaactccct gagcctatcg tctccactga   1260

cagccgcctc tgggttgaat tccgcagcag cagcaattgg gttggaaagg gcttctttgc   1320

agtctacgaa gccatctgcg gggtgatgt gaaaaaggac tatggccaca ttcaatcgcc   1380

caactaccca gacgattacc ggcccagcaa agtctgcatc tggcggatcc aggtgtctga   1440

gggcttccac gtgggcctca cattccagtc ctttgagatt gagcgccacg acagctgtgc   1500

ctacgactat ctggaggtgc gcgacgggca cagtgagagc agcaccctca tcgggcgcta   1560

ctgtggctat gagaagcctg atgacatcaa gagcacgtcc agccgcctct ggctcaagtt   1620

cgtctctgac gggtccatta acaaagcggg ctttgccgtc aacttttca aagaggtgga    1680

cgagtgctct cggcccaacc gcgggggctg tgagcagcgg tgcctcaaca ccctgggcag   1740

ctacaagtgc agctgtgacc ccgggtacga gctggcccca gacaagcgcc gctgtgaggc   1800

tgcttgtggc ggattcctca ccaagctcaa cggctccatc accagcccgg gctggcccaa   1860

ggagtacccc cccaacaaga actgcatctg gcagctggtg gcccccaccc agtaccgcat   1920

ctccctgcag tttgacttct ttgagacaga gggcaatgat gtgtgcaagt acgacttcgt   1980

ggaggtgcgc agtggactca cagctgactc caagctgcat ggcaagttct gtggttctga   2040

gaagcccgag gtcatcacct cccagtacaa caacatgcgc gtggagttca agtccgacaa   2100

caccgtgtcc aaaaagggct tcaaggccca cttcttctca gaaaagaggc cagctctgca   2160

gccccctcgg ggacgccccc accagctcaa attccgagtg cagaaaagaa accggacccc   2220

ccagtgaggc ctgccaggcc tcccggaccc cttgttactc aggaacctca ccttggacgg   2280

aatgggatgg gggcttcggt gcccaccaac cccccacctc cactctgcca ttccggccca   2340

cctccctctg gccggacaga actggtgctc tcttctcccc actgtgcccg tccgcggacc   2400

ggggaccctt ccccgtgccc tacccctcc cattttgatg gtgtctgtga catttcctgt    2460

tgtgaagtaa aagagggacc cctgcgtcct gctcctttct cttgca                  2506
```

<210> SEQ ID NO 37
<211> LENGTH: 3545
<212> TYPE: DNA
<213> ORGANISM: Homo sapiens

<400> SEQUENCE: 37

```
gccgccgccg ccgtcgccgc cgccggagtc ctcgccccgc cgcgctgcgc ccggctcgcg     60

ctgcgctagt cgctccgctt cccacacccc gccggggact ggcagccgcc gccgcacatc    120
```

```
tgccgccaca gcctccgccg gctacccgaa cgttctcggg gccagcgccg agtggatcac    180
cggggaccgc gaggcacccg cgcgccgcag accccgcgcg ggctggagca cccggcagag    240
cgcgccacag cgccgtggcc tctgctgccc gggctgcgcc agagccgcgg acgggcgcgc    300
agagcgccgg ggactccgga gccgatccct agcgccgcga tgcggagcac ctactgcagg    360
agatcggggg cctgggacgc gctggccgag gtgtgatcgg accccaggct agccacaaag    420
ggcacttggc cccagggcta ggagagcgag gggagagcac agccacccgc ctcggcggcc    480
cgggactcgg ctcgactcgc cggagaatgc gcccgaggac gacggggcgc cagagccgcg    540
gtgctttcaa ctggcgagcg cgaatggggg tgcactggag taaggcagag tgatgcgggg    600
gggcaactcg cctggcaccg agatcgccgc cgtgcccttc cctggacccg gcgtcgccca    660
ggatggctgc cccgagccat gggccgcggc ggagctagcg cggagcgccc gaccctcgac    720
ccccgagtcc cggagccggc cccgcgcggg gccacgcgtc cctcgggcgc tggttcctaa    780
ggaggacgac agcaccagct tctcctttct cccttccctt ccctgccccg cactcctccc    840
cctgctcgct gttgttgtgt gtcagcactt ggctggggac ttcttgaact tgcagggaga    900
ataacttgcg caccccactt tgcgccggtg cctttgcccc agcggagcct gcttcgccat    960
ctccgagccc caccgcccct ccactcctcg gccttgcccg acactgagac gctgttccca   1020
gcgtgaaaag agagactgcg cggccggcac ccgggagaag gaggaggcaa agaaaaggaa   1080
cggacattcg gtccttgcgc caggtccttt gaccagagtt tttccatgtg gacgctcttt   1140
caatggacgt gtccccgcgt gcttcttaga cggactgcgg tctcctaaag gtcgaccatg   1200
gtggccggga cccgctgtct tctagcgttg ctgcttcccc aggtcctcct gggcggcgcg   1260
gctggcctcg ttccggagct gggccgcagg aagttcgcgg cggcgtcgtc gggccgcccc   1320
tcatcccagc cctctgacga ggtcctgagc gagttcgagt tgcggctgct cagcatgttc   1380
ggcctgaaac agagacccac ccccagcagg gacgccgtgg tgccccccta catgctagac   1440
ctgtatcgca ggcactcagg tcagccgggc tcacccgccc cagaccaccg gttggagagg   1500
gcagccagcc gagccaacac tgtgcgcagc ttccaccatg aagaatcttt ggaagaacta   1560
ccagaaacga gtgggaaaac aacccggaga ttcttcttta atttaagttc tatccccacg   1620
gaggagttta tcacctcagc agagcttcag gttttccgag aacagatgca agatgcttta   1680
ggaaacaata gcagtttcca tcaccgaatt aatatttatg aaatcataaa acctgcaaca   1740
gccaactcga aattccccgt gaccagactt ttggacacca ggttggtgaa tcagaatgca   1800
agcaggtggg aaagttttga tgtcaccccc gctgtgatgc ggtggactgc acagggacac   1860
gccaaccatg gattcgtggt ggaagtggcc cacttggagg agaaacaagg tgtctccaag   1920
agacatgtta ggataagcag gtctttgcac caagatgaac acagctggtc acagataagg   1980
ccattgctag taacttttgg ccatgatgga aaagggcatc ctctccacaa aagagaaaaa   2040
cgtcaagcca aacacaaaca gcggaaacgc cttaagtcca gctgtaagag acaccctttg   2100
tacgtggact tcagtgacgt ggggtggaat gactggattg tggctccccc ggggtatcac   2160
gccttttact gccacggaga atgccctttt cctctggctg atcatctgaa ctccactaat   2220
catgccattg ttcagacgtt ggtcaactct gttaactcta agattcctaa ggcatgctgt   2280
gtcccgacag aactcagtgc tatctcgatg ctgtaccttg acgagaatga aaaggttgta   2340
ttaaagaact atcaggacat ggttgtggag ggttgtgggt gtcgctagta cagcaaaatt   2400
aaatacataa atatatatat atatatatat tttagaaaaa agaaaaaaac aaacaaacaa   2460
aaaaacccca ccccagttga cactttaata tttcccaatg aagactttat ttatggaatg   2520
```

-continued

```
gaatggaaaa aaaaacagct attttgaaaa tatatttata tctacgaaaa gaagttggga   2580

aaacaaatat tttaatcaga gaattattcc ttaaagattt aaaatgtatt tagttgtaca   2640

ttttatatgg gttcaacccc agcacatgaa gtataatggt cagatttatt ttgtatttat   2700

ttactattat aaccactttt taggaaaaaa atagctaatt tgtatttata tgtaatcaaa   2760

agaagtatcg ggtttgtaca taattttcca aaaattgtag ttgttttcag ttgtgtgtat   2820

ttaagatgaa aagtctacat ggaaggttac tctggcaaag tgcttagcac gtttgctttt   2880

ttgcagtgct actgttgagt tcacaagttc aagtccagaa aaaaaaagtg gataatccac   2940

tctgctgact ttcaagatta ttatattatt caattctcag gaatgttgca gagtgattgt   3000

ccaatccatg agaatttaca tccttattag gtggaatatt tggataagaa ccagacattg   3060

ctgatctatt atagaaactc tcctcctgcc ccttaattta cagaaagaat aaagcaggat   3120

ccatagaaat aattaggaaa acgatgaacc tgcaggaaag tgaatgatgg tttgttgttc   3180

ttctttccta aattagtgat cccttcaaag gggctgatct ggccaaagta ttcaataaaa   3240

cgtaagattt cttcattatt gatattgtgg tcatatatat ttaaaattga tatctcgtgg   3300

ccctcatcaa gggttggaaa tttatttgtg ttttaccttt acctcatctg agagctcttt   3360

attctccaaa gaacccagtt ttctaacttt ttgcccaaca cgcagcaaaa ttatgcacat   3420

cgtgttttct gcccaccctc tgttctctga cctatcagct tgcttttctt tccaaggttg   3480

tgtgtttgaa cacatttctc caaatgttaa acctatttca gataataaat atcaaatctc   3540

tggca                                                               3545
```

<210> SEQ ID NO 38
<211> LENGTH: 6087
<212> TYPE: DNA
<213> ORGANISM: Homo sapiens

<400> SEQUENCE: 38

```
ctctctctct catacacaca cacacacgca cacacgcgcg cgcgcgcgcg cacacacaca     60

cacacgtaca ctaaaaaact cggaccagcc gcgccgcagc tgctccaatc cctggaaaag    120

gcaatcgagc gccctccgga ccgctgcgca cagccccggc tccgacctgg cgcccaaaac    180

agagctagtc ctagtccctc gcgcggccag tttggccggg tgttcccaaa aataaagcga    240

ggagggaagg tacagacaga tcttgaaaac acccgggcca cacacgccgc gacctacagc    300

tctttctcag cgttggagtg gagacggcgc ccgcagcgcc ctgcgcgggt gaggtccgcg    360

cagctgctgg ggaagagccc acctgtcagg ctgcgctggg tcagcgcagc aagtggggct    420

ggccgctatc tcgctgcacc cggccgcgtc ccgggctccg tgcgccctcg ccccagctgg    480

tttggagttc aaccctcggc tccgccgccg gctccttgcg ccttcggagt gtcccgcagc    540

gacgccggga gccgacgcgc cgcgcgggta cctagccatg gctggggcga gcaggctgct    600

ctttctgtgg ctgggctgct tctgcgtgag cctggcgcag ggagagagac cgaagccacc    660

tttcccggag ctccgcaaag ctgtgccagg tgaccgcacg gcaggtggtg gcccggactc    720

cgagctgcag ccgcaagaca aggtctctga acacatgctg cggctctatg acaggtacag    780

cacggtccag gcggcccgga caccgggctc cctggaggga ggctcgcagc cctggcgccc    840

tcggctcctg cgcgaaggca acacggttcg cagctttcgg gcggcagcag cagaaactct    900

tgaaagaaaa ggactgtata tcttcaatct gacatcgcta accaagtctg aaaacatttt    960

gtctgccaca ctgtatttct gtattggaga gctaggaaac atcagcctga gttgtccagt   1020
```

-continued

```
gtctggagga tgctcccatc atgctcagag gaaacacatt cagattgatc tttctgcatg   1080
gaccctcaaa ttcagcagaa accaaagtca actccttggc catctgtcag tggatatggc   1140
caaatctcat cgagatatta tgtcctggct gtctaaagat atcactcaac tcttgaggaa   1200
ggccaaagaa aatgaagagt tcctcatagg atttaacatt acgtccaagg gacgccagct   1260
gccaaagagg aggttacctt ttccagagcc ttatatcttg gtatatgcca atgatgccgc   1320
catttctgag ccagaaagtg tggtatcaag cttacaggga caccggaatt ttcccactgg   1380
aactgttccc aaatgggata gccacatcag agctgccctt tccattgagc ggaggaagaa   1440
gcgctctact ggggtcttgc tgcctctgca gaacaacgag cttcctgggg cagaatacca   1500
gtataaaaag gatgaggtgt gggaggagag aaagccttac aagacccttc aggctcaggc   1560
ccctgaaaag agtaagaata aaaagaaaca gagaaagggg cctcatcgga agagccagac   1620
gctccaattt gatgagcaga ccctgaaaaa ggcaaggaga aagcagtgga ttgaacctcg   1680
gaattgcgcc aggagatacc tcaaggtaga ctttgcagat attggctgga gtgaatggat   1740
tatctccccc aagtcctttg atgcctatta ttgctctgga gcatgccagt tccccatgcc   1800
aaagtctttg aagccatcaa atcatgctac catccagagt atagtgagag ctgtgggggt   1860
cgttcctggg attcctgagc cttgctgtgt accagaaaag atgtcctcac tcagtatttt   1920
attctttgat gaaaataaga atgtagtgct taaagtatac cctaacatga cagtagagtc   1980
ttgcgcttgc agataacctg gcaaagaact catttgaatg cttaattcaa tcattagttt   2040
atttttatgg acttcttcct gttttttttt tttttttttt tgcactgcca atgcattttg   2100
tttcaaaaga ttatttctat agtcagaggg gaatgagcaa atagactgaa gattgccacc   2160
aaggaaaaga actgtatttg tttctgaatg taacttaaag caagattttt agtaaatatg   2220
gacatctatt tctctttttg taatcaaaca caacaactta tcaaactgtt tttagaactg   2280
ttagagaaca cactggttta tttttgtaat gttctttgaa aacagaatgg agaagcagca   2340
atagcttgtc atttatctca tttaatgact aatgggaaat agagaacaat ttcgcgtttt   2400
gaattaggct tattgcctta gaatcctgag aaagtgctaa ataatcaact ctgatgtttt   2460
tcttaagttc ttgagactct tgtttatcct tgtttttcct ccacaagtca ttgtctaagt   2520
gtaatggaaa gtttatgctg agcgttagtg tgtatgtatg tgcgtacatg cgccaggtgc   2580
ctgtgccctc tgtaggatgg tttgcttaat atggttttat aattcagttt acacaggatt   2640
ctttattttt tttaattttg tattttggca aacaccattc agttataaga actttgccaa   2700
atatgataga ataattcaag agcatataca gagagttacc acttgaccca gctatttaat   2760
tgcaaataca gttgttttca tttcatttcc taccagaaaa aggaatcaga aacctagttt   2820
ttgaaaacac aagtgtaatt cctcttttgt acttcttttt cacaaatgct tttatttatt   2880
ctaaattgaa tttaaaaatc cttcctaaag ccattaactc tttaattctc ctgatatgcc   2940
tttacttcct atgaagttat tggtagatgt tgaggcccaa aaactggtag aatattgaag   3000
atcttcttaa atgaccaatt taaccataac caaatattga atatcattct tcagtcacat   3060
ctaagtcagg cactttttca catagatcag ggcttttggc tcagtcacga aatctacaag   3120
ttagcaaagc ttacaaaaca ttattcgtca ggtatgggaa tcaaatatag acacttgttt   3180
gtctttgctt tccatttcta tgtgtcacat acatatatgt gtcctcttat aactttagtc   3240
ttcaaaatta tttcaatatc cttcttctca ctatatttat ttgtgtgatg gaaatgcttt   3300
caggccgtag atcattgttg gtgttaatct gtggttaatc ctcattttag ttccgtctta   3360
tctgatactt agaaatatct cagccatttt ggaggctgtg cagtatcaga agacgtggag   3420
```

-continued

```
tttgttctgt ctctgcctgt agctaattat ggtggttcag tcatttaata aatatgtttt   3480
gagcatctat tttgtgaaag gcactgtgtt acctgtgtgt ctttagtgtc ctcactggta   3540
aaatgaagag gctggccatg agctggaagg gttaagttta taattccagc tatttcacac   3600
ccgtcttcct tgaaggaatg atagtgatag atataaaaac actgtaagtc cctcttttaa   3660
taaactaaat gaaagaacat cctatacttc gctgtttgta aattagtatg gcattcgctt   3720
tggtttaagt ggtattttat tgcaaaccca ttaaaagaat aactcatgaa aagaagctct   3780
ttgacacctt ggggtacaca aatgttggtg tgggtgtgtg ttaattctgt gagtgagaca   3840
caccagttct aaaaaaaatg agtgaagttc tggtgcctga gttaccatgc tttcttctag   3900
ttcttacagt agcataaaat taaagattca aagtgagatg gaggataaaa ttacttttta   3960
atacatgttc tcaaacattt gaaaataaaa gtatatgata gaagggggcc agagtgtggc   4020
caccatcctg atcgtactgt ttttcaataa agaaaacttt ttcattggta gatttggtga   4080
aattctaaat ttaggttttt ttctagagct gtatcaacca aaacttctgg caattcccag   4140
tatcacttct tagccttctt atatccaaat gcctgtttat tacctttctt aatttgaatc   4200
aatgcctagt tattacagat tgcaccccac aatggccaaa aacccactac ataataaaat   4260
ttacaggtac taactagtta agattatatt ttaagtagca attgatataa aattacaaca   4320
caatgaaaga acttgggtaa tctcttagca atggaaatag gttttaacca gcagtttttc   4380
tgggtgcttt gtaactatca ttttactaat gaattgagga tgtattatgg tttaaattgg   4440
aagagtttta ttcccaaaga ataaagcaag attatctttc agtagtagag attgaagtaa   4500
atgtattaat attttaatta atacagattt actaagagta gttagaaaat ttagtaagtg   4560
cctgttttac aaattgttag gtactagttt ctgtataatt cctacacaga agctttagaa   4620
atctcctgat attaaattat taaattggca ttcatgaaaa gagaagctac aattataaac   4680
tccatttgct aaatcatgca taatactctc tctctctctt cccccacaag taatctctct   4740
accccatgca gtgtgcacac acacacacac acagtcagtt actgaaaaaa ataattcttt   4800
ttcttttttt ttttaaatgg agtttcactc ttgtcgccca ggctggagtg cagtggcgtg   4860
atctcggccc actgcaacct ccacctccca ggttcaagca gttctcctgc ctcagcctcc   4920
tgagtagctg ggattacagg tgtccgccac catgcctggc taattttttt atttgataaa   4980
aagaattctt tttctcaata actgttctct tgaattcaaa ttaagggact gccaaagtca   5040
attagaatat tttaaaaata ctttgttgta acctgtgtaa ataatataca atttacagga   5100
tttgggattg tagaacttaa actggaagac tggattcctc agatctcagg actataacat   5160
tccagataaa tttttacatt ccctttgctg tatattaact gatgatcatt tatatgttaa   5220
gattttttac cttaatattt ctgaataaaa ctcttattgc ccatttaata ttttcatagg   5280
caatcaaatg tgagtaatac tgctaagagt ctgatttatt aaaaatattt gtataattca   5340
ttcagtttag tttttcagtt tagtctttct gctttcactt ttctctgtgc taacaagtaa   5400
ctaatgtctg ggcattgact tcttattgaa tcaaagttgg gttaggcata gctatgcaca   5460
cctgatgtgt aagattaaag aagagattaa ataagaaatc ttgggtaagt tggacttttc   5520
tgtatagctc ttttttcctc tgagttgtat tttaatgtag tttataagtg ataaaatgat   5580
ccttgttttc taaaagccag tccttccctt cagctttcca cagtttctgt aaatgtttaa   5640
tacttgtaca gtcaatggca attttaaata tatatatata tataatatat gtatatggaa   5700
aaggttcaaa gatgctttta atttatttaa tgactattgc cttcctataa taataatttt   5760
```

```
catccttaat tatgataata cttttagcaa gaaaaattcc tttttactac agtttttaga   5820

tgcaaaatgc agtttggttc tttagtcaaa tccacttaga gggtatattg cagtgaaact   5880

gtgaaggata cttcactacc aatgtataag ctttgttgaa tttgtatcat tttctttcag   5940

taatgaaaag ctattcatta tacagtatgg aaataaaaat tgcttcattg accattcatt   6000

tttacttatt gggaaatact atatttccag acattttcaa gtgtgctgca tttaaaagag   6060

gtaataaagc ttaagcatag agttgaa                                       6087

<210> SEQ ID NO 39
<211> LENGTH: 1931
<212> TYPE: DNA
<213> ORGANISM: Homo sapiens

<400> SEQUENCE: 39

ggaagatgcg agaaggcaga ggaggaggga gggagggaag gagcgcggag cccggcccgg     60

aagctaggtg agtgtggcat ccgagctgag ggacgcgagc ctgagacgcc gctgctgctc    120

cggctgagta tctagcttgt ctccccgatg ggattcccgt ccaagctatc tcgagcctgc    180

agcgccacag tccccggccc tcgcccaggt tcactgcaac cgttcagagg tccccaggag    240

ctgctgctgg cgagcccgct actgcaggga cctatggagc cattccgtag tgccatcccg    300

agcaacgcac tgctgcagct tccctgagcc tttccagcaa gtttgttcaa gattggctgt    360

caagaatcat ggactgttat tatatgcctt gttttctgtc aagacaccat gattcctggt    420

aaccgaatgc tgatggtcgt tttattatgc caagtcctgc taggaggcgc gagccatgct    480

agtttgatac ctgagacggg gaagaaaaaa gtcgccgaga ttcagggcca cgcgggagga    540

cgccgctcag ggcagagcca tgagctcctg cgggacttcg aggcgacact tctgcagatg    600

tttgggctgc gccgccgccc gcagcctagc aagagtgccg tcattccgga ctacatgcgg    660

gatctttacc ggcttcagtc tggggaggag gaggaagagc agatccacag cactggtctt    720

gagtatcctg agcgcccggc cagccgggcc aacaccgtga ggagcttcca ccacgaagaa    780

catctggaga acatcccagg gaccagtgaa aactctgctt ttcgtttcct ctttaacctc    840

agcagcatcc ctgagaacga ggtgatctcc tctgcagagc ttcggctctt ccgggagcag    900

gtggaccagg gccctgattg ggaaaggggc ttccaccgta taaacattta tgaggttatg    960

aagcccccag cagaagtggt gcctgggcac ctcatcacac gactactgga cacgagactg   1020

gtccaccaca atgtgacacg gtgggaaact tttgatgtga gccctgcggt ccttcgctgg   1080

acccgggaga agcagccaaa ctatgggcta gccattgagg tgactcacct ccatcagact   1140

cggacccacc agggccagca tgtcaggatt agccgatcgt tacctcaagg gagtgggaat   1200

tgggcccagc tccggcccct cctggtcacc tttggccatg atggccgggg ccatgccttg   1260

acccgacgcc ggagggccaa gcgtagccct aagcatcact cacagcgggc caggaagaag   1320

aataagaact gccggcgcca ctcgctctat gtggacttca gcgatgtggg ctggaatgac   1380

tggattgtgg ccccaccagg ctaccaggcc ttctactgcc atggggactg cccctttcca   1440

ctggctgacc acctcaactc aaccaaccat gccattgtgc agaccctggt caattctgtc   1500

aattccagta tccccaaagc ctgttgtgtg cccactgaac tgagtgccat ctccatgctg   1560

tacctggatg agtatgataa ggtggtactg aaaaattatc aggagatggt agtagaggga   1620

tgtgggtgcc gctgagatca ggcagtcctt gaggatagac agatatacac accacacaca   1680

cacaccacat acaccacaca cacacgttcc catccactca cccacacact acacagactg   1740

cttccttata gctggacttt tatttaaaaa aaaaaaaaaa aaaggaaaaa atccctaaac   1800
```

attcaccttg accttattta tgactttacg tgcaaatgtt ttgaccatat tgatcatata 1860
ttttgacaaa atatatttat aactacgtat taaaagaaaa aaataaaatg agtcattatt 1920
ttaaaggtaa a 1931

<210> SEQ ID NO 40
<211> LENGTH: 3859
<212> TYPE: DNA
<213> ORGANISM: Homo sapiens

<400> SEQUENCE: 40
actctttaga tctctcttga agagggctgg tatatttgtg cctgctggag gtggaattaa 60
cagtaagaag gagaaaggga ttgaatggac ttacaggaag gatttcaagt aaattcaggg 120
aaacacattt acttgaatag tacaacctag agtattattt tacactaaga cgacacaaaa 180
gatgttaaag ttatcaccaa gctgccggac agatatatat tccaacacca aggtgcagat 240
cagcatagat ctgtgattca gaaatcagga tttgttttgg aaagagctca agggttgaga 300
agaactcaaa agcaagtgaa gattactttg ggaactacag tttatcagaa gatcaacttt 360
tgctaattca aataccaaag gcctgattat cataaattca tataggaatg cataggtcat 420
ctgatcaaat aatattagcc gtcttctgct acatcaatgc agcaaaaact cttaacaact 480
gtggataatt ggaaatctga gtttcagctt tcttagaaat aactactctt gacatattcc 540
aaaatattta aaataggaca ggaaaatcgg tgaggatgtt gtgctcagaa atgtcactgt 600
catgaaaaat aggtaaattt gtttttttcag ctactgggaa actgtacctc ctagaacctt 660
aggttttttt tttttttaag aggacaagaa ggactaaaaa tatcaacttt tgcttttgga 720
caaaaatgca tctgactgta tttttactta agggtattgt gggtttcctc tggagctgct 780
gggttctagt gggttatgca aaaggaggtt tgggagacaa tcatgttcac tccagtttta 840
tttatagaag actacggaac cacgaaagac gggaaataca aagggaaatt ctctctatct 900
tgggtttgcc tcacagaccc agaccatttt cacctggaaa acaagcgtcc tctgcacctc 960
tctttatgct ggatctctac aatgccatga ccaatgaaga aaatcctgaa gagtcggagt 1020
actcagtaag ggcatccttg gcagaagaga ccagaggggc aagaaaggga tacccagcct 1080
ctcccaatgg gtatcctcgt cgcatacagt tatctcggac gactcctctg accacccaga 1140
gtcctcctct agccagcctc catgatacca actttctgaa tgatgctgac atggtcatga 1200
gctttgtcaa cttagttgaa agagacaagg atttttctca ccagcgaagg cattacaaag 1260
aatttcgatt tgatcttacc caaattcctc atggagaggc agtgacagca gctgaattcc 1320
ggatatacaa ggaccggagc aacaaccgat ttgaaaatga aacaattaag attagcatat 1380
atcaaatcat caaggaatac acaaataggg atgcagatct gttcttgtta gacacaagaa 1440
aggcccaagc tttagatgtg ggttggcttg tctttgatat cactgtgacc agcaatcatt 1500
gggtgattaa tccccagaat aatttgggct tacagctctg tgcagaaaca ggggatggac 1560
gcagtatcaa cgtaaaatct gctggtcttg tgggaagaca gggacctcag tcaaaacaac 1620
cattcatggt ggccttcttc aaggcgagtg aggtacttct tcgatccgtg agagcagcca 1680
acaaacgaaa aaatcaaaac cgcaataaat ccagctctca tcaggactcc tccagaatgt 1740
ccagtgttgg agattataac acaagtgagc aaaaacaagc ctgtaagaag cacgaactct 1800
atgtgagctt ccgggatctg ggatggcagg ttcatctgat gtttcctgac cacgtaccaa 1860
agccttgttg tgctccaacc aaattaaatg ccatctctgt tctgtacttt gatgacagct 1920

-continued

```
ccaatgtcat tttgaaaaaa tatagaaata tggtagtacg ctcatgtggc tgccactaat   1980
attaaataat attgataata acaaaaagat ctgtattaag gtttatggct gcaataaaaa   2040
gcatactttc agacaaacgg ggaatttcct aaaattagtc tggctcattt tgactctttt   2100
cctatgtaca atatcatgta tatagtcatt tttatttatt taaacgtata tattctcttc   2160
tgtggaggct ttatcaataa aatctatttc ataggccact acattataca atagatcatc   2220
tagtataatt ttcaatgggt tatgctgagt ccattcaatt ccatttcaac attttttttct   2280
aatacaattt tacataattt tctgagatta gacagaactc ctttgactgt ttaatattgt   2340
ggaaggaaat tgaataattt agttatattg tgccaatgaa aaccatgata gaatatttat   2400
ttagaaataa gacttaaaaa aataacaacc caaacaaaaa ttcttggata aacacaattt   2460
ctcttttaga gttcctgctt cattagataa agtgaaatgt tgaactggat ttgaataaat   2520
aaacggtagg cagaacatag aagctgaaag attgcacaga attgttttaa ctgtttgctt   2580
taacagaagt ggtgtaactg taggagcatg ttcctttttg gcttgtggat tgtagatttt   2640
gcaaagagct caaagcttca ggagacaggc ttgagcctgt gtccatagct ttccaagtta   2700
acactaattg tagtacaacc ttcttacctc aaataaatca tgtctgccta ttatctagaa   2760
cactactgct gcagaatttt tttttcagat ttaaaaacct agtccaaaat aaagaaacat   2820
ttacatgtgc tccactttcc tccccacagg caagagtcac tgcatgcgta aaatgtacaa   2880
gagcagaaga tgccgaaaga accattttct ttagctctcc tttataactg agtttgctga   2940
ttgatgtgat gcaagggatt ttatttagaa gtaaaagcac tgaaactaaa ctggaggaaa   3000
ttaccaaaag tcccagaatg gctttgacag aattgccatt tctaaagaac agctgaaatt   3060
catttttcat atctttgaga gtgagctcaa tgaaaacctt attttgtaaa ggcattttgt   3120
aaaccttctt ccaagcacaa ataattccaa acaggaaggt tctgttgtgt gtgtgtgtgt   3180
gtgtgtgtct gtgtgtgcat gtgtgttctt ccctctaaaa ttaatttatt ttctctatct   3240
attagaatgc cctctaaggc ctttctttaa cacacactga ctttttgaag aatgatcttt   3300
agattgataa cttgctattt atggtgactc tgtggttagg cttatttacc gttaatctaa   3360
agtattcata aagcaccatt tattaatcat ccttttggat ctttcaaacc aaacgtatac   3420
caaaaatgtc ttcaaaaatg ttatggcttt gtttgtaatt cgggtatatt aaaatgttgt   3480
tttgaaatac agtttatctt aaagaaaatt tgacagtaac tatattaagg ggtacattaa   3540
gtaatatatt tttaattaat ggtgtaccat tgagagaata agaaatggaa gtctattgtt   3600
ttattcttta aatgtgctgt ttaaatatat ttccatattt taaaatatat taaacagatg   3660
ctaatttctg ctgttcttga tttggttctt tatttaaaag gaatacaaaa tgtaagtata   3720
tcataaattg agacaataag aatatttatc aaatgtaaac tgtttgtgga tcacatgatt   3780
ctttatgttg ttcttaattg ccaaaattgt tttttgtgtt gttaataatt atctcactat   3840
taaatgtgca aagcaacaa                                                3859
```

<210> SEQ ID NO 41
<211> LENGTH: 3784
<212> TYPE: DNA
<213> ORGANISM: Homo sapiens

<400> SEQUENCE: 41

```
agaaagccca cgttggccgc tgcggggagc gcggcgtgga gaggcgggag accgaattcc     60
ggcgccgccg ccgcggccgc tgctcggtgc actagccccc ttccttccca tcctttctgc    120
gagcgggttt gctgggcagc cgggcgaccg ccgaacggaa agcaagatcc tcgccgcctc    180
```

-continued

```
cgcttgagga ggcgtgcggc gcgcggagat tttgagtggg agcgacggtg cccgagagct    240
caggggcgcg gagttcgtga gcgagaagga agttaaacct cgcggaatag actggcattt    300
cgggacgcct tgtcgccgca gcctgggccc tgcaacgggg taaacttcat ggtggccctg    360
cgatctgggg aggggcgtgc gccacggtga tgccgggcat ctcccgcagc tcgtgagcgg    420
ccccgctccc cgctgccccg ggtcccactc agtcgccagg gagagcgcgg ggcagcgcac    480
gtgtgcggcc agcgaggccc agagtgaccg cgccgcgact cgcaggagcc agggcgcagg    540
ctgcagtgca gcccggactc agacgcacct ggcctggacc gcgcgcctct agagacctgc    600
gcgaggctgt gaggctcccc ttcctcccct ccaagcggtt ctcctggtga tcgccccttc    660
gccacctctc tagcctgggc aactgggggc gccccggacg accatgagag ataaggactg    720
agggccagga aggggaagcg agcccgccga gaggtggcgg ggactgctca cgccaagggc    780
cacagcggcc gcgctccggc ctcgctccgc cgctccacgc ctcgcgggat ccgcgggggc    840
agcccggccg ggcggggatg ccggggctgg ggcggagggc gcagtggctg tgctggtggt    900
gggggctgct gtgcagctgc tgcgggcccc cgccgctgcg gccgcccttg cccgctgccg    960
cggccgccgc cgccgggggg cagctgctgg gggacggcgg gagccccggc cgcacggagc   1020
agccgccgcc gtcgccgcag tcctcctcgg gcttcctgta ccggcggctc aagacgcagg   1080
agaagcggga gatgcagaag gagatcttgt cggtgctggg gctcccgcac cggccccggc   1140
ccctgcacgg cctccaacag ccgcagcccc cggcgctccg gcagcaggag gagcagcagc   1200
agcagcagca gctgcctcgc ggagagcccc ctcccgggcg actgaagtcc gcgcccctct   1260
tcatgctgga tctgtacaac gccctgtccg ccgacaacga cgaggacggg gcgtcggagg   1320
gggagaggca gcagtcctgg ccccacgaag cagccagctc gtcccagcgt cggcagccgc   1380
ccccgggcgc cgcgcacccg ctcaaccgca agagccttct ggcccccgga tctggcagcg   1440
gcggcgcgtc cccactgacc agcgcgcagg acagcgcctt cctcaacgac gcggacatgg   1500
tcatgagctt tgtgaacctg gtggagtacg acaaggagtt ctcccctcgt cagcgacacc   1560
acaaagagtt caagttcaac ttatcccaga ttcctgaggg tgaggtggtg acggctgcag   1620
aattccgcat ctacaaggac tgtgttatgg ggagttttaa aaaccaaact tttcttatca   1680
gcatttatca agtcttacag gagcatcagc acagagactc tgacctgttt ttgttggaca   1740
cccgtgtagt atgggcctca gaagaaggct ggctggaatt tgacatcacg gccactagca   1800
atctgtgggt tgtgactcca cagcataaca tggggcttca gctgagcgtg gtgacaaggg   1860
atggagtcca cgtccacccc cgagccgcag gcctggtggg cagagacggc ccttacgaca   1920
agcagccctt catggtggct ttcttcaaag tgagtgaggt gcacgtgcgc accaccaggt   1980
cagcctccag ccggcgccga caacagagtc gtaatcgctc tacccagtcc caggacgtgg   2040
cgcgggtctc cagtgcttca gattacaaca gcagtgaatt gaaaacagcc tgcaggaagc   2100
atgagctgta tgtgagtttc caagacctgg gatggcagga ctggatcatt gcacccaagg   2160
gctatgctgc caattactgt gatggagaat gctccttccc actcaacgca cacatgaatg   2220
caaccaacca cgcgattgtg cagaccttgg ttcaccttat gaaccccgag tatgtcccca   2280
aaccgtgctg tgcgccaact aagctaaatg ccatctcggt tctttacttt gatgacaact   2340
ccaatgtcat tctgaaaaaa tacaggaata tggttgtaag agcttgtgga tgccactaac   2400
tcgaaaccag atgctgggga cacacattct gccttggatt cctagattac atctgcctta   2460
aaaaaacacg gaagcacagt tggaggtggg acgatgagac tttgaaacta tctcatgcca   2520
```

```
gtgccttatt acccaggaag attttaaagg acctcattaa taatttgctc acttggtaaa   2580

tgacgtgagt agttgttggt ctgtagcaag ctgagtttgg atgtctgtag cataaggtct   2640

ggtaactgca gaaacataac cgtgaagctc ttcctaccct cctcccccaa aaacccacca   2700

aaattagttt tagctgtaga tcaagctatt tggggtgttt gttagtaaat agggaaaata   2760

atctcaaagg agttaaatgt attcttggct aaaggatcag ctggttcagt actgtctatc   2820

aaaggtagat tttacagaga acagaaatcg ggaagtgggg gggaacgcct ctgttcagtt   2880

cattcccaga agtccacagg acgcacagcc caggccacag ccagggctcc acggggcgcc   2940

cttgtctcag tcattgctgt tgtatgttcg tgctggagtt ttgttggtgt gaaaatacac   3000

ttatttcagc caaaacatac catttctaca cctcaatcct ccatttgctg tactctttgc   3060

tagtaccaaa agtagactga ttacactgag gtgaggctac aaggggtgtg taaccgtgta   3120

acacgtgaag gcaatgctca cctcttcttt accagaacgg ttctttgacc agcacattaa   3180

cttctggact gccggctcta gtaccttttc agtaaagtgg ttctctgcct ttttactata   3240

cagcatacca cgccacaggg ttagaaccaa cgaagaaaat aaaatgaggg tgcccagctt   3300

ataagaatgg tgttaggggg atgagcatgc tgtttatgaa cggaaatcat gatttccctt   3360

gtagaaagtg aggctcagat taaattttag aatattttct aaatgtcttt ttcacaatca   3420

tgtactggga aggcaatttc atactaaact gattaaataa tacatttata atctacaact   3480

gtttgcactt acagcttttt ttgtaaatat aaactataat ttattgtcta ttttatatct   3540

gttttgctgt aacattgaag gaaagaccag acttttaaaa aaaaagagtt tatttagaaa   3600

gtatcatagt gtaaacaaac aaattgtacc actttgattt tcttggaata caagactcgt   3660

gatgcaaagc tgaagttgtg tgtacaagac tcttgacagt tgtgcttctc taggaggttg   3720

ggttttttta aaaaaagaat tatctgtgaa ccatacgtga ttaataaaga tttcctttaa   3780

ggca                                                                3784
```

```
<210> SEQ ID NO 42
<211> LENGTH: 4021
<212> TYPE: DNA
<213> ORGANISM: Homo sapiens

<400> SEQUENCE: 42
```

```
actctggcgc tcccgaggcg gcctcttgtg cgatccaggg cgcacaaggc tgggagagcg     60

ccccggggcc cctgctatcc gcgccggagg ttggaagagg gtgggttgcc gccgcccgag    120

ggcgagagcg ccagaggagc gggaagaagg agcgctcgcc cgcccgcctg cctcctcgct    180

gcctccccgg cgttggctct ctggactcct aggcttgctg gctgctcctc ccacccgcgc    240

ccgcctcctc actcgccttt tcgttcgccg gggctgcttt ccaagccctg cggtgcgccc    300

gggcgagtgc ggggcgaggg gcccggggcc agcaccgagc agggggcggg ggtccgggca    360

gagcgcggcc ggccggggag gggccatgtc tggcgcgggc gcagcggggc ccgtctgcag    420

caagtgaccg agcggcgcgg acggccgcct gccccctctg ccacctgggg cggtgcgggc    480

ccggagcccg gagcccgggt agcgcgtaga gccggcgcga tgcacgtgcg ctcactgcga    540

gctgcggcgc cgcacagctt cgtggcgctc tgggcacccc tgttcctgct gcgctccgcc    600

ctggccgact tcagcctgga caacgaggtg cactcgagct tcatccaccg gcgcctccgc    660

agccaggagc ggcgggagat gcagcgcgag atcctctcca ttttgggctt gccccaccgc    720

ccgcgcccgc acctccaggg caagcacaac tcggcaccca tgttcatgct ggacctgtac    780

aacgccatgg cggtggagga gggcggcggg cccggcggcc agggcttctc ctacccctac    840
```

```
aaggccgtct tcagtaccca gggccccct ctggccagcc tgcaagatag ccatttcctc     900
accgacgccg acatggtcat gagcttcgtc aacctcgtgg aacatgacaa ggaattcttc     960
cacccacgct accaccatcg agagttccgg tttgatcttt ccaagatccc agaaggggaa    1020
gctgtcacgg cagccgaatt ccggatctac aaggactaca tccgggaacg cttcgacaat    1080
gagacgttcc ggatcagcgt ttatcaggtg ctccaggagc acttgggcag ggaatcggat    1140
ctcttcctgc tcgacagccg taccctctgg gcctcggagg agggctggct ggtgtttgac    1200
atcacagcca ccagcaacca ctgggtggtc aatccgcggc acaacctggg cctgcagctc    1260
tcggtggaga cgctggatgg gcagagcatc aaccccaagt tggcgggcct gattgggcgg    1320
cacgggcccc agaacaagca gcccttcatg gtggctttct tcaaggccac ggaggtccac    1380
ttccgcagca tccggtccac ggggagcaaa cagcgcagcc agaaccgctc caagacgccc    1440
aagaaccagg aagccctgcg gatggccaac gtggcagaga acagcagcag cgaccagagg    1500
caggcctgta agaagcacga gctgtatgtc agcttccgag acctgggctg gcaggactgg    1560
atcatcgcgc ctgaaggcta cgccgcctac tactgtgagg gggagtgtgc cttccctctg    1620
aactcctaca tgaacgccac caaccacgcc atcgtgcaga cgctggtcca cttcatcaac    1680
ccggaaacgg tgcccaagcc ctgctgtgcg cccacgcagc tcaatgccat ctccgtcctc    1740
tacttcgatg acagctccaa cgtcatcctg aagaaataca gaaacatggt ggtccgggcc    1800
tgtggctgcc actagctcct ccgagaattc agaccctttg gggccaagtt tttctggatc    1860
ctccattgct cgccttggcc aggaaccagc agaccaactg ccttttgtga gaccttcccc    1920
tccctatccc caactttaaa ggtgtgagag tattaggaaa catgagcagc atatggcttt    1980
tgatcagttt ttcagtggca gcatccaatg aacaagatcc tacaagctgt gcaggcaaaa    2040
cctagcagga aaaaaaaaca acgcataaag aaaaatggcc gggccaggtc attggctggg    2100
aagtctcagc catgcacgga ctcgtttcca gaggtaatta tgagcgccta ccagccaggc    2160
cacccagccg tgggaggaag gggcgtggc aaggggtggg cacattggtg tctgtgcgaa     2220
aggaaaattg acccggaagt tcctgtaata aatgtcacaa taaaacgaat gaatgaaaat    2280
ggttaggacg ttacagatat attttcctaa acaatttatc cccatttctc ggtttatcct    2340
gatgcgtaaa cagaagctgt gtcaagtgga gggcggggag gtccctctcc attccctaca    2400
gttttcatcc tgaggcttgc agaggcccag tgtttaccga ggtttgccca aatccaagat    2460
ctagtgggag gggaaagagc aaatgtctgc tccgaggagg gcggtgtgtt gatctttgga    2520
ggaaaaatat gttctgttgt tcagctggat ttgccgtggc agaaatgaaa ctaggtgtgt    2580
gaaatacccg cagacatttg ggattggctt ttcacctcgc cccagtggta gtaaatccat    2640
gtgaaattgc agaggggaca aggacagcaa gtaggatgga acttgcaact caaccctgtt    2700
gttaagaagc accaatgggc cgggcacagt agctcccacc tgtaatccca gcactttggg    2760
aggctgaggt gggcggatca tttgaggtca ggagttcgag accagcctgg ccaacatggt    2820
gaaaccccat ctctactaaa aatacaaaaa ttagccgggc atggtggcac gcacctgtaa    2880
tcccagctac tctggaggct gaggcaggag aattgcttga accccagagg tggaggttgc    2940
agtgagccaa gatcgtccca ctgcactcca gcttgggtga caaaacaaga ctccatctca    3000
aaagaaaaaa aaaacagcac caatgaagcc tagttctcca cgggagtggg gtgagcagga    3060
gcactgcaca tcgccccagt ggaccctctg gtctttgtct gcagtggcat tccaaggctg    3120
ggccctggca agggcacccg tggctgtctc ttcatttgca gaccctgatc agaagtctct    3180
```

```
gcaaacaaat ttgctccttg aattaagggg gagatggcat aataggaggt ctgatgggtg   3240
caggatgtgc tggacttaca ttgcaaatag aagccttgtt gagggtgaca tcctaaccaa   3300
gtgtcccgat ttggaggtgg catttctgac gtggctcttg gtgtaagcct gccttgcctt   3360
ggctggtgag tcccataaat agtatgcact cagcctccgg ccacaaacac aaggcctagg   3420
ggagggctag actgtctgca aacgttttct gcatctgtaa agaaaacaag gtgatcgaaa   3480
actgtggcca tgtggaaccc ggtcttgtgg gggactgttt ctccatcttg actcagacag   3540
ttcctggaaa caccggggct ctgtttttat tttctttgat gtttttcttc tttagtagct   3600
tgggctgcag cctccactct ctagtcactg gggaggagta tttttgtta tgtttggttt   3660
catttgctgg cagagctggg gctttttgtg tgatccctct tggtgtgagt tttctgaccc   3720
aaccagcctc tggttagcat catttgtaca tttaaacctg taaatagttg ttacaaagca   3780
aagagattat ttatttccat ccaaagctct tttgaacacc cccccccctt taatccctcg   3840
ttcaggacga tgagcttgct ttccttcaac ctgtttgttt tcttatttaa gactatttat   3900
taatggttgg accaatgtac tcacagctgt tgcgtcgagc agtccttagt gaaaattctg   3960
tataaataga caaaatgaaa agggtttgac cttgcaataa aaggagacgt ttggttctgg   4020
c                                                                   4021
```

<210> SEQ ID NO 43
<211> LENGTH: 5354
<212> TYPE: DNA
<213> ORGANISM: Homo sapiens

<400> SEQUENCE: 43

```
agagtaggct ggcagctgtc ctaactgcct actaaagcca aatgcttgag gagagagaga     60
gagtaaggag ccagccatga atcctttcca gaaaaatgag tccaaggaaa ctcttttttc    120
acctgtctcc attgaagagg taccacctcg accacctagc cctccaaaga agccatctcc    180
gacaatctgt ggctccaact atccactgag cattgccttc attgtggtga atgaattctg    240
cgagcgcttt tcctattatg gaatgaaagc tgtgctgatc ctgtatttcc tgtatttcct    300
gcactggaat gaagatacct ccacatctat ataccatgcc ttcagcagcc tctgttattt    360
tactcccatc ctgggagcag ccattgctga ctcgtggttg ggaaaattca aagtcctatc    420
attgatcggc ctgagtctaa tagctttggg gacaggaggc atcaaaccct gtgtggcagc    480
ttttggtgga gaccagtttg aagaaaaaca tgcagaggaa cggactagat acttctcagt    540
cttctacctg tccatcaatg cagggagctt gatttctaca tttatcacac ccatgctgag    600
aggagatgtg caatgttttg gagaagactg ctatgcattg gcttttggag ttccaggact    660
gctcatggta attgcacttg ttgtgtttgc aatgggaagc aaaatataca ataaaccacc    720
ccctgaagga aacatagtgg ctcaagtttt caaatgtatc tggtttgcta tttccaatcg    780
tttcaagaac cgttctggag acattccaaa gcgacagcac tggctagact gggcggctga    840
gaaatatcca aagcagctca ttatggatgt aaaggcactg accagggtac tattccttta    900
tatcccattg cccatgttct gggctctttt ggatcagcag ggttcacgat ggactttgca    960
agccatcagg atgaatagga atttggggtt ttttgtgctt cagccggacc agatgcaggt   1020
tctaaatccc cttctggttc ttatcttcat cccgttgttt gactttgtca tttatcgtct   1080
ggtctccaag tgtggaatta acttctcatc acttaggaaa atggctgttg gtatgatcct   1140
agcatgcctg gcatttgcag ttgcggcagc tgtagagata aaaataaatg aaatggcccc   1200
agcccagcca ggtccccagg aggttttcct acaagtcttg aatctggcag atgatgaggt   1260
```

gaaggtgaca gtggtgggaa atgaaaacaa ttctctgttg atagagtcca tcaaatcctt 1320
tcagaaaaca ccacactatt ccaaactgca cctgaaaaca aaaagccagg attttcactt 1380
ccacctgaaa tatcacaatt tgtctctcta cactgagcat tctgtgcagg agaagaactg 1440
gtacagtctt gtcattcgtg aagatgggaa cagtatctcc agcatgatgg taaaggatac 1500
agaaagcaga acaaccaatg ggatgacaac cgtgaggttt gttaacactt tgcataaaga 1560
tgtcaacatc tccctgagta cagatacctc tctcaatgtt ggtgaagact atggtgtgtc 1620
tgcttataga actgtgcaaa gaggagaata ccctgcagtg cactgtagaa cagaagataa 1680
gaacttttct ctgaatttgg gtcttctaga ctttggtgca gcatatctgt ttgttattac 1740
taataacacc aatcagggtc ttcaggcctg gaagattgaa gacattccag ccaacaaaat 1800
gtccattgcg tggcagctac cacaatatgc cctggttaca gctggggagg tcatgttctc 1860
tgtcacaggt cttgagtttt cttattctca ggctccctct agcatgaaat ctgtgctcca 1920
ggcagcttgg ctattgacaa ttgcagttgg gaatatcatc gtgcttgttg tggcacagtt 1980
cagtggcctg gtacagtggg ccgaattcat tttgttttcc tgcctcctgc tggtgatctg 2040
cctgatcttc tccatcatgg gctactacta tgttcctgta aagacagagg atatgcgggg 2100
tccagcagat aagcacattc ctcacatcca ggggaacatg atcaaactag agaccaagaa 2160
gacaaaactc tgatgactcc ctagattctg tcctgacccc aattcctggc cctgtcttga 2220
agcatttttt ttcttctact ggattagaca agagagatag cagcatatca gagctgatct 2280
cctccacctt tctccaatga cagaagttcc aggactggtt ttccagtaca tctttaaaca 2340
aggccccaga gactctatgt ctgcccgtcc atcagtgaac tcattaaaac ttgtgcagtg 2400
ttgctggagc tggcctggtg tctccaaatg accatgaaaa tacacacgta taatggagat 2460
cattctctgt gggtatgcaa agttatggga attcctttat aggtaactgc catttaggac 2520
tgatggccct aatttttgag gtgctgattt agaggcaaaa ttgcagaata acaaagaaat 2580
ggtatttcaa gttttttttt ttataagcaa tgtaattatg ctattcacag gggcctcaag 2640
aattggtatg tatgatgtga tctggtccag ccagggcctg gcttgtcagc tctctaggtt 2700
tgatatgact ttagtaaatt tgtcaatata gatggtagga agcagaatgc cattttatta 2760
aaacacagga gaagttatat ctctctgatt atgatagtat tttatttact tatccaaacc 2820
ctcctttctc agtatggata gatcatggaa accagattag agatagtaag cattagtaaa 2880
cattgttctg gagaacagga acaggtgtaa gttgtagaaa tcctgaagag ccagtcattc 2940
ttttacagag tacattcttc ttagcctcta tggcgctggt ctatgccctt cagtgaacag 3000
ttgtataaac aataattata atttgcaacc ttgtcttgtc aaccttgctg atccagcttt 3060
ttcttattat tacaccttgt cttgcttatt gcagcaaata ttcaataaca acaatgtttc 3120
tataagtcca acttccttta ttaatgtttc catttagcct caaaaatatc aaagtagttc 3180
ctttttgatg ttgttttcct gatttacttt tcccataagt tttaaatacc atttctgcct 3240
tgaagcctag aaattttctt tttattcaaa aaaagttaca ttaatgctct aggtttgagg 3300
ttctaaaatg gaaatgtcaa tagaggagca tggtcctatg tgaggttcct atcaaaattt 3360
gtgggagtag ggatggtaga gcatgagggt tttgtttgtg tatgtgtatg gtcatgaaaa 3420
aaaattgaga aacattacct catacacaat gaatgaatca gaggacagac acgggaatgg 3480
cacgactgtg cagtgtgtta ctaggaaaaa agttcagaat cactgttcta gagagcttca 3540
tttccattgg ttttaaaaca ttattctcat gtagaacagt gttgggtctc atactgttaa 3600

```
tgttaatacg taacaatgtt catgttaaca ggcacctgtt aatattaaca gataatgtta   3660

ctgttaacag gtaagagaaa ttgctctaag tgcccaaact ttatatactt cagttttaat   3720

gacaagcatt tcagaaatat aagagcggca gccagaccaa ccagtttttc cagatatctt   3780

gatgtgaacc tgaccctact cctttagaag acagcctgtt catttttaaa tagctttaac   3840

ccaaactgtt ctatgaccat tgtttcaaga gacattaaca cagttctgta aatagaagtg   3900

tctatggaca aataagtttg ggaaatgtgg catactgtat ccttttctta acatttgcat   3960

attaaagact ctgagatatc ctgcagtaaa gacacaagat accttgttta aattaacatg   4020

tacgctgcag aacattggtt tggaaaaaac tgttgagcag ttcttccttg taagtgctga   4080

gcttcctctc tgaaacctcc taccattgtt tttttcccc tgtagctaac aagaataagt    4140

ataacagccg gccaggcaca gtggctcatg cctgtaatcc cagcactttg ggaggctgag   4200

acaggtggat cacctgaggt caggagttcg agaccagcct ggccaacatg gtgaaaccgt   4260

gtctctacta aaagtacaaa aattagccag gtgtgatggc aggtgcctgt aatcccagct   4320

actcgggagg ctgaagcaga agaattgctt gaacccggga ggcagaggtt gcaatgagcc   4380

gagatcacgc catcacactc tagcctgggg gacaagagtg agacttcatc taaaaaaaaa   4440

aagaaaagaa tatgtatacc ccctttttca tgtggcagat gtttagctat ttggggagaa   4500

ctttcatggc tcttccctaa tcatcaagta ttcaaggtaa agattctcgg ttcctgtaat   4560

ggttcctcac caggcataat ttgtcctttt accatcctac tttctgtctt ctgaaaaaca   4620

ttctttatct gaaatacagc aattaatatt aagatatctt aatatgaagt gcctggagtc   4680

aaatataaca ttccaaagta gtctgactgg aagaactagc acctgccttt cttcaaacaa   4740

tgcacttctg ttaatgcagt gtaaggtaac atgagttgtt tttggaaact acatcataat   4800

gtgggcttac attctagcac ttatcactta atgacaggga tacatttgag gaatgcattg   4860

ttaggcaatt ttgtcattat gcaaacatca tagagtgtac ttacacaaac ctatggtata   4920

gcctactaca catctaagtt atatggtata gactgtttct ccagctatat ggtgtagact   4980

gtttctccta ggctacaaac ctgcacagca tgttactgta ttaaatgctg taggcaattg   5040

taacacaatg gtatttttat acttaaacat atctaaacat agaaacggta caaaaaactt   5100

tacacattat atagatgtat caaattattc atatgtgctc tgaaaatgtc tatatctgtt   5160

atgtatcaat tttttaaaaa gtgaatgaca taattcattt gaaaaaatgt ggacacacaa   5220

attggaaaag aggtataaat gcagtattat aatctaatgg gaccaccatc acatatttgg   5280

tctgtcattg actgaaactg caatatagag tttttcttaa catttgcata ttaaagactc   5340

tgactatata tgga                                                     5354
```

<210> SEQ ID NO 44
<211> LENGTH: 3884
<212> TYPE: DNA
<213> ORGANISM: Homo sapiens

<400> SEQUENCE: 44

```
atcacatacc ctaaagaacc ctgggatgac taaggcagag agagtctgag aaaactcttt     60

ggtgcttctg cctttagttt taggacacat ttatgcagat gagcttataa gagaccgttc    120

cctccgcctt cttcctcaga ggaagtttct tggtagatca ccgacacctc atccaggcgg    180

ggggttgggg ggaaacttgg caccagccat cccaggcaga gcaccactgt gatttgttct    240

cctggtggag agagctggaa ggaaggagcc agcgtgcaaa taatgaagga gcacgggggc    300

accttcagta gcaccggaat cagcggtggt agcggtgact ctgctatgga cagcctgcag    360
```

```
ccgctccagc ctaactacat gcctgtgtgt ttgtttgcag aagaatctta tcaaaaatta    420
gcaatggaaa cgctggagga attagactgg tgtttagacc agctagagac catacagacc    480
taccggtctg tcagtgagat ggcttctaac aagttcaaaa gaatgctgaa ccgggagctg    540
acacacctct cagagatgag ccgatcaggg aaccaggtgt ctgaatacat ttcaaatact    600
ttcttagaca agcagaatga tgtggagatc ccatctccta cccagaaaga cagggagaaa    660
aagaaaaagc agcagctcat gacccagata agtggagtga agaaattaat gcatagttca    720
agcctaaaca atacaagcat ctcacgcttt ggagtcaaca ctgaaaatga agatcacctg    780
gccaaggagc tggaagacct gaacaaatgg ggtcttaaca tctttaatgt ggctggatat    840
tctcacaata gacccctaac atgcatcatg tatgctatat tccaggaaag agacctccta    900
aagacattca gaatctcatc tgacacattt ataacctaca tgatgacttt agaagaccat    960
taccattctg acgtggcata tcacaacagc ctgcacgctg ctgatgtagc ccagtcgacc   1020
catgttctcc tttctacacc agcattagac gctgtcttca cagatttgga gatcctggct   1080
gccatttttg cagctgccat ccatgacgtt gatcatcctg gagtctccaa tcagtttctc   1140
atcaacacaa attcagaact tgctttgatg tataatgatg aatctgtgtt ggaaaatcat   1200
caccttgctg tgggtttcaa actgctgcaa gaagaacact gtgacatctt catgaatctc   1260
accaagaagc agcgtcagac actcaggaag atggttattg acatggtgtt agcaactgat   1320
atgtctaaac atatgagcct gctggcagac ctgaagacaa tggtagaaac gaagaaagtt   1380
acaagttcag gcgttcttct cctagacaac tataccgatc gcattcaggt ccttcgcaac   1440
atggtacact gtgcagacct gagcaacccc accaagtcct tggaattgta tcggcaatgg   1500
acagaccgca tcatggagga atttttccag cagggagaca aagagcggga gaggggaatg   1560
gaaattagcc caatgtgtga taaacacaca gcttctgtgg aaaaatccca ggttggtttc   1620
atcgactaca ttgtccatcc attgtgggag acatgggcag atttggtaca gcctgatgct   1680
caggacattc tcgatacctt agaagataac aggaactggt atcagagcat gatacctcaa   1740
agtccctcac caccactgga cgagcagaac agggactgcc agggtctgat ggagaagttt   1800
cagtttgaac tgactctcga tgaggaagat tctgaaggac ctgagaagga gggagaggga   1860
cacagctatt tcagcagcac aaagacgctt tgtgtgattg atccagaaaa cagagattcc   1920
ctgggagaga ctgacataga cattgcaaca gaagacaagt cccccgtgga tacataatcc   1980
ccctctccct gtggagatga acattctatc cttgatgagc atgccagcta tgtggtaggg   2040
ccagcccacc atgggggcca agacctgcac aggacaaggg ccacctggcc tttcagttac   2100
ttgagtttgg agtcagaaag caagaccagg aagcaaatag cagctcagga aatcccacgg   2160
ttgacttgcc ttgatggcaa gcttggtgga gagggctgaa gctgttgctg ggggccgatt   2220
ctgatcaaga cacatggctt gaaaatggaa gacacaaaac tgagagatca ttctgcacta   2280
agtttcggga acttatcccc gacagtgact gaactcactg actaataact tcatttatga   2340
atcttctcac ttgtcccttt gtctgccaac ctgtgtgcct tttttgtaaa acattttcat   2400
gtctttaaaa tgcctgttga atacctggag tttagtatca acttctacac agataagctt   2460
tcaaagttga caaacttttt tgactctttc tggaaaaggg aaagaaaata gtcttccttc   2520
tttcttgggc aatatccttc actttactac agttactttt gcaaacagac agaaaggata   2580
cacttctaac cacattttac ttccttcccc tgttgtccag tccaactcca cagtcactct   2640
taaaacttct ctctgtttgc ctgcctccaa cagtactttt aactttttgc tgtaaacaga   2700
```

-continued

```
ataaaattga acaaattagg gggtagaaag gagcagtggt gtcgttcacc gtgagagtct   2760

gcatagaact cagcagtgtg ccctgctgtg tcttggaccc tgccccccac aggagttgta   2820

cagtccctgg ccctgttccc tacctcctct cttcaccccg ttaggctgtt ttcaatgtaa   2880

tgctgccgtc cttctcttgc actgccttct gcgctaacac ctccattcct gtttataacc   2940

gtgtatttat tacttaatgt atataatgta atgttttgta agttattaat ttatatatct   3000

aacattgcct gccaatggtg gtgttaaatt tgtgtagaaa actctgccta agagttacga   3060

ctttttcttg taatgttttg tattgtgtat tatataaccc aaacgtcact tagtagagac   3120

atatggcccc cttggcagag aggacagggg tgggcttttg ttcaaagggt ctgccctttc   3180

cctgcctgag ttgctacttc tgcacaaccc ctttatgaac cagttttgga aacaatattc   3240

tcacattaga tactaaatgg tttatactga gcttttactt ttgtatagct tgataggggc   3300

agggggcaat gggatgtagt ttttacccag gttctatcca aatctatgtg ggcatgagtt   3360

gggttataac tggatcctac tatcattgtg gctttggttc aaaaggaaac actacatttg   3420

ctcacagatg attcttctga atgctcccga actactgact ttgaagaggt agcctcctgc   3480

ctgccattaa gcaggaatgt catgttccag ttcattacaa aagaaaacaa taaaacaatg   3540

tgaattttta taataaaatg tgaactgatg tagcaaatta cgcaaatgtg aagcctcttc   3600

tgataacact tgttaggcct cttactgatg tcagtttcag tttgtaaaat atgtttcatg   3660

ctttcagttc agcattgtga ctcagtaatt acagaaaatg gcacaaatgt gcatgaccaa   3720

tgtatgtcta tgaacactgc attgtttcag gtggacattt tatcattttc aaatgtttct   3780

cacaatgtat gttatagtat tattattata tattgtgttc aaatgcattc taaagagact   3840

tttatatgag gtgaataaag aaaagcatga ttagattaaa aaaa                    3884
```

<210> SEQ ID NO 45
<211> LENGTH: 6036
<212> TYPE: DNA
<213> ORGANISM: Homo sapiens

<400> SEQUENCE: 45

```
taaaccttcc tggcttggcc taggagctcg agcggagtca tgggctctct ggtcctgaca     60

ctgtgcgctc ttttctgcct ggcagcttac ttggtttctg gcagccccat catgaaccta    120

gagcagtctc ctctggaaga agatatgtcc ctctttggtg atgttttctc agagcaagac    180

ggtgtcgact ttaacacact gctccagagc atgaaggatg agtttcttaa gacactaaac    240

ctctctgaca tccccacgca ggattcagcc aaggtggacc caccagagta catgttggaa    300

ctctacaaca aatttgcaac agatcggacc tccatgccct ctgccaacat cattaggagt    360

ttcaagaatg aagatctgtt ttcccagccg gtcagtttta atgggctccg aaaataccc     420

ctcctcttca atgtgtccat tcctcaccat gaagaggtca tcatggctga acttaggcta    480

tacacactgg tgcaaaggga tcgtatgata tacgatggag tagaccggaa aattaccatt    540

tttgaagtgc tggagagcaa aggggataat gagggagaaa gaaacatgct ggtcttggtg    600

tctggggaga tatatggaac caacagtgag tgggagactt ttgatgtcac agatgccatc    660

agacgttggc aaaagtcagg ctcatccacc caccagctgg aggtccacat tgagagcaaa    720

cacgatgaag ctgaggatgc cagcagtgga cggctagaaa tagataccag tgcccagaat    780

aagcataacc ctttgctcat cgtgttttct gatgaccaaa gcagtgacaa ggagaggaag    840

gaggaactga atgaaatgat ttcccatgag caacttccag agctggacaa cttgggcctg    900

gatagctttt ccagtggacc tggggaagag gctttgttgc agatgagatc aaacatcatc    960
```

```
tatgactcca ctgcccgaat cagaaggaac gccaaaggaa actactgtaa gaggaccccg   1020
ctctacatcg acttcaagga gattgggtgg gactcctgga tcatcgctcc gcctggatac   1080
gaagcctatg aatgccgtgg tgtttgtaac taccccctgg cagagcatct cacacccaca   1140
aagcatgcaa ttatccaggc cttggtccac ctcaagaatt cccagaaagc ttccaaagcc   1200
tgctgtgtgc ccacaaagct agagcccatc tccatcctct atttagacaa aggcgtcgtc   1260
acctacaagt ttaaatacga aggcatggcc gtctccgaat gtggctgtag atagaagaag   1320
agtcctatgg cttatttaat aactgtaaat gtgtatattt ggtgttccta tttaatgaga   1380
ttatttaata agggtgtaca gtaatagagg cttgctgcct tcaggaaatg gacaggtcag   1440
tttgttgtag gaaatgcata ttttcctctc cagttaagtc cctttcaatc tgttttctct   1500
ttggacttgc catttcctgg caatgccacc tccctgttga tttgaaaaca acccctaggc   1560
aaaatacagt gtcaaaagac acacacttgt gtatgtatat ttgtacatac atgaacttac   1620
aaaaatcttt tggttctatg caggcaggtt atactcatct acatgcatga ctcactcaaa   1680
tgtatgcata ttaaaggcca atggtatgtt ctctgttacc tcttctctga gtaggattta   1740
agtcaagata attgacatca gggttttaat catcctagga agtattaccc ttcctaaata   1800
ctctggaaat gtaagtgtag cttttgtcag ttgagtttct gtagttgctc agagaggagg   1860
ggcctggcaa aggatgcttg aagggaaggg ttaattgata cagaaaccaa atggacttaa   1920
gaggtcttag aggtacaaca ggaaaaaatg aacccatgga ggaccaatgt gctccagagg   1980
gcaactcctg gtcaaggcag gaaaacagaa gaaaccagca tgaaatctgt tcctgagaca   2040
ataggaaagc aaggccatga gtactggcca ttgctgctgc agagagtaga ggggttggga   2100
gggtacttga aggggagaaa gggagaaagg gaagaggata ttgatgttat cctcagaggc   2160
tatcctcaga tgtgtctgta aaaccaaaag tggttctgtt taaagaatta aatcttttgg   2220
acaaaataga agtatcaaag actaagagga ggaaaatcag aaggggtctg tctgttggaa   2280
gaaaggatgt taatatcttt cttcacctgt taacactgtt cccttgtctc agcacccctg   2340
ctttcctctg ctccatcttc ttccttccct ctttcttctt ggccctagtg cctctcacct   2400
tcctcccatc cctgtgtccc tgctcttccc tggccttcat gatgcatgct gtgaactgga   2460
aagggacacc taagtgcctt tgctctcagg gtgaaaggag ttagtgttct aatttctaaa   2520
tcttcccgtg atatttaatt tgattttatt ttaataatat cctttatcaa atgttttgtt   2580
catgaagaat acttagatat aagagaaaag aaaaccagaa taagtaagta taagaaaaag   2640
aaaaccagag tccaaatgaa tggatttaaa taaacgaatt tatgaataga cacacaagca   2700
aatgactcaa aagccaagcc tgaattttga aatcatgatt gtttcatggt agaaacccag   2760
taactttccc atcttctcat cttaccatct tcccattttg caactggcca ggactgaaag   2820
tggtgaggaa gtgttctgca caggaagggt ccggtgggtt ttcctggcag gtggcagcct   2880
ccagtcttaa cccctaacca tttccctcta cctggcaagc atattctggg ctttgtgcag   2940
gaggaaccag agcagagcag agcagtttcc aaactgttcc agcatctcca ggcagggaac   3000
atggatggtt cctgttagaa ccaggaatgt ggtttccagt acgtcatccc ccattcaccc   3060
ctactcatct taaggaatgc ttccttaaga agtctgacac ttttttcttt tttttaccct   3120
ggaaaacaat cagtcccctt ttacaaatct cttaaggtta taaactcaaa ctgcactaga   3180
caatagaggc aaggaaaact attttgaaga aggcccaatt tgaacctcag ctcgctagat   3240
ctgttgtctg ctgggtgaat cctggggaat tcattgctca tggaagagtg gtgttttgac   3300
```

-continued

```
cgtcagtggg tatacagtga ttgatgcttt gagaaagcca tgcaactcag aatcactatt   3360
tgtggaacag cctccatata acatgatgtg tgtatgtgtg tgtgatgtat agctggcttt   3420
gaataaccac gcttaatacc ctcagtggaa cgtggtgcat ccttcatact ccatggtaca   3480
caatgtatac tcacatactc caaggtactt cttatccttt ctaaaggaca ctgtaataca   3540
tacacagtaa aacctcagct gaccaggata gtcctggtta gataaaaatt aagcaaattt   3600
tctttatgtc taatacatat gacagtggtg tgctggtaaa acccttacaa ccagcaatcc   3660
agggggagaa aaagccctga tttgtggatt tcaatgctgc aaacgctcct acatggtcta   3720
tcttgagctg ccaaggtgat gtcaactggc ttgcaaaact tctaaaacct aagtcagctc   3780
ttgggagctg tgcactggtg ctggcacacc gctgacattt agtatcccac tgacattagc   3840
acaccgctga cattagcacc ctgatactag aatgttaagg atgtgccagc cctgctttcc   3900
actgtgtgcg ctgctggctc cgggcttctg gagaaatctt gtctcgagca cttatagtca   3960
ctcttctgtt aaagagatat gaaaatatag gctgttggcg atcaggctgc atagcccagt   4020
tgtttctttc tgcccatcca gatgtaaacc tgcatttcta tgattttctg cttccctgtg   4080
gaaagggagt gcagagagca acatattgtt attcaaatgt tgctagttgt atttttttgg   4140
ctttttgtca gaaagtgaaa agacacagcc cgtagaggag ttctcccagc tcccaccgga   4200
accccggcag cacaccggtg tcactttcaa ctcctgcatt gacaggaagc cagaatattg   4260
tcagatcctt aaaaaggtag aatcttacta atgtttctct ggtcatagac cttcttctgg   4320
gtcccatgcc agtttttttc cccctttat tgcagaatta tcatcaccga agttgatata   4380
gctaaacaac tcttgaggag aattatagca gagggacttg ggcagcccac agccaaaata   4440
ttcatgtaag agtttctagg cttcccacta tttattgatt gatatattta tttttgtaaa   4500
atattgtaga ataccaaata ttttattttt atgtctgtga ttccctttg gatagagagt   4560
cttctgggct tcagagtatg gctcacatat aatatatggc ctgtatttcc atctctctct   4620
ttttgcatca gaatattcta ttggtttaag gaatcttgcc atagcttgcc ataattttgt   4680
atatttgtgt cttgcaggca tgctgtgcct acaagcatgc tttgtagtat attttctgat   4740
ttgtaaatag tacagtttta actgaagtgt agatgttcca ggaaatattt aaccaataca   4800
ttgtcatgca gtttcataaa gtgatgttgt cagtttatca tgagaagcaa atattgtcag   4860
gctgtgagag aatgtgattg ctactcagta aacggagatg ctatttaaat gaatcttttc   4920
atcccccaaa tctggtactt cccctctgaa ttcacctgtt gccgtcactg acccagaaat   4980
tcagagatgt gattggtcaa attcatttgt aattggacca attactttgt aaatgtcaaa   5040
aatgttagct tagtgatttc caaaagagtc agccccaaag tgccgaattc tttcctgatg   5100
tgtaaatttt ggtccgggga attaatgaca aaaacctttt ttttttaaga actgttacta   5160
aatgtttcag tatttgttat gatttatatt cttcaagtaa aagatatttt catataagag   5220
aattttatgt attcttctta cttgattcat caacagatta tgaagcctag cagtgttctg   5280
gcaaaacctt tttaacttgc ctagaacaca gaagggatgt tgccctttt aaggttgtag   5340
atcttttcag agtcactgtg ggtcattctc aacccttgc agttctgcaa gctcacatat   5400
ggtgcaagag gaaatgctgg tatgactctg tgcattttct tgcccccaaa caggaacagt   5460
tgatttccta cattaaatgg aaggtagatg tgactatgga agagaagtac acaggggtgt   5520
ttctgcatgt gaaatatttg tcataagtta aaaacccatc atggaataac tgtttgttgt   5580
gatcagcatg tttttatcac acatgggcac tggttttgtg agcacctggc ttgatagtgg   5640
tggggcggcc aatgtgccag cgcccgccta ctgagcattc atggacattg gaaatcagcg   5700
```

```
aacaccacag acacaccgaa tcagctgatg cacggtcatg ttctggggta aaacctgttc   5760

attatccatg tccacatttg tatagttatc actagactaa aatgaagatg gaaataaata   5820

ttttaccctg tgttcatgaa ccaaatgtgt accttcagag tctttttaag taaaataaaa   5880

aaattatttt ggtgataatt atttgcagct tatttttcct tgaggtaagg tatttaattt   5940

tgcacactcc ccactttttc atgtttctac ttgataacat atcccgatgg aataaaacta   6000

attgctatat taataaagaa tggtctgaag aaacca                             6036


<210> SEQ ID NO 46
<211> LENGTH: 6652
<212> TYPE: DNA
<213> ORGANISM: Homo sapiens

<400> SEQUENCE: 46

gccagattag cggacgcggt gcccgcggtt gcaacgggat cccgggcgct gcagcttggg     60

aggcggctct ccccaggcgg cgtccgcgga gacacccatc cgtgaacccc aggtcccggg    120

ccgccggctc gccgcgcacc aggggccggc ggacagaaga gcggccgagc ggctcgaggc    180

tgggggaccg cgggcgcggc cgcgcgctgc cgggcgggag gctggggggc cggggccggg    240

gccgtgcccc ggagcgggtc ggaggccggg gccggggccg ggggacggcg gctccccgcg    300

cggctccagc ggctcgggga tcccggccgg gccccgcagg gaccatggca gccgggagca    360

tcaccacgct gcccgccttg cccgaggatg gcggcagcgg cgccttcccg cccggccact    420

tcaaggaccc caagcggctg tactgcaaaa acgggggctt cttcctgcgc atccaccccg    480

acggccgagt tgacggggtc cgggagaaga gcgaccctca catcaagcta caacttcaag    540

cagaagagag aggagttgtg tctatcaaag gagtgtgtgc taaccgttac ctggctatga    600

aggaagatgg aagattactg gcttctaaat gtgttacgga tgagtgtttc tttttgaac    660

gattggaatc taataactac aatacttacc ggtcaaggaa atacaccagt tggtatgtgg    720

cactgaaacg aactgggcag tataaacttg gatccaaaac aggacctggg cagaaagcta    780

tactttttct tccaatgtct gctaagagct gattttaatg gccacatcta atctcatttc    840

acatgaaaga agaagtatat tttagaaatt tgttaatgag agtaaaagaa aataaatgtg    900

tatagctcag tttggataat tggtcaaaca attttttatc cagtagtaaa atatgtaacc    960

attgtcccag taaagaaaaa taacaaaagt tgtaaaatgt atattctccc ttttatattg   1020

catctgctgt tacccagtga agcttaccta gagcaatgat ctttttcacg catttgcttt   1080

attcgaaaag aggcttttaa aatgtgcatg tttagaaaca aaatttcttc atggaaatca   1140

tatacattag aaaatcacag tcagatgttt aatcaatcca aaatgtccac tatttcttat   1200

gtcattcgtt agtctacatg tttctaaaca tataaatgtg aatttaatca attcctttca   1260

tagttttata attctctggc agttccttat gatagagttt ataaaacagt cctgtgtaaa   1320

ctgctggaag ttcttccaca gtcaggtcaa ttttgtcaaa cccttctctg tacccataca   1380

gcagcagcct agcaactctg ctggtgatgg gagttgtatt ttcagtcttc gccaggtcat   1440

tgagatccat ccactcacat cttaagcatt cttcctggca aaaatttatg gtgaatgaat   1500

atggctttag gcggcagatg atatacatat ctgacttccc aaaagctcca ggatttgtgt   1560

gctgttgccg aatactcagg acggacctga attctgattt tataccagtc tcttcaaaaa   1620

cttctcgaac cgctgtgtct cctacgtaaa aaaagagatg tacaaatcaa taataattac   1680

acttttagaa actgtatcat caaagatttt cagttaaagt agcattatgt aaaggctcaa   1740
```

-continued

```
aacattaccc taacaaagta aagttttcaa tacaaattct ttgccttgtg gatatcaaga   1800
aatcccaaaa tattttctta ccactgtaaa ttcaagaagc ttttgaaatg ctgaatattt   1860
ctttggctgc tacttggagg cttatctacc tgtacatttt tggggtcagc tctttttaac   1920
ttcttgctgc tctttttccc aaaaggtaaa aatatagatt gaaaagttaa aacattttgc   1980
atggctgcag ttcctttgtt tcttgagata agattccaaa gaacttagat tcatttcttc   2040
aacaccgaaa tgctggaggt gtttgatcag ttttcaagaa acttggaata taaataattt   2100
tataattcaa caaaggtttt cacattttat aaggttgatt tttcaattaa atgcaaattt   2160
gtgtggcagg atttttattg ccattaacat atttttgtgg ctgctttttc tacacatcca   2220
gatggtccct ctaactgggc tttctctaat tttgtgatgt tctgtcattg tctcccaaag   2280
tatttaggag aagcccttta aaaagctgcc ttcctctacc actttgctgg aaagcttcac   2340
aattgtcaca gacaaagatt tttgttccaa tactcgtttt gcctctattt ttcttgtttg   2400
tcaaatagta aatgatattt gcccttgcag taattctact ggtgaaaaac atgcaaagaa   2460
gaggaagtca cagaaacatg tctcaattcc catgtgctgt gactgtagac tgtcttacca   2520
tagactgtct tacccatccc ctggatatgc tcttgttttt tccctctaat agctatggaa   2580
agatgcatag aaagagtata atgttttaaa acataaggca tttgtctgcc atttttcaat   2640
tacatgctga cttcccttac aattgagatt tgcccatagg ttaaacatgg ttagaaacaa   2700
ctgaaagcat aaaagaaaaa tctaggccgg gtgcagtggc tcatgcctat attccctgca   2760
ctttgggagg ccaaagcagg aggatcgctt gagcccagga gttcaagacc aacctggtga   2820
aaccccgtct ctacaaaaaa acacaaaaaa tagccaggca tggtggcgtg tacatgtggt   2880
ctcagatact tgggaggctg aggtgggagg gttgatcact tgaggctgag aggtcaaggt   2940
tgcagtgagc cataatcgtg ccactgcagt ccagcctagg caacagagtg agactttgtc   3000
tcaaaaaaag agaaattttc cttaataaga aaagtaattt ttactctgat gtgcaataca   3060
tttgttatta aatttattat ttaagatggt agcactagtc ttaaattgta taaaatatcc   3120
cctaacatgt ttaaatgtcc atttttattc attatgcttt gaaaaataat tatggggaaa   3180
tacatgtttg ttattaaatt tattattaaa gatagtagca ctagtcttaa atttgatata   3240
acatctccta acttgtttaa atgtccattt ttattcttta tgtttgaaaa taaattatgg   3300
ggatcctatt tagctcttag taccactaat caaaagttcg gcatgtagct catgatctat   3360
gctgtttcta tgtcgtggaa gcactggatg ggggtagtga gcaaatctgc cctgctcagc   3420
agtcaccata gcagctgact gaaaatcagc actgcctgag tagttttgat cagtttaact   3480
tgaatcacta actgactgaa aattgaatgg gcaaataagt gcttttgtct ccagagtatg   3540
cgggagaccc ttccacctca agatggatat ttcttcccca aggatttcaa gatgaattga   3600
aatttttaat caagatagtg tgctttattc tgttgtattt tttattattt taatatactg   3660
taagccaaac tgaaataaca tttgctgttt tataggtttg aagaacatag gaaaaactaa   3720
gaggttttgt ttttattttt gctgatgaag agatatgttt aaatatgttg tattgttttg   3780
tttagttaca ggacaataat gaaatggagt ttatatttgt tatttctatt ttgttatatt   3840
taataataga attagattga aataaaatat aatgggaaat aatctgcaga atgtgggttt   3900
tcctggtgtt tccctctgac tctagtgcac tgatgatctc tgataaggct cagctgcttt   3960
atagttctct ggctaatgca gcagatactc ttcctgccag tggtaatacg attttttaag   4020
aaggcagttt gtcaatttta atcttgtgga tacctttata ctcttagggt attattttat   4080
acaaaagcct tgaggattgc attctatttt ctatatgacc ctcttgatat ttaaaaaaca   4140
```

```
ctatggataa caattcttca tttacctagt attatgaaag aatgaaggag ttcaaacaaa   4200
tgtgtttccc agttaactag ggtttactgt ttgagccaat ataaatgttt aactgtttgt   4260
gatggcagta ttcctaaagt acattgcatg ttttcctaaa tacagagttt aaataatttc   4320
agtaattctt agatgattca gcttcatcat taagaatatc ttttgtttta tgttgagtta   4380
gaaatgcctt catatagaca tagtctttca gacctctact gtcagttttc atttctagct   4440
gctttcaggg ttttatgaat tttcaggcaa agctttaatt tacactaagc ttaggaagta   4500
tggctaatgc caacggcagt ttttttcttc ttaattccac atgactgagg catatatgat   4560
ctctgggtag gtgagttgtt gtgacaacca caagcacttt tttttttttt aaagaaaaaa   4620
aggtagtgaa tttttaatca tctggacttt aagaaggatt ctggagtata cttaggcctg   4680
aaattatata tatttggctt ggaaatgtgt ttttcttcaa ttacatctac aagtaagtac   4740
agctgaaatt cagaggaccc ataagagttc acatgaaaaa aatcaattta tttgaaaagg   4800
caagatgcag gagagaggaa gccttgcaaa cctgcagact gctttttgcc caatatagat   4860
tgggtaaggc tgcaaaacat aagcttaatt agctcacatg ctctgctctc acgtggcacc   4920
agtggatagt gtgagagaat taggctgtag aacaaatggc cttctctttc agcattcaca   4980
ccactacaaa atcatctttt atatcaacag aagaataagc ataaactaag caaaaggtca   5040
ataagtacct gaaaccaaga ttggctagag atatatctta atgcaatcca ttttctgatg   5100
gattgttacg agttggctat ataatgtatg tatggtattt tgatttgtgt aaaagtttta   5160
aaaatcaagc tttaagtaca tggacatttt taaataaaat atttaaagac aatttagaaa   5220
attgccttaa tatcattgtt ggctaaatag aataggggac atgcatatta aggaaaaggt   5280
catggagaaa taatattggt atcaaacaaa tacattgatt tgtcatgata cacattgaat   5340
ttgatccaat agtttaagga ataggtagga aaatttggtt tctatttttc gatttcctgt   5400
aaatcagtga cataaataat tcttagctta ttttatattt ccttgtctta aatactgagc   5460
tcagtaagtt gtgttagggg attatttctc agttgagact ttcttatatg acattttact   5520
atgttttgac tacctgacta ttaaaaataa atagtagata caattttcat aaagtgaaga   5580
attatataat cactgcttta taactgactt tattatattt atttcaaagt tcatttaaag   5640
gctactattc atcctctgtg atggaatggt caggaatttg ttttctcata gtttaattcc   5700
aacaacaata ttagtcgtat ccaaaataac ctttaatgct aaactttact gatgtatatc   5760
caaagcttct cattttcaga cagattaatc cagaagcagt cataaacaga agaataggtg   5820
gtatgttcct aatgatatta tttctactaa tggaataaac tgtaatatta gaaattatgc   5880
tgctaattat atcagctctg aggtaatttc tgaaatgttc agactcagtc ggaacaaatt   5940
ggaaaattta aatttttatt cttagctata aagcaagaaa gtaaacacat taatttcctc   6000
aacattttta agccaattaa aaatataaaa gatacacacc aatatcttct tcaggctctg   6060
acaggcctcc tggaaacttc cacatatttt tcaactgcag tataaagtca gaaaataaag   6120
ttaacataac tttcactaac acacacatat gtagatttca caaaatccac ctataattgg   6180
tcaaagtggt tgagaatata ttttttagta attgcatgca aaatttttct agcttccatc   6240
ctttctccct cgtttcttct ttttttgggg gagctggtaa ctgatgaaat cttttcccac   6300
cttttctctt caggaaatat aagtggtttt gtttggttaa cgtgatacat tctgtatgaa   6360
tgaaacattg gagggaaaca tctactgaat ttctgtaatt taaaatattt tgctgctagt   6420
taactatgaa cagatagaag aatcttacag atgctgctat aaataagtag aaaatataaa   6480
```

```
tttcatcact aaaatatgct attttaaaat ctatttccta tattgtattt ctaatcagat   6540

gtattactct tattatttct attgtatgtg ttaatgattt tatgtaaaaa tgtaattgct   6600

tttcatgagt agtatgaata aaattgatta gtttgtgttt tcttgtctcc ca           6652


<210> SEQ ID NO 47
<211> LENGTH: 695
<212> TYPE: DNA
<213> ORGANISM: Mus musculus

<400> SEQUENCE: 47

ggccccgggc cgttgtacac tcaaggggct ctctcggctt caggaagagt ccggctgcac     60

tgggctggga gcccggcggg acacggactg ggaggctggc agcccgcggg cgagccgcgc    120

tggggggccg aggccggggt cggggccggg gagccccaag agctgccaca gcggggtccc    180

ggggccgcgg aagggccatg gctgccagcg gcatcacctc gcttcccgca ctgccggagg    240

acggcggcgc cgccttccca ccaggccact tcaaggaccc caagcggctc tactgcaaga    300

acggcggctt cttcctgcgc atccatcccg acggccgcgt ggatggcgtc cgcgagaaga    360

gcgacccaca cgtcaaacta caactccaag cagaagagag aggagttgtg tctatcaagg    420

gagtgtgtgc caaccggtac cttgctatga aggaagatgg acggctgctg gcttctaagt    480

gtgttacaga agagtgtttc ttctttgaac gactggaatc taataactac aatacttacc    540

ggtcacggaa atactccagt tggtatgtgg cactgaaacg aactgggcag tataaactcg    600

gatccaaaac gggacctgga cagaaggcca tactgtttct tccaatgtct gctaagagct    660

gactcacttt tgacactgtc actgagacac tgtca                               695


<210> SEQ ID NO 48
<211> LENGTH: 1016
<212> TYPE: DNA
<213> ORGANISM: Rattus norvegicus

<400> SEQUENCE: 48

ggcaccccat tcctggcctc tgtctcccgc accctatccc ttcacagcct gtgctctagg     60

ggactggaga tttccaaaac ctgacccgat ccctccccag ttcagttcct tctactgctt    120

tgggtggaag gctggtcgtt gtgttaaaag gcaggaaggg agaaagttgc atttaaactt    180

taggagctgc gtcacggcag tctcctggag aaagctccgc cgaacgggac agattctttt    240

tgcaacttgg aggcgccggg cgtggggagg aggcggcgcg tggggcgggg gcgcgcgggg    300

ccggggtgca ggcggggacg cggggtgacg cgggcccggg ccgctgtagc acacaggggc    360

tcggtctctc ggcttcaggc ggagtccggc tgcactaggc tgggagcgcg gcgggacgcg    420

aaccgggagg ctggcagccc gcgggcgagc cgcgctgggg ggccgaggcc ggggtcgggg    480

ccggggagcc ccgagagctg ccgcagcggg gtcccggggc cgcggagggg ccatggctgc    540

cggcagcatc acttcgcttc ccgcactgcc ggaggacggc ggcggcgcct tcccacccgg    600

ccacttcaag gatcccaagc ggctctactg caagaacggc ggcttcttcc tgcgcatcca    660

tccagacggc cgcgtggacg gcgtccggga gaagagcgac ccacacgtca aactacagct    720

ccaagcagaa gagagaggag ttgtgtccat caagggagtg tgtgcgaacc ggtacctggc    780

tatgaaggaa gatggacggc tgctggcttc taagtgtgtt acagaagagt gtttcttctt    840

tgaacgcctg gagtccaata actacaacac ttaccggtca cggaaatact ccagttggta    900

tgtggcactg aaacgaactg ggcagtataa actcggatcc aaaacggggc ctggacagaa    960

ggccatactg tttcttccaa tgtctgctaa gagctgactc tctttagaca ctgtca       1016
```

<210> SEQ ID NO 49
<211> LENGTH: 6594
<212> TYPE: DNA
<213> ORGANISM: Bos taurus

<400> SEQUENCE: 49
ccggggccgc gccgcggagc gcgtcggagg ccggggccgg ggcgcggcgg ctccccgcgc 60
ggctccaggg gctcggggac cccgccaggg ccttggtggg gccatggccg ccgggagcat 120
caccacgctg ccatccctgc cggaggacgg cggcagcggc gctttcccgc cgggccactt 180
caaggacccc aagcggctgt actgcaagaa cgggggcttc ttcctgcgca tccaccccga 240
cggccgagtg gacggggtcc gcgagaagag cgacccacac atcaaactac aacttcaagc 300
agaagagaga ggggttgtgt ctatcaaagg agtgtgtgca aaccgttacc ttgctatgaa 360
agaagatgga agattactag cttctaaatg tgttacagac gagtgtttct tttttgaacg 420
attggagtct aataactaca atacttaccg gtcaaggaaa tactccagtt ggtatgtggc 480
actgaaacga actgggcagt ataaacttgg acccaaaaca ggacctgggc agaaagctat 540
actttttctt ccaatgtctg ctaagagctg atcttaatgg cagcatctga tctcatttta 600
catgaagagg tatatttcag aaatgtgtta atgaaaaaag aaaaatgtgt acagtgagct 660
gctcagtttg ggtaactgtt cagataaccg tttatctaag agtaaaatat ttaaccattg 720
ccttagtttt tttttaaaga aaaaacacaa taacagcaaa aattcctgga aaatgtatac 780
atttccactt tttatacagc atttcctttt atccagtgaa acttacttaa agctacaatc 840
tttcatacag ttgcttcatt tgaagaggct tttaaaatgt gtacaaacaa gttttcttca 900
tggaaattat agacattaga aaattaaagt catatttagt tattaaccca aatgtccact 960
acttcctata atatggcaca cattaatcta catgtacaac ttacttaaac atgtacaact 1020
tacttaaaca ttttaaaaac atgtaaatat gaatttaatc cattcctgtc atagttttgt 1080
aattgtctgg cagtttcttg tgatagagtt tatagaacaa gcctgtgtaa actgctggca 1140
gttcttccat ggtcagatca attttgtcaa acccttcttt gtacccatac agcagcagcc 1200
ttgcaactct gcttgttatg ggagtcgtat ttttagtctt gactagatcg ctgagattca 1260
tccactcaca ctttaagcat tcacgctggc aaaaatttat ggtgaatgaa tatggcttta 1320
agcggcagat aatatacata tctgacttcc caaaagctcc tggatgggtg tgctgttgcc 1380
gaatactcag gagggatctg aattcggatt ttataccagt ctcttcaaaa acttctcgaa 1440
ctgctgtatc tcctacataa aagaaaatgt acaaatcaat aacgattata cttttagaaa 1500
tttaatcaaa gattttcaga taaggaagca ttattatgta aagattcaaa aggtaaaaat 1560
ttaccctaag aaaagaaagc tttccctgta aactctgtcc tctggacatc ctgaaaaaac 1620
aaagtatttt cttaccactg tatagctaag aagcttttga aataatattt ctttggcttc 1680
tacttgcaag cttacccatc tatatatatg tattttggga gtcacatatt tttaaattct 1740
tcctgcttta tttcccaaaa gttaatattc ctgtatattt tttcattatt atcttgttcc 1800
tgattatcca ttaaaactgc ctaaactgat aaacatttga agtaagaaaa agtgatccat 1860
tcttctttac aaaagtctgt agagctgcag aatatataga actaggaaat gattcaaatc 1920
atccctggtc tctcctggga ctgtcaggcc tctgaagtca taggtcggat ttcgttataa 1980
ccattttgtt atgctcttct agttattctg tcagtggaat cccaccatgg taatttctgg 2040
cattttcttt gtttcttgct gtttcaaaga acttggattc attcttctaa caccaaaatg 2100
ctacagtcat cagaagttta aaaaaaaact tgcaatttac agaattttat aatattacca 2160
ggcttttcac attttataaa gttgattttt aaataatatg caaatttcta ggacaggatt 2220
tttattgcca ttaacttatt tttgtggctg ctctttctaa atatccagat gaacctccta 2280
cctgggattt ctgtaatttt ctgatgctgt cattgtctcc caaagtgttt atgaaaagcc 2340
ctaaaaaagc tgccttcctt gtctattttc tgggaagttt cacaattgcc acaagtatag 2400
atttttgttt aaatatcttt taatgccttc attttcttgt ttgtcaggtt gtaaactgta 2460
tttggcttct cagtagtcct gctagtgagg aataggcaag gaagagcaag taaacaagaa 2520
atgttgcagt gtttttttcta ataacagctc tggaaataag cacaggaaga gtagtgtgta 2580
aaatatgaca tctgtctacc atatttgaat tctgtgtgaa cgaacttttt aattgagatt 2640
tgctaaagat caaatcaaca tggttagaaa ttatattttt aaactgaaaa tatagaaaaa 2700
tatatgttaa gaaaaggaaa acttggctta agaaaaataa tttttgttgt attaaaaaac 2760
ttgtattaag tttgttacag attgtggcac tagtcttaaa ttttacatgt catttgctga 2820
tctgacttaa aaattgttca aatgtttaaa aagttcttta aacattttaa aatgaccatg 2880
gggatcttgt ttagctctta ataacactag tcaagagttt aacatttagt tcctgtgtct 2940
agcctgcttg tatgttatag aagcacagga tggggctggt gagtgaatct gccaggctta 3000
gccatcacca cagcagctga ttcaaaatca gcactgcctg gatagtttga tccatttaac 3060
ttgaatcatg atgtcattaa ctagattaaa aattaaatgg gcaaataagt gcttttagat 3120
ctagaggaac caaccccttc tatattaaaa ttgaaatctc ttctccaagg attttatgat 3180
gaattaaaaa ttttaattta ggtaaagtgc gttatttgct ggtattattt taaatgtact 3240
gtaagtaaac tgaataacgg ttttatagat ttgaagaata taggaaaacc aagagggttt 3300
tgtttttatt tttgctggtt gaaagatgtt taaaaacatc atagtgtttt atttagttaa 3360
aggacagtac tgaaatggag tttatatttg ttacttctat tttgtaatat ttaataacag 3420
gattaggttg aaataaaata ataggaaaaa ctgtgcagaa tgtggatttt cctggtgtct 3480
ccccctcact ctggtacact gatgagctct gagcagaccc cactgcttta cagacctttg 3540
gctatacagg gagttctctt cctgttagtg ctaatgagat tttccccccc ccagaaaggc 3600
agcttctgtt tttaacctta tctatagata ggcttatcgg agaaggcaat ggcaccccac 3660
tccagaactc ttgcctggaa aatcccatgg atggaggagc ctggtgggct gcagtccatg 3720
gggtcgctaa gagttggaca cgactgagcg acttcacttt cacttttcac tttcatgcat 3780
tggagaagga aatggcaacc cactccggtg ttcttgcctg gagaatccgg gggacgaggg 3840
agcctggtga gctgctgtct atggggtcgc agagtcggac atgactgaag tgacttagca 3900
gcagcataga taccttttttg tactctgctt catttaccta atacttatca aagaatgaag 3960
gattccaaac aaatgagctt cttattttaa ctagtattta ctgcttaaca gccagtatga 4020
acatttgcac atttatgatg gcggcagtcc tattacatac tttcctaaaa acagagttta 4080
aagaaaataa ataattcctg gttgatttgg cttcatcatt aagagtaatc tattactata 4140
ctgttacaaa acagaaatgt actctacata gacatggtct ttcagatctc tatgtctctt 4200
atcatttcta gctgctttca gagttttatc acttctgagg caatgcttca gtttttccta 4260
ctcctaggca atatggtaaa tgccagttgc tgcttttttc ttaattccat gtggctggag 4320
gcattaaaaa caatctctga ctaggtgggt tgttgttata cccacaagta tttttaaaaa 4380
gtagtgaatt tctagttata tggacttgaa atgttctgga gtacactcaa acctaaagtg 4440
tacttattta catggtgtgg aaatgtgttt atttacattt aaatatatct gaaattcaga 4500
atatcaatga aaactcaaat gaaaaaagtt attcatttga aagaaaaaaa aaaaaaaagt 4560
tattcatttg agaaggcaag gttcagaaga ggaagttata caaacttcct atagactgct 4620
atttgcccag tatggattag ataaggatgt aaaacagaca cttaactagt tcacatgatc 4680
tcatatcaca tgatagtgtg agataaccgg gaattctaga gtaaatggct ttttctttca 4740
gcactggcac tactacaaaa tccttttatt tcaacagaag acctagggaa gactaagcta 4800
aaggtcagtg agcacctaaa aaccaaaatc tgctatgata tatttgtagt gaaatttatt 4860
tataggatgt taggagttgg ctgtatacta caaataggac attttcatct gtggaacatt 4920
aaaaaaaaat catttcaagt atatatatat acatttaaaa ataatttagg gcactgcctt 4980
catataaatg atggctaaag agaatagggt acatatacac agtgaggaca aagtcataga 5040
aaaatagtta agtatgaaat gagttatcta ttgatttatt atgataagga ctgtgcctga 5100
cacaatggtt taaggaagag acaggaaaac tcaatttcta ctctcgattt cctgtaaaat 5160
cagtgacaaa gaattcttag attatttcaa acttccctta gatactgagc tcagtaaatt 5220
gttctaggaa attatctctc atttcagact ttctcacatg agacatgtta ccatcttttg 5280
gctttctgac tatcgaaaaa aatagataaa atttccataa acagaagaat tataccacca 5340
ctgttcaata attgccttta aaatatttca catttcattt aaaagttctc ttcaaccttg 5400
tgataaaatg gtcaagaatt tttctaatag taaagttcca acaattttgt tatgccgagt 5460
tgctcagttg tgtctgactc ttgtgactcc atggactgta gcccaccagg ctcttctgtc 5520
catggggatt ctccaggcaa gaatactgga gtgggttgcc atgccctcct ccaggggata 5580
tttccaacca agggatcaaa cccaggtctc cctcattgta ggcagattct taattgtctg 5640
acctaccagg gaaaccctcc aacaatttta gtcaaattca aaatatccct taatgctaac 5700
cttaactgta tatccaaagt ttctcatttc caaattatct agaagcagtc ctaagccaaa 5760
aaacaggtgt tatgctctga atggtattat ttatactaat ggaataaatt gtagtgttaa 5820
gttttgctat taattttata tcagcactga ataacttctt tgaaattttc tgacttagtc 5880
taaaccaatt agaaagtgta aaatctcatt ctcagctcta gagcaagaaa gtaaacacat 5940
aaatttattc agcattttca agtcaattat aaatatataa gatacccacc aatatcttct 6000
ccaggctctg acaggcctcc tgggaacttc cacatgtttt tcagctgtag tattaaatca 6060
gaaagcaaag ttaacacagc tcttatttac taacatacac atacgtagag atgccacaga 6120
agctacccat aattgatcaa ggtggttgag aatttatttt ttcgtaactg ccaccaattt 6180
ttttcagctt ccttcctcac tcctttcttc tctcgggaaa ctgctgactt gtgaaatctt 6240
tcctatcttt ttatttagga aatagaagtg gttttttttta tgttaatgtg ataaattctg 6300
tatgagtgaa acagtggggg gaacatctac tgaatttgta tagttaaaaa tttttgctgc 6360
tagtttatta aagaatacat gaatcttact gatgctgcta taaattagta gaaaatatat 6420
aaatgtaatc actaaagtat gctattttta attttcaatt tactttctat attgtgtgtc 6480
taatcagata tattaatctt aagagttttc ttgttctctg tgttaatgat tttatgtaaa 6540
aatataattg tctttcctgg gaagtgtgaa taaaattgat ttaagtttct ggct 6594

<210> SEQ ID NO 50
<211> LENGTH: 574
<212> TYPE: DNA
<213> ORGANISM: Gallus gallus

<400> SEQUENCE: 50

```
gaggctggac ggccgcggca gggggcgagc ccgcccggcg ctggcggcgg cggccggcgg     60
gggcccgggg cggcggggag ccgccggggc ccggcgcatg gcggcggggg cggcggggag    120
catcaccacg ctgccggcgc tgcccgacga cgggggcggc ggcgcttttc cccccgggca    180
cttcaaggac cccaagcggc tctactgcaa gaacggcggc ttcttcctgc gcatcaaccc    240
cgacggcagg gtggacggcg tccgcgagaa gagcgatccg cacatcaaac tgcagcttca    300
agcagaagaa agaggagtag tatcaatcaa aggcgtaagt gcaaaccgct ttctggctat    360
gaaggaggat ggcagattgc tggcactgaa atgtgcaaca gaggaatgtt tctttttcga    420
gcgcttggaa tctaataact ataacactta ccggtcacgg aagtactctg attggtatgt    480
ggcactgaaa aggactggac agtacaagcc cggaccaaaa actggacctg gacagaaagc    540
tatccttttt cttccaatgt ctgctaaaag ctga                                574
```

<210> SEQ ID NO 51
<211> LENGTH: 6684
<212> TYPE: DNA
<213> ORGANISM: Sus scrofa

<400> SEQUENCE: 51

```
atgtcgtttg ggtggcgcgg ggttgggctg gggcgccttc tggggaaccg gcggggtcga     60
gggctctgga gctgcggagg ccttggcttt ggcctcctgc cgcgcccccg catctccccc    120
gcccgcgact gccttccaac tccctttgga tgtcgcgcgc ttgcggggcg gcgcgctgga    180
agggaggagg gccgggggcg tgggggttgg tgggcgtttg ggggtggaga tgtagaagat    240
gtgacgccgc gcggctcggc cggtgccaga ccagcggact cagagcccgc agttgcaagc    300
cgatcccggg cgctgcagtt tggggaggcg gccctgccga gagtggcggc cgccgagaaa    360
cccagcccta acccgcagct ccagggccgg cggagagcga agcggccaaa cagcacgagg    420
ctgggggccc gcgggcgcgg ccgcgtgccg cggggcggga ggctgggggg ccggggccgg    480
ggccgcgctc cggagcgcgt cggaggccgg ggccgggggt cggcggcggc ggcggcggcg    540
gctccccgcg cggctccagg ggctcgggga ccccggcaga gccctggtgg ggccatggca    600
gccgggagca tcaccacgct gcccgccctg ccggaggacg gcggcagcgg cgccttcccg    660
cccggccact tcaaggatcc taagcggttg tactgcaaaa acggaggctt cttcctgcgc    720
atccaccccg acggccgagt ggatggggtc cgggagaaga gcgaccctca catcaaacta    780
caacttcaag cagaagagag aggggttgtg tctatcaaag gagtgtgtgc aaaccgttat    840
cttgctatga aggaagatgg aagattactg gcttctattc tctgcttcat ccacactggc    900
cttctttctg cccttcacac actctggcct gatcctgttg tggcttaccc tccctttgcc    960
tggaagctct tctctgaaat ctggacggtt aactccttca cctccttcga gaaatgtgtt   1020
acagacgagt gtttcttttt tgaacgactg gaatctaata actacaatac ttaccggtcg   1080
aggaaatact ccagttggta tgtggcactg aaacgaacgg ggcagtataa acttggaccc   1140
aaaacaggac ctgggcagaa agctatactt tttcttccaa tgtctgctaa gagctgatct   1200
taacggcagc atctgatctc atgtcacatg aaagaagagg tttattttag aaacttgtta   1260
atgaaagaaa aatatataca gctatctgct cagtttggta actggtcaga taatctttta   1320
tctaataata aaatatttaa ccattgcctt agtaaataac aaacaaaaat tcctggaaaa   1380
tgtatatact tctgcttttt atatagcatt taccattatc cagtaaagct tacttagagc   1440
tataatcttt tcatacattt gaagagaggc ttttaaaatg tgcacactta caaacaagtt   1500
ttcttcatga aaatcacagg cattagaaaa ttaacatcag acatacagtt aacccaaatg   1560
```

```
tctactactt attatggcaa acattaatct acgtgtacaa tgtactaaca ttttttaga   1620
catgttagta tgaatttaat ccattcctgt cacagttttg taattgtctg gcagttcctt   1680
gtgatagagt ttataggaca agcctgtgta aactgctgga agttcttcca tggtcagatc   1740
aatcttgtca aacccttcct tgtacccata gagcagcagc cgagcaaccc tgctagtgat   1800
gggagtcgta ttttcactct tgaccaggtc actgagatcc atccactcac accttaaaca   1860
ttcatgctgg caaaaattta tgatgaatga acgtggcttt aagcggcata taatatacat   1920
atctgacttc ccaaaagctc caggattggt gtgctgttgc cgaatactca ggagggacat   1980
gaattctgac tttataccag tctcttcaaa aacttctcga actgctgtat ctcctacatt   2040
aaaaaaatta tacagacact aatcaataag atcatctttt tgaaatttaa tccaagattt   2100
tcagataaag tagcattagc taaaggttca aaagcaaaac tctacctaag aaatgaagtt   2160
ttcaatgtaa attcgttgcc ttctggatat cctgaaatat caaagtattt tcttaccacc   2220
atatagctaa ggctgctctt tgtgtaggct tacccatctg tttattttgg gagtcacata   2280
tttttaaact cttcctgctg tatatcccaa aaggtgaaaa catacattgt aatgttgtag   2340
ttaatattcc tacatatttt ttcataatta tcctgtttct gatcatcaaa cctgcctaaa   2400
tttatacaca ttagcattga ggaaaaagtg atacatttgt ctttataaag tgtgtagagc   2460
tagagactct actgaactat gaaaagatgc aaatttcccc tggttcctcc tgggactgtc   2520
aagcctctga agtcagagca gatttcttct gagtcatttt gttatgctct tctagttatc   2580
ctgttaatgg aaccctagca tggtaatttt tggcattttc ttttgtttct tgcaatttca   2640
aagaacttgg attcattttc ctagcaccaa tatgctataa tcatctcata tgaagttttc   2700
aaaaagcttg ttggaattta cagaatttta taatatgacc agggttttca cattttacaa   2760
gggtgatttt tttattaata tgtaaacttc tgggacagga tttttattgc cattaactta   2820
tttttgtggc tgctttttct aaatatccag atgagcctcc taggtgagat ttccctaatt   2880
ttgtgttgct ctgtcattgt ctcccaaagt gtttatgaga agccctttaa aaagctgcct   2940
tccttgccta tttacagaga agtttcacaa ctgccacagg tatagatttc tgttcaacta   3000
cccttaaatg cctccactta tttgtctgtc aaattgtaaa ttatatttgc cttctcagta   3060
gccctccttg tgaggtacag gcaaggaaag taaagtgaag gaaaaagtct caatgttttt   3120
ctcatacaga gttctggaaa tgtgcacagg aagagaggaa agtgttaaaa tgtaagacat   3180
ttgtttgcca tttttgaatt acatgctgac tttccttgcc atagagtaaa catggttaga   3240
aattatattt tttaaaccaa aaagatgaaa aaagaattta tgtgttaagg aaaacttgcc   3300
ttaataagaa aaataacatg gttgttatta aacttgttaa agattgtggc actagccata   3360
attttacatg atatttgttg atcggactta aaaattgttt aaatgttaat ttttattttg   3420
aaacactttg aaaaatgacc atgggatctt gtttagcttt tagtgacact aaccaagaat   3480
ttggcattta gtttacctga gtcttatttg tattttatgg atgcacagac ctggctagtg   3540
agctaatctg tcctgctcat tagtcaccac agtagttgat tcaaaataag tgttacatga   3600
gtagtttgat cagtttaatt tgaatcatga catcgttgac ttgactaaaa gttgaatggg   3660
caaataagtg cttttatatc taaaggaacc ccttctatct caagattgaa atctcttgac   3720
caaggatttt actatgaatt taaaattttt atctaaagtg ctttttttctt gtacctttcc   3780
tattttatgt actgtaagct aaactgaaat aacatttact gttttatagg tttgaagaat   3840
ataggaaaaa ccaaaagggt tttgttttta tttttgctgg ttgaaagata atgtttaaat   3900
```

-continued

```
aagtcaatga aatggagttt atatttgtta attctatttt gtaatattta ataataggat   3960
taggttgaaa taaaataaaa taataggaaa aactgcagaa tgtgggtttt cctggtgttc   4020
ccctctgact tggatatact gatgaacttt ggtcagaccc caactgcttt acagtccttt   4080
aaaactatgc agggagattc tcttccagtc agtggaaatg agattttttt tgaggaaggc   4140
cgcttttgca tttttaacct tgtagatacc tttgtatagg gtattatatt agagtctgag   4200
gattgcatta tattttgtat atgccccctt aatgtttttt aaaacattat ggacaataac   4260
acttcattta cctagtatta tcaaagaatg aagaattcca aacaaatgtg cttctcagtc   4320
aactagtgtt tactacttaa gagccaatat gaatgtttgc acatacttcc ctaaaaacag   4380
cctaaagaaa ataatttaaa taattcttgg atgattaggc ttcatcatta agaataatct   4440
gttattgtac tgtgttacaa aacagaaatg cccttgtata gacagtcttt cagatctctg   4500
tcagttatca tttctagctg cttttagggt tttatcattt ctaaagcaaa gctccaattt   4560
ttattactca taggcagtat agataatgcc agttgctgtt tttttcttaa ttccacatag   4620
ctgaggtgtg tatgtgacct ctgaataggt gggttgtgac aaccacagat tttaaaaaaa   4680
tgtagtgaat ttcttactta tgtggacttg gaggttctgg agtacaatca gacctacaat   4740
ttatactatt tggcttggaa atgtgtttct tcctttatgt ttaaatatat ctgaaattca   4800
gaagatccat aaaaacacaa atgaaaacat caattcattt gagaaggcaa gactcggaag   4860
cagaagctac ataaaccttt tcctataaat tattgtttat atggattggc taaggatata   4920
aaacctaaac ttaactagtt caaatgacct catatcacat aaggatagtg tgagataatc   4980
agatgttcta gaataaatgg ccttctcttt tagcactccc accactacaa aatcctctct   5040
tatttcaaca gaagacctag cagactctga gcaaaaggtc agtaagttta agtacctaaa   5100
acccaaaatt tgctatgtat atatctgaat gtagtaaatt tacttataag ttgttaggcg   5160
ttggctctgt actgtgtata ggacatttta atctgtggaa cattaaaaga aaagttgagt   5220
atatatatat attcaaaatt ttaaaaaatg atttaggaaa ttgccttcat ataaatgatg   5280
gctaaagaga aataagggac atacactttg aggaaaaagt cagagaaata atattggtat   5340
caaatgagtt acctcttgat ttattatggt ggggactgca tgcatctgac cttaaggaat   5400
aggtaggaaa actcaatttc tattccttcc tctatttcct gtaaaatcgg tgacataaga   5460
aattcttagc ttattttgta tttctctgtc ttaaacaatg agctcagtaa atcgtttcag   5520
aaagttatat ctaatttgat actttttcat gaggcatttt actataaaat acaggctttc   5580
tgactagccc aaataaaata gtagataaaa ttttcataaa aagaacaatg tcaccattgc   5640
tctgtaactg actttataaa taacacttct cagttcattt aaatattatt atttatcaaa   5700
aattttctca cagtttaatt acagtaattt tagttatatt ccaaataacc tttaatgata   5760
aacttgacag atgtatatcc aaagcttttc attttcaaac aaattaatat agaagcagtc   5820
ctaagcagaa aaacaggtgt tatactccta agggtatacc ttatattaat gggataagtt   5880
gtaatgttat aaggtttgcc actaatttta tatcagccct gaagtaactt cactgaaatt   5940
ttctgactta gtagaaaagt tgaaaatcct attctcggct ctatagcaag aaaagtaata   6000
aacacatgaa tttcctcaac attttcaagc cagttaaaga tatgtaagat acacaccaat   6060
atcttctcca ggctccgaca ggcctcctgg aaatttccac atatttttca actgcagaat   6120
aaaaatcaga aaatacagtt aatatagctt ttattcatta acacacaaac atggagatgc   6180
cacaaaatct actcaaaatt tgtcaagttg tttgagaatt tattttttgg tacctgcacc   6240
ccaatttttt ccagcttcct tcctctcact cctttttttgg agaaattggt gatttgtgaa   6300
```

gtcttttccc acctttttct tcaggaaata taagtggttt tgtttggtta atgggttaat 6360
gtgataaatt ctgtatgaat aaaaacagta gggaaagggg acatctactg aatttgtata 6420
gtttaaaaaa tcttgctgct actttattaa aaaaaataga ggaatcttac tgatgctgct 6480
ataagtaaat agaaaatata gtataatttt aatcattaaa atatgctatt tttaattttc 6540
acacttattt tctatattgt gtgtctaatc agatatatta accttaagat ttctcttgtt 6600
ctctgtgtta aagaccttat gtaaaaatgt aattgctttt catgagaagt tgtgaataaa 6660
actgatacag ttttaagttt gtga 6684

<210> SEQ ID NO 52
<211> LENGTH: 6513
<212> TYPE: DNA
<213> ORGANISM: Canis lupus familiaris

<400> SEQUENCE: 52
atgatgcata ggtttgaatg ctacttcctg acagccctca tctgtgggac tagtgctccc 60
cgagcccgag cccgagcccg agcccgagcg cagcatcccg gcccgcgcgc agctccccag 120
ggcagccggc gaggggagcg gccgggcggc gcgaggctgg gggcccgcgg gcgcggccgc 180
gcgctgccgg gcgggaggct ggggggccgg ggccgtggcc gcgcccccgga ccgggtcggg 240 ggccggggcc ggggggcggc ggcggctcct cgcgcggctc cgggggcgcg gacaccccgg 300
cagagccccg gggcgccat ggcagccggg agcatcacca cgctgcccgc cctgccggag 360
gacggcggca gcggcgcctt cccgcccggc cacttcaagg accccaagag gctgtactgc 420
aaaaacgggg gcttcttcct gcggatccac cccgacggcc gggtggacgg ggtccgggag 480
aagagcgatc cccacgtcaa attgcaactt caagcagaag agagaggcgt tgtgtccatc 540
aaaggagtat gtgcaaatcg ctatcttgct atgaaggaag atggaagatt actggcttct 600
aaatgtgtta ctgacgagtg cttctttttt gaacgattgg aatctaataa ctacaatact 660
taccggtcaa ggaaatactc cagttggtat gtggcactga aacgaactgg gcagtataaa 720
cttggaccaa aaacaggacc tgggcagaaa gctatacttt ttcttccaat gtctgctaag 780
agctgatcta aatggcagca tcttatctca tttcacatga aagaagacgt atattttaga 840
aatttgttaa tggaagaaaa gaaaaaatgt gtacagtgat ctgctctgtt tggataaatg 900
gtcagataac cttttatcta atagtaaata tttaatcatt gccttactaa agaaaaagca 960
acaaaaatgc ctggaaaatg tatagacttc caccttttat attgcatttg cctttatcta 1020
gtgaagctta cttagagcta caatcttttt cttacatttg cttcatttga aaagaggctt 1080
ttaaaatttg cacattttct tcaagtaagt tttcttcatg taaattatac tcatgagaaa 1140
attaaaatca gatatttagt taaccccaaa tgtccactac tttttataat atggcacaca 1200
tttttctgca tgtacaattt acttaagatt ttttaaaatg tgcaaatatg gatttaattc 1260
attcctgtca tagttctgta attgtctggc agtttcttgt gatagagttt atagaacaag 1320
cctgtgtaaa ctgccggaag ttcttccatg gtgaaatcaa tcttgtcaaa gccttctcta 1380
tacccataga gcagcagcct agcaactctg ctggtgatag gagttgtatt ttcagtcttg 1440
atcaggtcat tgagatccat ccattcacac cttaagcatt catgctggca aaaatttatg 1500
gtgaatgaat atggctttaa gcgacagatg atatacatat ctgacttccc aaaagctcca 1560
ggactggcgt gctgttgccg aatgctcagg agggacttga actctgattt tataccagtc 1620
tcttcaaaaa cttctcgaac tgctgtgtct cctacataaa agataggtgt acaaatcagt 1680

```
aaggatctgg atttgccttc tggacatcct gaaataccaa agtattttct tacaactata   1740
tatcttagaa gcttttgaaa tatcgaatat ttctttggct gctatttgta gacttaccca   1800
cctggtatgt atattttggg ggtcacattt ttaacctctt ctgactctat ttcccaaaag   1860
ttgaaaatac aggttcttgc agttaacatt cttacatatt tcttcattat ttcctgtttg   1920
tgatcatcca tcaaaactac ttaaatttat acatatcagt attgagaaaa attgattcat   1980
tcttcctttg tctgtagagc tgcagaatgt actgagctgt gaaaagttca aaaccttcct   2040
ggtgatcttg ggtgggactg tcaagcctct aaagtcatag aacagtttca tttataacca   2100
ttttgttatg ctcccctaat tattctgtca gtggaatccc attagtaatt tttggcattt   2160
ccttggtttc ttgagattcc aaagaactat tttatcaaaa gtgttaaaaa aaaaaaaaaa   2220
aaagaaaagc ttgcaattta cagaatttta taatacgaca tggatttcac attttataag   2280
gttgattttt caatattatg caaatttctg ggacaggatt ttgattgcca ttaatatttc   2340
tgtggttgct ctttctaaat ctccagaaga accccctaaa tgggctttct ctaattttgt   2400
gatgctttgt cactgtctcc taaagtgttt atgagaaact ctttaaatag ctgccttctt   2460
tgctcagttt gcttagaagc ttcccaattt cacaattgtc acaggcatag atttttgttc   2520
aaagacctct attcaatgct tctatttcct tgtcaaatag aaaattatac tggtgaagaa   2580
taggtaagga agaagaaatc aaggaaaaaa tctcaatttt cctgtagttg ggctattgcc   2640
ttgtcttaac aattgcctac ataagctcat gtttgtttgt tttttaagaa acagctatag   2700
caatatgcac aggaaaaaca aagtgttcta aaatgtaaga catttgtcca ccattttgaa   2760
ttaattacat gctgacttcc ccttgagatt tttcatagat taaacatggt ttgaaattac   2820
tgttttaaac taaaaacata aaaaaggaat ttatgtgaat aaaaggaaaa tcttccttaa   2880
gaaagataat tttcagctgg gaatacaata gatgtttgtt attaaatttg ttacaggttg   2940
tggcactagt cttaagtgaa atcagcaaat gagatttaca atttattgtt taaatgttta   3000
ctctgttagc actttaaaaa aaataaccat gggggttccg ttaagctctt actacaacta   3060
atcaagaatt tggcatttca tttggaatct agccttttta tgtatcatgg aggcacagga   3120
cagactagtg agtgaatcta ccttactcag cagtcacctt agctgttgat tagaaatcag   3180
caccgcctgg gtagtttgat cagtttaact tgagtcaaca tattattgac tagactaaaa   3240
attgactggg tatataagtg ctttttcatc caggatatga gtgactcctt cctcctcaaa   3300
atggaaatct ttaccccaca gctttttttgc catgaattta gattttatta tccagataaa   3360
ctgctttatt ctgttgtacc tttattttaa tgtactgtaa gctcaagtga aataacattt   3420
actattttat atgtttaagg aacataggaa aaaccaagaa gttttcattt ttatttttgc   3480
tgattgagag atatgtttaa atatgtcaca gtgtttttgt ttagttacgg gacagtgaaa   3540
tggagtttat tttgttattt ctagtttgta atatttaaca ataggatcag gttgaaataa   3600
aataggaaaa actgtgcaga atgtgggttt ccctggtgtt tccctctgat tctggtgcac   3660
tgatgagctc tgaacagacc ccctgctgct ttctggtcct ttgaccatgc aggagattct   3720
cttcctgtcg atggtaatga tgatttttta ggaaggcatt ttctctgttt ttaaccttgt   3780
agatactttt gtactattag ggtattatat taaagcctga agattgtatt ctattttata   3840
tatgccaccg ccccccctta atttttttaa gtgcttcatt tacctagtat tatcaaagaa   3900
tgaaggattc caaacaaacg tgtttcccag ttaactagag tttactactc aagagctaat   3960
atgaatgtgt gcacatttgt gatggttgta ttcctaaaat aaatacactc ctaaatacag   4020
agtttaaaga aaataatttc aatacttagg taatttggct catcctcaag gatattctgt   4080
```

```
tgtgttataa gacagaaatg ctctaatatg gacatagtct ccagaactct attgtcagtt   4140
atcatttcta gctgctttca gggttttatc agttctaagg gaaagcttta atttacatac   4200
tcctaagcaa tatgatgaat gccatctgct tttcttgtaa ctcctcatgg ttgaggtata   4260
tatatgctct ctagataggt ggggtggttg tgccaaccac aaatacttaa ttcagaattc   4320
actacttttt ttgttgtttt taatttggac ttgaagtgtt ctggagtaca cttaaaccta   4380
aaattatgta tacttgactt gaaaatgtgt tcttcatttg catttaaata taagtaaact   4440
gaaaattcac aagatccata aaaactcaaa aggaaaaagt caattaattt aagaaggcaa   4500
gctacaggaa gctaaacata cttcctgtag cctgattttt gtccaatatg gattgggtaa   4560
ggatgtaaga cataaattta actagttcac acacactctc atatatcaca taaggatagt   4620
atgaaataat taggtgttcc aaaataagtg gccctctctt tcactacttg caccaccaca   4680
aaatctgtta tttcaacaga agacctaagc aatagaatct aggcagaaga tccttaaggc   4740
caaaatttgc tatggacata tctcagtgta gtaaatttac ttatggtttg ttaggagttg   4800
gctatttact gtttacaggg cattttcatc tgggtaacat ttttaaaaaa tcaagtttca   4860
aatatatata catttttaaa tatttataaa gaacctagga agttgccttt atatataaat   4920
gttggctaag taggggacat gcatatgaga aaaaaaatca tggagaaata atactgagat   4980
caaatgaggc atcttgattt attatgatgc agactgcatt tgacccagtc aagggtcagg   5040
aataggtagg aaaactctgt ctttattctt tcttctattt actgtaaaat cagtaacatg   5100
gagagttctt agcttatttc acattttctt gtttgaaaaa caagagctga ttgagctcag   5160
gaagttgttt tagggaattc tcatttgaga ctttcttgta tgggacattt tactaagttt   5220
gacttcctat ttaaaataaa tagtaaataa agaggagaat taagtcacta ctgctctata   5280
ggtgacttta taaatactta ttttgaggtt catttaaaag ttactgttca tccttgtggg   5340
gtgaaatggt caagaatttg tgttttctta tagtttaatt ccagtaacaa tattagtcaa   5400
atccaaaata acccttattg ctaaaatttc ctaatgtata tgcaaagctt tttcttttt    5460
tttttaata ttttatttat ttattcatga gagacagaga gagagagaga gagagacaca   5520
gagacacacg cagagagaga agcaggctcc atgcagggcg cctgatgcgg gactcgatcc   5580
cgggtctcca gaatcacgcc ctgggccaaa gggaggcgct aaaccgctga gccacccagg   5640
gatccccaaa gctttttatt tcaaacaaat taacctagga gcaattctaa acagaatagg   5700
tgttgtgctc ctaatggtat tttttatact agtggggtaa gttgtaatat tacaagtttt   5760
gctgctaatt ttgtagtagc tctgaagaaa cctctctgaa atttctcagt ataaaccagt   5820
tagaaaattt taaatcttat tttcagctat agagcaaaaa agtaaacaca aatttcctga   5880
acattttcaa gccagttaaa aatatgtaag gtgtacacac caatatcttc tccaggctct   5940
gacaggcctc ctggaaactt ccacatattt ttcaactgca acataaagtc aggaaataaa   6000
gttaacatag cttcattcac taacacacac ggagactcca caaaatccac ccataattcg   6060
tcaagaggct gagaatttac tttttggtaa ttgcatgcaa atttctttca ccttcctttc   6120
acactccacc ctttcttttt cttgggggaa actggtaact tatgaaatat tttcctattt   6180
ttttctttag gaaatagatg tggttttgtt tgattaatgt gataaattct gtttgaatga   6240
aacagtggag ggaaacatct actgagtttg tgtaattttt aaaattttgc tgctagttaa   6300
ctattaacag atagaggaat catacagatg ctgctataaa taagtagaaa gtacagtata   6360
agtttaataa ctaaaatgct atttttaatt ttcacactta tttttctgta ttgtatgtct   6420
```

aatcagattt ctcttgttct gtgttaatga ttttatgtac aaatgtaatt gcttttcgtg 6480
ggtagtatga ataaatttga taagtataag ttt 6513

<210> SEQ ID NO 53
<211> LENGTH: 468
<212> TYPE: DNA
<213> ORGANISM: Ovis aries

<400> SEQUENCE: 53
atggccgccg ggagcatcac cacgctgcca gccctgccgg aggacggcgg cagcagcgct 60
ttcccgcccg gccactttaa ggaccccaag cggctgtact gcaagaacgg gggcttcttc 120
ctgcgcatcc accccgacgg ccgagtggac ggggtccgcg agaagagcga ccctcacatc 180
aaactacaac ttcaagcaga agagagaggg gttgtgtcta tcaaaggagt gtgtgcaaac 240
cgttaccttg ctatgaaaga agatggaaga ttactagctt ctaaatgtgt tacagacgag 300
tgtttctttt ttgaacgatt ggagtctaat aactacaata cttaccggtc aaggaaatac 360
tccagttggt atgtggcact gaaacgaact gggcagtata aacttggacc caaaacagga 420
cctgggcaga aagctatact ttttcttcca atgtctgcta agagctga 468

<210> SEQ ID NO 54
<211> LENGTH: 651
<212> TYPE: DNA
<213> ORGANISM: Oryctolagus cuniculus

<400> SEQUENCE: 54
cggcgcgccc cggttccccg gcaggggccc ggcaggtgag ccatggcagc cgagagcatc 60
accacgctgc ccgccctgcc ggaggatgga ggcagcggcg ccttcccgcc cggccacttc 120
aaggacccca agcggctgta ctgcaaaaac gggggtttct tcctgcgtat ccaccccgac 180
ggccgcgtgg acggggtccg ggagaagagc gacccacaca tcaaattaca acttcaagca 240
gaagagagag gagttgtatc catcaaaggt gtgtgtgcaa accgttacct tgctatgaag 300
gaagatggaa gactgctggc ttctaaatgt gttacagacg agtgcttctt ttttgaacga 360
ctggagtcta ataactacaa tacttaccgg tcaaggaaat attccagctg gtatgtggca 420
ctgaaacgaa ctgggcagta taaacttgga tccaaaacag gacctgggca gaaggctata 480
ctttttcttc caatgtctgc taagagctga ttttaatggc accatctaat ctcatttcac 540
atgaagaaag agaaacatat atttgttaat gagaggaaaa caaatgtcta cagctcagct 600
ttgttgaatg gccaggcaac tttttatcta ataataaaat gtttaaccat t 651

<210> SEQ ID NO 55
<211> LENGTH: 1115
<212> TYPE: DNA
<213> ORGANISM: Xenopus laevis

<400> SEQUENCE: 55
gaattccgta gcatctcctt gcctgcccct ggctcatggc tgctgctgtt gaactttctc 60
tgcctttgaa ttacaggaga tgacagattt gccaagggct gctgaaaggt gcttttactg 120
atgctgctga ggcactgtag gagggctgca tgtgaatacc tcacaaaggg aaaagtttgt 180
cagacttcca attgaatgaa ctgtgaggcc ctgagcaggg aaactgaggc gagacacagg 240
gctattatca gaaaacgaac tgctgctacc tgttggacct cgcctgggct ctgagaggct 300
gctgggaagg cagggctgaa acattgttgc agggatggcg gcagggagca tcacaactct 360
gccaactgaa tccgaggatg gggaaacac tcctttttca ccagggagtt ttaaagaccc 420
caagaggctc tactgcaaga acgggggctt cttcctcagg ataaactcag acgggagagt 480
ggacgggtca agggacaaaa gtgactcgca cataaaatta cagctacaag ctgtagagcg 540
gggagtggta tcaataaagg gaatcactgc aaatcgctac cttgccatga aggaagatgg 600
gagattaaca tcgctgaggt gtataacaga tgaatgcttc tttttgaac gactggaagc 660 taataactac aacacttacc ggtctcggaa atacagcagc tggtatgtgg cactaaagcg 720
aaccgggcag tacaaaaatg gatcgagcac tggaccggga caaaaagcta ttttatttct 780
cccaatgtcc gcaaagagct gatctgaaat gactgatttt tttaggtcaa gagaaaccct 840
ttctaagacc agaaaatcct tttatatctg taatattaaa tgtgaggctg aggtacagca 900
ttgttttatt gtatatttgt gcaggctctt gagctagtgt ttgagagtga tgaaactaaa 960
ctacagttgt ccactcagta tttaatctac acgttaatat attgaatatt atacatgcat 1020
ttctaaatta agtgtctgga atttttacat gaaaattcct taaatactat aaaagtagag 1080
taccgtagta aaaggagaat taaaatgtga agctt 1115

<210> SEQ ID NO 56
<211> LENGTH: 6113
<212> TYPE: DNA
<213> ORGANISM: Homo sapiens

<400> SEQUENCE: 56
gacatttaga ctccaggctt caacctgttt acaagcggac tttccaaagg aagggggtgg 60
gagatagggc catacaaaac accagccgcc gtcccccaaa acaaaaagtg actttcggca 120
gccttcaaat cggcaggcac cactaaaaac agaaaggaag agagggaaga aaacaacggc 180
gactgggcag ctgcctccac ttctgacaac tccaaaggga tatacttgta gaagtggctc 240
gcaggctggg gctccgcaga gagagaccag aaggtgccaa ccgcagaggg gtgcagatat 300
ctccccctat tccccacccc acctcccttg ggttttgttc accgtgctgt catctgtttt 360
tcagaccttt ttggcatcta acatggtgaa gaaaggagta aagaagagaa caaagtaact 420
cctgggggag cgaagagcgc tggtgaccaa caccaccaac gccaccacca gctcctgctg 480
ctgcggccac ccacgtccac catttaccgg gaggctccag aggcgtaggc agcggatccg 540
agaaaggagc gaggggagtc agccggcttt tccgaggagt tatggatgtt ggtgcattca 600
cttctggcca gatccgcgcc cagagggagc taaccagcag ccaccacctc gagctctctc 660
cttgccttgc atcgggtctt acccttccag tatgttcctt ctgatgagac aatttccagt 720
gccgagagtt tcagtacaat gtggaaatgg atactgacac attgtgcctc agcctttccc 780
cacctgcccg gctgctgctg ctgctgcttt ttgttgctgt tcttggtgtc ttccgtccct 840
gtcacctgcc aagcccttgg tcaggacatg gtgtcaccag aggccaccaa ctcttcttcc 900
tcctccttct cctctccttc cagcgcggga aggcatgtgc ggagctacaa tcaccttcaa 960
ggagatgtcc gctggagaaa gctattctct ttcaccaagt actttctcaa gattgagaag 1020
aacgggaagg tcagcgggac caagaaggag aactgcccgt acagcatcct ggagataaca 1080
tcagtagaaa tcggagttgt tgccgtcaaa gccattaaca gcaactatta cttagccatg 1140
aacaagaagg ggaaactcta tggctcaaaa gaatttaaca atgactgtaa gctgaaggag 1200
aggatagagg aaaatggata caatacctat gcatcattta actggcagca taatgggagg 1260
caaatgtatg tggcattgaa tggaaaagga gctccaagga gaggacagaa aacacgaagg 1320
aaaaacacct ctgctcactt tcttccaatg gtggtacact catagaggaa ggcaacgttt 1380

-continued gtggatgcag tagaaccaat ggctcttttg ccaagaatag tggatattct tcatgaagac 1440
agtagattga aaggcaaaga cacgttgcag atgtctgctt gcttaaaaga aagccagcct 1500
ttgaaggttt ttgtattcac tgctgacata tgatgttctt ttaattagtt ctgtgtcatg 1560
tcttataatc aagatatagg cagatcgaat gggatagaag ttattcccaa gtgaaaaaca 1620
ttgtggctgg gttttttgtt gttgttgtca agtttttgtt tttaaacctc tgagatagaa 1680
cttaaaggac atagaacaat ctgttgaaag aacgatcttc gggaaagtta tttatggaat 1740
acgaactcat atcaaagact tcattgctca ttcaagccta atgaatcaat gaacagtaat 1800
acatgcaagc atttactgga aagcacttgg gtcatatcat atgcacaacc aaaggagttc 1860
tggatgtggt ctcatggaat aattgaatag aatttaaaaa tataaacatg ttagtgtgaa 1920
actgttctaa caatacaaat agtatggtat gcttgtgcat tctgccttca tccctttcta 1980
tttctttcta agttatttat ttaataggat gttaaatatc ttttggggtt ttaaagagta 2040
tctcagcagc tgtcttctga tttatctttt ctttttattc agcacaccac atgcatgttc 2100
acgacaaagt gtttttaaaa cttggcgaac acttcaaaaa taggagttgg gattagggaa 2160
gcagtatgag tgcccgtgtg ctatcagttg acttaatttg cacttctgca gtaataacca 2220
tcaacaataa atatggcaat gctgtgccat ggcttgagtg agagatgtct gctatcattt 2280
gaaaacatat attactctcg aggcttcctg tctcaagaaa tagaccagaa ggccaaattc 2340
ttctctttca atacatcagt ttgcctccaa gaatatacta aaaaaaggaa aattaattgc 2400
taaatacatt taaatagcct agcctcatta tttactcatg atttcttgcc aaatgtcatg 2460
gcggtaaaga ggctgtccac atctctaaaa accctctgta aattccacat aatgcatctt 2520
tcccaaagga actatcaaag aatttggtat gaagcgcaac tctcccaggg gcttaaactg 2580
agcaaatcaa atatatactg gtatatgtgt aaccatatac aaaaacctgt tctagctgta 2640
tgatctagtc tttacaaaac caaataaaac ttgttttctg taaatttaaa gagctttaca 2700
aagttccata atgtaaccat atcaaaattc attttgttag agcaggtata gaaaagagta 2760
cataagagtt taccaatcat catcacattg tattccacta aataaataca taagccttat 2820
ttgcagtgtc tgtagtgatt ttaaaaatgt agaaaaatac tatttgttct aaatactttt 2880
aagcaataac tataatagta tattgatgct gcagttttat cttcatattt cttgttttga 2940
aaaagcattt tattgtttgg acacagtatt ttggtacaaa aaaaaagact cactaaatgt 3000
gtcttactaa agtttaacct ttggaaatgc tggcgttctg tgattctcca acaaacttat 3060
ttgtgtcaat acttaaccag cacttccagt taatctgtta tttttaaaaa ttgctttatt 3120
aagaaatttt ttgtataatc ccataaaagg tcatattttt cccattcttc aaaaaaactg 3180
tatttcagaa gaaacacatt tgaggcactg tcttttggct tatagtttaa attgcatttc 3240
atcatacttt gcttccaact tgctttttgg caaatgagat tataaaaatg tttaattttt 3300
gtggttggaa tctggatgtt aaaatttaat tggtaactca gtctgtgagc tataatgtaa 3360
tgcattccta tcaaaactag gtatcttttt ttcctttatt ttaaaataat aattgcacct 3420
gacacataaa catagaccac ccacaaccaa aattaaatgt ttggtaagac aaatacacat 3480
tggatgacca cagtaacagc aaacagggca caaactggat tcttatttca catagacatt 3540
tagattacta aagagactat gtgtaaacag tcatcattat agtactcaag acactaaaac 3600
agcttctagc aaaatatatt aaagcttgca gaggccaaaa atagaaaaca tctccctgtc 3660
tctcccacat ttccctcaca gaaagacaaa aaacctgcct ggtgcagtag ctcacacctg 3720
taatcccagc agtttgggag actgtgggaa gatggcttga gtccaggagt tctagacagg 3780

```
cctgagaaac ctagtgagac atccttctct taaacaaaac aaaacaaaac aaatgtagcc   3840
atgcgtggtg gcatatacct gtggtcccaa ctactcagga ggctgaaacg gaaggatctc   3900
ttgggcccag gagtttgagg ctgcagtgag ctataatctt gccattgcac tccagcctgg   3960
gtgaaaaaga gccagaaaga aaggaaagag agaaaagaga aaagaaagag agaaaagaca   4020
gaaagacagg aaggaaggaa ggaaggaagg aaggaaggaa ggaaggaagg aaggaagcaa   4080
ggaaagaagg aaggaaggaa agaagggagg gaaggaagga gagagaaaga aagattgttt   4140
ggtaaggagt aatgacattc tcttgcattt aaaagtggca tatttgcttg aaatggaaat   4200
agaattctgg tcccttttgc aactactgaa gaaaaaaaaa agcagtttca gccctgaatg   4260
ttgtagattt gaaaaaaaaa aaaattggag ctattgagag atctgcctct gtaggagtat   4320
ggtcccaggc ccacaaagtt aaagtgcatc agccacaaat atgtgtccat ttgagttttg   4380
gttctgagaa tactcctcat aaagatatag aatcactccc tcctcctaac tcgcaaaagg   4440
ctgaacagtg tatagtatgt tacatttaaa taaaaacaat aaaaatgttg ggaaaagaaa   4500
attaaaatat tgtccttgtt tgttttatta gtcagaaact ctacctggta ataaagagag   4560
aagctcaagt gtgtgcatgg caggatgtgg ttaaatgccc cacagcccca aacaacaaca   4620
acagaaaaaa aaattactca aacatttgta agttttctct aatgtttcac atgtgtgagt   4680
tagctatctt tactctaata acaaccaaat gctttcaatc ttttctaaat attcaggtcc   4740
acctaattta cacagtggat aaagaaaaat gaattggaaa cgaggatggc ttatgaaaca   4800
atggaagact tttggaggaa agccaggtgg ctgcagaatc tgatttcaag gggatgaatg   4860
accaatgaat ttgatttgaa aattagagag aaaaaataca taataatgca agttgcttcc   4920
agggcccaag caagtttatg aacccaattt acatagatca gcattaatgc tgcacagttc   4980
taataatttg gatgctgcca attcaaggtt tgtgattatt cagtgaagta aaatttacct   5040
ttttcatatt actgaagggt tcagctggtc caaactttgt ctaaataaag ttatatatgt   5100
agcttaaaat atttaagaga agatgtctag tacattagaa gtaggacata tacatgcaaa   5160
cagataccat attgattaag agttcttgtt tatttcatga agcaggactt ttccaactta   5220
aactgaaaaa aaaataaaaa ggaagaggaa tatctttgaa ggatgctcag gagaaaaagg   5280
aactctgagt tctatgagta cttagaaatg aagtaacgaa gatctgcttc ttctcagaca   5340
ttcattttct gttacccttc attggtttta tttggttagg ccagattgct tctagtctac   5400
ttctttccta ctccaaaacc caaaacccca aactccttta ctacaagatc caaaaaggta   5460
aacatcctag atataactct tattggccag gtttggataa cataccaacc tctagaccaa   5520
tcagtataag agatttggga attgtgattg accaatcttc agtgacatga ccacagagag   5580
gcaaggtgaa gattttggca gcccacacaa ccgcaactag tgaagaagag tacaccaagg   5640
agacagcagt gctgcaggtg caaaaaccaa atggttgttt gctacatctt attaaatgaa   5700
gctgtgacat aaaaacattt tctattccta tatttcccac caattccaat tattcttcac   5760
ctgtttgttt gtccaagtta gagaggtttt aagatcattc tctttcatat gttctttacc   5820
attgaaagat tacatttgca ttgttttgtt ttaagccaag agtagggccc tggatatagc   5880
taggctcact gtggttttgc aaactttata ttgggatgaa tgcaagtttt cactgaataa   5940
aaagctggtc ctcctacttc aacctgtatc acaatatgat gttataaatg tttctttcag   6000
tttatcccaa gagtatgtgc tagtattttc aagtgtatcg acatatagaa aaaatctgaa   6060
accctgatgt cattcattgt ttaagtgtaa aataaaaaaa aaacagaaaa aaa          6113
```

<210> SEQ ID NO 57
<211> LENGTH: 4572
<212> TYPE: DNA
<213> ORGANISM: Mus musculus

<400> SEQUENCE: 57
ggctttccaa gggacttgga ggtggagaga agggcccaac aaaacgccag ccgccagccg 60
ccccccaaac aagaagtggc tttcggaaga cttcacatca acaggcacca ccaaaaagag 120
aaaggaagga gaagacaaca gcgcctgggc agctgcctcc agttctgaca actccaaaga 180
gacacttttt aagtggccag caggctggga ctctgcagag aaggaccaga aggtgccaac 240
cgcagagggg cgcagatgtc ttcctgcacc cccaccccac ccactttggg ttttgttcac 300
cgtcctgtca tctgtttttc agacctcttt tgcatctaac atggtgaaga aaggagtgaa 360
gaagagaaca aagtaacccc cggggggagc gaagagctct ggtgaccgac accaccagtt 420
cctactgccg cggccaccca cgtccactgt tcaccctgag actggagaga cgcaggcagc 480
ggatccgagg acggagcgag gacaggcagc cggtccttcc tagaagttat ggatgttggt 540
gcactcgctt ctggccagat ccgtacccag agggagctat ccagaagcca ccacctccag 600
ctgtctctct gcctcgcagc aggtcttacc cttccagtat gttccttctg atgagacaat 660
ttccagtgcc gagagtttca gtacaatgtg gaaatggata ctgacacatt gtgcctcagc 720
ctttccccac ctgccgggct gctgttgctg cttcttgttg ctctttttgg tgtcttcgtt 780
ccctgtcacc tgccaagctc ttggtcagga catggtgtca caggaggcca ccaactgctc 840
ttcttcctcc tcgtccttct cctctccttc cagtgcggga aggcatgtgc ggagctacaa 900
tcacctccaa ggagatgtcc gctggagaag gctgttctcc ttcaccaagt actttctcac 960
gattgagaag aacggcaagg tcagcgggac caagaatgaa gactgtccgt acagtgtcct 1020
ggagataaca tcagtggaaa tcggagttgt tgccgtcaaa gccatcaaca gcaactatta 1080
cttagccatg aacaagaagg ggaaactcta tggctcaaaa gagtttaaca acgactgtaa 1140
gctgaaagag agaatagagg aaaatggata caacacctat gcatctttta actggcagca 1200
caatggcagg caaatgtatg tggcattgaa tggaaaagga gctcccagga gaggacaaaa 1260
aacaagaagg aaaaacacct ctgctcactt cctccccatg acgatccaaa catagaagaa 1320
aacactgttg gtggatgcag tacaaccaat gactctttgg acagaaagag atggtatcct 1380
cactgaagac tgtagctcaa aaggcaaaga catagccctg aattcagctt gtttaaagga 1440
aggaaggctt tggatgtttt tgtactcact gctgacatac aaagttcttt tcactagctc 1500
tgtgtcattg tgtcatgcct tataatcaag atagaggcaa gtcaagtttg gatggaagtt 1560
atcctcaagt gaacaatgtt gtggtggggg ctgggcttt tttgtttgtt tgtttgtttc 1620
atttttaagt ttttgttttt gaacttctga gatagaactt aaagaacatg gaacactctg 1680
ttgaatgatc tttgggaaag ttatttatgg aatatgaaca catatcaaag actttcattg 1740
ctcattcaag cctgatgatt caatgagcag taagacacgc aagcatttac tggaaagcac 1800
ttgggtcata tcatatgcac aaccaaagga gctttgggtg tggcaccatg gaagaattgg 1860
atcagattta caaatataaa catagtagta tgaaactgtc ctaatacaaa tagtatggta 1920
tgcttgtgca ttctgtctcc atccttttct atttccttct aagttattta tttaatagga 1980
tgttaaatat cttttggggt ttaaagagta tcttcaatgc tgccctctgg tttacctttt 2040
ctctctctct ctctctctct ctctctctct ctctctctct ctctctctct ctctctctct 2100
ctctctctct ctccctctct ctccctccct cccccctctg gcaccatacg cacattcatg 2160

-continued

```
acaaagtgtt ttaaaacctt ggcaaacact tcagaaatag gagatgagat caaggaagca   2220
gtatgaatgc cccatgcgct ctcagttgac ttaatttgca cttctgcaat aaaaaacacc   2280
agcaatgact atggcagaat tctgctatag attatgtaac agatatctgt catcatttgt   2340
caacatatat cagtccagag ggacccttac cttaaaatgt agaaggccaa attctctttc   2400
attgtcttat ttcatcttca agaatatact aaaagaagaa aaaatgaatt gttagactaa   2460
cattgttggg ttttttttt cctactgatg atggcttgcc acaggtcaca atggcaaatg   2520
atgcaaaggt tatctgcaca tacatgagcc ctttgtaagg cccacagaat ccttctccct   2580
caaaagaacc aaaaaaggaa atttggtatg aagtgcaact ctccctgggg cttaacctga   2640
gcaaatatat cctagtatat gagtaaccat atactgacac ctgttcaagc tgaatggtct   2700
agtctttaca gaaccacata aaccttgttt tctgtaaatt taaaatgttc tagaaggttc   2760
cataatataa ccacattgaa attcattttc ttagaaaagg tatagaaagc agtatgtaag   2820
tgtgccatgc accctcgctc tgtagatcac taaataaaca cgtaagcctt atttgcagtg   2880
tctgtagtga ttttaagaat gtaggaaaca cttctaaaaa aattttaaag gataactctg   2940
agatgatatt gatgctgcag tcttctttct tgtttggaaa tgtctgttta ttttcattgt   3000
ttggattcag tattttgata ggaacaaaaa gactcaccaa atgtgtctgt ttactaaaat   3060
ttaacctcta gagaggctag tgatttgtga tcctcttcta acttatttgt gctgatgctt   3120
gaccagtaca aatcagcttt ttaaaatatt attattaaag gttgatcagt cattttaaaa   3180
ttggcctttt ttttcagaat gttcctacag gtcataattt atgatttctt tgaaaagctt   3240
gcatttcaag agaaaagcac agaggcacaa tgctttggtt tatgggtata ggttgcattt   3300
tgtggtgttc tttcaacttg ttttctgaca aatgggattt ttaaaatgta tacttcttgt   3360
ggttggattc tgtatgttag agtttaattg gtaactgagt ctaaaggctc taatgtaatg   3420
aatctctaga agaactaggt atcttttttt acttttattt taaaataata attatacctg   3480
acacatgacc atggaccacc cacaaccaaa attaaatgtt tggggagaca aactatagta   3540
ttcagtgaca agggtaacag caaatagtgc agacgttgga ttcttatttc actttgccat   3600
ttagattact aaagagacta tgtgtaaaca gtcatcatta tagtactcaa gacattaaac   3660
agcttctagc aaaatgtatc aaagcttgca gagtccaaaa atagaaaaca tctttccccc   3720
tctcccaccc tacatttccc cctgtatgca tcctaacaga gataaataca aaatgaattc   3780
ggtaaggaga gaggagattc ttcttcactt catatttgtt tgatattaat agagaattct   3840
ggtccttttt acaactactg aaagaaaaga agttcagtcc taaattttgt gtgttaaaaa   3900
aagaaaagat tttgtgagtt ctgcctccgt gggaagtgtg ggcactgctc caccatgctg   3960
aagtgtgtta gccacgggta cagagcatat gactgttgac atcagactcc ttaaagatac   4020
agaatcgctt ccctcctcct aatcctcaaa aggctgaaca gtgtatatta tgttacattt   4080
aaataaaggc aataaaaatg ctgggaaaag agaataaaag tactgttctt attttatttc   4140
ctttctttct tctcttctct tttcttttct ttccttttct tttttttttc cttttttttt   4200
cttttttttt tttattagcc taaaactata cctggtaatg agatcagctc cagggctgtg   4260
tgcatggcag gatgtggtta aatgccccac agccccaaac aacaacaaca gaaaaaaaaa   4320
ttactcaaac atttgtaagg tttctttaat gttttacatg tgtgagccgg ctatccttac   4380
cctaataaca accaaatgct ttcgggttct cctaactact caggtccacc tagtttacac   4440
agtggataaa gaagaatgaa ttgaaaacaa ggatggcttg tgcaacaatg agaggctctt   4500
```

ggaggaaagc caggagctgc aaacgttgac ttccagggca tggaaaagac caacgaattt 4560
gatttgaaaa gt 4572

<210> SEQ ID NO 58
<211> LENGTH: 648
<212> TYPE: DNA
<213> ORGANISM: Rattus norvegicus

<400> SEQUENCE: 58
atgtggaaat ggatactgac acattgtgcc tcagcctttc cccacctgcc gggctgctgt 60
tgctgcttct tgttgctctt cttggtgtct tccgtccctg tcacctgcca agctcttggt 120
caggacatgg tgtcaccgga ggctaccaac tcctcttcct cctcctcttc ctcctcctcg 180
tcctcttcct tctcctctcc ttccagcgcg gggaggcatg tgcgaagcta caatcacctc 240
cagggagatg tccgctggag aaagctgttc tccttcacca agtactttct caagattgaa 300
aagaacggca aggtcagcgg gaccaagaag gaaaactgtc cgtacagtat cctagagata 360
acatcagtgg aaatcggagt tgttgccgtc aaagccatta acagcaacta ttacttagcc 420
atgaacaaga aggggaaact ctatggctca aaagaattta acaatgactg taaactgaaa 480
gagaggatag aggaaaatgg atacaacacc tatgcatctt ttaactggca gcacaacggc 540
aggcaaatgt atgtggcatt gaatggaaaa ggagctccca ggagaggaca aaaaacaaga 600
aggaaaaaca cctccgctca cttcctcccc atggtggtcc actcatag 648

<210> SEQ ID NO 59
<211> LENGTH: 2013
<212> TYPE: DNA
<213> ORGANISM: Danio rerio

<400> SEQUENCE: 59
ggaaaaatgc ccctcgtcgc ctcttattct gacgcacaca tgcaagcaaa acatgcatgc 60
gcacatgcgg atcttcaaag ctgactgcct cttatagtct ccctattagt taaagagatt 120
acatctgggg ccctgaacca aataaataag gtgagaggag tgtcagagct cagtctgctc 180
cacctcggga ttctctcagc acttcagtgg taagcagaag ggaaacactc ttaatcagaa 240
ggacattgag agagctggac acagcaggga ttacactttt ttcctcctac tgtggattcc 300
tctcatttca tcaagaacag atttgctacc ctgttgaatt tgggtcattt ttgccattct 360
tttccagaac attttcattg cttcttgcag tccttgtttt ctcccatccg acagaggttc 420
tgcagtggat tgtatgtggg agagcaggag gaggtgaagc ggtttcccac agaggtgttt 480
tgagttatgg atgttgacac attccttctg gacacgaggg gaaatggatc cagcctgagc 540
agcctaagca gacacgatca ctacggacgc tttacggggc ttcacctcct tgcatcaccc 600
tttctcccat ccagctcttc agcatgtacc tttctgtgag gctcttccca gttttccgag 660
ctccaggaca atgtgcaaat ggaaagtgac taagggtgcc tcagcctggt tccgtctgtc 720
ctgcctttcc ctgccgctgc tgcttctgtt cctgtgttcg gctctgcctg tggcctgcca 780
tgacacccac agggccatcc gtgccccgag gggcaccaac tcctcatcgt ctgccgtggt 840
ggggcggcat gtgcgcagct acaaccacct cacgggggac gtgcgcagga ggaaactctt 900
ctcctaccag aagttctttc tcaggatcga taagaacgga aaagtcaatg gcaccaaaag 960
caaggacgat ccgtacagta cactcgaaat caagtctgtg gatgtgggca tcgttgccat 1020
caaggggatt caaagcaatt actaccttgc aattaacaag aaaggggtgg tctacggggc 1080
gagggatttc ggcattgact gcaagctgat agagaggata gaggagaaca ggtacaacac 1140
ctatgcctcg gcagaatgga tgaacaagaa gaagcacatg ttcgtaggtc tgagcgccaa 1200
cgggaggccg atgagggcca aaaagacccg gagaaaaaac acagccacac actttctccc 1260
cattcctatc gtgtagctac aaccccacca aagggaacat ttaactgcac tgaggaaaga 1320
cttggaattt tttttcgtca gtataaatgg aaccatttgg agaagaaggc actatgtaaa 1380
gaaactacaa gaactcatta tcactgagtc aaatcgttgt tgcatatttt gtttaagtta 1440
ttggcaccag ggaaaaaata tacttttttta gtaaaggaaa ggttggacac atggacgaga 1500
ggaatcggac attgcaacct cccagaatga actggagaga cctttcacgg agtgtattgc 1560
ttgtgtgtat ttgtgtgtgt gacctttgga tgcagttatt tatgctgtac taactcatac 1620
gaaacattct aacagactct caagctctgt gactcagtgg actgaaagtt atgcaaacac 1680
ttactggaag cacttgctca aggtgcaaga ctgagaagcc gagacggaga cccagcatcc 1740
taccatccga atttagtcaa gctagcacca ttagcgtaaa gaactctaac ataattaaca 1800
tgcaraagcc actgtattta atatctccat tctttacctg actgctttgg aataaattat 1860
ttattttatg taatatttaa agaaaaacaa aaggcaaaaa acacatggaa tggacatttt 1920
tttatcattt atgctcctct tttaaaaaaa gctattctat cggttacaca tgaataaata 1980
aatatatttc tccttaaaaa aaaaaaaaaa aaa 2013

<210> SEQ ID NO 60
<211> LENGTH: 5018
<212> TYPE: DNA
<213> ORGANISM: Gallus gallus

<400> SEQUENCE: 60
ggaaagagac acaataaatc ttgagaggct taaaaggaag agcaggctaa agtgtgaact 60
ttttatttca gcaacggaag tgagaaatca gtgattcatt aaaggaggga gaaagacctc 120
catggaagtt ggcaaagaag aaggaaaagg agctaattat gtctcttccc ctttttactc 180
tctccgacca gcctataatc tgctctcgca gggtctgctt gcagcatgta cttcttccca 240
acctttccac tcaacccctc ctccagcagg ggggaggggg aggtctagca ggcaacaagc 300
tccaggtggc tttctcaacc gctccgctgc caaaaaaata aaatccttcg ctagaaaaca 360
agtttctttt cttttttttc ttttcttttt tttttttttt tttttttttg gctggtgcgg 420
ggggagcctc cctggagggg attggttcag cctgcaagac agggaaatta gtaaggcatg 480
agtctccaag ccatgctggt ggccagcact ccgaggagcg gagcgcttta ggagcaatta 540
gcagcgagcc gaaggcggcg gcggctgccg ccgctgcagc tcgggaggaa gcgagggcag 600
ctcctggggc tccctccgca gcaggcactg ctcgctccaa ctgcaaaagg gtttcagatg 660
tcccaccgct gcttgacctc ctgcaaataa gggttgacca ccagaggcac atcccacctc 720
tgatttgtaa tcgctgacat ttaggctaca gcttccaacc tgtttacaac caaaggggag 780
ggaaaggaaa ggaagagaag agaagagggg gcttgggggg agaaacaaat tgggattttt 840
tccccccctc tctctttcac tctctttctc tctctctctg ggtggttttt tttttgtttt 900
tttttttgtt tgtttgcttg tttgtttgtg tgttttttgt tgctgttgtt tgttttttttt 960 tattttttttt taatactgtt ctggagaatt caaagcaaaa caaagaaact gcctcctcta 1020
gggttgtcag tgagaaagga cgagttgtgc aactggtttg ggatttgcaa gagggcgagg 1080
gggtggggat cagaagaagg tgcaaagcca cgaagtgtga gcgcaagtgt gtgtgtaaag 1140
gggtgtgtgt gaaaaatccc ttccagcacc cctttccact ggttgttatt tattgttgtt 1200
gttgttcatt ctgctgtcat ctatttttca gacctttctg cttctaagat ggtgaagaaa 1260
ggagtgagga agagagcaaa ataactactg ggaagtctca aaccagctct tttttctgag 1320
ggaggactcg aaggattaaa aggcagcaac ttctgaggcg atctgtcccc tgagttatgg 1380
atgttggtgc acttacttca ggccagatca gagctcagag ggatctaacc agaagcagca 1440
accaccggct ctccacttgc cttttaccag gttttaccca tccagtatgt ttcttttgat 1500
aagacatttt ccaacgccca gagtttcagt acaatgtgca aatggatact gacaaatggt 1560
gcctcagcct tttcccacct gccttgttgc tgcttgctgc tgctcttctt ggtgtcttct 1620
gtgcctgtca cctgccatga cctcggccag gacatgctgt ccccggaggc caccaactct 1680
tcttcttcat catcctcctc cttcccctcg tccttctcct ctccttccag tgcggggaga 1740
cacgtgcgga gctacaatca cctccaagga gacgtgcgca agaggaagct ctactcttac 1800
aacaaatact ttctcaagat cgagaagaac ggcaaggtca gcggcaccaa gaaggagaac 1860
tgccccttca gcatattgga gataacatct gtagaaattg gagttgtggc agttaagtcc 1920
atcaaaagca actattattt agctatgaac aagaaaggaa aagtctacgg ctctaaggag 1980
tttaatagtg attgcaaatt gaaggaaaga atagaagaaa atggatacaa tacatatgca 2040
tccttaaatt ggaagcacaa tggaaggcaa atgtttgttg ctctgaatgg aaggggagcc 2100
acaaagaggg gacaaaaaac aagaaggaaa aacacttcag ctcactttct tccaatggta 2160
gtaatgtcat agatgaagga actattttat caatgcagtt gaaccaaagg ctcttatgtc 2220
actaagaatt ggtagtcttc ttgaagaata attgcaaaga aatagtgcag acatctgctt 2280
gtttgaaaag agcaggggaa gcctctgaag tttttgtatt cattgctggc aaatgaaata 2340
cttttattta attcagtgtt ctatcttaag agcaagatag aagctgaatc aaaggggata 2400
taagtcattg ccagtatgaa cattttttc tctctgcaac agaacttaag gaatgtgaga 2460
caatctaatg aatgatcttc gtggggaaag ttatttatgg aatactaact catatcaaag 2520
acctgaattg ctcattcaag cctatgaaca gttagacatg caagtattta ctggaagcac 2580
ttgggtcata tgcacaaata aagatgcttc tggagaagcc ttgtggaaga atggatagga 2640
ttaaggaata taagcaaagc agtatcaaac tgttctaaca aaacgaatac tatggtttgc 2700
ttgtatgttc taacttcact ccttttattt tctctctaag ttatttattt aataggatgt 2760
taaatatctt tttttttttt atttgaaacg ttttcctcat ttgctttttt gttgttttcc 2820
ctttttctca gtacttcaca cagggttgat acgttaaaat atcagaacct tgtaagtact 2880
gttagaatag gtgatggaca aggctttaaa gacagaattt aatgtgtata atccgttgtt 2940
tttttttcct aactctcttg cacttaagca aaagaccaaa catgcagtgc ttggattaat 3000
ggtactgtgt gtctttatgt ttgagaggtt ttcttacttg ttagcactca aaaacaaact 3060
tcatgaaata cttgcttcaa agggactctc tgctattttt aaactgagag caggggccac 3120
ctctgtactt gggtataaat gcatctgcat gtatattcat ctgactttga tttcagtgtg 3180
gatttaataa caaatgcatt gcaatcagta agaaattttg cagtaagcac tgggctggaa 3240
cctagctgtg gacagtcctg ttaaaatcac tgataatacc attcttaaaa ttaaatagta 3300
tgaaattttc aggtgttaaa tttggtctct gaaagatgag agagcaacac aatcctgcac 3360
tccttattca attaatacaa cctttcagca tgtttgtcct tgttaagagc ttgaagagtc 3420
acagaaaaag agtcagagca atacctaaat aaggactgag gaatagggaa tccaaaatca 3480
tgctcatgca tttatcagag attattactc acatgtatat tatatatgag agccaacaaa 3540
aaagctgtgc tggtatccag ctttagcatg cctttcatat ccaccatagt cactgaaggc 3600

```
tccaaatgca taatatccag cacattttca ttaagtgtta ctagtcccat ggcttaactt   3660
gagcaactgc agtataacaa aattaagcat aatatgaagt ctgttcaatt aaaagtacat   3720
aaggtttgtt ttatgttttg ctttactctg taattttata gagctctgga tagctcacca   3780
atgtaaccat attgagattc attttgttag agcagataaa tagaaagcaa tacaacaaat   3840
aatttgtacc actgtcttca cattgtattc cactaaataa ataaataagc ctttgcagtg   3900
tctgtagtaa gaaacaaaag tagtataata ttattttgtt ctaaatactt ttaagtgata   3960
actatgagat tatattgatg atgcagtttt atcttcaata tttcttgttg tgaaaaagtc   4020
atttttattt ttattatttg gaaactgtat tttggtacaa aggagagcct tgcttaatgt   4080
ttctttttga gaatgtttaa cctctataaa ggctggtgtt gttggaatct tttctaagtt   4140
atttaagtca atgtttaacc agcacttcaa tcttaatctg ttatttaaat attagctgtt   4200
aacaaaaaaa aaaatagctt tcccataaaa tacgaagtgg tcagactgta tttcctgtct   4260
ttaaataaag ccaactcttt taaaaccaga aagtaattcg agacacaaca ttctaactga   4320
cagctaacat tacatttcat ggtactttat atccagcttg cttcttcaca aatgagggtc   4380
tctagaaagg gaaaaaagaa cttccgattt taaatgtagt ttcaggtgat cagcaaaact   4440
taatgaccat aataaaagtg agtttctgtt gttaaaaatt tgtaatcagt aattaaaact   4500
gacaagatat agtggaccac ctacagtgag cattcaatgt tagcctgggc aaatgcagta   4560
ctagatgact acttaaagaa catttagggt acaaatgtgg ttctcttgac agaattacct   4620
agtttatatg atcaggggag gatttttgca taaatattat catagtactc aaaatactat   4680
gctgctcaga ggccaaaatc atggaaaaca tcacttttcc taagtccatc aggaaccatg   4740
tctgacatga atttcttaga ataaaccaga acaaaacgtc cttgaaggaa atgattcctg   4800
catgattagc atactgtaat acccactggt ggtgggagca aaatgctgac cttttttcta   4860
gagtctcaca gttccttgac catatcctct gttctctgtc agacagactc tgaggaggag   4920
agatttaaaa aagaaaagaa aaacaagaat cactgagcaa caatgtatag catggtatat   4980
ttcaataaaa ataataaaat atggggaata gagaataa                           5018
```

<210> SEQ ID NO 61
<211> LENGTH: 3384
<212> TYPE: DNA
<213> ORGANISM: Bos taurus

<400> SEQUENCE: 61

```
atgtggaaat ggattctgac acattgtgcc tcagcctttc cccacctgtc cggctgctgc     60
tgctgcttct tgttgctgtt cttggtgtct tccgtccctg tcacctgcca agccctcgat    120
caggacatgg tgtcaccagg ggccaccaac tcctcttctt cttcctcgtc ctcgtcctcc    180
tcgtccgtct ccttgccttc cagtgcgggg aggcatgtgc ggagctacaa tcacctccaa    240
ggagatgtcc gctggagaaa gctattctct ttcaccaagt actttctcaa gattgagaac    300
gggaaggtca gcggtaccaa gaaggagaac tgcccgtaca gtatcctgga gataacttca    360
gtggaaatcg gagttgttgc tgtgaaagcc attaacagca actattattt agccatgaac    420
aagaagggga aactctatgg ctcgaaagaa tttaataatg actgtaagct gaaggagagg    480
atagaggaaa acggatacaa tacctatgca tcttttaact ggcagcacaa tgggaggcag    540
atgtatgtgg cattgaatgg aaaaggagct cctagaagag gacagaaaac acgaaggaaa    600
aacacctcag ctcattttct tccgatggtg gtacactcat agaagaaggc aatgattgca    660
```

-continued

```
gatgcagtat aaccaaaggc tctttatgag gcacagttgg tattctttat gaagacagta    720
cttcacaagg caaagacaca ttgcaaatgt ctgcttgctt gaaagaaagg aagcctttga    780
aggtttttgt actctctgct gacatatgat gttctcttag ttagttctgt gtcctgcctt    840
gtgatcacaa tataagcaga tcaaatggat ggaatttatt cccaagtgaa caatattgtg    900
gctgagtttt ggggtcaagt tttgtttat gtttttgttt ttatcctctg agatagaact    960
taaaggacaa ggaacgatct gttgaatgaa tttcgggaaa gttatttatg gaatacgaac   1020
tcatatcaaa gacattcatt gctcattcaa gcctaatgat tcaatgagca gtaagacatg   1080
caagcattta ctggaaagca cttgggtcat atcatatgca caaccaaagg agctttgcgc   1140
gtgatatcat ggaagaatcg gataggatta acaaatataa acatggtagt gtaaaactgt   1200
tctaaccaaa caaatagtaa tggtatgctt gtgcattctg ccttcatcct tttctatttc   1260
cttctaagtt atttatttaa taggatgtta aatatctttt ggggttttaa agagtatcct   1320
cagcagctgc tctctgtttt accttttctt tttctttagc acaccacatg catattcatg   1380
acaaagtgtt tttaaaactt ggcaaacact tcaagaatag gagataaaat tggggaaaga   1440
gtgtgagtgc cccacgtgct gtctgttgac ttcacctgca cttctgccat aagaaccatc   1500
aacaagaaac atgacaatac tacgacatgg cctgagtgag agatatccgc catcatttac   1560
aaacatacat cactcctaag gcttcctttc ctaagcaata gacccaaaaa ccaaattctt   1620
ctcttaatca atcagtgagc ctccaaaagt acagtaaaag aaagaaaatt aattgtcaag   1680
tgcattttag tagcataggc tcattattta ctaatgattt ctgccgtatg tcacagtggt   1740
aaatgatgac gaggctgtct gcctatgtaa gaacacttta caagtctcac atagtgtatc   1800
tccccacagg aactgtcaag gaatttggta tgaagtgcaa ccctcctccc ccacaggggc   1860
ttaaactgag caaatatatc ctggtatatg tgtaactata tgctgaaatt tgttcaaatg   1920
gtatgatcta gtctttgcaa aaccaaataa aacttatttt ctgtaaattt taagagcttt   1980
ggaaggttcc ataatgtaac cttattgaaa ttcattttgt tagagcaggt atagaaaaca   2040
gtacagaaaa gcataccagt catcatcaca ttgtattcca ctaaataaat acttaaacct   2100
tatttgcagt gtctgtagtg atttttaaaa gtgtagaaaa atactatttg ttctaaatac   2160
tttaagtgat aactataaaa ttatactgat actgcagttt tatcttaata tttcttgttt   2220
tgaaaaggtc tgtttatttt tattatttga cacagtattt tggtacaaag gaaagactta   2280
ctaaatgtgt ctttttacta aagtttaagc tctagaaagt ctggtgtttt atcatcttct   2340
ctaataactt aattgtgtcg atgcttaacc agcacttcca gttaatctgt tattgaaaaa   2400
ttagctttat tgagaaattt tcccataaag taattccatt aaagatcata tttttctcat   2460
tccttaaaaa agttgggatt tcaaaggaaa tgcatttgag gcagaatgtt ttggcttatg   2520
ataaacttgc attttatggt acttggcttc caagttgctt tttgacaaat gggattctaa   2580
aaatgtttaa ttttgtggtt ggaatctgta tgttgaaatt tcattggtaa ctgagtctga   2640
acgctatact gtaatgcatt cctatgagaa ctagattatc tttgttgttt tattttaaaa   2700
taataattgc acctgacaca tgaacatgga ccacccgcaa ccaaaattaa atgtttggtg   2760
agacaaatac agtattagat gaccatggta acagcacata gggtgcacac tggattcgta   2820
tttcacatag ccattcagat taccaagaga ctgtgtgtaa acagtcatca tcctagtact   2880
caaaacactg aaacagcttc tagcaaaatg tatcaaagct tgcagaagcc aaaaatagaa   2940
aacatctcct ttacctctcc cctgtctcac ccccagaata aacacatgga cagaaaaaaa   3000
gatagaaaca gtttagtaaa gagtaattag attctcctgc atttaaaatg gcatctttgc   3060
```

-continued

```
ttgatattga gatagaaatc tggtcccccc cttgcagctg gattgtgcta ctgaaggaaa   3120

agcagctccg gtcctgaatg gttttttgtt ttttgttttt tgtttttaaa tcatgatttt   3180

ggtagctctg cctctgtagg aagtgtgagc cctggctaca atgtcagggt gcatcagcca   3240

caaatgtgta tccatctgaa tgttgatttc aaggagactc ctcataaaga tatagattcc   3300

ctccctcctc ctacctccca aaaggctgaa cagtgtatag tatgttacat ttgaataaat   3360

caataaaaat actgggtaaa gaaa                                          3384


<210> SEQ ID NO 62
<211> LENGTH: 20
<212> TYPE: DNA
<213> ORGANISM: Unknown
<220> FEATURE:
<223> OTHER INFORMATION: Description of Unknown:
      TP63 target seqeunce

<400> SEQUENCE: 62

tgcgcgtggt ctgtgttata                                                  20


<210> SEQ ID NO 63
<211> LENGTH: 20
<212> TYPE: DNA
<213> ORGANISM: Unknown
<220> FEATURE:
<223> OTHER INFORMATION: Description of Unknown:
      Target sequence

<400> SEQUENCE: 63

accattaaag aaaatatcat                                                  20
```

GENERATION OF AIRWAY BASAL STEM CELLS FROM HUMAN PLURIPOTENT STEM CELLS

CROSS REFERENCE TO RELATED APPLICATIONS

This application claims under 35 U.S.C. 119(e) claims the benefit of U.S. Provisional Patent Application Ser. No: 62/978,514 filed on Feb. 19, 2020, the contents of which are incorporated herein by reference in their entirety.

GOVERNMENT SUPPORT

This invention was made with Government Support under Contract No. HL139799 and HL139876 awarded by the National Institutes of Health. The Government has certain rights in the invention.

SUPPORT

Work on this invention was supported by awards from Cystic Fibrosis Foundation Therapeutics.

SEQUENCE LISTING

The instant application contains a Sequence Listing which has been submitted electronically in ASCII format and is hereby incorporated by reference in its entirety. Said ASCII copy, created on Feb. 19, 2021, is named 701586-097050USPT_SL.txt and is 210,302 bytes in size.

FIELD OF THE INVENTION

The invention described herein relates to iPSC-derived airway basal stem cells, and personalized medicine for the treatment of pulmonary and respiratory diseases and assays comprising iPSC-derived airway basal stem cells.

BACKGROUND

The Center for Disease Control (CDC) reports that more than 6.2 million children in the United States, or about 8% of all American kids, have asthma. Induced pluripotent stem cells (iPSCs) offer unprecedented opportunities to advance the understanding and treatment of childhood diseases. Disease modelling using human patient derived and genetically modified respiratory cells will provide improved insight into the mechanisms of respiratory diseases, such as cystic fibrosis, asthma, and lung malformations. In particular, human airway basal cells in the trachea are mediators of airway epithelium regeneration in the adult human airway and promote normal mucus secretion and protection from lung injury and microorganisms. However, there is currently an unmet need for human-derived airway basal cells that adequately recapitulate the physiology and pathophysiology of the healthy and diseased epithelial barrier function of the native airway. Furthermore, there is also a great need for airway basal cells that can be used for a variety of applications in an unlimited capacity without the need for harsh cell isolation protocols and that can be maintained in culture long-term for a better understanding of the progression of respiratory diseases.

SUMMARY

The technology as described herein relates to methods of generating a population of engineered airway basal cells (BCs), their compositions and disease models thereof.

Primary human bronchial epithelial cells are essential human basal cells and methods are in use to access these cells from patients either via bronchoscopy or from explanted lungs. However, the ability to obtain and expand such cells ex vivo is needed. To date there are no protocols that generate a bone-fide basal cell population, e.g., that includes the ability to selectively expand these cells. The methods described herein provide the ability to generate patient-specific basal cells and airway epithelium from PSCs, something which is no possible with prior art methods.

Described herein is the generation of a tissue-specific stem cells from PSCs and those properties of self-renewal and multi-lineage differentiation; thereby increasing the net yield of cells, the applicability of these cells to disease modeling, and the ability to cryopreserve cells as a ready to go product that overcomes the lengthy, complicated PSC protocols.

In one aspect of any of the embodiments, described herein is a method comprising:

(a) culturing a population of Nkx2-$1^+$ lung progenitor cells in a first culture medium, wherein the first culture medium comprises, or the Nkx2-$1^+$ lung progenitor cells are contacted with, one or more of: at least one Wnt agonist; at least one retinoic acid or a derivative thereof; and at least one bone morphogenic protein (BMP) agonist;

(b) re-suspending the Nkx2-$1^+$ lung progenitor cells in a hydrogel to form epithelial spheres;

(c) culturing the epithelial spheres in a second culture medium, wherein the second culture medium comprises, or the epithelial spheres are contacted with one or more of: at least one fibroblast growth factor (FGF) agonist; at least one steroid; 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells; and (d) passaging and re-suspending the airway progenitor cells in the second culture medium, thereby expanding the airway progenitor cells.

In some embodiments of any of the aspects, the method further comprises culturing the airway progenitor cells from step (d) in a third culture medium, wherein the third culture medium comprises, or the airway progenitor cells from step (d) are contacted with one or more of: at least one inhibitor of SMAD; at least one inhibitor of transforming growth factor β (TGF-β); at least one bone morphogenetic protein (BMP) inhibitor; and at least one ROCK inhibitor; thereby differentiating the airway progenitor cells into airway basal cells (BCs).

In one aspect of any of the embodiments, one or more of the 3-dimensional culturing steps, e.g., the resuspension steps can be omitted. Accordingly, described herein is a method comprising:

In one aspect of any of the embodiments, described herein is a method comprising:

(a) culturing a population of Nkx2-$1^+$ lung progenitor cells in a first culture medium, wherein the first culture medium comprises, or the Nkx2-$1^+$ lung progenitor cells are contacted with, one or more of: at least one Wnt agonist; at least one retinoic acid or a derivative thereof; and at least one bone morphogenic protein (BMP) agonist;

(b) optionally re-suspending the Nkx2-$1^+$ lung progenitor cells in a hydrogel to form epithelial spheres;

(c) culturing the epithelial spheres in a second culture medium, wherein the second culture medium comprises, or the epithelial spheres are contacted with one or more of: at least one fibroblast growth factor (FGF) agonist; at least one steroid; 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells; and (d) passaging and optionally re-suspending the airway progenitor cells in the second culture medium, thereby expanding the airway progenitor cells.

In some embodiments of any of the aspects, the method further comprises culturing the airway progenitor cells from step (d) in a third culture medium, wherein the third culture medium comprises, or the airway progenitor cells from step (d) are contacted with one or more of: at least one inhibitor of SMAD; at least one inhibitor of transforming growth factor β (TGF-β); at least one bone morphogenetic protein (BMP) inhibitor; and at least one ROCK inhibitor; thereby differentiating the airway progenitor cells into airway basal cells (BCs).

In some embodiments of any of the aspects, the Nkx2-1$^+$ lung progenitor cells are generated by a method comprising:

(a) culturing a population of stem cells in a serum-free medium;

(b) culturing the population of stem cells in a culture medium wherein the culture medium comprises or the stem cells are contacted with, a Wnt agonist or a Wnt polypeptide;

(c) culturing the population of stem cells in a culture medium wherein the culture medium comprises or the stem cells are contacted with, a bone morphogenic protein (BMP) and a Wnt agonist, thereby inducing the differentiation of the stem cells into a population of lung progenitor cells; and (d) sorting and/or isolating a population of Nkx2-1$^+$ lung progenitor cells from the population of lung progenitor cells generated in (c).

In some embodiments of any of the aspects, the airway basal cells (BCs) generated in step (d) express one or more markers selected from the group consisting of: Nkx2-1; tumor protein 63 (TP63); cytoskeletal protein keratin 5 (KRT5); and nerve growth factor receptor (NGFR). In some embodiments of any of the aspects, the method further comprises a step of sorting and/or isolating airway BCs that express one or more markers selected from the group consisting of: Nkx2-1; tumor protein 63 (TP63); cytoskeletal protein keratin 5 (KRT5); and nerve growth factor receptor (NGFR).

In some embodiments of any of the aspects, the Nkx2-1$^+$ lung progenitor cells are genetically modified.

In some embodiments of any of the aspects, the hydrogel comprises one or more extracellular matrix components. In some embodiments of any of the aspects, the hydrogel comprises an extracellular matrix composition comprising a gelatinous protein mixture secreted by Engelbreth-Holm-Swarm (EHS) mouse sarcoma cells (MATRIGEL™).

In some embodiments of any of the aspects, the Wnt agonist is an inhibitor of GSK-3. In some embodiments of any of the aspects, the Wnt agonist is CHIR 99021. In some embodiments of any of the aspects, the BMP is BMP4. In some embodiments of any of the aspects, the fibroblast growth factors are FGF2 and FGF10. In some embodiments of any of the aspects, the ROCK inhibitor is Y-27632 (Y).

In some embodiments of any of the aspects, the first culture medium comprises CHIR99021, retinoic acid, and BMP4, or the cells in the first culture medium are contacted with CHIR99021, retinoic acid, and BMP4.

In some embodiments of any of the aspects, the second culture medium comprises FGF2, FGF10, dexamethasone, IBMX, 3',5'-cyclic monophosphate sodium salt, and Y-27632; or the cells in the second culture medium are contacted with FGF2, FGF10, dexamethasone, IBMX, 3',5'-cyclic monophosphate sodium salt, and Y-27632.

In some embodiments of any of the aspects, the cells in steps (b) and/or (d) are cultured in a 3-dimensional microenvironment.

In some embodiments of any of the aspects, the airway BCs are differentiated from induced pluripotent stem cells or embryonic stem cells. In some embodiments of any of the aspects, the airway BCs are differentiated from human induced pluripotent stem cells.

In some embodiments of any of the aspects, the third culture medium comprises A83-01 and DMH1; or the cells in the third culture medium are contacted with A83-01 and DMH1. In some embodiments of any of the aspects, the third culture medium comprises bronchial epithelial growth medium, A83-01, and DMH1.

In some embodiments of any of the aspects, the inhibitor of SMAD is A83-01. In some embodiments of any of the aspects, the inhibitor of transforming growth factor β (TGF-β) is selected from the group consisting of: ALK5 inhibitor II, SB431542, LY364947, and A83-01. In some embodiments of any of the aspects, the inhibitor of BMP is selected from the group consisting of: dorsomorphin or DMH1.

In one aspect of any of the embodiments, described herein is a method of generating a population of engineered airway basal cells (BCs), the method comprising:

(a) culturing a population of Nkx2-1+ lung progenitor cells in a first culture medium, wherein the first culture medium comprises, or the lung progenitor cells are contacted with, one or more of: at least one Wnt agonist; at least oneretinoic acid or a derivative thereof; and at least one bone morphogenic protein (BMP) agonist;

(b) re-suspending the Nkx2-1+ lung progenitor cells in a hydrogel to form epithelial spheres;

(c) culturing the epithelial spheres in a second culture medium, wherein the second culture medium comprises, or the epithelial spheres are contacted with, one or more of: at least one fibroblast growth factor (FGF) polypeptide; at least one steroid; and at least one Rho kinase (ROCK) inhibitor, thereby differentiating the epithelial spheres into airway progenitor cells;

(d) passaging and re-suspending the airway progenitor cells in the second culture medium; and (e) culturing the airway progenitor cells from step (d) in a third culture medium, wherein the third culture medium comprises, or the airway progenitor cells are contacted with, one or more of: at least one inhibitor of SMAD; at least one inhibitor of transforming growth factor β (TGF-β); at least one bone morphogenetic protein (BMP) inhibitor; and at least one ROCK inhibitor thereby differentiating the airway progenitor cells into airway basal cells (BCs). In some embodiments of any of the aspects, the inhibitor of SMAD is A83-01. In some embodiments of any of the aspects, the inhibitor of transforming growth factor β (TGF-β) is selected from the group consisting of: ALK5 inhibitor II, SB431542, LY364947, DMH1, and A83-01. In some embodiments of any of the aspects, the inhibitor of BMP is selected from the group consisting of: dorsomorphin or DMH1.

In some embodiments of any of the aspects, the cells are cultured for a time period of at least 24 hours or more, at least 36 hours or more, at least 48 hours or more, or at least 72 hours or more in each of the cell culture media.

In some embodiments of any of the aspects, the method further comprises, during or following step (d), sorting the population of Nkx2-1+ lung progenitor cells for F3+/EGFR+ lung/airway progenitor cells.

In some embodiments of any of the aspects, the method further comprises a step of cryopreserving the airway BCs.

In some embodiments of any of the aspects, the stem cells are human induced pluripotent stem cells or human embryonic stem cells. In some embodiments of any of the aspects, the stem cells are derived from a healthy subject. In some embodiments of any of the aspects, the stem cells are derived from a subject with a pulmonary disease. In some embodiments of any of the aspects, the pulmonary disease is selected from the group consisting of: asthma, cystic fibrosis, primary ciliary dyskinesia, interstitial lung disease, and genetic lung malformations.

In some embodiments of any of the aspects, the lung epithelial progenitor cells are genetically modified. In some embodiments of any of the aspects, the genetically modified lung epithelial progenitor cells comprise a nucleic acid encoding at least one airway BC marker operably linked to a promoter. In some embodiments of any of the aspects, the BC marker is one or more of the BC markers selected from the group consisting of: Nkx2-1; TP63; KRT5; and/or NGFR. In some embodiments of any of the aspects, the nucleic acid further comprises a reporter gene.

In one aspect of any of the embodiments, provided herein is an airway basal cell or cell line generated by the method described herein. In some embodiments of any of the aspects, the airway basal cell line is cryopreserved.

In one aspect of any of the embodiments, provided herein is a disease model comprising a cell or cell line described herein. In some embodiments of any of the aspects, the airway basal cell (line) is genetically modified. In some embodiments of any of the aspects, the airway basal cell (line) is derived from a subject with a pulmonary disease. In some embodiments of any of the aspects, the pulmonary disease is selected from the group consisting of: asthma, cystic fibrosis, primary ciliary dyskinesia interstitial lung disease, and genetic lung malformations.

In one aspect of any of the embodiments, described herein is a transplant composition comprising the airway basal cell (line) described herein. In some embodiments of any of the aspects, the composition further comprises a pharmaceutically acceptable carrier. In some embodiments of any of the aspects, the composition further comprises a scaffold.

In one aspect of any of the embodiments, described herein is a nucleic acid comprising:

(a) a promoter;

(b) one or more basal cell markers selected from Nkx2-1; TP63; KRT5; and NGFR; and (c) at least one reporter gene.

In some embodiments of any of the aspects, the basal cell marker is TP63. In some embodiments of any of the aspects, the reporter gene is green fluorescent protein (GFP) or tdTomato. In one aspect of any of the embodiments, described herein is a cell comprising the foregoing nucleic acid.

In one aspect of any of the embodiments, described herein is a method of treating a subject with a pulmonary disease, the method comprising: administering to the trachea of the subject the transplant composition described herein. In some embodiments of any of the aspects, the pulmonary disease is selected from the group consisting of: asthma, cystic fibrosis, primary ciliary dyskinesia interstitial lung disease, and genetic lung malformations. In some embodiments of any of the aspects, the transplant composition is an autologous transplant composition. In some embodiments of any of the aspects, the transplant composition is an allogenic transplant composition.

A BRIEF DESCRIPTION OF THE DRAWINGS

FIGS. 1A-1H show generation of a Dual-Fluorescent NKX2-1GFP; TP63tdTomato iPSC Reporter to Track and Purify Putative Basal Cells. FIG. 1A shows adult human airway immunolabeled with the antibodies indicated (DNA stained with Hoechst; scale bar represents 10 μm). FIG. 1B shows a schematic of gene-editing strategy to insert tdTomato sequence into one allele of the TP63 locus of NKX2-1GFP iPSCs. See FIG. 8 for further details. FIG. 1C shows a schematic of airway-directed differentiation protocol. FIG. 1D shows a representative image of BU3 NGPT spheroid on day 36 of differentiation demonstrating GFP and tdTomato fluorescence (scale bar represents 50 μm). FIG. 1E shows representative flow cytometry plots of NKX2-1GFP versus TP63tdTomato expression on days 0, 15, and 35 of directed differentiation. FIG. 1F shows the quantification of the percentage of cells (mean±SD), calculated by flow cytometry, co-expressing NKX2-1GFP and TP63tdTomato between days 15 and 16 and 40-42 of differentiation (n=6). FIG. 1G shows qRT-PCR quantification of TP63 mRNA levels ($2^{-DDCt}$) in GFP+/TOM+, GFP−/TOM−, and GFP+/TOM− populations sorted by fluorescence-activated cell sorting (FACS) compared to presort levels on day 36 of directed differentiation (*p<0.05). FIG. 1H shows immunolabeling of BU3 NGPT with antibodies against TP63 and RFP on day 30 of directed differentiation. The cells remained in 2D culture from day 15 to facilitate antibody labeling (DNA stained with DAPI; scale bar represents 50 μm).

FIGS. 2A-2H demonstrate that NKX2-1GFP+/TP63tdTomato+ Cells Adopt a Molecular Signature Similar to Primary Basal Cells. FIG. 2A shows schematic of experiment: GFP+/TOM+-sorted cells were suspended in 3D Matrigel between days 30-35 of differentiation in FGF2+FGF10+DCI+Y or primary BC media. After 12-14 days, morphology and tdTomato fluorescence were assessed (left panel) and the expression of NKX2-1GFP, TP63tdTomato, and NGFR quantified by flow cytometry (middle and right panel, representative plots). See FIG. 9 for additional details. FIG. 2B shows kinetics of NGFR induction, quantified by flow cytometry in response to primary BC medium compared to continued FGF2+FGF10+DCI+Y over 8 days between days 33-41 (n=3). FIG. 2C shows NGFR protein immunostaining of BU3 NGPT cells in primary BC medium compared to TP63tdTomato fluorescence (scale bar represents 20 μm).

FIG. 2D shows Percentage of NGFR+ cells (mean±SD) quantified by flow cytometry between days 40-50 (n=12) (**p<0.0001). FIG. 2E shows scRNA-seq of day 46 cells from BC or FGF2+FGF10+DCI+Y media. UMAP (left panel) displays the distribution based on culture conditions used to treat cells. Louvain clustering (res=0.25) identifies 6 clusters (1-6). FIG. 2F shows UMAP of canonical BC (TP63, NGFR, and KRT5) and SC (SCGB3A2) markers. FIG. 2G shows UMAP of the expression of BC signature (left) and graph of BC gene signature enrichment score ("basal"=0.84±0.24; "proliferative TP63+"=0.52±0.24; "secretory"=0.51±0.18 "TP63+/NGFR−"=0.51±0.15; "SCGB3A2+"=0.32±0.15; mean enrichment score±SD). See also FIGS. 10-11. FIG. 2H** shows heatmap showing all calculated pairwise PCCs between freshly isolated primary human airway cells (without culturing) and all iPSC-derived cells on day 46 grown in either FGF2+FGF10+DCI+Y or BC medium. Ten fetal and adult primary airway epithelial cell types are shown. The best fit annotations represent the epithelial cell type with the highest PCCs for each iBC in each cultured sample.

FIGS. 3A-3I demonstrate that iBCs Undergo Self-Renewal and Multi-Lineage Differentiation. FIG. 3A shows a schematic of the experiment: GFP+/TOM+ cells sorted on approximately day 40 of differentiation expanded in BC medium and then characterized in terms of self-renewal and multi-lineage differentiation in ALI. FIG. 3B shows representative flow cytometry plots of NKX2-1GFP versus TP63tdTomato expression in cells at passage 7, following expansion in 3D culture with BC medium (left panel). Per input sorted GFP+/Tom+ cell on day 45, the yield up to 123 days of directed differentiation was calculated (right panel). FIG. 3C shows immunolabeling of representative spheroid on day 83 of differentiation in either BC medium (left and middle panel) or after 10 days in ALI differentiation medium (right panel) with antibodies indicated (DNA stained with Hoechst; scale bar represents 50 tm). See also FIG. 12. FIG. 3D-3E show GFP+/TOM+ cells were expanded in BC medium until day 46 and plated on transwells with (FIG. 3E) or without (FIG. 3D) GFP/TOM/NGFR sorting. Representative images of the endogenous TP63tdTomato fluorescence during culture of BU3 NGPT-derived ALI are shown. Stitched image of whole transwell insert (Ø=6.5 μm; 1st column) and zoom in (2nd column) is shown. Immunolabeling with antibodies indicated after 16 days of ALI culture is shown (3rd and 4th columns; DNA stained with DRAQ5; scale bar represents 100 μm). FIG. 3F shows confocal microscopy of BU3 NGPT-derived ALI cultures shown in (FIG. 3E) and immunolabeled with antibodies indicated (DNA stained with DRAQ5; scale bar represents 100 μm). FIG. 3G shows transverse section of BU3 NGPT-derived ALI cultures shown in (FIG. 3E) and stained with hematoxylin and eosin or antibodies indicated (DNA stained with DAPI; scale bar represents 100 μm). FIG. 3H shows TEER measurements (mean±SD) of Transwell ALI cultures, comparing GFP+/TOM+ from FGF2+10+DCI+Y (n=5), BC medium with (n=4) or without (n=5) NGFR sorting, and primary HBEC controls (n=21). FIG. 3I shows TP63tdTomato fluorescence in BU3 NGPT iBCs after cryopreservation and thaw (scale bar represents 200 tm; left panel). Immunolabeling of ALI cultures generated from cryopreserved iBCs with antibodies indicated is shown (scale bar represents 100 μm).

FIGS. 4A-4F show. scRNA-Seq Profiling of iBCs and Their Differentiated Progeny. FIG. 4A shows a schematic of scRNA-seq experiment and UMAP with Louvain clustering (clusters 1-6) of iBC-derived ALI. See also FIG. 11 and FIG. 14. FIG. 4B shows the top 20 differentially expressed genes (DEGs) per cluster. FIG. 4C shows UMAPs of primary BC, SC, and MCC gene signatures applied to iBC-derived ALI (upper row). FIG. 4D shows Violin plots of the enrichment score of clusters 1-6 for BC, SC, and MCC gene signatures (lower panel). FIG. 4E shows UMAPs of the canonical BC, SC, and MCC markers across clusters 1-6. Violin gene expression plots of same panel of markers are shown in (FIG. 4D). FIG. 4F shows qRT-PCR validation of key airway markers in iBC-derived ALI (iBC-ALI) compared to primary HBEC-derived ALI (HBEC-ALI) in PneumaCult ALI medium. Fold change is 2-DDCt normalized to undifferentiated iPSCs (*p<0.05; **p<0.01, error bars represent mean±SD).

FIGS. 5A-5C show that iBCs Establish Pseudostratified, Well-Differentiated Airway Epithelium in Vivo in Tracheal Xenografts. FIG. 5A shows a schematic of experimental procedure used to generate tracheal xenografts. FIG. 5B shows a magnified image (left panel; scale bar represents 50 μm) of xenograft epithelium established from BU3 NGPT iBCs stained with hematoxylin and eosin; the location of this region within the transverse section of the xenograft is shown in the right panel. White arrows indicate examples of MCCs. FIG. 5C shows immunolabeling of the xenograft epithelium with the indicated antibodies. Anti-GFP and anti-RFP antibodies were used to detect the expression of each fluorochrome reporter that had been targeted to the donor human cell loci, NKX2-1GFP, and TP63tdTomato, respectively. DAPI staining indicates DNA (scale bar represents 50 μm).

FIGS. 6A-6G demonstrate a Surface Marker Strategy for Purifying iBCs Using NGFR Replaces the Need for Fluorescent Reporters. FIG. 6A shows a schematic of NKX2-1GFP/TP63tdTomato reporter versus surface marker iBC protocols. FIG. 6B shows representative flow cytometry plots of BU3 NGPT iBCs on day 40 of differentiation and labeled with antibodies against NGFR and EpCAM. Arrow indicates sorted NGFR+/EpCAM+ cells are 94.5% GFP+/TOM+. Enrichment is quantified (mean±SD) in the right panel (n=3). FIG. 6C shows representative images of the endogenous TP63tdTomato fluorescence in whole Transwell filters (Ø=6.5 μm) seeded with sorted (NGFR+/EpCAM+) or unsorted cells during submerged culture and after ALI culture. FIG. 6D shows a representative flow cytometry plot of a non-reporter iPSC line (DD001m) stained for NGFR. FIG. 6E shows a representative image of sorted NGFR+ cells plated on transwell filters and after 7 days immunolabeled with an anti-TP63 antibody (DNA stained with Hoechst; scale bar represents 100 μm). FIG. 6F shows confocal microscopy of DD001m iPSC-derived ALI cultures immunolabeled with antibodies indicated (scale bar represents 200 μm). FIG. 6G depicts a representative image of RUES2 ESC-derived ALI immunolabeled with an anti-ACT antibody (DNA stained with DRAQ5; scale bar represents 200 μm; upper left) and confocal microscopy of it immunolabeled with antibodies indicated (DNA stained with DRAQ5; scale bar represents 100 μm).

FIGS. 7A-7I show that iBCs enable in vitro modeling of acquired and genetic respiratory diseases. FIG. 7A shows representative images of BU3 NGPT iBC-derived ALI cultures, with or without IL-13 treatment, immunolabeled with antibodies indicated (DNA stained with Hoechst; scale bar represents 200 μm). FIG. 7B shows quantification of the number of MUC5AC+ cells (mean±SD) per high power field for IL-13-treated versus untreated wells (n=3) (**p<0.01). FIG. 7C shows qRT-PCR quantification of mRNA expression levels of MUC5AC, SPDEF, and MUC5B in IL-13 treated (+IL-13) versus untreated cells (no IL-13; n=3). Data are preselected as fold change over untreated iBC-derived ALI cultures (*p<0.05; p<0.01; *p<0.001). Error bars represent mean±SD. FIG. 7D shows a schematic of CF and PCD disease-modeling experiments, relying on surface markers. See also FIG. 14. FIGS. 7E-7F show representative electrophysiological traces from Ussing chamber analysis of ALI cultures generated from CF iPSCs and corrected CF iPSCs (con CF) (FIG. 7E). Mean and SD of electrophysiological values from (FIG. 7F) (n=3). FIG. 7G shows immunolabeling of MCCs in ALI cultures generated from DNAH5 mutant nasal epithelial cells, iPSCs, non-diseased primary HBECs, and BU3 NGPT iPSCs with antibodies indicated (DNA stained with DAPI; scale bar represents 10 μm). Transmission electron microscopy of cilia is shown (right column). FIGS. 7H-7I shows the number of outer dynein arms detected in cross sections of cilia (H, mean±SD) or ciliary beat frequency (I, mean±SEM) from the samples detailed in (FIG. 7G) (***p<0.001).

FIGS. 8A-8E show the characterization of the BU3 NKX2-1GFP; TP63tdTomato iPSC line. FIG. 8A shows a schematic of targeting strategy to introduce a 2A-tdTomato cassette at a double-stranded break site within exon 4 of one allele of TP63. The donor vector includes a floxed PGK promoter-driven antibiotic selection cassette (puroTK, consisting of a fused Puro resistance-thymidine kinase [TK] cassette) which is excised following transient Cre recombinase exposure. Negative selection was performed by adding ganciclovir to kill clones without successful PuroR-TK cassette excision. FIG. 8B shows TP63 locus targeting screening by inside-outside PCR of gDNA from iPSCs. FIG. 8C shows karyotyping of BU3 iPSC line with successful monoallelic integration of the 2A-tdTomato cassette (clone 5) and after Cre-mediated excision of the antibiotic selection cassette (clone 22, abbreviated as "c5-cre22"). Normal 46,XY karyotype is shown. FIG. 8D shows immunolabeling of BU3 NGPT c5-cre22 iPSCs for pluripotency markers (NANOG, SSEA4, SOX2, OCT4 and TRA1-81) and DAPI to counterstain nuclei (scale bar=100 μm). Phase microscopy of a representative BU3 NGPT iPSC colony (scale bar=400 μm). FIG. 8E shows immunolabeling of BU3 NGPT iPSCs for classic endoderm (SOX17), primitive streak (Brachyury) and ectodermal markers (TUJ1, NESTIN). Nuclei are stained with DAPI. Scale bar=100 μm.

FIGS. 9A-9G show assessment of the differentiation capacity and NGFR expression of NKX2-1GFP+; TP63tdTomato+ cells in FGF2+FGF10+DCI+Y medium. FIG. 9A shows representative images of ALI cultures generated from sorted GFP+/TOM+ cells (day 40-42) in FGF2+10+DCI+Y medium immunolabelled with antibodies against ACT and MUC5AC and with nuclear labelling using Hoechst (upper panel). Merge images iPSC-derived ALI compared to primary HBEC-derived ALI (lower panel). Scale bars=100 μm. FIG. 9B shows TEER of iPSC-derived ALI (n=4) from (FIG. 9A) compared to HBEC-derived ALI (n=4). (****=p<0.0001). FIG. 9C shows schematic of experiment. GFP+/TOM+ cells were sorted on day 30 of differentiation and cultured in FGF2+10+DCI+Y medium until day 53. FIG. 9D shows representative flow cytometry plots from the experiment depicted in (FIG. 9C) analyzing the expression of GFP, tdTomato and NGFR on days 30, 41 and 53. FIG. 9E shows the quantification of the percent GFP+/TOM+ cells on days 41 (87.0±1.5, mean±SD, n=3) and 53 (73.8±0.7) of the experiment summarized in (C) and the frequency of NGFR+ cells within GFP+/TOM+ population (days 41=0.8±0.3 and day 53=8.0±3.3). On day 35 of differentiation (see FIG. 2A schematic) GFP+/TOM+ cells were sorted and plated in continued FGF2+10+DCI+Y medium, PneumaCult-EX medium supplemented with Y-27632 (Pn-Ex+Y), PneumaCult-EX medium supplemented with A83-01, DMH-1, and Y-27632 (Pn-Ex+SMADi+Y), or PneumaCult-EX Plus medium supplemented with A83-01, DMH-1, and Y-27632 (Pn-Ex Plus+SMADi+Y) until day 50. FIG. 9F shows representative flow cytometry plots of GFP and tdTomato expression are shown. FIG. 9G shows NGFR+ cell on day 50 per input cell GFP+/TOM+ cell on day 35 of differentiation in PneumaCult-EX medium supplemented with A83-01, DMH-1, and Y-27632 (Pn-Ex), or PneumaCult-EX Plus medium supplemented with A83-01, DMH-1, and Y-27632 (Pn-Ex Plus).

FIGS. 10A-10E show Sc-RNA-Seq analysis of airway epithelial organoids in FGF2+FGF10+DCI+Y or BC media. FIG. 10A shows ScRNA-Seq of day 45 cells from primary BC or FGF2+FGF10+DCI+Y media (identical to FIG. 2E). UMAP (left panel) displays the culture conditions used to treat cells. Louvain clustering (res=0.25) identifies 6 clusters (1-6). See also FIGS. 2E-2H. FIG. 10B shows UMAPs of key markers used to classify the identity of cell clusters including proliferation (TOP2A and MKI67), secretory (SCGB1A1) and multiciliated (FOXJ1) cells and non-lung endoderm (ALB and AFP). FIG. 10C shows a gene-expression heatmap of the top 20 DEGs across clusters 1-6. Selected canonical lineage and proliferation markers for each cluster are highlighted. FIG. 10D shows UMAPs of the expression pattern of additional basal cell markers and tdTomato. See also FIG. 2F. FIG. 10E shows gene expression violin plots of additional secretory and basal markers across clusters 1-6.

FIGS. 11A-11D show Sc-RNA-Seq of primary HBECs and their differentiated progeny. FIG. 11A shows a schematic of scRNA-Seq experiment profiling P0 primary HBECs (DD001m) in BEGM medium and after 20 days of differentiation into a mucociliary epithelium in ALI culture. These data were used to generate the gene-signatures for BC, SC, MCC and ionocytes (FIG. 15) applied to iBCs (FIG. 2) and iBC-derived ALI (FIG. 4). From this scRNA-Seq experiment we performed immunolabeling of DD001m HBEC cultures with antibodies against basal cell markers TP63 and KRT5 (scale bar=50 μm) and ALI cultures with antibodies against ACT and EpCAM (scale bar=100 μm). FIG. 11B shows UMAP of cells from P0 and ALI conditions after filtering out doublets and degraded cells. 3,943 cells from P0 HBECs and 3160 cells from ALI culture were analyzed. UMAPs labelled with original identity (left graph) and after Louvain clustering and annotation of clusters (right panel) are shown. FIG. 11C shows a gene-expression heatmap of the top 20 DEGs across 8 clusters. Select canonical lineage and proliferation markers for each cluster are highlighted. FIG. 11D shows UMAPs of the gene-expression of a panel of canonical markers of basal, secretory, immature multiciliated, multiciliated cells and ionocytes.

FIGS. 12A-12D shows expansion, cryopreservation and multi-lineage differentiation of iBCs. FIG. 12A showed representative images, phase (left) and fluorescence (right), of iBCs after 9 passages in 3D MATRIGEL culture. FIG. 12B shows a Normal karyotype (46, XY) of BU3 NGPT iPSC-derived iBCs on day 82 of directed differentiation. FIG. 12C shows representative images of 1000 cells/μl and 200 cell/μl concentrations from the limiting dilution assay used for plating density to allow clonal outgrowth of spheres (see FIG. 3C). iPSC-derived airway progenitors were infected with one of three lentiviral vectors designed to constitutively express either GFP, BFP or dsRed. Transduced cells were sorted, combined and replated in 3D MATRIGEL at a range of concentrations. The number of clonal and non-clonal spheres at each density was quantified (middle graph). Clonal spheres from iBCs cultured in ALI differentiation medium were immunolabelled with an antibody against ACT and nuclei labelled with Hoechst. The series are, in order, "dsRed only", GFP "only", "BFP only" and "Mixed". FIG. 12D shows ALI cultures from BU3 NGPT derived iBCs after 10 passages in 3D culture immunolabelled with antibodies against ACT and MUC5AC (nuclei stained with Hoechst; scale bar=100 μm).

FIGS. 13A-13B show Sc-RNA-Seq of iBC-derived ALI. FIG. 13A shows a UMAP of iBC-derived ALI with Louvain clustering (clusters 1-6) and annotation (identical to FIG. 4A). The expression of additional genes identified as highly differentially expressed genes within in FIG. 4B are presented. See also FIG. 4E. FIG. 13B shows UMAP and violin plots of the gene expression of cell cycle genes TOP2A and MKI67

FIGS. 14A-14E show the characterization of CF and PCD iPSCs and their airway epithelial derivatives. FIG. 14A shows G-band karyotyping of F508del iPSCs demonstrating a normal 46,XY karyotype. FIG. 14B shows G-band karyotyping of mutant DNAH5 iPSCs demonstrating a normal 46,XX karyotype. FIG. 14C shows characterization of mucociliary differentiation with antibodies against ACT and MUC5B in ALI cultures generated from F508del iPSCs (using the protocol summarized in FIG. 6A) in the experiments described in FIGS. 7B-7C. Nuclei stained with Hoechst. Scale bar=50 μm. FIG. 14D shows characterization of mucociliary differentiation with antibodies against ACT and MUC5AC in ALI cultures generated from DNAH5 mutant iPSCs in the experiments described in FIGS. 7D-G. Nuclei stained with Hoechst. Scale bar=100 μm. FIG. 14E shows immunolabeling of multiciliated cells from the samples detailed in FIG. 7D with antibodies against ACT and DNALI1 (nuclei stained with DAPI; scale bar=10 μm).

FIG. 15 shows a table of ranked gene expression signatures of the top 30 DEGs in human BCs, SCs, MCCs, and ionocytes based on scRNA-Seq profiling of primary P0 HBECs and after differentiation in ALI culture.

Figure 20A:
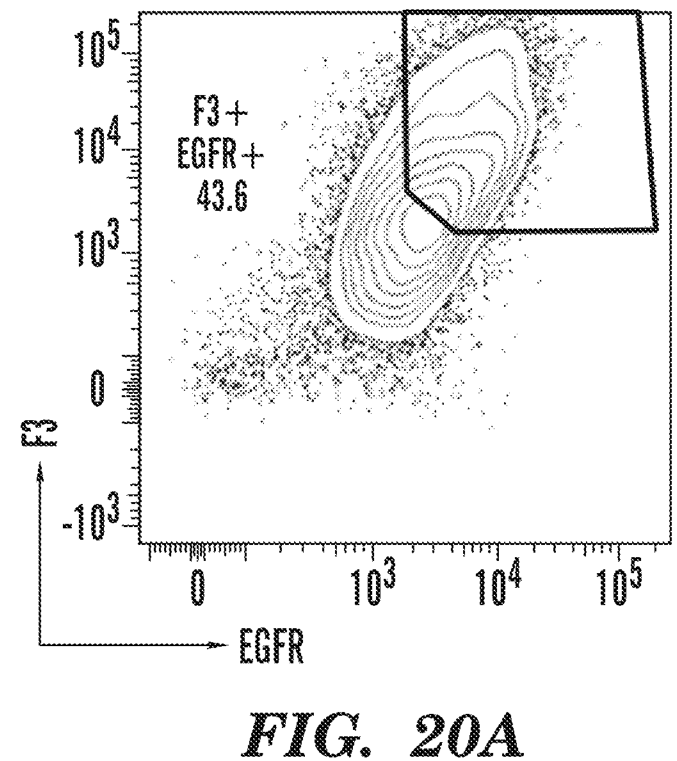
Figure 20B:
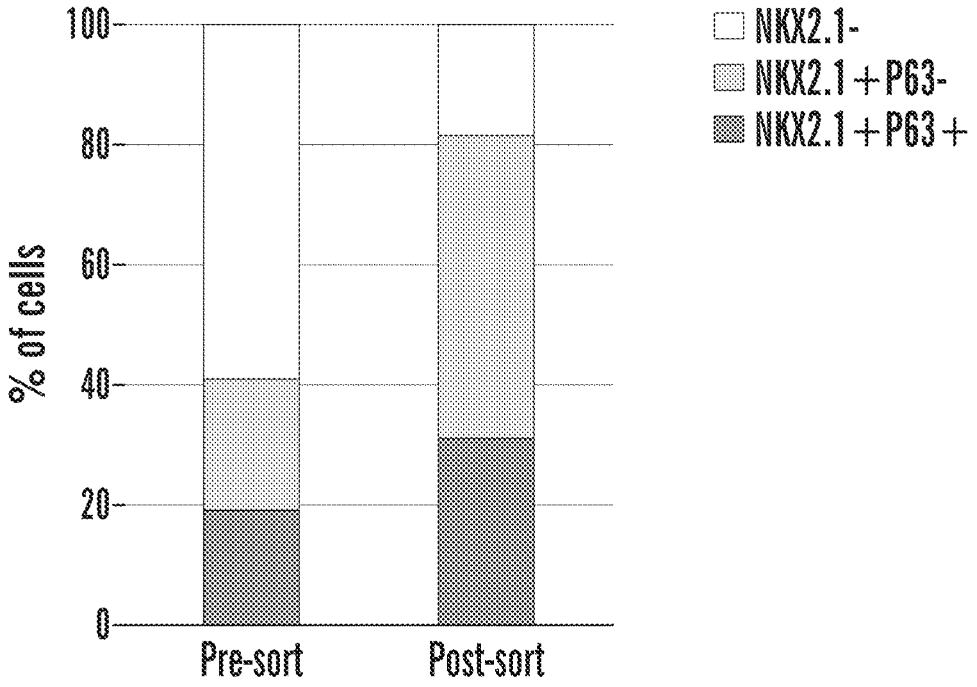
Figure 20C:
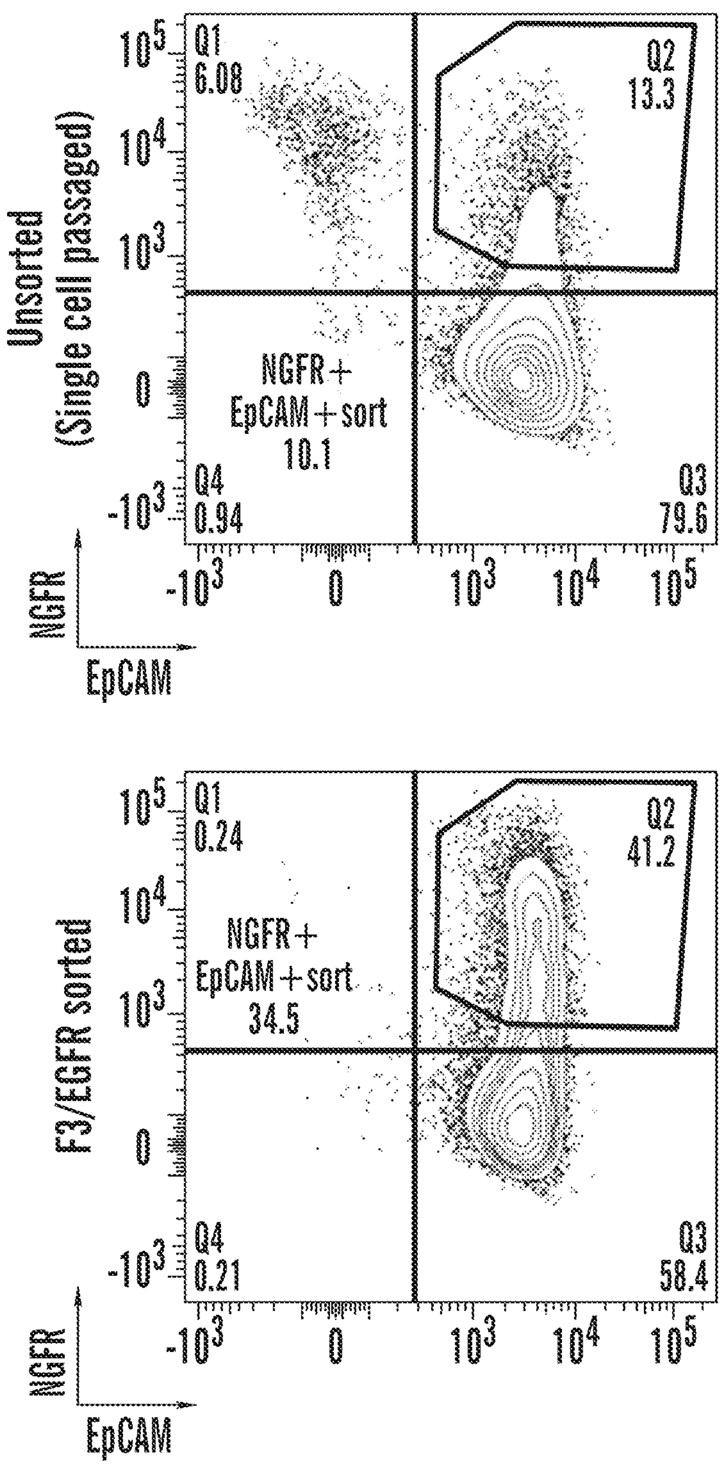

FIG. 20A-20C show that isolation of lung/airway progenitor cells in hPSC-derived airway epithelial organoids. FIG. 20A shows a representative plot of F3 and EGFR expression at ~Day 30 of airway differentiation protocol in a non-reporter cell line. Top right gate is used to sort F3 and EGFR-expressing population. FIG. 20B shows the % of NKX2.1 and TP63 positive cells on ~Day 30 in pre- and post-F3+EGFR+ sorting. The cell line shown poorly retains NKX2.1 expression on Day 30. By sorting F3 and EGFR expressing cells, we highly enrich the NKX2.1+ population and consequently remove the majority of undesired non-lung/airway lineage cells. FIG. 20C shows representative plots of NGFR and EpCAM expression on Day 40 of airway differentiation protocol in a non-reporter cell line. The top plot shows the NGFR and EpCAM expression in cells from B that were simply passaged on ~Day 30 and exposed to the Basal Cell medium (previously described methodology): the low % of NKX2.1+ and in particular of NKX2.1+TP63+ cells result in a poor induction of NGFR+EpCAM+ population representing the desired target cells, iBCs. The bottom plot shows the NGFR and EpCAM expression in cells from B that were sorted for F3+EGFR+ on Day 30 and exposed to the Basal Cell medium: the enrichment of NKX2.1+ and consequent higher % of NKX2.1+TP63+ cells result in a significantly higher induction of NGFR+EpCAM+ population.

DETAILED DESCRIPTION

The process of lung development in vivo is highly complex and relies on the precise coordination of epithelial-mesenchymal interactions, extracellular matrix (ECM) communications, as well as a myriad of multiple intricate pathways of epithelial-mesenchymal interactions controlled by a number of complex signaling cascades, including bone-morphogenic proteins (BMPs), fibroblast growth factors (FGFs), sonic hedgehog (SHH) and the wingless-type MMTV integration site family (MINT).

Basal cells (BCs) of the adult mouse and human airways are capable of self-renewal and multi-lineage differentiation in vivo and after culture expansion ex vivo, thereby fulfilling the definition of a tissue-specific adult stem cell. BCs are highly abundant in the pseudostratified epithelium extending from the trachea to the terminal bronchioles of the respiratory system. This is further described in detail e.g., by Rock et al., 2010, which is incorporated herein by reference in its entirety.

BCs can regenerate the airway epithelium by serving as precursors for essential specialized epithelial cell types, including secretory cells (SCs) and multiciliated cells (MCCs). These stem cell properties make BCs a highly desirable cell type to generate ex vivo for modeling airway diseases and a leading candidate for cell-based therapies designed to reconstitute the airway epithelium.

The technology described herein relates to methods of generating stem cell-derived airway basal cells (BCs), compositions, and disease models thereof.

Accordingly, the methods and compositions described herein are based on the discovery of an improved directed differentiation of human iPSCs via an NKX2-1+ lung progenitor intermediate into functional airway basal cells (BCs) in response to cyclical modulation of the canonical Wnt signaling pathway, formation of epithelial spheres, and cell sorting steps to produce highly enriched stem cell-derived airway BCs (also referred to herein as iBCs). In particular, the iBCs described herein recapitulate hallmark stem cell properties of primary basal stem cells, including self-renewal and multi-lineage differentiation, thus enabling modeling of airway diseases in vitro and repopulation of tracheal xenografts in vivo. Thus, the methods and compositions described herein are highly promising for the treatment of pulmonary diseases such as cystic fibrosis (CF), asthma, and others.

In one aspect, described herein is a method of generating a population of engineered airway basal cells (BCs).

In another aspect, described herein is a method of generating a population of engineered airway basal cells (BCs), the method comprising:

(a) culturing a population of Nkx2-1+ lung progenitor cells in a first culture medium, wherein the first culture medium comprises, or the Nkx2-1+ lung progenitor cells are contacted with, one or more of: at least one Wnt agonist; at least one retinoic acid or a derivative thereof; and at least one a bone morphogenic protein (BMP) agonist (e.g., a BMP polypeptide);

(b) re-suspending the Nkx2-1+ lung progenitor cells in an extracellular matrix composition to form epithelial spheres;

(c) culturing the epithelial spheres in a second culture medium, wherein the second culture medium comprises, or the epithelial spheres are contacted with, one or more of: at least one fibroblast growth factor (FGF) agonist (e.g., a FGF polypeptide); at least one steroid, 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells; and (d) passaging and re-suspending the airway progenitor cells in the second culture medium, thereby generating a population of engineered airway basal cells (BCs) and/or expanding the airway progenitor cells.

In another aspect, described herein is a method of generating a population of engineered airway basal cells (BCs), the method comprising:

(a) culturing a population of Nkx2-1+ lung progenitor cells in a first culture medium, wherein the first culture medium comprises, or the Nkx2-1+ lung progenitor cells are contacted with, one or more of: at least one Wnt agonist; at least one retinoic acid or a derivative thereof; and at least one a bone morphogenic protein (BMP) agonist (e.g., a BMP polypeptide);

(b) re-suspending the Nkx2-1+ lung progenitor cells in an extracellular matrix composition to form epithelial spheres;

(c) culturing the epithelial spheres in a second culture medium, wherein the second culture medium comprises, or the epithelial spheres are contacted with, one or more of: at least one fibroblast growth factor (FGF) agonist (e.g., a FGF polypeptide); at least one steroid, 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells; and (d) passaging and re-suspending the airway progenitor cells in a third culture medium, thereby generating a population of engineered airway basal cells (BCs) and/or expanding the airway progenitor cells.

In another aspect, described herein is a method of generating a population of engineered airway basal cells (BCs), the method comprising:

(a) culturing a population of Nkx2-1+ lung progenitor cells in a first culture medium, wherein the first culture medium comprises, or the lung progenitor cells are contacted with, one or more of: at least one Wnt agonist; at least one retinoic acid or a derivative thereof; and at least one a bone morphogenic protein (BMP) agonist (e.g., a BMP polypeptide);

(b) re-suspending the Nkx2-1+ lung progenitor cells in an extracellular matrix composition to form epithelial spheres;

(c) culturing the epithelial spheres in a second culture medium, wherein the second culture medium comprises, or the epithelial spheres are contacted with, one or more of: at least one fibroblast growth factor (FGF) agonist (e.g., a FGF polypeptide); at least one steroid, 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells;

(d) passaging and re-suspending the airway progenitor cells in the second culture medium; and (e) culturing the airway progenitor cells from step (d) in a third culture medium, wherein the third culture medium comprises, or the airway progenitor cells are contacted with, one or more of: an at least one inhibitor of SMAD; at least one inhibitor of transforming growth factor β (TGF-β); at least one bone morphogenic protein (BMP) inhibitor; and at least one ROCK inhibitor, thereby differentiating the airway progenitor cells into airway basal cells (BCs).

In some embodiments of any of the aspects, the method comprises providing and/or culturing a population of Nkx2-1+ lung progenitor cells in a first culture medium as described herein.

In some embodiments of any of the aspects, the Nkx2-1$^+$ lung progenitor cells described herein are generated by a method comprising:

(a) culturing a population of stem cells in a serum-free medium;

(b) culturing the population of stem cells in a culture medium wherein the culture medium comprises, or the stem cells are contacted with at least one Wnt agonist and/or a Wnt polypeptide;

(c) culturing the population of stem cells in a culture medium wherein the culture medium comprises, or the stem cells are contacted with, at least one bone morphogenic protein (BMP) agonist (e.g., a BMP polypeptide) and at least one Wnt agonist (e.g., a Wnt polypeptide), thereby inducing the differentiation of the stem cells into a population of lung progenitor cells; and (d) sorting and/or isolating a population of Nkx2-1$^+$ lung progenitor cells from the population of lung progenitor cells generated in (c).

Methods of generating Nkx2-1$^+$ lung progenitor cells are known in the art and further described below and e.g., U.S. Pat. No. 10,590,392 B2, which is incorporated herein by reference in its entirety.

In some embodiments of any of the aspects, the stem cell is an embryonic stem cell. For example, in some embodiments of any of the aspects, the Nkx2-1$^+$ lung progenitor cells and/or airway basal cells (BCs) described herein are derived from human embryonic stem cells as the starting material. Such pluripotent cells can be cells that originate from the morula, embryonic inner cell mass or those obtained from embryonic gonadal ridges.

A cell is defined as having the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli.

Human embryonic stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein in their entireties by reference.

In some processes, hESCs are maintained on a feeder layer. In such processes, any feeder layer which allows hESCs to be maintained in a pluripotent state can be used. One commonly used feeder layer for the cultivation of human embryonic stem cells is a layer of mouse fibroblasts.

More recently, human fibroblast feeder layers have been developed for use in the cultivation of hESCs (see US Patent Application No. 2002/0072117, the disclosure of which is incorporated herein by reference in its entirety). Alternative processes permit the maintenance of pluripotent hESC without the use of a feeder layer. Methods of maintaining pluripotent hESCs under feeder-free conditions have been described in US Patent Application No. 2003/0175956, the disclosure of which is incorporated herein by reference in its entirety.

Human embryonic stem cells used herein can be maintained in culture either with or without serum. In some embryonic stem cell maintenance procedures, serum replacement is used. In others, serum free culture techniques, such as those described in US Patent Application No. 2003/0190748, the disclosure of which is incorporated herein by reference in its entirety, are used. Stem cells are maintained in culture in a pluripotent state by routine passage until it is desired that they be differentiated into definitive lung progenitor cells.

In some embodiments of any of the aspects, the stem cell is an induced pluripotent stem cell. For example, in some embodiments of any of the aspects, the Nkx2-1+ lung progenitor cells which are differentiated into airway basal cells according to the methods described herein, can be derived from reprogrammed cells, e.g., induced pluripotent stem cells (iPS cells) derived from differentiated or somatic cells. In such an embodiment, the iPS cells can be derived from, for example, but not limited to, skin cells, urine cells, neoplastic cells, tumor cells and cancer cells. In some embodiments, the de-differentiated cells are from a subject, and in some embodiments, the de-differentiated stem cells are obtained from a biopsy, e.g., a patient with a respiratory disease, cystic fibrosis (CF) or asthma. Thus, in some embodiments of any of the aspects, the iPS cells are human iPS cells.

A somatic cell can be obtained from a subject, reprogrammed to an induced pluripotent stem cell, and then re-differentiated into an airway basal cell to be administered to the subject (e.g., autologous cells). Since the airway BCs (or their differentiated progeny) are essentially derived from an autologous source, the risk of engraftment rejection or allergic responses is reduced compared to the use of cells from another subject or group of subjects. In addition, the use of iPSCs negates the need for cells obtained from an embryonic source. Thus, in one embodiment, the stem cells used to generate airway basal cells for use in the compositions and methods described herein are not embryonic stem cells.

In some embodiments, the airway basal cells useful for the compositions described herein are derived from non-autologous sources.

In some embodiments of any of the aspects, an iPS cells used for generation of the airway BCs according to the methods described herein, can be produced by any method known in the art can be used, for example virally-induced or chemically induced generation of iPS cells are described in Mauritz et al., Circulation. 2008; 118:507-517, and disclosed in International Application WO2008/088882, EP1970446, US2009/0047263, 052009/0068742, and 2009/0227032, which are incorporated herein in their entireties by reference.

iPS cells can also be generated using other methods commonly known in the art, such as, including but not limited to uses of non-viral methods, polycistronic vectors, mRNA species, miRNA, and proteins, including International Patent Applications WO2010/019569, WO2009/149233, WO2009/093022, WO2010/022194, WO2009/101084, WO2008/038148, WO2010/059806, WO2010/057614, WO2010/056831, WO2010/050626, WO2010/033906, WO2009/126250, WO2009/143421, WO2009/140655, WO2009/133971, WO2009/101407, WO2009/091659, WO2009/086425, WO2009/079007, WO2009/058413, WO2009/032456, WO2009/032194, WO2008/103462, JP4411362, EP2128245, and U.S. Patent Applications US2004/0072343, US2009/0253203, US2010/0112693, US2010/07542, US2009/0246875, US2009/0203141, US2010/00625343, US2009/0269763, which are incorporated herein in their entireties by reference.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fth117; Sal 14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The Nkx2-1+ lung progenitor cells described herein can be isolated from tissue including solid tissues (the exception to solid tissue is whole blood, including blood, plasma and bone marrow) which were previously unidentified in the literature as sources of stem cells. In some embodiments, the tissue is lung tissue. In other embodiments, the tissue is for example but not limited to, umbilical cord blood, placenta, bone marrow, or chondral villi.

An adult stem cell is structurally distinct from an embryonic stem cell not only in markers it does or does not express relative to an embryonic stem cell, but also by the presence of epigenetic differences, e.g. differences in DNA methylation patterns.

In some embodiments of any of the aspects, airway BCs generated according to the methods described herein are generated and maintained using the culture media and methods described in WO2010/090513, WO2012/168930, and U.S. Pat. No. 10,590,392 B2.

In one aspect, the methods described herein comprise culturing a population of cells (e.g., anterior foregut endoderm cells or Nkx2-1+ lung progenitor cells) in a first culture medium. In some embodiments of any of the aspects, the first culture medium comprises one or more of a Wnt agonist, retinoic acid, and a bone morphogenic protein (BMP). In some embodiments of any of the aspects, the cells are contacted with one or more of: a Wnt agonist, retinoic acid, and a bone morphogenic protein (BMP).

In some embodiments, the first culture medium comprises one or more Wnt agonists. In some embodiments, when the cells are cultured in the first culture medium, they are contacted with one or more Wnt agonists.

In some embodiments, one or more agents that activate or enhance the Wnt pathway, are herein termed "Wnt activating agents" or "activating agents" or "Wnt agonists".

The Wnt/β-catenin pathway, also called the canonical Wnt pathway, plays a critical role in embryonic developmental programs and stem cell differentiation of the respiratory system through the regulation of cell proliferation and migration. The molecular mechanisms of the Wnt/β-catenin pathway are further described, e.g., in Joerg Huelsken, Juergen Behrens, "The Wnt signalling pathway" *Journal of Cell Science* (2002), and Pongracz, J. E., Stockley, R. A. "Wnt signalling in lung development and diseases." *Respir Res* 7, 15 (2006), the contents of each of which are incorporated herein by reference in their entireties.

Wnt withdrawal (or Wnt inhibition) results in the cells differentiating along a proximal differentiation pathway to become NXK2-1+/SOX2+ airway epithelial cells, whereas sustained Wnt activation results in the cells differentiating along a distal differentiation pathway to become NXK2-1+/SOX9+ epithelial cells. Closely regulated control of Wnt signaling can be used to differentiate human Nxk2-1 lung epithelial progenitor intermediates derived from iPSC or ESCs in vitro, allowing the development of airway basal cells described herein.

In some embodiments, Wnt activating agents activate the Wnt/β-catenin pathway directly, for example Wnt activating agents include Wnt or wnt3a or homologues and variants thereof, as well as β-catenin and components of the Wnt/β-catenin signaling pathway. In other embodiments, Wnt activating agents activate Wnt/β-catenin pathway by inhibiting negatively acting components of the Wnt/β-catenin-GSK3 pathway. For example, a Wnt activating agent can suppress or inhibit the activity and/or expression of Wnt/β-catenin endogenous suppressors, for example a Wnt activating agent can be an inhibitor of GSK3β.

In some embodiments of any of the aspects, "activating agent" or "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, Wnt/beta-catenin signaling, e.g. its ability to increase the level and/or activity of Wnt/beta-catenin signaling can be determined, e.g. by measuring the level of an expression product of Wnt/beta-catenin signaling pathway and/or the activity of Wnt/beta-catenin signaling. Methods for measuring the level of a given mRNA and/or polypeptide are known to one of skill in the art, e.g. RT-PCR with primers can be used to determine the level of RNA, and Western blotting with an antibody can be used to determine the level of a polypeptide. Antibodies to Wnt/beta-catenin signaling pathway proteins are commercially available. Assays for measuring the activity of Wnt/beta-catenin signaling are known in the art, e.g., WNT Signaling Pathway RT2 Profiler PCR Array Cat. No. PAHS-043Z from Qiagen; Hilden Germany or Wnt/β-Catenin Activated Targets Antibody Sampler Kit Cat No. 8655 from Cell Signaling Technologies Danvers, Mass. Exemplary methods that can be used to determine the activity of a β-catenin/Wnt pathway agonist include, without limitation, monitoring the expression of a reporter gene under the control of a TCF/LEF family transcription factor, as well as TOPFlash luciferase reporter assays, as described in US 2014/0044763.

Wnt activating agents of the present invention include, but are not limited to polynucleotides, polypeptides, proteins, peptides, antibodies, small molecules, aptamers, nucleic acids, nucleic acid analogues and other compositions that are capable of activating or enhancing the wnt/β-catenin pathway, or increasing the activity and/or expression of wnt, wnt-dependent genes/proteins and/or β-catenin. Alternatively, wnt activating agents of the present invention are agents that inhibit the activity and/or expression of genes and/or gene products that suppress the activity and/or expression of wnt or the wnt/β-catenin pathway including, but not limited to, agents that inhibit GSK-3 or GSK-3β, or sFRP, DKK1, WIF-1 etc. In alternative embodiments, Wnt activating agents include but are not limited to disheveled WLS/Evi, (dsh), LRP-5, LRP-6, Dally (division abnormally delayed), Dally-like, PAR1, β-catenin, TCF, lef-1 and Frodo or homologues or genetically modified versions thereof that retain wnt activating activity. In some embodiments of any of the aspects, Wnt activating agents are inhibitory molecules to endogenous extracellular inhibitors of Wnt/β-catenin signalling, for example inhibitors that inhibit their activity and/or expression, for example inhibitory nucleic acid of WIF-1, cerberus, Dickkopf-1 (DKK1), Dapper, pertussis toxin, disabled-2 (dab-2), naked cuticle (naked), Frzb-related proteins, FrzA, frzB, sizzled sFRP (secreted frizzled-related proteins), sRFP-1, sFRP-2, collagen 18 (XVIII), endostatin, carboxypeptidase Z, receptor tyrosine kinase, corin etc.

Non-limiting examples of agonists of Wnt/beta-catenin signaling can include CHIR99021; a recombinant Wnt polypeptide; a Wnt polypeptide (e.g., a polypeptide expression product of human Wnt-1, 2A, 2B, 3, 3A, 4, 5A, 5B, 7A, 7B, 8A, 8B, 9A, 9B, 10A, 10B, and/or 11A); an exogenous Wnt polypeptide; BIO; WAY-316606; a (hetero) arylpyrimidine; IQ1; QS11; SB-216763; DCA; R-spondin; and an inhibitor of Axin2 (e.g., NCBI Gene ID: 8313 and orthologs thereof) and/or APC (e.g., NCBI Gene ID: 324 and orthologs thereof).

In one embodiment, wnt activating agents activate and/or increase the activity of wnt homologues and/or wnt/β-catenin signaling. In some embodiments, wnt activating agents are a wnt gene and/or wnt gene product, or homologues or genetically modified versions and fragments thereof having wnt signaling activity. Wnt genes and proteins useful as wnt activating agents in the present invention are well known to a person of ordinary skill in the art, and include, for example, human and mouse wnt genes, wnt homologues and fragments and genetically modified versions thereof that have wnt signaling activity. Wnt genes include, but are not limited to human Wnt-1, 2A, 2B, 3, 3A, 4, 5A, 5B, 7A, 7B, 8A, 8B, 9A, 9B, 10A, 10B, 11A, and murine Wnt genes, Wnt-1, 2, 3A, 3B, 4, 5A, 5B, 6, 7A, 7B, 8A, 8B, 10B, 11 and 12. Gene or nucleic acid sequences encoding the polypeptides are disclosed in U.S. Pat. Nos. 5,851,984 and 6,159,462, which are incorporated herein by reference in their entirety.

In some embodiments, the wnt activating agent comprises one or more wnt gene and/or gene products as mentioned above. In some embodiments, the wnt activating agent is Wnt3A gene or Wnt3A gene product or a modified version, homologue or fragment thereof, that has wnt signaling activity, including, but not limited to SEQ ID NO: 1 (GenBank accession #NM_009522), SEQ ID NO:2 (GenBank accession #NM_030753); and/or SEQ ID NO:3 (GenBank accession #NM_033131). In some embodiments, the wnt activating agent is a nucleic comprising a sequence having at least 60%, at least 65%, at least 70%, at least 75%, at least 80%, at least 85%, at least 90%, at least 95%, or greater sequence identity to SEQ ID NO: 1 (GenBank accession #NM 009522), SEQ ID NO:2 (GenBank accession #NM_030753); and/or SEQ ID NO:3 (GenBank accession #NM_033131) and retaining the wild-type wnt signaling activity of the reference sequence. In some embodiments, the wnt activating agent is a polypeptide comprising a sequence having at least 60%, at least 65%, at least 70%, at least 75%, at least 80%, at least 85%, at least 90%, at least 95%, or greater sequence identity to one or more of the polypeptides encoded by SEQ ID NO: 1 (GenBank accession #NM_009522), SEQ ID NO:2 (GenBank accession #NM_030753); and/or SEQ ID NO:3 (GenBank accession #NM_033131) and retaining the wild-type wnt signaling activity of the reference sequence. Other wnt activating agents that activate wnt/β-catenin signaling can be used, for example compositions listed and discussed in U.S. Pat. Nos. 5,851,984 and 6,159,462 which are incorporated herein by reference in their entirety.

Thus, in another embodiment, wnt activating agents useful in the present invention are inhibitors of GSK-3 and/or GSK-3β. Examples of inhibitors of GSK-3 inhibitors include but are not limited to BIO (6-bromoindirubin-3'oxime), acetoxime analogue of BIO, 1-azakenpaullone or analogues or modified versions thereof, as shown in the Examples. In some embodiments, wnt activating agents can be substrate competitive GSK3 peptides, for example, a cell permeable substrate competitive GSK3 peptide. Any agent which inhibits GSK3β is potentially useful as a wnt activating agent in the methods described herein, and includes, for example lithium, LiCl, Ro31-8220, as disclosed in International Patent Application No: PCT97/41854, which is incorporated herein in its entirety by reference, and retinoic acid. Inhibitors of glycogen synthase kinase 3 (GSK3) can also include 6-bromo-indirubin-3'-oxime (BIO) (Meijer et al. Chemistry and Biology 10:1255 (2003); Goessling et al. Cell 136:1136 (2009)), AR-A014418 (Bhat et al. Journal of Biological Chemistry 278:45937 (2003), the organometallic GSK-3 inhibitor DW21 (Williams et al. Angewandte Chemie International Edition 44:1984 (2005)); and FGF2 (e.g., recombinant mouse FGF2), the disclosures of which are incorporated herein by reference.

In some embodiments, the Wnt agonist is CHIR99021. CHIR99021 acts as an inhibitor of the enzyme, GSK3. The function and cellular regulation of glycogen synthase kinase-3 (GSK3) are described, e.g., in Beurel et al. "Glycogen synthase kinase-3 (GSK3): regulation, actions, and diseases." *Pharmacol Ther.* 2015; 148:114-131. doi: 10.1016/j.pharmthera.2014.11.016, which is incorporated herein by reference in its entirety. As used herein, "CHIR99021" refers to a compound having the structure of Formula I or a pharmaceutically acceptable salt thereof. The synthesis of CHIR99021 as well as the structure and synthesis of related compounds, e.g., derivatives, including those with similar biological activity are known in the art, see, e.g. WO 1999/065897; WO 2002/020495; WO 2005/003948; WO 2006/001863; WO 2006/117212; WO 2007/016485; WO 2007/075911; WO 2007/083978; and US 2002/0156087; each of which is incorporated by reference herein in its entirety.

Formula I

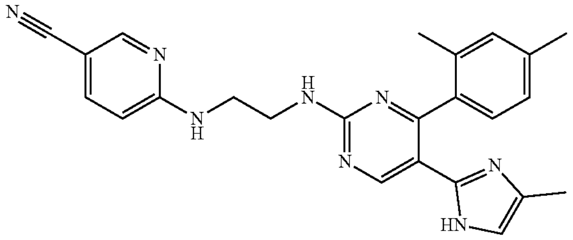

In some embodiments, other wnt activating agents that inhibit GSK-3 can be used, for example compositions disclosed in U.S. Pat. No. 6,411,053, which is incorporated herein by reference in its entirety. Further examples include GSK-3 inhibitors identified by the methods disclosed in International Patent Application No: PCT97/41854, which is incorporated herein in its entirety by reference.

In further aspects, Wnt activating agents trigger Wnt/β-catenin signaling by activating and/or increasing the activity of β-catenin, for example, that stabilize and/or increase cytosolic accumulation of β-catenin and/or inhibit its phosphorylation. In some embodiments of any of the aspects, Wnt activating agents are β-catenin gene and/or β-catenin gene product, or homologues, genetically modified version or fragments thereof that retain wnt activating activity. β-catenin gene and gene product are known to persons of ordinary skill in the art, and include but are not limited to (GenBank accession #XM_208760). In some embodiments of any of the aspects, writ activating agents are stabilized versions of β-catenin, for example versions where serine residues of the GSK-3β phosphorylation consensus motif of β-catenin have been substituted, resulting in inhibition of ubiquitination and stabilization of the protein. Examples of stabilized β-catenins include, but are not limited to those with the amino acid changes D32Y; D32G; S33F; S33Y; G34E; S37C; S37F; T41I; S45Y; and deletion of AA 1-173 relative to human β-catenin. A number of publications describe stabilized β-catenin mutations, for example, see Morin et al., 1997; Palacios et al., 1998; Muller et al., 1998; Miyoshi et al., 1998; Zurawel et al., 1998; Voeller et al., 1998; and U.S. Pat. No. 6,465,249, etc., which are incorporated herein in their entirety by reference. In alternative embodiments, other Wnt activating agents that activate β-catenin can be used, for example compositions discussed in U.S. Pat. No. 6,465,249, which is incorporated herein in its entirety by reference.

In some embodiments of any of the aspects, Wnt activating agents are any β-catenin binding partners that increase the stability of β-catenin and/or promote β-catenin localization in the nucleus. In alternative embodiments, Wnt activating agents include, but are not limited to Frodo, TCF, pitx2, Reptin 52, legless (lgs), pygopus (pygo), hyrax/parafbromin, LKBI/XEEK1 or homologues or modified versions or fragments thereof that retain Wnt activating activity. In alternative embodiments, Wnt activating agents are inhibitors of negative factors, for example inhibitory nucleic acids and/or peptides that inhibit the activity and/or gene expression of, for example but not limited to APC, Axin, dab-2, grucho, PP2A, chibby, pontin 52, Nemo/LNK kinases etc.

Antagonist antibodies have also been developed that inhibit β-catenin phosphorylation by virtue of propagating the Wnt signal transduction cascade. Such antibodies may bind the Wnt receptors including Frizzled and LRP family proteins and trigger concomitant conformational changes that stimulate the propagation of the Wnt signaling pathway, which includes distinct molecular events that inhibit β-catenin phosphorylation by GSK3. For instance, the antibody 1D9 has been developed as an agonist of Wnt signal transduction, and is described in detail in US 2014/0044717, the disclosure of which is incorporated herein by reference.

It is encompassed in the present methods provided herein that wnt activating agents activate or enhance Wnt/β-catenin signaling in the Nkx2-1+ lung progenitor cells described herein. For example, wnt activating agents can be delivered to the culture media of the Nkx2-1+ lung progenitor cells, and in some embodiments the wnt activating agent is delivered to the Nkx2-1+ lung progenitor cells as a polynucleotide and/or a polypeptide. The polynucleotide can be comprised in a vector, (i.e., a viral vector and/or non-viral vector). Examples of the viral vectors include, but are not limited to adenoviral vectors, adeno-associated vectors, retroviral vectors or lentiviral vectors. Alternatively, wnt activating agents may be delivered to a feeder layer, such that the wnt/β-catenin signaling is promoted in the feeder layer. In one embodiment, the feeder layer may comprise 'wnt activating agent-producing cells'. In alternative embodiments, wnt activating agents are delivered to the Nkx2-1+ lung progenitor cells and/or the feeder layer. In some embodiments, more than one wnt activating agent is delivered to the Nkx2-1+ lung progenitor cells and/or feeder layer, and in some embodiments, the wnt activating agents delivered to the Nkx2-1+ lung progenitor cells are different from those delivered to the feeder cell layer. In some embodiments, the wnt activating agent can be encoded in a nucleic acid operatively linked to a promoter, and in some embodiments the promoter is, for example, a tissue-specific promoter, or an inducible promoter.

In some embodiments of any of the aspects, the first culture medium comprises retinoic acid (also known as vitamin A) or a derivative thereof. As used herein, the term "retinoic acid" refers to Formula II or a pharmaceutically acceptable salt thereof.

Formula II

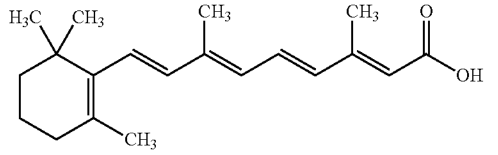

Various derivatives of retinoic acid are known in the art, e.g., such as beta-carotene, retinal, retinol, all-trans-retinoic acid, 9-cis-retinoic acid and 13-cis retinoic acid. Methods of synthesizing retinoic acid and its derivatives are described e.g., in WO2003037385A1 and U.S. Pat. No. 4,826,871 A, the contents of each of which are incorporated herein by reference in their entireties.

In some embodiments, the first culture medium comprises one or more a bone morphogenetic protein (BMP)s or BMP agonists. In some embodiments, when the Nkx2-1+ lung progenitor cells are cultured in the first culture medium, they are contacted with one or more bone morphogenetic proteins (BMP) or BMP agonists. BMP polypeptides are members of the transforming growth factor-beta superfamily and BMP signaling regulates a variety of embryonic patterning during fetal and embryonic development. For example, BMP4 (e.g., a polypeptide of NCBI Gene ID: 652 or an ortholog thereof), is found in early embryonic development in the ventral marginal zone and directs lung development. Signal transduction of BMPs and methods of measuring such activity are further described, e.g., in Miyazono K, et al. "Bone morphogenetic protein receptors and signal transduction." *J Biochem.* 2010 January; 147(1):35-51. doi: 10.1093/jb/mvp148. Epub 2009 Sep. 17. PMID: 19762341, which is incorporated herein by reference in its entirety. Sequences for BMPs are known in the art, e.g., human BMPs can include the sequences associated with NCBI Gene ID: 649 (SEQ ID NO: 10), 650 (SEQ ID NO: 11), 651 (SEQ ID NO: 12), 652 (SEQ ID NO: 13), 653 (SEQ ID NO: 14), 654 (SEQ ID NO: 15), 655 (SEQ ID NO: 16), 6565 (SEQ ID NO: 17), 5142 (SEQ ID NO: 18), and 27302 (SEQ ID NO: 19). In some embodiments, the BMP agonist is a nucleic comprising a sequence having at least 60%, at least 65%, at least 70%, at least 75%, at least 80%, at least 85%, at least 90%, at least 95%, or greater sequence identity to a nucleotide sequence associated with NCBI Gene ID: 649 (SEQ ID NO: 36), 650 (SEQ ID NO: 37), 651 (SEQ ID NO: 38), 652 (SEQ ID NO: 39), 653 (SEQ ID NO: 40), 654 (SEQ ID NO: 41), 655 (SEQ ID NO: 42), 6565 (SEQ ID NO: 43), 5142 (SEQ ID NO: 44), or 27302 (SEQ ID NO: 45) and retaining the wild type BMP activity of the reference sequence. In some embodiments, the BMP is a polypeptide comprising a sequence having at least 60%, at least 65%, at least 70%, at least 75%, at least 80%, at least 85%, at least 90%, at least 95%, or greater sequence identity to one or more of the polypeptides associated with NCBI Gene ID: 649 (SEQ ID NO: 10), 650 (SEQ ID NO: 11), 651 (SEQ ID NO: 12), 652 (SEQ ID NO: 13), 653 (SEQ ID NO: 14), 654 (SEQ ID NO: 15), 655 (SEQ ID NO: 16), 6565 (SEQ ID NO: 17), 5142 (SEQ ID NO: 18), or 27302 (SEQ ID NO: 19) and retaining the wild-type BMP activity of the reference sequence.

In some embodiments, the first culture medium comprises a bone morphogenetic protein (BMP) or BMP agonist. BMP polypeptides are members of the transforming growth factor-beta superfamily and BMP signaling regulates a variety of embryonic patterning events during fetal and embryonic development. For example, BMP4 is found in early embryonic development in the ventral marginal zone and directs lung development. Signal transduction of BMPs are further described, e.g., in Miyazono K, et al. "Bone morphogenetic protein receptors and signal transduction." *J Biochem.* 2010 January; 147(1):35-51. doi: 10.1093/jb/mvp148. Epub 2009 Sep. 17. PMID: 19762341, which is incorporated herein by reference in its entirety.

In some embodiments of any of the aspects, the first culture medium comprises one or more of CHIR99021, retinoic acid, BMP4 or any combination thereof. In some embodiments of any of the aspects, first culture medium comprises CHIR99021, retinoic acid, and BMP4.

In some embodiments of any of the aspects, the first culture medium comprises about 10 nM to about 100 μM CHIR99021. In some embodiments of any of the aspects, the first culture medium comprises 10 nM to 100 μM CHIR99021. In some embodiments of any of the aspects, the first culture medium comprises about 100 nM to about 100 μM CHIR99021. In some embodiments of any of the aspects, the first culture medium comprises 100 nM to 100 μM CHIR99021. In some embodiments of any of the aspects, the first culture medium comprises at least about 1 μM CHIR99021 or more. In some embodiments of any of the aspects, the first culture medium comprises at least about 3 μM CHIR99021 or more. In some embodiments of any of the aspects, the first culture medium comprises at least 1 μM CHIR99021 or more. In some embodiments of any of the aspects, the first culture medium comprises at least 3 μM CHIR99021 or more. In some embodiments of any of the aspects, the first culture medium comprises about 1 μM to about 3 μM CHIR99021. In some embodiments of any of the aspects, the first culture medium comprises 1 μM to 3 μM CHIR99021.

In some embodiments the first culture medium comprises at least about 0.1 ng/ML to about 1,000 ng/mL BMP4. In some embodiments the first culture medium comprises 0.1 ng/ML to 1,000 ng/mL BMP4. In some embodiments the first culture medium comprises at least about 1 ng/ML to about 100 ng/mL BMP4. In some embodiments of any of the aspects, the first culture medium comprises at least about 10 ng/mL recombinant human BMP4. In some embodiments the first culture medium comprises 1 ng/ML to 100 ng/mL BMP4. In some embodiments of any of the aspects, the first culture medium comprises 10 ng/mL recombinant human BMP4. In some embodiments the first culture medium comprises about 10 ng/ML to about 20 ng/mL BMP4. In some embodiments the first culture medium comprises 10 ng/ML to 20 ng/mL BMP4.

In some embodiments the first culture medium comprises about 0.1 nM to about 10 μM retinoic acid. In some embodiments the first culture medium comprises 0.1 nM to 10 μM retinoic acid. In some embodiments the first culture medium comprises about 1 nM to about 100 nM retinoic acid. In some embodiments the first culture medium comprises 1 nM to 100 nM retinoic acid. In some embodiments the first culture medium comprises about 10 nM to about 100 nM retinoic acid. In some embodiments the first culture medium comprises 10 nM to 100 nM retinoic acid. In some embodiments the first culture medium comprises about 50 nM to about 100 nM retinoic acid. In some embodiments the first culture medium comprises 50 nM to 100 nM retinoic acid. In some embodiments the first culture medium comprises at least about a concentration of about 50 nM to about 100 nM retinoic acid. In some embodiments the first culture medium comprises at least about a concentration of about 10 nM to about 100 nM retinoic acid. In some embodiments the first culture medium comprises at least about a concentration of about 50 nM to about 100 nM retinoic acid.

In some embodiments of any of the aspects, the first culture medium consists of or consists essentially of Ham's F12 (Thermo Fisher) with B27 Supplement with N2 Supplement (Invitrogen), Monothioglycerol, ascorbic acid, Iscove's Modified Dulbecco's Medium, Ham's F-12 Nutrient Mixture, B-27™ supplement, and N2™ supplement L-alanyl-L-glutamine dipeptide, bovine serum albumin, one or more antibiotics, and one or more of: CHIR99021, retinoic acid, BMP4 or any combination thereof. In some embodiments of any of the aspects, first culture medium the first culture medium consists of or consists essentially of Ham's F12 (Thermo Fisher) with B27 Supplement with N2 Supplement (Invitrogen), Monothioglycerol, ascorbic acid, Iscove's Modified Dulbecco's Medium, Ham's F-12 Nutrient Mixture, B-27™ supplement, and N2™ supplement L-alanyl-L-glutamine dipeptide, bovine serum albumin, one or more antibiotics CHIR99021, retinoic acid, and BMP4.

In some embodiments of any of the aspects, when the Nkx2-1+ lung progenitor cells are cultured in the first culture medium, they are contacted with one or more of CHIR99021, retinoic acid, BMP4 or any combination thereof. In some embodiments of any of the aspects, when the Nkx2-1+ lung progenitor cells are cultured in the first culture medium, they are contacted with CHIR99021, retinoic acid, and BMP4.

In some embodiments of any of the aspects, the Nkx2-1+ lung progenitor cells described herein are cultured in the first culture medium for at least about 8 days or more, 9 days or more, 10 days, or more, 11 days or more, 12 days or more, 13 days or more, 14 days or more, 15 days or more, 16 days or more. In some embodiments of any of the aspects, the Nkx2-1+ lung progenitor cells described herein are cultured in the first culture medium for at least about 15 days. In some embodiments of any of the aspects, the Nkx2-1+ lung progenitor cells described herein are cultured in the first culture medium for at least 8 days or more, 9 days or more, 10 days, or more, 11 days or more, 12 days or more, 13 days or more, 14 days or more, 15 days or more, 16 days or more. In some embodiments of any of the aspects, the Nkx2-1+ lung progenitor cells described herein are cultured in the first culture medium for at least 15 days.

In some embodiments of any of the aspects, the Nkx2-1+ lung progenitor cells described herein are cultured in the first culture medium for no more than 40 days, 35 days, 30 days, 25 days, or 20 days.

In some embodiments of any of the aspects, the Nkx2-1+ lung progenitor cells described herein are cultured in the first culture medium for about 4 days to about 20 days. In some embodiments of any of the aspects, the Nkx2-1+ lung progenitor cells described herein are cultured in the first culture medium for 4 days to 20 days. In some embodiments of any of the aspects, the Nkx2-1+ lung progenitor cells described herein are cultured in the first culture medium for about 6 days to about 16 days. In some embodiments of any of the aspects, the Nkx2-1+ lung progenitor cells described herein are cultured in the first culture medium for 6 days to 16 days. In some embodiments of any of the aspects, the Nkx2-1+ lung progenitor cells described herein are cultured in the first culture medium for about 8 days to about 14 days. In some embodiments of any of the aspects, the Nkx2-1+ lung progenitor cells described herein are cultured in the first culture medium for 8 days to 14 days.

In some embodiments of any of the aspects, the Nkx2-1+ lung progenitor cells described herein are purified by cell sorting.

As will be appreciated by one of skill in the art, a Nkx2-1+ lung progenitor cell described herein or a progeny thereof will lack markers of embryonic stem cells or induced pluripotent stem cells. In one embodiment of the methods described herein, one or more cell surface markers are used to determine the degree of differentiation along the spectrum of embryonic stem cells or iPSCs to e.g., fully differentiated airway basal cells.

In some embodiments, antibodies or similar agents specific for a given marker, or set of markers, can be used to separate and isolate the desired cells using fluorescent activated cell sorting (FACS), panning methods, magnetic particle selection, particle sorter selection and other methods known to persons skilled in the art, including density separation (Xu et al. (2002) *Circ. Res.* 91:501; U.S.S.N. 20030022367) and separation based on other physical properties (Doevendans et al. (2000) *J Mol. Cell. Cardiol.* 32:839-851). Negative selection can be performed, including selecting and removing cells with undesired markers or characteristics, for example fibroblast markers or muscle cell markers, etc.

Thus, in some embodiments of any of the aspects, the Nkx2-1+ lung progenitor cells described herein and/or their differentiated progeny express Nkx2-1. In some embodiments of any of the aspects, the Nkx2-1+ lung progenitor cells described herein and/or their differentiated progeny express $CD47^{hi}/CD26^{lo}$ markers.

In some embodiments of any of the aspects, the method of generating airway basal cells described herein comprises a step of re-suspending the Nkx2-1+ lung progenitor cells in a hydrogel, (e.g., in extracellular matrix composition) to form epithelial spheres, e.g., after the step of culturing in the first culture medium. As used herein, “hydrogel” refers to a network of hydrophilic polymer chains. In some embodiments of any of the aspects, the hydrogel comprises one or more extracellular matrix components, e.g., laminin, nidogen, collagen, growth factors (e.g., TGF-beta and EGF) and proteoglycans with cell adhesive peptides. In some embodiments of any of the aspects, the hydrogel comprises laminin, nidogen, collagen, growth factors (e.g., TGF-beta and EGF) and proteoglycans with cell adhesive peptides. In some embodiments of any of the aspects, the hydrogel comprises laminin, nidogen, and collagen. In some embodiments of any of the aspects, the hydrogel comprises laminin, nidogen, collagen, and proteoglycans with cell adhesive peptides. In some embodiments of any of the aspects, the hydrogel comprises or consists essentially of MATRIGEL™

The extracellular matrix composition can be any composition that permits the formation of the epithelial spheres and maintains cell viability. In addition to the treatments described above, an extracellular matrix protein can be added to the media or culture vessel to promote further cellular adhesion, differentiation, and/or induce a desired cell signaling pathway (e.g., via integrin signaling). Examples of extracellular matrix proteins include but are not limited to collagen, fibronectin, fibrinogen, poly-lysine, vitronectin, laminin, elastin, tenascin, and Matrigel®. Other extracellular matrix formulations and proteins are known in the art. In some embodiments of any of the aspects, the extracellular matrix composition comprises a gelatinous protein mixture secreted by Engelbreth-Holm-Swarm (EHS) mouse sarcoma cells. In some embodiments, the ECM composition comprises one or more of laminin, Collagen W, heparan sulfate proteoglycans, entactin/nidogen, fibronectin, or any combination thereof. In some embodiments of any of the aspects, the gelatinous protein mixture secreted by Engelbreth-Holm-Swarm (EHS) mouse sarcoma cells is MATRIGEL™. MATRIGEL™ is commercially available, for example, from CORNING® [MATRIGEL® Matrix (Catalog #356231)].

In some embodiments of any of the aspects, the method comprises culturing the Nkx2-1+ lung progenitor cells, epithelial spheres, and/or differentiated progeny in a 3-dimensional (3D) microenvironment. The phrase “cultured in a 3-dimensional microenvironment” refers to a cell culture comprising a population of cells described herein that has more than one layer of cells in any given plane. A 3-dimensional tissue is not a monolayer or laminar in structure. Rather, 3-dimensional tissues possess a shape with a larger volume compared with monolayer tissues. The hydrogel and extracellular matrix compositions described herein can aid in the formation of 3-D tissue structures. The 3-dimensional (3D) hydrogel (e.g., extracellular matrix (ECM)) environment promotes the differentiation of the Nkx2-1+ lung progenitor cells into airway progenitor cells. See, e.g., Hawkins, F., et al. (2017). “Prospective isolation of Nkx2-1-expressing human lung progenitors derived from pluripotent stem cells.” *J. Clin. Invest.* 127, 2277-2294, which is incorporated herein by reference in its entirety. Similarly, devices and transwells can also be used to generate and culture 3-D tissues. See, e.g., U.S. Pat. Nos. 5,160,490 A; 7,029,689 B2; US Pg. 2019/0376024 A1; which are incorporated herein by reference in their entirety. It should be noted that the 3D culture of cells can be applied at any step of the methods described herein and at any time point in the process of generating the airway basal cells described herein.

In some embodiments of any of the aspects, the Nkx2-1+ lung progenitor cells are cultured in a 3-dimensional microenvironment. In some embodiments of any of the aspects, the airway progenitor cells are cultured in a 3-dimensional microenvironment. In some embodiments of any of the aspects, the airway basal cells are cultured in a 3-dimensional microenvironment. In some embodiments of any of the aspects, the step involving a first culture medium and the step of resuspending in the hydrogel (e.g., culturing in a 3-dimensional microenvironment) occur concurrently. In some embodiments of any of the aspects, the step involving a second culture medium and the step of resuspending in the hydrogel (e.g., culturing in a 3-dimensional microenvironment) occur concurrently. In some embodiments of any of the aspects, the cells are resuspended in a hydrogel and then cultured in a first culture medium (e.g., cultured in the first culture medium in a 3-dimensional microenvironment). In some embodiments of any of the aspects, the cells are resuspended in a hydrogel and then cultured in a second culture medium (e.g., cultured in the second culture medium in a 3-dimensional microenvironment).

In some embodiments of any of the aspects, the methods described herein further comprise culturing the epithelial spheres in a second culture medium.

In some embodiments of any of the aspects, the second culture medium consists of or consists essentially of Ham’s F12 (Thermo Fisher) with B27 Supplement with N2 Supplement (Invitrogen), monothioglycerol, ascorbic acid, Iscove’s Modified Dulbecco’s Medium, Ham’s F-12 Nutrient Mixture, B-27™ supplement, and N2™ supplement L-alanyl-L-glutamine dipeptide, bovine serum albumin, cAMP, IBMX, one or more antibiotics and one or more of: at least one fibroblast growth factor (FGF) agonist (e.g., FGF polypeptide); at least one steroid; and at least one ROCK inhibitor or any combination thereof. In some embodiments of any of the aspects, the second culture medium consists of or consists essentially of Ham’s F12 (Thermo Fisher) with B27 Supplement with N2 Supplement (Invitrogen), monothioglycerol, ascorbic acid, Iscove’s Modified Dulbecco’s Medium, Ham’s F-12 Nutrient Mixture, B-27™ supplement, and N2™ supplement L-alanyl-L-glutamine dipeptide, bovine serum albumin, cAMP, IBMX, one or more antibiotics, at least one fibroblast growth factor (FGF) agonist (e.g., FGF polypeptide), at least one steroid, and at least one ROCK inhibitor. In some embodiments of any of the aspects, the second culture medium comprises one or more fibroblast growth factor (FGF) agonists, e.g., FGF polypeptides. Fibroblast growth factor polypeptides are regulators of cell proliferation and differentiation for various of cell types. The members of the FGF family of polypeptides and their function in cell signaling are described in detail, e.g., in Ornitz D M, Itoh N (2001). “Fibroblast growth factors”. *Genome Biology.* 2 (3): reviews3005.1-reviews3005.12, and Luigi Maddaluno et al. “Fibroblast growth factors: key players in regeneration and tissue repair" *Development* (2017) 144: 4047-4060; doi: 10.1242/dev.152587, the contents of each of which are incorporated herein by reference in their entireties.

In some embodiments of any of the aspects, the second culture medium comprises an FGF2 polypeptide. Nucleic acid and amino acid sequences for FGF2 are known in the art, e.g., can include the sequences associated with NCBI Gene IDs: 2247 (SEQ ID NO: 20), 14173 (SEQ ID NO: 21), 54250 (SEQ ID NO: 22), 281161 (SEQ ID NO: 23), 396413 (SEQ ID NO: 24), 397643 (SEQ ID NO: 25), 403857 (SEQ ID NO: 26), 443306 (SEQ ID NO: 27), 100009068 (SEQ ID NO: 28), 100101279 (SEQ ID NO: 29), or an ortholog thereof. In some embodiments, the FGF2 is a nucleic acid comprising a sequence having at least 60%, at least 65%, at least 70%, at least 75%, at least 80%, at least 85%, at least 90%, at least 95%, or greater sequence identity to a nucleotide sequence associated with NCBI Gene IDs: 2247 (SEQ ID NO: 46), 14173 (SEQ ID NO: 47), 54250 (SEQ ID NO: 48), 281161 (SEQ ID NO: 49), 396413 (SEQ ID NO: 50), 397643 (SEQ ID NO: 51), 403857 (SEQ ID NO: 52), 443306 (SEQ ID NO: 53), 100009068 (SEQ ID NO: 54), 100101279 (SEQ ID NO: 55), and retaining the wild-type FGF2 activity of the reference sequence. In some embodiments, the FGF2 is a polypeptide comprising a sequence having at least 60%, at least 65%, at least 70%, at least 75%, at least 80%, at least 85%, at least 90%, at least 95%, or greater sequence identity to one or more of the polypeptides associated with NCBI Gene IDs: 2247 (SEQ ID NO: 20), 14173 (SEQ ID NO: 21), 54250 (SEQ ID NO: 22), 281161 (SEQ ID NO: 23), 396413 (SEQ ID NO: 24), 397643 (SEQ ID NO: 25), 403857 (SEQ ID NO: 26), 443306 (SEQ ID NO: 27), 100009068 (SEQ ID NO: 28), 100101279 (SEQ ID NO: 29), and retaining the wild-type FGF2 activity of the reference sequence.

In some embodiments of any of the aspects, the second culture medium comprises an FGF10 polypeptide. Nucleic acid and amino acid sequences for FGF10 are known in the art, e.g., can include the sequences associated with NCBI Gene IDs: 2255 (SEQ ID NO: 30), 14165 (SEQ ID NO: 31), 25443 (SEQ ID NO: 32), 359830 (SEQ ID NO: 33), 395432 (SEQ ID NO: 34), 326285 (SEQ ID NO: 35), or an ortholog thereof. In some embodiments, the FGF10 is a nucleic acid comprising a sequence having at least 60%, at least 65%, at least 70%, at least 75%, at least 80%, at least 85%, at least 90%, at least 95%, or greater sequence identity to a nucleotide sequence associated with NCBI Gene IDs: 2255 (SEQ ID NO: 56), 14165 (SEQ ID NO: 57), 25443 (SEQ ID NO: 58), 359830 (SEQ ID NO: 59), 395432 (SEQ ID NO: 60), 326285 (SEQ ID NO: 61) and retaining the wild-type FGF10 activity of the reference sequence. In some embodiments, the FGF10 is a polypeptide comprising a sequence having at least 60%, at least 65%, at least 70%, at least 75%, at least 80%, at least 85%, at least 90%, at least 95%, or greater sequence identity to one or more of the polypeptides associated with NCBI Gene IDs: 2255 (SEQ ID NO: 30), 14165 (SEQ ID NO: 31), 25443 (SEQ ID NO: 32), 359830 (SEQ ID NO: 33), 395432 (SEQ ID NO: 34), 326285 (SEQ ID NO: 35) and retaining the wild-type FGF10 activity of the reference sequence.

In some embodiments of any of the aspects, the second culture medium used to direct the differentiation of Nkx2-1+ lung epithelial progenitors along a proximal differentiation pathway and into airway basal stem cells comprises FGF2 and/or FGF10 polypeptides. In some embodiments of any of the aspects, during culture in the second culture media, the epithelial spheres are contacted with one or more FGF polypeptides. In some embodiments of any of the aspects, the one or more FGF polypeptides comprise FGF2 and/or FGF10. In some embodiments, the one or more FGF polypeptides comprise, consist of, or consist essentially of FGF2. In some embodiments, the one or more FGF polypeptides comprise, consist of, or consist essentially of FGF10. In some embodiments, the one or more FGF polypeptides comprise, consist of, or consist essentially of FGF2 and FGF10 polypeptides. In some embodiments of any of the aspects, the second culture media comprises FGF10 at about a concentration of 10 ng/mL to 100 ng/mL. In some embodiments of any of the aspects, the media comprises FGF2 and does not comprise FGF10. In some embodiments of any of the aspects, the second culture media comprises a concentration of about 0-250 ng/mL of FGF2.

In some embodiments of any of the aspects, the second culture medium comprises a Rho kinase (ROCK) inhibitor. In some embodiments of any of the aspects, the epithelial spheres or differentiated progeny thereof (e.g., airway progenitor cells and airway basal cells) are contacted with at least one ROCK inhibitor. Rho-associated coiled Kinases or Rho kinases refers to a family of serine/threonine kinases involved in the regulation of the cellular cytoskeleton. The structure and function of ROCK polypeptides are further described, e.g, in Gervaise Loirand "Rho Kinases in Health and Disease" *Pharmacological Reviews* (2015), 67 (4) 1074-1095; DOI: https://doi.org/10.1124/pr.115.010595, Mackay and Hall *J Biol Chem* 1998, 273, 20685; Aspenstrom *Curr Opin Cell Biol* 1999, 11, 95; Amano, et al. *Exp Cell Res* 2000, 261, 44, each of which is incorporated herein by reference in their entireties. Nucleic acid and amino acid sequences for ROCK1 and ROCK2 are known in the art and can include, e.g., the sequences associated with NCBI Gene IDs: 6093, 9475, 19877, 19878, or an ortholog thereof. Inhibitors of ROCK1 and/or ROCK 2 can include but are not limited to those described, e.g., in Feng Y et al. "Rho Kinase (ROCK) Inhibitors and Their Therapeutic Potential." *J Med Chem.* 2016 Mar. 24; 59(6):2269-300. doi: 10.1021/acs.jmedchem.5b00683, and WO2002076977A2, each of which is incorporated herein by reference their entireties.

In some embodiments of any of the aspects, the media comprises the ROCK inhibitor Y-27632, for example, at a concentration of about 10 μM, or between about 2-20 μM to promote cell survival post-sorting.

As used herein, "Y-27632" refers to a compound having the structure of Formula III or a pharmaceutically acceptable salt thereof. Y-27632 inhibits both ROCK1 and ROCK2 by competing with ATP for binding to the catalytic site. The structure and function of Y-27632 is further described, e.g, in Ishizaki T, et al. "Pharmacological properties of Y-27632, a specific inhibitor of rho-associated kinases." *Mol Pharmacol.* 2000 May; 57(5):976-83. PMID: 10779382, Watanabe, K., et al. "A ROCK inhibitor permits survival of dissociated human embryonic stem cells." *Nature Biotechnology* 25(6), 681-686 (2007), and Davies, S. P., et al. "Specificity and mechanism of action of some commonly used protein kinase inhibitors." *Biochem. J.* 351(1), 95-105 (2000), the contents of each of which are incorporated herein by reference in their entireties.

Formula III

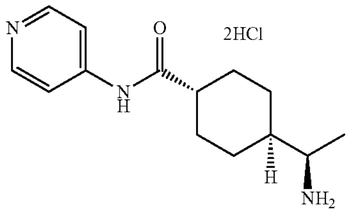

The synthesis of Y-27632 as well as the structure and synthesis of related compounds, e.g., derivatives, including those with similar biological activity are known in the art, see, e.g., WO2002076977A2; US-2004028716-A1; EP-2628482-A1; and Paleček J, et al. "A practical synthesis of Rho-Kinase Inhibitor Y-27632 and fluoro derivatives and their evaluation in human pluripotent stem cells." *Org Biomol Chem.* 2011 Aug. 7; 9(15):5503-10. doi: 10.1039/c1ob05332a, the contents of each of which are incorporated herein by reference in their entireties.

In some embodiments of any of the aspects, the second culture media comprises one or more steroids. In some embodiments of any of the aspects, the epithelial spheres or differentiated progeny thereof (e.g., airway progenitor cells and airway basal cells) described herein are contacted with one or more steroids. The structure, function, and synthesis of steroids are known in the art, e.g., U.S. Pat. Nos. 8,846,650; 9,149,486; 6,359,016; 6,284,804; 6,726,918; 6,899,717; 8,034,366; 8,506,987; 9,012,437; 8,043,628; the contents of each of which are incorporated herein by reference in their entireties. Exemplary steroids for use include, but are not limited to; dexamethasone, hydrocortisone, corticosterone, betnesol, prednisolone, celestone, fluorocortisone, orapred, prednisone, analogs, and derivatives thereof.

In some embodiments of any of the aspect, the second culture medium comprises dexamethasone. In some embodiments of any of the aspects, the epithelial spheres described herein are contacted with dexamethasone.

As used herein, "dexamethasone" refers to a compound having the structure of Formula IV or a pharmaceutically acceptable salt thereof.

Formula IV

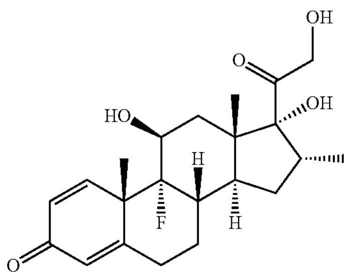

In some embodiments of any of the aspects, the second culture medium comprises 3',5'-cyclic monophosphate sodium salt. In some embodiments of any of the aspects, the epithelial spheres or differentiated progeny thereof (e.g., airway progenitor cells and airway basal cells) are contacted with 3',5'-cyclic monophosphate sodium salt. As used herein, "3',5'-cyclic monophosphate sodium salt" refers to a compound having the structure of Formula V or a pharmaceutically acceptable salt thereof.

Formula V

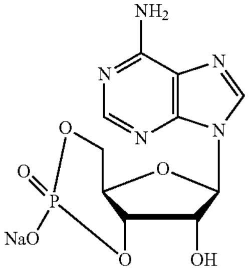

In some embodiments, the concentration of 3',5'-cyclic monophosphate sodium salt is at least about 10 nM to about 200 nM. In some embodiments, the concentration of 3',5'-cyclic monophosphate sodium salt is at least about 100 nM.

In some embodiments of any of the aspects, the second culture medium comprises 3-isobutyl-1-methyxanthine (IBMX). In some embodiments of any of the aspects, the epithelial spheres or differentiated progeny thereof (e.g., airway progenitor cells and airway basal cells) are contacted with 3-isobutyl-1-methyxanthine (IBMX). IBMX is an inhibitor of cyclic nucleotide phosphodiesterases (PDEs). When PDEs are inhibited, cellular cyclic AMP and cyclic GMP levels increase, thereby activating protein kinases, e.g., protein kinase A. As used herein "IBMX" refers to a compound having the structure of Formula VI or a pharmaceutically acceptable salt thereof.

Formula VI

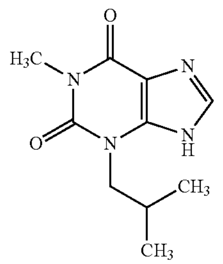

Synthesis and the mechanism of action of IBMX is described, e.g., in WO-9967403-A1; U.S. Pat. No. 10,702,588 B2; and Miao J Y, et al. "1-Methyl-3-isobutylxanthine delays apoptosis induced by deprivation of growth factors in vascular endothelial cells." *Acta Pharmacol Sin.* 2000 Oct. 21 (10):936-8. PMID: 11501048, the contents of each of which are incorporated herein by reference in their entireties. In some embodiments of any of the aspects, the IBMX concentration is about 25 to about 200 nM. In some embodiments of any of the aspects, the IBMX concentration is about 50 nM.

In some embodiments of any of the aspects, the methods described herein further comprise culturing the epithelial spheres in a second culture medium, wherein the second culture medium comprises one or more of fibroblast growth factor (FGF) polypeptides, one or more steroids (e.g., dexamethasone), and a Rho kinase (ROCK) inhibitor, thereby differentiating the epithelial spheres into airway progenitor cells. In some embodiments of any of the aspects, the methods described herein further comprise culturing the epithelial spheres in a second culture medium, wherein the second culture medium comprises one or more of fibroblast growth factor (FGF) polypeptides, one or more steroids (e.g., dexamethasone), 3',5'-cyclic monophosphate sodium salt, 3-isobutyl-1-methyxanthine (IBMX), and a Rho kinase (ROCK) inhibitor, thereby differentiating the epithelial spheres into airway progenitor cells. In some embodiments of any of the aspects, the methods described herein further comprise culturing the epithelial spheres in a second culture medium, wherein the epithelial cells are contacted with one or more of fibroblast growth factor (FGF) polypeptides, one or more steroids (e.g., dexamethasone), 3',5'-cyclic monophosphate sodium salt, and a Rho kinase (ROCK) inhibitor, thereby differentiating the epithelial spheres into airway progenitor cells.

In some embodiments of any of the aspects, the methods described herein further comprise culturing the epithelial spheres in a second culture medium, wherein the epithelial cells or differentiated progeny thereof (e.g., airway progenitor cells or airway basal stem cells) are contacted with one or more of fibroblast growth factor (FGF) polypeptides, one or more steroids (e.g., dexamethasone), 3',5'-cyclic monophosphate sodium salt, 3-isobutyl-1-methyxanthine (IBMX), and a Rho kinase (ROCK) inhibitor, thereby differentiating the epithelial spheres into airway progenitor cells.

In some embodiments of any of the aspects, the second culture medium described herein comprises FGF2, one or more steroids (e.g., dexamethasone), 3',5'-cyclic monophosphate sodium salt, 3-isobutyl-1-methyxanthine (IBMX), and a ROCK inhibitor. In some embodiments of any of the aspects, the culture media comprises FGF10, one or more steroids (e.g., dexamethasone), 3',5'-cyclic monophosphate sodium salt, 3-isobutyl-1-methyxanthine (IBMX), and a ROCK inhibitor. In some embodiments of any of the aspects, the second culture medium comprises FGF2, FGF10, one or more steroids (e.g., dexamethasone), 3',5'-cyclic monophosphate sodium salt, 3-isobutyl-1-methyxanthine (IBMX), and a ROCK inhibitor.

In some embodiments of any of the aspects, the epithelial spheres or differentiated progeny thereof (e.g., airway progenitor cells or airway basal stem cells) are contacted with FGF2, one or more steroids (e.g., dexamethasone), 3',5'-cyclic monophosphate sodium salt, 3-isobutyl-1-methyxanthine (IBMX), and a ROCK inhibitor. In some embodiments of any of the aspects, the epithelial spheres or differentiated progeny thereof (e.g., airway progenitor cells or airway basal stem cells) are contacted with FGF10, one or more steroids (e.g., dexamethasone), 3',5'-cyclic monophosphate sodium salt, 3-isobutyl-1-methyxanthine (IBMX), and a ROCK inhibitor. In some embodiments of any of the aspects, the epithelial spheres or differentiated progeny thereof (e.g., airway progenitor cells or airway basal stem cells) are contacted with FGF2, FGF10, one or more steroids (e.g., dexamethasone), 3',5'-cyclic monophosphate sodium salt, 3-isobutyl-1-methyxanthine (IBMX), and a ROCK inhibitor.

In some embodiments of any of the aspects, the epithelial spheres or differentiated progeny thereof (e.g., airway progenitor cells or airway basal stem cells) are cultured in the second culture medium for at least about 8 days or more, 9 days or more, 10 days or more, 11 days or more, 12 days or more, 13 days or more, 14 days or more, or 15 days or more. In some embodiments of any of the aspects, the epithelial spheres or differentiated progeny thereof (e.g., airway progenitor cells or airway basal stem cells) are cultured in the second culture medium for at least 8 days or more, 9 days or more, 10 days or more, 11 days or more, 12 days or more, 13 days or more, 14 days or more, or 15 days or more.

In some embodiments of any of the aspects, the epithelial spheres or differentiated progeny thereof (e.g., airway progenitor cells or airway basal stem cells) are cultured in the second culture medium for no more than 40 days, 35 days, 30 days, 25 days, or 20 days.

In some embodiments of any of the aspects, the epithelial spheres or differentiated progeny thereof (e.g., airway progenitor cells or airway basal stem cells) are cultured in the second culture medium for about 6 days to about 20 days. In some embodiments of any of the aspects, the epithelial spheres or differentiated progeny thereof (e.g., airway progenitor cells or airway basal stem cells) are cultured in the second culture medium for 6 days to 20 days. In some embodiments of any of the aspects, the epithelial spheres or differentiated progeny thereof (e.g., airway progenitor cells or airway basal stem cells) are cultured in the second culture medium for about 8 days to about 18 days. In some embodiments of any of the aspects, the epithelial spheres or differentiated progeny thereof (e.g., airway progenitor cells or airway basal stem cells) are cultured in the second culture medium for 8 days to 18 days. In some embodiments of any of the aspects, the epithelial spheres or differentiated progeny thereof (e.g., airway progenitor cells or airway basal stem cells) are cultured in the second culture medium for about 8 days to about 15 days. In some embodiments of any of the aspects, the epithelial spheres or differentiated progeny thereof (e.g., airway progenitor cells or airway basal stem cells) are cultured in the second culture medium for 8 days to 15 days.

In some embodiments of any of the aspects, the methods described herein comprise isolating or sorting airway progenitor cells produced by any of the methods described herein using one or more airway basal cell markers. In some embodiments of any of the aspects, the airway progenitor cells or airway BCs described herein express one or more BC markers. A BC marker can include but is not limited to: NK2 homeobox 1 (Nkx2-1); tumor protein 63 (TP63); cytoskeletal protein keratin 5 (KRT5); and nerve growth factor receptor (NGFR). For example, the sorting step can be used to enrich for specific airway progenitor cell populations, e.g., airway basal cells, from a heterogeneous population of cells comprising undifferentiated cells (e.g., iPS cells) and various sub-types of lung progenitor cells. In some embodiments of any of the aspects, the airway basal cell marker is TP63. In some embodiments of any of the aspects, the airway basal cell marker is NGFR. In some embodiments of any of the aspects, the airway basal cell markers are TP63 and NGFR. In some embodiments of any of the aspects, the airway basal cell markers are TP63, NGFR, and KRT5. In some embodiments of any of the aspects, the methods described herein further comprise isolating or sorting lung progenitor cells, epithelial spheres, and/or airway progenitor cells described herein using Coagulation factor III (F3) and/or Epidermal growth factor receptor (EGFR). Methods of sorting cells based on a particular cell surface marker can include, e.g. fluorescence-activated cell sorting (FACS) and others as described above or known in the art.

The airway basal cell marker, TP63 or tumor protein 63, is a member of the p53 family of transcription factors, is essential to the BC program in the airway but also other organs. The molecular function of T63 is further described, e.g., in Yang et al., *Nature* 1999, which is incorporated herein by reference in its entirety. In animal models of lung development, Tp63 expression is gradually restricted to the developing airways, where it is initially broadly expressed in immature airway progenitors and later restricted to a subset of tracheal cells that localize to the basement membrane and upregulate markers of adult BCs, including Krt5 and Ngfr.

In some embodiments of any of the aspects, the methods described herein comprise passaging and re-suspending the airway progenitor cells in the second culture medium described herein, thereby expanding the airway progenitor cells to generate the airway basal cells described herein.

It is contemplated herein that during extended 3D culture in the second culture medium that spontaneous differentiation of the airway progenitor cells to engineered airway BCs and secretory and MCCs can occur.

In some embodiments, the airway progenitor cells are passaged. In some embodiments, the airway progenitor cells are not passaged. In some embodiments, the airway progenitor cells are passaged at least 5 times or more, 6 times or more, 7 times or more, 8 times or more, 9 times or more, or 10 times or more.

In some embodiments of any of the aspects, the methods described herein comprise culturing the airway progenitor cells described herein in a third culture medium, thereby generating the airway basal cells described herein. In some embodiments of any of the aspects, the methods described herein comprise culturing the airway basal cells described herein in the third culture medium. It is contemplated herein that inhibition of SMAD and Rho-associated protein kinase (ROCK) signaling induce a proliferative state of airway BCs and significantly increase overall yield from serially passaged cultures while maintaining, to an extent, their differentiation capacity. Compositions of the third culture medium used in the methods described herein are discussed further below.

In some embodiments of any of the aspects, the third culture medium consists of or consists essentially of Pneumacult ExPlus™ (StemCell Technologies, Inc.); and one or more of: at least one inhibitor of SMAD, at least one inhibitor of transforming growth factor β (TGF-β), at least one bone morphogenetic protein (BMP) inhibitor, and at least one ROCK inhibitor, or any combination thereof. In some embodiments of any of the aspects, the third culture medium consists of or consists essentially of Pneumacult ExPlus™, at least one inhibitor of SMAD, at least one inhibitor of transforming growth factor β (TGF-β), at least one bone morphogenetic protein (BMP) inhibitor, and at least one ROCK inhibitor In some embodiments, the third culture medium comprises at least one inhibitor of transforming growth factor β (TGF-β). TGF-β is a cytokine having three isoforms and which activates TGF-β receptors, thereby triggering kinase signaling caseds that control, e.g., differentiation, chemotaxis proliferation, and immune cell activation. Sequences for TGF-β are known for a number of species, e.g., human TGF-β sequences can be found under the NCBI Gene ID 7040. Exemplary assays that can be used to determine the inhibitory activity of a TGFβ signaling pathway inhibitor include, without limitation, electrophoretic mobility shift assays, antibody supershift assays, as well as TGFβ-inducible gene reporter assays, as described in WO 2006/012954, among others.

In some embodiments of any of the aspects, an inhibitor of transforming growth factor β (TGF-β) is a TGFβ receptor inhibitor. In some embodiments, the TGFβ receptor inhibitor is selected from the group consisting of ALK5 inhibitor II, SB431542, LY364947, DMH1, and A83-01. In some embodiments, the TGFβ receptor inhibitor is A83-01.

Several structurally distinct classes of small molecules inhibitors of TGFβ signaling have been reported. These agents can be classified on the basis of the core molecular scaffolds of these molecules. For example, TGFβ signaling inhibitors may contain a dihydropyrrlipyrazole, imidazole, pyrazolopyridine, pyrazole, imidazopyridine, triazole, pyridopyrimidine, pyrrolopyrazole, isothiazole or oxazole functionality as the core structural fragment of the molecule. Some non-limiting examples of small molecule inhibitors of TGFβ signaling include ALK5 inhibitor II (also referred to as E-616452), LY364947 (also referred to as ALK5 Inhibitor I, TbR-I Inhibitor, Transforming Growth Factor-b Type I Receptor Kinase Inhibitor), A83-01, and DMH1, described above. Other examples of small molecules that can be used to modulate TGFβ signaling in conjunction with the compositions and methods of the invention include SB431542 (4-(5-Benzol[1,3]dioxol-5-yl-4-pyridin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate, an Alk5 inhibitor), Galunisertib (LY2157299, an Alk5 inhibitor), LY2109761(4-[2-[4-(2-pyridin-2-yl-5,6-dihydro-4H-pyrrolo[1,2-b]pyrazol-3-yl) quinolin-7-yl]oxyethyl]morpholine, an Alk5/TGFβRII inhibitor), SB525334 (6-[2-tert-butyl-5-(6-methylpyridin-2-yl)-1H-imidazol-4-yl]quinoxaline, an Alk5 inhibitor), GW788388 (N-(oxan-4-yl)-4-[4-(5-pyridin-2-yl-1H-pyrazol-4-yl)pyridin-2-yl]benzamide, an Alk5 inhibitor), K02288 (3-[6-amino-5-(3,4,5-trimethoxyphenyl)pyridin-3-yl]phenol, an Alk4/Alk5 inhibitor), SD-208 (2-(5-chloro-2-fluorophenyl)-N-pyridin-4-ylpteridin-4-amine, an Alk5 inhibitor), EW-7197 (N-((4-([1,2,4]triazolo[1,5-a]pyridin-6-yl)-5-(6-methylpyridin-2-yl)-1H-imidazol-2-yl)methyl)-2-fluoroaniline, an Alk4/Alk5 inhibitor), and LDN-212854(5-[6-[4-(1-Piperazinyl)phenyl]pyrazolo[1,5-a]pyrimidin-3-yl]-quinoline, an Alk4/Alk5 inhibitor).

Additional examples of small molecule TGFβ modulators include antagonists of TGFβ receptors, such as 2-(3-(6-Methylpyridin-2-yl)-1H-pyrazol-4-yl)-1,5 napththyridine, [3-(Pyridin-2-yl)-4-(4-quinolyl)]-1H-pyrazole, and 3-(6-Methylpyridin-2-yl)-4-(4-quinolyl)-1-phenylthiocarbamoyl-1H-pyrazole. Other small molecule inhibitors include, but are not limited to, SB-431542, (4-[4-(1,3-Benzodioxol-5-yl)-5-(2-pyridinyl)-1H-imidazol-2-yl]-benzamide, described in Halder et al. Neoplasia 7:509 (2005)), SM16, a small molecule inhibitor of TGFβ receptor ALK5, the structure of which is shown below (Fu et al. Arteriosclerosis, Thrombosis and Vascular Biology 28:665 (2008)), SB-505124 (an Alk4/Alk5 inhibitor, structure shown below, described in Dacosta Byfield et al. Molecular Pharmacology 65:744 (2004)), and 6-bromo-indirubin-3'-oxime (described in U.S. Pat. No. 8,298,825), the disclosures of each of which are incorporated herein by reference.

Formula IX

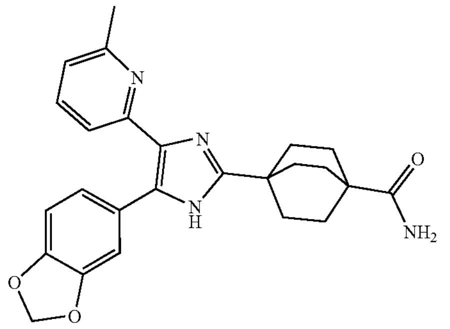

SM16

-continued

Formula X

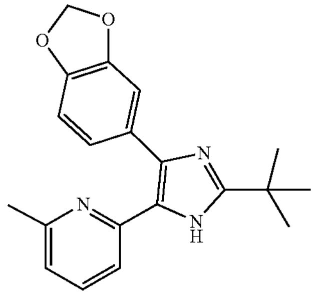

SB-505124

In some embodiments of any of the aspects, the at least on TGFβ inhibitor comprises SB431542. As used herein, "SB431542" refers a compound having the structure of Formula VII or a pharmaceutically acceptable salt thereof. SB431542 is an inhibitor of ALK5, ALK4, and ALK7, and therefore inhibits the TGFβ/Smad signaling pathway. Synthesis and mechanisms of action of SB431542 are described, e.g., in Laping N J, et al. Inhibition of transforming growth factor (TGF)-beta1-induced extracellular matrix with a novel inhibitor of the TGF-beta type I receptor kinase activity: SB-431542. *Mol Pharmacol.* 2002 July; 62(1):58-64. doi: 10.1124/mol.62.1.58. PMID: 12065755, the content of which is incorporated herein by reference in its entirety. The TGFβ/Smad signaling pathway is further discussed below.

Formula VII

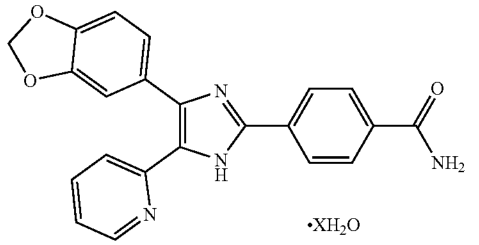

Additional examples of inhibitors of TGF-β signaling are described in, e.g., Callahan et al. Journal of Medicinal Chemistry 45:999 (2002); Sawyer et al. Journal of Medicinal Chemistry 46:3953 (2003); Gellibert et al. Journal of Medicinal Chemistry 47:4494 (2004); Tojo et al. Cancer Science 96:791 (2005); Petersen et al. Kidney International 73:705 (2008); Yingling et al. Nature Reviews Drug Discovery 3:1011 (2004); Byfield et al. Molecular Pharmacology 65:744 (2004); Dumont et al. Cancer Cell 3:531 (2003); WO 2002/094833; WO 2004/026865; WO 2004/067530; WO 2009/032667; WO 2004/013135; WO 2003/097639; WO 2007/048857; WO 2007/018818; WO 2006/018967; WO 2005/039570; WO 2000/031135; WO 1999/058128; U.S. Pat. Nos. 6,509,318; 6,090,383; 6,419,928; 7,223,766; 6,476,031; 6,419,928; 7,030,125; 6,943,191; US 2005/0245520; US 2004/0147574; US 2007/0066632; US 2003/0028905; US 2005/0032835; US 2008/0108656; US 2004/015781; US 2004/0204431; US 2006/0003929; US 2007/0155722; US 2004/0138188; and US 2009/0036382, the disclosures of each which are incorporated herein by reference. Inhibitory antibodies capable of attenuating TGFβ receptor activity include Lerdelimumab, and an antibody that binds the TGFβ receptor type II. Other examples include GC-1008, an antibody that binds and antagonizes all isoforms of human TGFβ, as well as ID11, an antibody that binds all isoforms of murine TGFβ. These antibodies are described in detail, e.g., in U.S. Pat. No. 8,603,818, the disclosure of which is incorporated herein by reference.

Furthermore, a variety of proteins that antagonize the TGFβ signaling cascade can be used in the methods described herein, including Decorin, an extracellular matrix proteoglycan that negatively regulates TGFβ activity, as well as Lefty1, Lefty2, Follistatin, Noggin, Chordin, Cerberus, Germlin, Inhibin, Cystatin C, Recombinant Mouse Lefty-1 (an ACVR2B inhibitor), as well as the Smad proteins Smad6 and Smad7, which serve to prevent the phosphorylation of the R-Smad proteins or recruit ubiquitin ligases to the TGFβ receptor type I so as to promote the degradation of the receptor. These proteins are described in detail in U.S. Pat. No. 8,298,825, the disclosure of which is incorporated by reference herein.

A variety of inhibitory agents that operate by a mechanism of RNA interference have been developed to antagonize the biological processes described by the methods of the invention. For instance, TGFβ receptor type II siRNA polynucleotides have been reported that are derived from the human TGFβRII sequence (Genbank Accession Number: M85079). The siRNA duplex sequences were developed against particular target sequences within the TGFβ receptor type II gene and have been used to knock down expression of the receptor in a variety of whole cell models. These siRNA sequences are described in detail in U.S. Pat. No. 8,067,389, the disclosure of which is incorporated herein by reference. Other oligonucleotide-based modulators of TGFβ signaling, such as siRNAs and antisense oligonucleotides, are described in U.S. Pat. Nos. 5,731,424; 6,124,449; US 2008/0015161; US 2006/0229266; US 2004/0006030; US 2005/0227936; and US 2005/0287128, the disclosures of each of which are incorporated herein by reference. siRNAs useful for targeting TGFβR or ALK5 expression can be readily designed and tested. A database of siRNA sequences and a predictor of siRNA sequences has been established (Chalk et al. (Nucleic Acids Research 33: D131 (2005). This database can be used to predict the thermodynamic parameters of a particular siRNA-target mRNA interaction, as well as to evaluate the propensity of designed siRNA sequences for off-target interactions. The database is available as an electronic resource at www.siRNA.cgb.ki.se.

In some embodiments, the third culture medium comprises at least one inhibitor of SMAD. SMADs comprise a family of polypeptides that regulate cell development and cell growth. SMAD signaling pathways are further described, e.g., in Miller et al, (2020), and U.S. Pat. No. 8,298,825, which are incorporated herein by reference in its entirety. Inhibitors of SMAD are known in the art. For example, A 83-01 is a potent inhibitor of activin receptor-like kinase (ALK) including ALK5 (type I transforming growth factor-β receptor), ALK4 (type IB activin receptor), and ALK7 (type I NODAL receptor). Inhibition of Alk-5 inhibits SMAD signaling.

In some embodiments of any of the aspects, the inhibitor of SMAD is A83-01 or a derivative thereof. As used herein, the term "A83-01" refers to a compound with the structure of Formula XI or a pharmaceutically acceptable salt thereof.

Formula XI

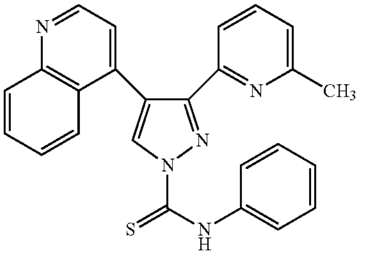

Methods of synthesizing A83-01 and pharmacological mechanisms of action are further described, e.g., Tojo et al (2005) "The ALK5 inhibitor A-83-01 inhibits smad signaling and epithelial-to-mesenchymal transition by transforming growth factor-β." *Cancer.Sci.* 96 791 PMID: 16271073; and WO-2017206837-A1, the contents of each of which are incorporated herein by reference in their entireties.

In some embodiments of any of the aspects, the third culture medium comprises at least one inhibitor of a bone morphogenic protein (BMP). BMPs are discussed elsewhere herein. In some embodiments of any of the aspects, the airway progeniptor cells or differentiated progeny thereof (e.g., airway basal cells) are contacted with an inhibitor of BMP. BMP inhibitors are known in the art. For example, BMP inhibitors can include dorsomorphin. Exemplary BMP inhibitors include DMH1 (4-[6-(4-Isopropoxyphenyl)pyrazolo[1,5-a]pyrimidin-3-yl]quinoline, 4-[6-[4-(1-Methylethoxy)phenyl]pyrazolo[1,5-a]pyrimidin-3-yl]-quinoline), K02288 (3-(6-amino-5-(3,4,5-trimethoxyphenyl)pyridin-3-yl)phenol), LDN-212854 (5-[6-[4-(1-Piperazinyl)phenyl] pyrazolo[1,5-a]pyrimidin-3-yl]-quinoline), LDN-193189 (4-[6-[4-(1- Piperazinyl)phenyl]pyrazolo[1,5-a]pyrimidin-3-yl]-quinoline), LDN-214117 (1-(4-(6-Methyl-5-(3,4,5-trimethoxyphenyl)pyridin-3-yl)phenyl)piperazine), and ML347 (5-[6-(4-methoxyphenyl)pyrazolo[1,5-a]pyrimidin-3-yl]quinoline). In some embodiments of any of the aspects, the BMP inhibitor is DMH1.

As used herein, the term "DMH1" refers to the compound also known as 4-[6-(4-Isopropoxyphenyl)pyrazolo [1,5-a] pyrimidin-3-yl] quinoline with the structure of Formula XII or any pharmaceutically acceptable salt thereof. DMH1 is a dorsomorphin homolog that selectively inhibits ALK2 and promotes differentiation of pluripotent stem cells. DMH1 is also an inhibitor of BMP. See, e.g., Hao J, et al. DMH1, a small molecule inhibitor of BMP type I receptors, suppresses growth and invasion of lung cancer. PLoS One. 2014; 9(6):e90748. (2014), which is incorporated herein by reference in its entirety.

Formula XII

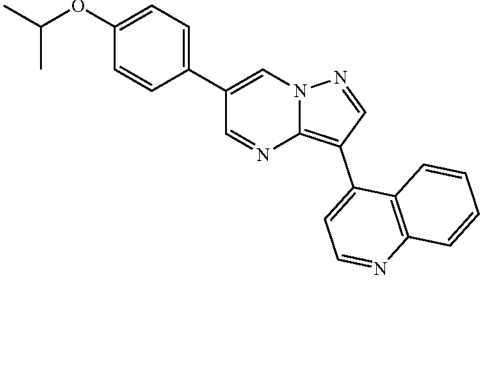

In some embodiments of any of the aspects, the at least one BMP inhibitor comprises dorsomorphin. As used herein, "dorsomorphin" refers to the compound of Formula VIII or a pharmaceutically acceptable salt thereof. Dorsomorphin inhibits bone morphogenetic protein (BMP) signaling via inhibition of ALK2, ALK3, and ALK6. See, also, e.g., Yu P B, et al. "Dorsomorphin inhibits BMP signals required for embryogenesis and iron metabolism." *Nat Chem Biol.* 2008 Jan. 4(1):33-41. doi: 10.1038/nchembio.2007.54. Epub 2007 Nov. 18. PMID: 18026094; PMCID: PMC2727650, the contents of which is incorporated herein by reference in its entirety.

Formula VIII

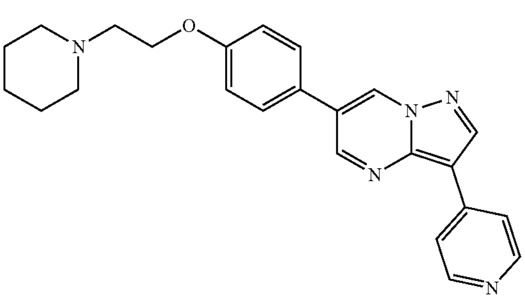

In some embodiments of any of the aspects, the third culture medium comprises A83-01, DMH1, and Y-27632. In some embodiments of any of the aspects, the airway progenitor cells or the airway basal cells described herein are contacted with A83-01, DMH1, and Y-27632. In some embodiments of any of the aspects, the third culture medium comprises 1 μM A83-01, 1 μM DMH1, and 10 μM Y-27632.

In some embodiments of any of the aspects, the third culture medium comprises from about 10 nM to about 100 μM A83-01. In some embodiments of any of the aspects, the third culture medium comprises from about 100 nM to about 10 μM A83-01. In some embodiments of any of the aspects, the third culture medium comprises about 1 μM A83-01. In some embodiments of any of the aspects, the third culture medium comprises from 10 nM to 100 μM A83-01. In some embodiments of any of the aspects, the third culture medium comprises from 100 nM to 10 μM A83-01. In some embodiments of any of the aspects, the third culture medium comprises 1 μM A83-01.

In some embodiments of any of the aspects, the third culture medium comprises from about 10 nM to about 100 μM DMH1. In some embodiments of any of the aspects, the third culture medium comprises from about 100 nM to about 10 μM DMH1. In some embodiments of any of the aspects, the third culture medium comprises about 1 μM DMH1. In some embodiments of any of the aspects, the third culture medium comprises from 10 nM to 100 μM DMH1. In some embodiments of any of the aspects, the third culture medium comprises from 100 nM to 10 μM DMH1. In some embodiments of any of the aspects, the third culture medium comprises 1 μM DMH1.

In some embodiments of any of the aspects, the third culture medium comprises from about 100 nM to about 1,000 μM Y-27632. In some embodiments of any of the aspects, the third culture medium comprises from about 1 μM to about 100 μM Y-27632. In some embodiments of any of the aspects, the third culture medium comprises about 10 μM Y-27632. In some embodiments of any of the aspects, the third culture medium comprises from 100 nM to 1,000

μM Y-27632. In some embodiments of any of the aspects, the third culture medium comprises from 1 μM to 100 μM Y-27632. In some embodiments of any of the aspects, the third culture medium comprises 10 μM Y-27632.

In some embodiments of any of the aspects, the cells are cultured in the third culture medium for at least about 24 hours or more, at least about 2 days or more, at least about 3 days or more, at least about 4 days or more, at least about 5 days or more, at least about 6 days or more, at least about 7 days or more, at least about 8 days or more, at least about 9 days or more, at least about 10 days or more, at least about 11 days or more, at least about 12 days or more, at least about 13 days or more, at least about 14 days or more, or at least about 15 days or more.

In some embodiments of any of the aspects, the cells described herein are genetically modified. In some embodiments of any of the aspects, the cells described herein comprise a nucleic acid encoding at least one Nkx2-1+ lung progenitor cell marker and/or at least one airway BC marker operably linked to at least one inducible promoter. Nucleic acids can be stably integrated in the genome of the cell and operably linked to a promoter active in the cell. Alternatively, nucleic acids encoding the markers (e.g., polypeptides) described herein can be operably linked to a promoter in an expression construct. Expression constructs include any nucleic acid constructs capable of directing expression of a gene or other nucleic acid sequence of interest (e.g., Nkx2-1-GFP). In some embodiments of any of the aspects, the lung progenitor cells described herein are contacted with a nucleic acid comprising: Nxk2-1; at least one reporter gene, and optionally, an inducible promoter. Methods of producing a stable cell line of Nkx2-1+ lung progenitor cells are further described, e.g., McCauley, et al. (2017). "Efficient derivation of functional human airway epithelium from pluripotent stem cells via temporal regulation of Wnt signaling." *Cell Stem Cell* 20, 844-857.e6. A stable cell line allows for fascile isolation of Nkx2-1+ lung progenitor cells from a heterogeneous population of cells by methods known in the art, e.g., flow cytometry sorting.

In some embodiments of any of the aspects, a vector is capable of driving expression of one or more nucleic acid sequences in a mammalian cell. Suitable expression vectors include plasmid vectors (such as those available from Stratagene, Madison Wis.), viral vectors (such as replication defective retroviral vectors, herpes virus, adenovirus, adenovirus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205).

In some embodiments, the gene encoding the Nkx2-1+ lung progenitor cell marker is targeted and replaced with a gene encoding at least one airway basal cell marker. Thus, in another aspect, described herein is a nucleic acid comprising: (a) a promoter; (b) one or more airway basal cell markers selected from Nkx2-1; TP63; KRT5; and NGFR; and (c) at least one reporter gene. In some embodiments, the nucleic acid comprises an inducible promoter.

A "reporter gene" as used herein encompasses any gene that is genetically introduced into a cell that adds to the phenotype of the stem cell. Reporter genes as disclosed in this invention are intended to encompass fluorescent, enzymatic and resistance genes, but also other genes which can easily be detected by persons of ordinary skill in the art. In some embodiments of the invention, reporter genes are used as markers for the identification of particular stem cells, lung progenitor cells, airway basal cells and their differentiated progeny.

In some embodiments the reporter gene is or encodes a selectable marker. The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene.

In some embodiments of any of the aspects, the reporter gene encodes a detectable marker or a fluorescent marker. Detectable markers include green fluorescent protein (GFP) blue, sapphire, yellow, red, orange, and cyan fluorescent proteins and variants of any of these. Luminescent proteins such as luciferase (e.g., firefly or Renilla luciferase) are also of use. As will be evident to one of skill in the art, the term "selectable marker" as used herein can refer to a gene or to an expression product of the gene, e.g., an encoded protein.

In some embodiments of any of the aspects, the reporter gene is green fluorescent protein (GFP) and/or tdTomato. In some embodiments the nucleic acid comprises two reporter genes.

In some embodiments of any of the aspects, the methods described herein further comprise gene editing to correct a mutation. In some embodiments of any of the aspects, the method comprises gene editing prior to delivering a nucleic acid described herein.

Methods of gene editing in a host cell are known in the art. Non-limiting examples of gene knockdown, inhibition, and alteration include CRISPR/Cas9 systems, Transcription Agonist-Like Effectors Nucleases (TALENS), and inhibitory nucleic acids. One of ordinary skill in the art can design and test an gene editing agent or system that targets the Nkx2-1-GFP gene described herein. Methods of preparing and delivering gene editing systems are described, e.g., in WO2015/013583A2; U.S. Pat. No. 10,640,789 B2; US Pg. No. US2019/0367948 A1; US Pg. No. 2017/0266320 A1; US Pg No. 2018/0171361 A1; US Pg. No. 2016/0175462 A1; and US Pg. No. 2018/0195089 A1, the contents of each of which are incorporated herein by reference in their entirety.

In another approach, base editing can be used to introduce point mutations in cellular DNA or RNA without making double-stranded breaks. In some embodiments, the method of altering an endogenous nucleic acid described herein is by cytosine base editing, adenine base editing, antisense-oligonucleotide-directed A to I RNA editing, or Cas 13 base editing. Methods of base editing are known in the art and described, e.g., in Rees et al. *Nature Rev Genet.* 19(12); 770-788 (2018) and Kopmor et al. *Nature* 533, 420-424 (2016), which are incorporated herein by reference in their entireties.

In some embodiments, a cell as described herein is transiently transfected with the components of a gene editing system (such as by transient transfection of one or more vectors, or transfection with RNA), and modified through the activity of a CRISPR or base editing complex, to establish a new cell or cell line comprising cells containing a modification to the host cell gene. The airway basal cell markers introduced to the cell can then be used to select for populations of airway progenitor cells that will differentiate to an airway basal cell described herein (e.g., a TP63+ airway basal cell).

In some embodiments of any of the aspects, described herein is a cell comprising a nucleic acid as described herein. In some embodiments of any of the aspects, described herein is a cell comprising a nucleic acid comprising: (a) an inducible promotor; (b) one or more basal cell markers selected from Nkx2-1; TP63; KRT5; and NGFR; and (c) at least one reporter gene.

In another aspect, described herein is an airway basal cell line generated by any of the methods or embodiments of said methods described herein. In another aspect, the airway basal cell line comprises a population of airway basal cells generated by any of the methods described herein. An airway basal cell produced by the methods described herein can be distinguished from a naturally-occurring airway basal cell by that fact that the airway basal cells produced by the methods described herein give rise to differentiated progeny (secretory and ciliated cells) that have transcriptional signatures more similar to fetal secretory and ciliated cells than to their adult counterparts (e.g., when placed in air liquid interface culture). In this respect, the iBCs exhibit a differentiation pattern distinct from that of primary adult airway basal cells.

In some embodiments of any of the aspects, an airway basal cell generated by the methods described herein has clonal self-renewal capacity. In some embodiments of any of the aspects, an airway basal cell generated by the methods described herein have the ability to differentiate into multiple lineages, e.g., in ALI culture and/or in tracheal xenografts.

In some embodiments of any of the aspects, the airway basal cell line is cryopreserved. As used herein, the term "cryopreserved" refers to a viable cell frozen in aqueous solution, where the aqueous solution is formulated to protect the cell during the freezing process. Cells and tissues are frequently cryopreserved to temporally extend their viability and usefulness in biomedical applications. The process of cryopreservation involves, in part, placing cells into aqueous solutions containing electrolytes and chemical compounds that protect the cells during the freezing process (cryoprotectants). Such cryoprotectants are often small molecular weight molecules, such as glycerol, propylene glycol, ethylene glycol or dimethyl sulfoxide (DMSO), which prevent or limit intracellular ice crystal formation upon freezing of the cells. In this protocol, airway basal cells are cryopreserved in medium three with 10% DMSO. Protocols for both cryopreservation and thawing or re-establishing previously frozen cells in culture are known in the art, e.g., U.S. Pat. No. 9,877,475 B2; Karlsson J. O., Toner M. Long-term storage of tissues by cryopreservation: critical issues. Biomaterials. 1996; 17:243-256; and D.E. Principles of cryopreservation. Methods Mol Biol. 2007; 368:39-57, which are incorporated herein by reference in their entireties.

In another aspect, described herein is a kit comprising one or more of the culture media and/or cell populations described herein. In some embodiments, the kit comprises first cell culture medium described herein. In some embodiments the kit comprises the second cell culture medium described herein. In some embodiments the kit comprises the third cell culture medium described herein. In some embodiments the kit comprises the airway basal cells described herein. In some embodiments, the kit comprises the airway basal cells described herein and a hydrogel. In some embodiments, the kit comprises the airway basal cells described herein; and one or more of: the first culture medium described herein, the second culture medium described herein, and the third culture medium described herein; and materials and packaging therefore. In some embodiments, the kit comprises the airway basal cells described herein; a hydrogel; one or more of: the first culture medium described herein, the second culture medium described herein, and the third culture medium described herein; and materials and packaging therefore. In yet another aspect, described herein is a kit comprising cryopreserved airway basal cells described herein. In another aspect, described herein is a kit comprising cryopreserved airway basal cells described herein; one or more of: the first culture medium described herein, the second culture medium described herein, and the third culture medium described herein; and materials and packaging therefore.

A kit is an assemblage of materials or components, including at least one of the media, cell, or other reagents described herein. The exact nature of the components configured in the kit depends on its intended purpose. In some embodiments of any of the aspects, a kit includes instructions for use. "Instructions for use" typically include a tangible expression describing the technique to be employed in using the components of the kit, e.g., to differentiate and/or expand cells. Still in accordance with the present invention, "instructions for use" may include a tangible expression describing the preparation of a medium, such as dilution, mixing, or incubation instructions, and the like, typically for an intended purpose. Optionally, the kit also contains other useful components, such as, measuring tools, diluents, buffers, pharmaceutically acceptable carriers, or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components. Thus, for example, a package can be a glass vial used to contain suitable quantities of a composition containing a volume of a medium, cell, or other reagent described herein. The packaging material generally has an external label which indicates the contents and/or purpose of the kit and/or its components.

In another aspect, described herein is a disease model comprising the airway basal cell line or a population of airway basal cells generated by the methods described herein.

In some embodiments of any of the aspects, the airway basal cell line is derived from a subject with a pulmonary disease. Exemplary pulmonary diseases that can be modeled using the airway basal cell line prepared as described herein include those discussed, for example, mucus metaplasia of asthma, the chloride transport defects of cystic fibrosis (CF), and the ciliary dysfunction of primary ciliary dyskinesia (PCD), and lung malformations.

Reliable methods of generating, differentiating, and maturing human in-vitro differentiated airway basal cells are necessary, for example, to ensure that disease phenotypes represent, where appropriate, onset and functional phenotypes of diseases and disorders described herein in order to identify therapeutics to treat these diseases and disorders effectively. The methods described herein can reliably produce mature iBCs that can be used to study tracheal and respiratory function in both health and disease. Additional examples of diseases that can be modeled using the airway basal cells generated by the methods described herein include but are not limited to those described in Al-Qadi et al. *Respiratory Medicine* Volume 107, Issue 9, (2013) which is incorporated herein by reference in its entirety.

For example, in asthma, the epithelium plays a sentinel role in pathogenesis, and there is significant interest in understanding epithelial dysfunction and the contribution of genetic variants to asthma susceptibility (See, e.g., Loxham et al., 2014). The working examples demonstrate that a mucus meta-plasia phenotype is induced in iPSC-derived airway epithelium in response to stimulation with the Th-2 cytokine IL-13. In CF, where many mutations in one gene necessitate individual models of disease for predicting personalized therapeutics, the working examples demonstrate that patient-specific iPSCs or their gene-edited progeny can be differentiated into iBCs and give rise to airway epithelia exhibiting quantifiable CFTR-dependent currents of sufficient magnitude for disease modeling using the gold-standard Ussing chamber assay of CFTR function.

The airway basal cells generated by the methods described herein permit the evaluation of the response of airway BCs to various treatments or stimuli. In addition, the disease model described herein can be used to determine the toxicity and therapeutic outcomes of candidate drugs or agents.

In various embodiments, quantifiable parameters of airway basal cells can include structure, barrier function, marker expression, capacity to self-renew and proliferate, cilia beat frequency, metabolic respiratory capacity, oxygen consumption, electrophysiological and biophysical parameters (e.g., Cl− currents). In some embodiments, quantifiable parameters include survival and/or division or regeneration of the e.g., stem cell-derived airway BCs described herein.

While most parameters will provide a quantitative readout, in some instances a semi-quantitative or qualitative result will be acceptable. Methods of measuring the various parameters useful for evaluating airway basal cell status or function include but are not limited to: immunoassays, cellular morphology assays, electrophysiology (e.g., Ussing chamber voltage clamp), metabolic assays (e.g., cellular bioenergetics assays and oxygen consumption tests), video microscopy (e.g., high speed video-microscopy), transmission electron microscopy, and limiting dilution tracheosphere assays.

In some embodiments of any of the aspects, the airway basal cell line is contacted with an agent that induces a pathological phenotype. For example, Interleukin-13 (IL-13) is an inflammatory cytokine in asthma and can induce mucus metaplasia. Mucus metaplasia is characterized by increased MUC5AC+ cell numbers via the activation of STATE and SPDEF, at the expense of multicillieated cells (MCCs) and MUC5B+ cell frequencies. See, e.g., Kondo et al., 2002; Seibold, 2018; Woodruff et al., 2009, which are incorporated herein by reference in their entireties. The working examples demonstrate that IL-13 can induce this pathological phenotype in the airway basal cells generated by the methods described herein.

In some embodiments of any of the aspects, the airway basal cell line is genetically modified. In some embodiments of any of the aspects, the airway basal cell line is genetically modified to express a mutation in the CFTR gene. The CFTR gene encodes the cystic fibrosis transmembrane conductance regulator (CFTR) polypeptide. CFTR is an ABC transporter-class ion channel protein that conducts chloride ions across epithelial cell membranes. Mutations of the CFTR gene affecting chloride ion channel function lead to dysregulation of epithelial fluid transport in the lung, pancreas and other organs, resulting in cystic fibrosis. Cystic fibrosis is discussed in further detail below.

In some embodiments, the mutation in CFTR is selected from the group consisting of: CFTR-AF508 (also known as CFTR-delF508) CTFR-G551D, CFTR-G542X, CFTR-L927P, CFTR-E60X, CFTR-4015delATTT, and CFTR-A455E. The airway basal cell line can be genetically modified to express a genetic defect or genetic lesion in the CFTR gene e.g., as disclosed in Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451), or any of the >1000 disease causing mutations in the CF gene identified and disclosed on the database site at: world-wide-web: genet.sickkids.on.ca/cftr/. In some embodiments, the airway basal cells described herein are genetically modified to correct one or more of these CFTR mutations.

In some embodiments of any of the aspects, the airway basal cell line is genetically modified to express a mutation in the DNAH5. Mutations in DNAH5 have been associated with primary ciliary dyskinesia (PCD). DNAH5 encodes the dynein heavy chain 5 polypeptide, a member of the dynein family of polypeptides. Dyneins are involved in moving cytoskeletal proteins called, microtubles, in cells by converting chemical energy stored in adenosine triphosphate (ATP) to mechanical function, e.g., beating of cilia in the respiratory tract, cellular cargo transport, and mitosis. The structure and function of DNAH5 is further described, e.g., in Ibanez-Tallon, I. et al. "Loss of function of axonemal dynein Mdnah5 causes primary ciliary dyskinesia and hydrocephalus." Hum. Molec. Genet. (2002), which is incorporated herein by reference in its entirety. In some embodiments, the mutation in DNAH5 is c.12617G>A, p.Trp4206Ter. In some embodiments, the airway basal cells described herein are genetically modified to correct a DNAH5 mutation.

In another aspect, described herein is a transplant composition comprising the airway basal cells produced by the methods described herein. The transplant composition can be administered to a subject in need of treatment of a pulmonary disease.

As used herein, the terms "administering," "introducing" and "transplanting" are used interchangeably in the context of the placement of cells, e.g. airway basal cells, as described herein into a subject, by a method or route which results in at least partial localization of the introduced cells at a desired site, such as a site of injury or repair, such that a desired effect(s) is produced. The airway BCs can be implanted directly to the lung, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment.

In other embodiments, the cells can be administered via an indirect systemic route of administration, such as an intraperitoneal or intravenous route.

In some embodiments of any of the aspects, the composition and/or cells are administered by transplantation or implantation. In some embodiments of any of the aspects, the composition and/or cells are administered by a catheter. In some embodiments of any of the aspects, the composition and/or cells are administered by having a medical professional physically place the composition and/or cells at the desired location, e.g., by swabbing, microsurgery, laparoscope use, endoscope use, or other method known in the art.

In some embodiments of any of the aspects, the compositions and/or cells described herein can be administered by inhalation, e.g., as a vapor or aerosol formulation or by nebulization. For use as aerosols, a composition described herein can be provided in solution or suspension may be packaged in a pressurized aerosol container together with suitable propellants, for example, hydrocarbon propellants like propane, butane, or isobutane with conventional adjuvants. A composition described herein can also be administered in a non-pressurized form such as in a nebulizer or atomizer. In some embodiments, a composition can also be administered directly to the airways in the form of a dry powder, e.g., by use with an inhaler. Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

In some embodiments of the aspects described herein, the population of cells being administered according to the methods described herein comprises allogeneic cells or their obtained from one or more donors. As used herein, "allogeneic" refers to a cardiomyocyte obtained from or derived from (e.g., differentiated from) one or more different donors of the same species, where the genes at one or more loci are not identical. For example, cells being administered to a subject can be derived from umbilical cord blood obtained from one more unrelated donor subjects, or from one or more non-identical siblings. In some embodiments, syngeneic cell populations can be used, such as those obtained from genetically identical animals, or from identical twins. In other embodiments of this aspect, the airway basal cells described herein are autologous cells; that is, the cells are obtained or isolated from a subject (or derived from) and administered to the same subject, i.e., the donor and recipient are the same.

A transplant composition for humans may include one or more pharmaceutically acceptable carriers or materials as excipients. In contrast, a cell culture composition (not for human transplant) typically will use research reagents like cell culture media as an excipient. airway BCs described herein could also be administered in an FDA-approved matrix/scaffold or in combination with FDA-approved drugs.

In general, the compositions comprising airway BCs described herein are administered as suspension formulations where the cells are admixed with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the Nkx2-1$^{+}$ human lung progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

In another aspect, described herein is a method of treating a pulmonary disease, respiratory disease, lung injury, or lung malformation the method comprising administering to the subject an airway basal cell, e.g., an airway basal cell produced according to a method described herein. In some embodiments, the methods and compositions are provided herein for the prevention of an anticipated disorder, e.g., mucus metaplasia.

As used herein "lung disease" refers to any pathology or condition affecting and/or arising in the lungs (e.g., including the bronchi, alveoli, pleura, muscles and/or nerves of the lung). In some embodiments of any of the aspects, the lung disease is not an infectious lung disease. In some embodiments of any of the aspects, a lung disease can be an airway basal cell-associated lung disease, e.g., a disease characterized by damage to and/or dysfunction of the airway epithelium or trachea and in particular, the airway basal cells lining the tracheal epithelium.

In some embodiments of any of the aspects, a therapeutically effective amount of airway basal cells are administered to the subject. In some embodiments of any of the aspects, the airway basal cells are derived from cells obtained from the subject. In some embodiments of any of the aspects, the airway basal cell is autologous to the subject. In some embodiments of any of the aspects, the NKX2-1+ lung progenitor cell or the less differentiated cell the NKX2-1+ lung progenitor cell is derived from was genetically modified to correct a mutation that contributed to the lung disease. Such mutations are known in the art and readily identified by one of ordinary skill in the art and/or, e.g., by genetic testing of the subject.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions and formulations as disclosed herein will be decided by the attending physician within the scope of sound medical judgment. The exact amount required will vary depending on factors such as the type of disease being treated.

The term "effective amount" as used herein refers to the amount of a population of airway BCs described herein needed to alleviate at least one or more symptoms of a disease or disorder, including but not limited to an injury, disease, or disorder. An "effective amount" relates to a sufficient amount of a composition to provide the desired effect, e.g., treat a subject with asthma, PCD, CF, etc. The term "therapeutically effective amount" therefore refers to an amount of human airway BCs described herein or a composition of such cells that is sufficient to promote a particular effect when administered to a typical subject, such as one who has, or is at risk for, a pulmonary disease or disorder. An effective amount as used herein would also include an amount sufficient to prevent or delay the development of a symptom of the disease, alter the course of a disease symptom (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting the lungs prior to administering the cells according to the methods described herein. In some embodiments, the subject is first diagnosed as being at risk of developing a disease or disorder prior to administering the cells.

For use in the various aspects described herein, an effective amount of human airway BCs described herein comprises at least $1\times10^3$, at least $1\times10^4$, at least $1\times10^5$, at least $5\times10^5$, at least $1\times10^6$, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $1\times10^7$, at least $1.1\times10^7$, at least $1.2\times10^7$, at least $1.3\times10^7$, at least $1.4\times10^7$, at least $1.5\times10^7$, at least $1.6\times10^7$, at least $1.7\times10^7$, at least $1.8\times10^7$, at least $1.9\times10^7$, at least $2\times10^7$, at least $3\times10^7$, at least $4\times10^7$, at least $5\times10^7$, at least $6\times10^7$, at least $7\times10^7$, at least $8\times10^7$, at least $9\times10^7$, at least $1\times10^8$, at least $2\times10^8$, at least $5\times10^8$, at least $7\times10^8$, at least $1\times10^9$, at least $2\times10^9$, at least $3\times10^9$, at least $4\times10^9$, at least $5\times10^9$ or more airway BCs described herein.

In one embodiment of any of the aspects, the transplant composition described herein is administered directly into the trachea or locally (e.g., to the lungs). In another embodiment of any of the aspects, the composition is administered continuously, in intervals, or sporadically. The route of administration of the composition will be optimized for the type of composition being delivered and can be determined by a skilled practitioner.

In some embodiments, an effective amount of airway BCs described herein are administered to a subject by tracheal engraftment transplantation. In some embodiments, an effective amount of airway BCs described herein are administered to a subject by systemic administration, such as intravenous administration.

The phrases "systemic administration," "administered systemically", "peripheral administration" and "administered peripherally" are used herein refer to the administration of a population of airway BCs described herein other than directly into a target site, tissue, or organ, such as the trachea, such that it enters, instead, the subject's circulatory system.

The choice of formulation will depend upon the specific composition used and the number of airway BCs described herein to be administered; such formulations can be adjusted by the skilled practitioner. However, as an example, where the composition is airway BCs described herein in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells. Alternatively, the formulation can comprise a scaffold, such as a biodegradable scaffold or extracellular matrix composition as described herein.

In some embodiments, additional agents to aid in treatment of the subject can be administered before or following treatment with the airway BCs as described. Such additional agents can be used to prepare the target tissue for administration of the progenitor cells. Alternatively, the additional agents can be administered after the airway BCs described herein to support the engraftment and growth of the administered cell into the lungs, or other desired administration site. In some embodiments, the additional agent comprises growth factors, such as FGF. In some embodiments, the additional agents area pulmonary disease therapeutic.

Therapeutics currently used to treat or prevent a pulmonary disease include, but are not limited to, antibiotics (e.g. aminosalicylic acid, norfloxacin, penicillin, cephalosporin), antivirals (e.g. zanamivir, oseltamivir), vaccines, corticosteroids (e.g. hydrocortisone, prednisone, prednisolone, budesonide), vasoconstrictors, anti-hypertensive agents, inhalers (e.g. albuterol, formoterol, salmeterol, tiotropium), surfactants (e.g. CUROSURF®) oxygen therapy, and any other treatments for pulmonary diseases known in the art.

When administered in combination, the composition and the additional agent or composition (e.g., second or third agent), or all, can be administered in an amount or dose that is higher, lower or the same as the amount or dosage of each agent used individually, e.g., as a monotherapy. In certain embodiments, the administered amount or dosage of the transplant composition described herein and the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of a pulmonary disease) is lower (e.g., at least 20%, at least 30%, at least 40%, or at least 50% lower) than the amount or dosage of each composition individually required to achieve the same therapeutic effect.

In some embodiments of any of the aspects, the methods described herein comprise administering an effective amount of a transplant composition described herein to a subject in order to alleviate at least one symptom of the pulmonary disease. As used herein, “alleviating at least one symptom of the pulmonary disease” is ameliorating any condition or symptom associated with the disease (e.g., difficulty breathing, too much or too little mucus, coughing, wheezing, gasping for air, shortness of breath, inability to breath without a support device). As compared with an equivalent untreated control, such reduction is by at least 5%, 10%, 20%, 40%, 50%, 60%, 80%, 90%, 95%, 99% or more as measured by any standard technique. A variety of means for administering the agents and compositions described herein to subjects are known to those of skill in the art.

The efficacy of treatment can be determined by the skilled clinician. However, a treatment is considered “effective treatment,” as the term is used herein, if any one or all of the symptoms, or other clinically accepted symptoms or markers of disease, e.g., pulmonary dysfunction is reduced, e.g., by at least 10% following treatment with a composition comprising human airway BCs as described herein. Methods of measuring these indicators are known to those of skill in the art and/or described herein.

Non-limiting examples of clinical tests that can be used to assess pulmonary dysfunction include but are not limited to blood tests (e.g., an immunoreactive trypsinogen (IRT) test) sweat chloride test, sputum test, chest X-ray, CT scan, and pulmonary function tests, (e.g., spirometry, plethysmography test, or a diffusion capacity test).

Where necessary or desired, animal models of a pulmonary disease can be used to gauge the effectiveness of a particular composition as described herein. Animal models of respiratory function are useful for determining tissue morphologies, ciliary beat frequencies, pulmonary function, immunoreactivity, etc.

The technology developed and described here constitutes a protocol to derive airway basal cells from pluripotent stem cells. Airway basal cells are stem cells for the human airways capable of regenerating the airway epithelium and its complement of specialized cell types including but not limited to multiciliated cells, secretory cells, and ionocytes. In addition to their biological importance in vivo airway basal cells are very useful in in vitro for modeling airway diseases and drug development for airway diseases including but not limited to cystic fibrosis, asthma, chronic bronchitis and primary ciliary dyskinesia. Furthermore, basal cells are potential candidates for cell-based therapies for airway regeneration.

Provided herein are methodologies to derive airway basal cells from human pluripotent stem cells (PSCs). PSCs included induced pluripotent stem cells (iPSCs) and embryonic stem cells (ESCs). These methodologies include 1) a directed differentiation protocol that include step-wise signaling pathway manipulation using different media including key information on the role of FGF in basal cell specification, and the effect of SMAD inhibitors and bronchial epithelial media to expand and mature a basal cell population 2) cell-surface marker strategy to isolate PSC-derived basal cells (iBCs) (Nerve growth factor receptor, NGFR), 3) techniques to expand inculture, cryopreserve, thaw and differentiate iBCs from any iPSC or ESC line and 4) a basal cell reporter iPSC line (see below). This provides a near unlimited source of patient-specific cells that have similar marker expression and functional characteristics as endogenous basal cells. This technology has widespread potential applications including as a potential source of autologous cell-based therapy, modeling of airway diseases including but not limited to cysticfibrosis (CF), primary ciliary dyskinesia (PCD), asthma, chronic bronchitis, idiopathic pulmonary fibrosis (IPF), environmental/occupational/infectious insults to airway epithelium. This technology can be applied to drug screening, drug development, testing novel technologies aimed at the airways including gene-correction, gene-therapy, modified RNA therapies.

Described herein is a basal cell reporter line to identify, track and purify basal cells generated from pluripotent stem cells. The strategy was to insert fluorescent reporters into the endogenous locus of two genes, NKX2-1 and TP63, that are important in basal cell development. The inventors inserted a GFP sequence into the NKX2-1 locus and a tdTomato sequence into the TP63 locus in a wild-type iPSC line (BU3). The resulting iPSC line, BU3 NKX2-1GFP; TP63tdTomato (BU3 NGPT) was confirmed to appropriately targeted, faithful and specific for both reporters and have a normal karyotype. Using this basal cell reporter tool primordial the key milestones or airway basal cell development can be recapitulated including NKX2-1GFP+ cells can be sorted to purity and subsequently differentiated into immature airway progenitors (NKX2-1GFP+/TP63tdTomato+). NKX2-1GFP+/TP63tdTomato+ can be sorted to purity and further matured to express NGFR.

Potential products and services contemplated as embodiments of the technology described herein include but are not limited to:

iPSC basal cell reporter line: NKX2-1GFP+/TP63tdTomato+, "BU3 NGPT"

Protocol to generate airway basal cells and airway epithelium from induced pluripotent stem cells.

Methods to cryopreserve airway stem cells from any healthy individual or patient with genetic diseases that can be expanded in vitro and differentiated into airway epithelium. These methods will allow banking of highly valuable human, patient specific samples.

Platform for drug screening and development for airway injuries and diseases: infectious, inflammatory, genetic, noxious Precision medicine approaches to airway disease—individualized predictions of drug responsiveness.

iPSC-derived basal cell and their progeny as a cell-based therapy.

Platform to test and develop novel therapies for airway diseases including gene-editing, gene-therapy, modified RNA approaches including delivery, efficacy and safety.

In one aspect, provided herein is a protocol for directed differentiation of hPSCs into airway organoid. This protocol is based on previously described approaches to derive airway organoid from hPSCs (Hawkins et al., 2017; McCauely et al., 2017 and 2018).

Generating primordial lung progenitors (day 0-15):

Stage 1: NKX2-1+ lung progenitors were generated from hPSCs first by inducing definitive endoderm with STEMdiff Definitive Endoderm Kit (Stem Cell Technologies) for 60-72 hr. Endoderm-stage cells were dissociated and passaged in small clumps to hES-qualified Matrigel-coated (Corning) tissue culture plates (Corning) in base media of IMDM (ThermoFisher, Waltham, Mass.) and Ham's F12 (ThermoFisher) with B27 Supplement with retinoic acid (Invitrogen, Waltham, Mass.), N2 Supplement (Invitrogen), 0.1% bovine serum albumin Fraction V (Invitrogen), monothioglycerol (Sigma, St. Louis, Mo.), Glutamax (ThermoFisher), ascorbic acid (Sigma), and antibiotics (complete serum free differentiation medium, cSFDM), containing 10 μM SB431542 (Tocris, Bristol, United Kingdom) and 2 μM Dorsomorphin (Stemgent, Lexington, Mass.) for 72 hr to pattern cells toward anterior foregut endoderm. Cells were then cultured for 9-11 additional days (typically, 144 hr—day 15) in cSFDM containing with 3 μM CHIR99021 (Tocris), 10 ng/mL recombinant human BMP4 (rhBMP4, R&D Systems), and 50 nM retinoid acid (Millipore-Sigma) or with CHIR, 10 ng/mL recombinant human FGF10 (rhFGF10, R&D Systems, Minneapolis, Minn.), 10 ng/mL recombinant human KGF (rhKGF, R&D Systems), BMP4, and retinoic acid to induce a NKX2-1 highly expressing lung progenitor fate.

Stage 2: Generating immature airway progenitors (~day 15-30):

After specification of the NKX2-1+ lung progenitor identity, the NKX2-1+ lung progenitors were sorted by NKX2-1GFP expression for BU3-NGPT or enriched based on the expression of cell surface markers CD47hi/CD26− for non-reporter iPSC (see below) and then were resuspended in three-dimensional growth factor reduced Matrigel at 400 cells per μl of density and replated 25-50 μl per droplet in tissue culture dishes. Cells were then cultured in airway medium, cSFDM containing 250 ng/ml FGF2 (rhFGFbasic; R&D Systems), 100 ng/ml FGF10, 50 nM dexamethasone, 100 nM 8-Bromoadenosine 3',5'-cyclic monophosphate sodium salt (cAMP; Millipore-Sigma), 100 nM 3-Isobutyl-1-methylxanthine (IBMX; Millipore-Sigma), and 10 μM Y-27632 (Y; Tocris) (FGF2+FGF10+DCI+Y) to drive airway program and to form airway organoid containing airway progenitors. In particular, we identify FGF signaling being necessary for the emergence of population of cells similar to immature, TP63+, airway basal cells.

Stage 3: Maturation of airway progenitor/immature basal cells into iBCs (key new protocol to derive basal cells)

After the formation of airway organoid (typically ~day 30 of directed differentiation), cells in 3D Matrigel with FGF2+FGF10+DCI+Y were dissociated as described above. NKX2-1GFP and TP63tdTomato expressing cells were purified via cell sorting, replated at 400 cells per μl of density in Matrigel and cultured in FGF2+FGF10+DCI+Y. One day after (unless indicated), culture medium was switched to Pneumacult ExPlus (Stemcell technologies) supplemented with inhibitors of the SMAD signaling pathway: 1 μM A83-01 (Tocris) (TGF-b pathway), 1 μM DMH1 (Tocris) (BMP pathway), and 10 μM Y-27632 (Basal cell medium) to maturate and expand iPSCs-derived basal cells (iBCs). We identify a key new factors that generate mature basal cells from immature airway progenitors including roles for inhibition of SMAD signaling (both inhibitors of TGFb and BMP signaling individually or in combination), Y-27632 and bronchial epithelial cell growth media. In particular, the active ingredients contained in commercially available bronchial epithelial growth media (BEGM) products including Pneumacult Ex media and Pneumacult Ex Plus media. This includes upregulation of the surface receptor NGFR which can be used to sort purify basal cells. In some cases, Pneumacult Ex (Stemcell technologies) supplemented with 1 μM A83-01 (Tocris), 1 μM DMH1 (Tocris), and 10 μM Y-27632 was used as indicated in figures or its legends.

For non-reporter iPSCs, single cells dissociated from airway organoid in FGF2+FGF10+DCI+Y was replated without sorting and then started to culture in Basal cell medium one day after replating. iBCs were maintained with Basal cell medium every other day feeding. On ~day 30 or later, cells cultured in 3D Matrigel were harvested by incubation with 1 U/mL Dispase (Stemcell technologies) for ~60 min at 37 C. then subsequent incubation with 0.05% trypsin at 37 C. until a single cell suspension was achieved. Single cells were prepared for sorting as above in FACS buffer.

iBSCs at ~Day 40 of directed differentiation or later were sorted based on NKX2-1GFP/TP63tdTomato/Nerve growth factor receptor (NGFR) (Biolegend) for BU3-NGPT, or by staining NGFR alone or NGFR and EpCAM (Biolegend) for non-reporter iPSCs or ESCs. These cells can be passaged for at least 170 days in our hands, possibly longer, cryopreserved (see below) while retaining their basal markers and differentiation capacity.

Stage 4: Air Liquid Interface culture of iBCs or other iPSCs-derived airway epithelial cells.

iPSCs-derived airway epithelial cells including iBCs were seeded on air-liquid interface filters (for example 6.5 mm Transwell with 0.4 μm pore polyester membrane inserts (Corning Inc., Corning, N.Y.)) at 40,000-200,000 cells per insert with Pneumacult Ex medium supplement with SMAD inhibitors and Y-27632 for 3 to 8 days approximately. When the cells had formed a confluent layer the culture medium was switched to Pneumacult ALI medium (Stemcell technologies) or BEGM ALI media in both top and bottom chambers. The following day, the medium from top chamber was removed and the cells were further differentiated in air-liquid interface conditions for ~2 weeks or longer before analysis.

Airway epithelium generated from iBCs recapitulated key features of goblet cell hyperplasia of asthma, CFTR current important in CF and cilia dysfunction of PCD.

Cryopreservation: a novel feature of this technology is the ability to cryopreserve and store iBCs with viability and durability. These iBCs can be thawed according to established protocols, expanded and differentiation for airway epithelial assays. Specifically, after single cell dissociation of cells in stage 3 or 4 (see above) the cells are centrifuged at 300G, resuspended in a mixture of Pneumacult-Ex Plus medium or other BEGM supplemented with SMAD inhibitors e.g. 1 μM A83-01, 1 μM DMHL ROCK inhibitors e.g. 10 μM Y-27632 and 10% DMSO. This suspension is transferred to cryovials, for example at 400,000 cells per 1 ml, and transferred to a ~80 degrees celsius freezer for 24 hours followed by transfer to a ~150 degrees celsius freezer for longterm storage. Cryovials are thawed by heating to 37 degrees celsius in a water bath or bead bath (1-2 min). Once the ice pellet has melted of close to melted the suspension is diluted in Basal cell medium (see above) and centrifuged at 300 G for 5 min. Aspirate supernatant and then resuspend the cell pellet in in undiluted Matrigel, for example at 400-1000 cells per microliter, and place the MATRIGEL in droplet form in tissue culture plates. After Matrigel has solidified at 37 degrees celsius, 10-20 min, add basal cell medium.

Possible variations contemplated herein include:

iBCs can be sorted based on the classic marker NGFR but we also identified many other basal cell markers by single cell RNA sequencing that could be used as in addition to NGFR or potentially in place of NGFR.

Passaging/expansion of iBCs in 3-MATRIGEL is the standard but 2D culture is also feasible and possible with these cells.

FGF is important in the generation of immature airway progenitors. In some embodiments, FGF2 (250 ng/ml) and FGF10 (100 ng/ml) was used, however, immature airway progenitors emerge at lower efficiency with lower concentrations or with FGF2 or FGF10 alone.

While surface marker sorting with CD47/CD26 and NGFR increase the efficiency of the protocol, iBCs emerge without these sorting steps.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in stem cell and molecular biology can be found in Molecular Biology of the Cell, W. W. Norton & Company; Sixth edition, 2014 (ISBN-10: 9780815344322); Karp's Cell and Molecular Biology, Wiley; 9th edition (2020) (ISBN-10: 1119598249); The Merck Manual of Diagnosis and Therapy, 20th Edition, published by Merck Sharp & Dohme Corp., 2018 (ISBN 9780911910421, 0911910425); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the term "engineered" refers to a cell described herein or a population thereof as having been manipulated by the hand of man. For example, a cell is considered to be "engineered" when at least one aspect of the cell, e.g., function, morphology, or structure, or gene expression has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, the term "culturing" refers to maintaining cells described herein in conditions suitable for cell viability, proliferation, and/or differentiation. For example, the lung progenitor cells described herein can be maintained in a culture medium, whether it be on plates, a tissue culture dish, a flask, a hydrogel or a polymer.

The term "contacting" or "contact" as used herein as in connection with contacting a population of airway epithelial cells, airway progenitor cells, epithelial spheres, or lung progenitor cells as disclosed herein, can be in vitro, for example, in conditioned media or exogenously added agent or growth factor.

The term "cell culture medium" (also referred to herein as a "culture medium" or "medium" or "media") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. The appropriate cell culture media, for a particular cell type, is known to those skilled in the art.

The term "isolated" as used herein signifies that the cells described herein are placed into conditions other than their natural environment. The term "isolated" does not preclude the later use of these cells thereafter in combinations or mixtures with other cells.

As used herein, the term "expanding" refers to increasing the number of like cells through cell division (mitosis). The term "proliferating" and "expanding" are used interchangeably.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "enriching" or "sorting" is used synonymously with "isolating" cells, means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not airway epithelial cells as disclosed herein, that are any of: Nkx2-1; TP63; KRT5; and NGFR cells.

As used herein, the terms "treat," "treatment," "treating," or "amelioration" refers to therapeutic treatments, wherein the object is to reverse, alleviate, ameliorate, inhibit, slow down or stop the progression or severity of a condition associated with a pulmonary disease, e.g. asthma or cystic fibrosis. The term "treating" includes reducing or alleviating at least one adverse effect or symptom of respiratory disease, for example, difficulty breathing Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein the term "pulmonary disease" or "respiratory disease" refers to any disease that affects the lungs and other parts of the respiratory system or a subject's ability to breathe. The pulmonary disease can cause at least one symptom of the disease. These symptoms can include but are not limited to, difficulty breathing, too much or too little of surfactant in the lungs, wheezing, tightness in the chest, or any other symptom associated with a pulmonary disease in a subject. Non-limiting examples of pulmonary diseases include asthma, cystic fibrosis (CF), primary ciliary dyskinesia interstitial lung disease, genetic lung malformations. pneumonia, respiratory failure, chronic obstructive pulmonary disease (COPD), and lung infections.

As used herein, the terms "airway basal cell", airway basal stem cell", or "BCs" are used interchangeably to refer to a cell that is from the airway or trachea; or a cell that comprises phenotypic and/or structural features associated with the airway or trachea (e.g., Nkx2-1; TP63; KRT5; and NGFR expression, self-renewal, multi-lineage differentiation, etc.). The airway basal cell can be a native basal cell isolated from an organism or subject (e.g., a primary airway basal cell) or a basal cell that is differentiated from a stem cell or a lung progenitor cell by the methods described herein (e.g., in-vitro differentiated basal cells or iBCs).

As used herein, the term "airway progenitor cell" is used to refer to a cell that is from the airway or trachea; or a cell that comprises phenotypic and/or structural features associated with the airway or trachea and expresses at least one airway progenitor cell marker selected from the group consisting of: Coagulation factor III (F3) and Epidermal growth factor receptor (EGFR), NKX2-1, and TP63.

As used herein the term "human stem cell" refers to a human cell that can self-renew and differentiate to at least one cell type. The term "human stem cell" encompasses human stem cell lines, human-derived induced pluripotent stem (iPS) cells, human embryonic stem cells, human pluripotent cells, human multipotent stem cells, amniotic stem cells, placental stem cells, or human adult stem cells.

As used herein, the terms "induced pluripotent stem cell," "iPSC," "hPSC," and "human pluripotent stem cell" are used interchangeably herein and refer to a pluripotent cell artificially derived from a differentiated somatic cell. iPSCs are capable of self-renewal and differentiation into cell fate-committed stem cells, including cells of the lung progenitor cell lineages, as well as various types of mature cells.

As used herein, the term "a progenitor cell" refers to an immature or undifferentiated cell that has the potential later on to mature (differentiate) into a specific cell type, for example, a blood cell, a skin cell, a bone cell, or a hair cells. Progenitor cells have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. A progenitor cell also can proliferate to make more progenitor cells that are similarly immature or undifferentiated. Accordingly, as used herein, "lung progenitor cell" refers to a progenitor cell with the differentiation potential to form one or more types of lung cells. In some embodiments of any of the aspects, lung progenitor cells can be NKX2-1$^+$ FOXA2$^+$ cells. In some embodiments of any of the aspects, lung progenitor cells can be NKX2-1$^+$ FOXA2$^+$ epithelial cells. In some embodiments of any of the aspects, lung progenitor cells can be NKX2-1$^+$ FOXA2$^+$ epithelial cells that can give rise to cells that express mature lung epithelial markers (e.g., SFTPC, SCGB3A2, P63, SFTPB, HOPX, PDPN, SCGB1A1, FOXJ1). In some embodiments of any of the aspects, a lung progenitor cell is NKX2-1$^+$ and STPC$^-$. In some embodiments of any of the aspects, a lung epithelial progenitor cell is NKX2-1$^+$ FOXA2$^+$ and STPC$^-$.

As used herein, "NKX2-1", "NK2 homeobox 1", "or thyroid transcription factor 1 (TTF-1) refers to a transcription factor that controls gene expression specifically in the thyroid, lung, and diencephalon. It is also known as thyroid specific enhancer binding protein. Sequences are known for the sequence of NKX2-1 genes and polypeptides for a number of species, e.g., human NKX2-1 (NCBI Gene ID No: 7080) mRNA (e.g., NCBI Ref Seq: NM_001079668.2 and NM_003317.3) and polypeptide (e.g., NCBI Ref Seq: NP_001073136.1 and NP_003308.1).

In some embodiments of any of the aspects, a NKX2-1+ cell is a cell expressing a detectable quantity of NKX2-1 polypeptide. In some embodiments of any of the aspects, a NKX2-$1^{Hi}$ cell belongs to a first subpopulation (NKX2-$1^{Hi}$) of cells expressing a relatively higher amount of NKX2-1 polypeptide as compared to a second subpopulation (NKX2-$1^{Lo}$) of cells expressing a relatively lower amount of NKX2-1 polypeptide, wherein both subpopulations are part of the same total population (e.g. a population of cells obtained from the same source). In some embodiments of any of the aspects wherein a NKX2-1+ cell is referred to, a NKX2-$1^{Hi}$ cell can be used as an alternative embodiment.

In some embodiments of any of the aspects, the NKX2-1+ lung epithelial progenitor cell is a CD47hi/CD26lo cell, wherein CD47 is a polypeptide of NCBI Gene ID: 961 or an ortholog thereof and CD26 is a polypeptide of NCBI Gene ID: 1803 or an ortholog thereof. In some embodiments of any of the aspects, a CD47hi/CD26lo cell is a cell sorted from a population of cells for a CD47hi/CD26lo phenotype. In some embodiments of any of the aspects, the NKX2-1+ lung epithelial progenitor cell is provided by sorting lung epithelial progenitor cells to isolate a CD47hi/CD26lo population.

NKX2-1+ lung progenitor cells can be obtained from any source known in the art, e.g., by isolating such cells from a subject or tissue and/or by differentiating such cells from a less differentiated cell type, e.g., a stem cell or epithelial progenitor cell type. In some embodiments of any of the aspects, the NKX2-1+ lung progenitor cell is derived from a stem cell, an induced pluripotent stem cell (iPSC), an embryonic stem cell, and/or a somatic stem cell. In some embodiments, the NKX2-1+ lung progenitor cell is derived from a cell obtained from a subject, e.g., a subject having, diagnosed as having, or in need of treatment for a lung disease.

In some embodiments of any of the aspects, the NKX2-1+ lung progenitor cell is derived from a less differentiated cell by contacting the less differentiated cell with CHIR99021, BMP4 (e.g., a polypeptide of NCBI Gene ID: 652 or an ortholog thereof), and retinoic acid (RA).

The term "marker" as used herein is used to describe a characteristic and/or phenotype of a cell. Markers can be used for selection of cells comprising characteristics of interest and can vary with specific cells. Markers are characteristics, whether morphological, structural, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in or on a cell, including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological or structural characteristics. In one embodiment, the marker is a cell surface marker. In some embodiments, an airway basal cell marker is selected from the group consisting of: Nkx2-1; tumor protein 63 (TP63); cytoskeletal protein keratin 5 (KRT5); and nerve growth factor receptor (NGFR).

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues provided herein are preferred to be in the "L" isomeric form. However, residues in the "D" isomeric form may be substituted for any L-amino acid residue provided the desired properties of the polypeptide are retained.

The term "differentiate", or "differentiating" is a relative term that indicates a "differentiated cell" is a cell that has progressed further down the developmental pathway than its precursor cell. Thus in some embodiments, a stem cell as the term is defined herein, can differentiate to lineage-restricted precursor cells (e.g., a Nkx2-$1^+$ lung progenitor cell), which in turn can differentiate into other types of cells further down the pathway (such as a tissue specific precursor or airway basal cells), and then to an end-stage differentiated cell (e.g., lung epithelial cells), which plays a characteristic role in a certain tissue type, and may or may not retain the capacity to proliferate further. Methods for in vitro differentiation of stem cells to Nkx2-$1^+$ lung progenitor cells are known in the art and/or described herein.

The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse and teratoma formation assay. Pluripotency is also evidenced by the expression of embryonic stem (ES) cell markers, although the preferred test for pluripotency is the demonstration of the capacity to differentiate into cells of each of the three germ layers.

The term "reprogramming" as used herein refers to a process that alters or reverses the differentiation state of a differentiated cell (e.g. a somatic cell). Stated another way, reprogramming refers to a process of driving the differentiation of a cell backwards to a more undifferentiated or more primitive type of cell. The cell to be reprogrammed can be either partially or terminally differentiated prior to reprogramming. In some embodiments, reprogramming encompasses complete reversion of the differentiation state of a differentiated cell (e.g., a somatic cell) to a pluripotent state. In some embodiments, reprogramming also encompasses partial reversion of the differentiation state of a differentiated cell (e.g., a somatic cell) to a multipotent state. In some embodiments, reprogramming encompasses complete or partial reversion of the differentiation state of a differentiated cell (e.g., a somatic cell) to an undifferentiated cell. Reprogramming also encompasses partial reversion of the differentiation state of a somatic cell to a state that renders the cell more susceptible to complete reprogramming to a pluripotent state when subjected to additional manipulations.

Reprogramming involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "genetically modified" cell, as used herein refers to a population of cells or transplant compositions as described herein into which an exogenous nucleic acid has been introduced by a process involving the hand of man (or a descendant of such a cell that has inherited at least a portion of the nucleic acid). For example, a genetically modified population of Nkx2-1+ lung progenitor cells, their progeny, and/or airway basal cells and compositions thereof as described herein. The nucleic acid may for example, contain a sequence that is exogenous to the cell, it may contain native sequences (e.g., sequences naturally found in the cells) but in a non-naturally occurring arrangement (e.g., a coding region linked to a promoter from a different gene), or altered versions of native sequences, etc., e.g., a correction of a genetic lesion or mutation in the CFTR gene that causes CF. The process of transferring the nucleic acid into the cell is referred to as "transducing a cell" and can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "tissue" refers to a group or layer of similarly specialized cells which together perform certain special functions. The term "tissue-specific" refers to a source or defining characteristic of cells from a specific tissue.

The term "derived from," used in reference to a stem cell means the stem cell was generated by reprogramming of a differentiated cell to a stem cell phenotype. The term "derived from," used in reference to a differentiated cell means the cell is the result of differentiation, e.g., in vitro differentiation, of a stem cell. As used herein, "iBCs" or "induced pluripotent stem cell-derived airway basal cells" are used interchangeably to refer to airway basal cells differentiated from an induced pluripotent stem cell. In some embodiments, the induced-pluripotent stem cell is a human cell.

As described herein, a "genetically modified cell" is a cell which either carries a heterologous genetic material or construct, or which comprises a genome that has been manipulated, e.g., by mutation, including but not limited to site-directed mutation. The introduction of a heterologous genetic material generally results in a change in gene or protein expression relative to an un-modified cell. Introduction of RNA can transiently promote expression of a foreign or heterologous product, as can the introduction of a vector that does not integrate or replicate within the cell. Introduction of a construct that integrates into a cell's genome or replicates with the cell's nucleic acid will be more stable through successive cell divisions. In one embodiment, genetic modification is in addition to or separate from the introduction of a construct or constructs that reprogram a somatic cell to a stem cell phenotype, such as an iPS cell phenotype. Genetic modifications are known to those of skill in the art and can include, but are not limited to, the introduction of genetic material via viral vector or modification using CRISPR/Cas or similar system for site specific recombination.

The term "agent" or "agonist" as used herein means any compound or substance such as, but not limited to, a small molecule, nucleic acid, polypeptide, peptide, drug, ion, etc. An "agent" can be any chemical, entity or moiety, including without limitation, synthetic and naturally-occurring proteinaceous and non-proteinaceous entities. In some embodiments of any of the aspects, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

The term "antagonist" or "inhibitor" refers to any agent or entity capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct or indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide.

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment of any of the aspects, the subject is human. In another embodiment, of any of the aspects, the subject is an experimental animal or animal substitute as a disease model. In another embodiment, of any of the aspects, the subject is a domesticated animal including companion animals (e.g., dogs, cats, rats, guinea pigs, hamsters etc.). A subject can have previously received a treatment for a disease, or has never received treatment for a disease. A subject can have previously been diagnosed with having a disease, or has never been diagnosed with a disease.

As used herein, a "subject in need" of treatment for a particular condition can be a subject having that condition, diagnosed as having that condition, or at risk of developing that condition.

The term "allograft" or "allogenic" refers to a transplanted cell, tissue, or organ derived from a different animal of the same species.

The term "autologous" refers to a transplanted cell, tissue, or organ derived from the same animal of the same species. In some embodiments, the airway basal cells described herein are derived from a subject in need of treatment of a pulmonary disease.

The term "agent" refers to any entity which is normally not present or not present at the levels being administered in the cell. Agent may be selected from a group comprising, for example chemicals; small molecules; nucleic acid sequences; nucleic acid analogues; proteins; peptides; peptidomimetics, aptamers; antibodies; or fragments thereof. A nucleic acid sequence may be RNA or DNA, and may be single or double stranded, and can be selected from a group comprising; nucleic acid encoding a protein of interest, oligonucleotides, antisense oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), short-temporal RNAi (stRNA), dsRNA antisense oligonucleotides etc. A chemical entity or biological product is preferably, but not necessarily a low molecular weight compound, but may also be a larger compound, or any organic or inorganic molecule, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Agents can be, without limitation an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. The agent may be applied to the media, where it contacts the ovarian cell and induces its effects. Alternatively, the agent may be intracellular within the cell as a result of introduction of the nucleic acid sequence into the cell and its transcription resulting in the production of the nucleic acid and/or protein agent within the cell.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals including humans.

The term "derivative" as used herein means any chemical, conservative substitution, or structural modification of an agent. The derivative can improve characteristics of the agent or small molecule such as pharmacodynamics, pharmacokinetics, absorption, distribution, delivery, targeting to a specific receptor, or efficacy. For example, for a small molecule, the derivative can consist essentially of at least one chemical modification to about ten modifications. The derivative can also be the corresponding salt of the agent. The derivative can be the pro-drug of the small molecule as provided herein.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media.

The term "pharmaceutically acceptable" can refer to compounds and compositions which can be administered to a subject (e.g., a mammal or a human) without undue toxicity.

The term "pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., “Pharmaceutical Salts”, *Journal of Pharmaceutical Science,* 1977, 66, 1-19). Certain specific compounds of the present invention contain both basic and acidic functionalities that allow the compounds to be converted into either base or acid addition salts.

The term “expression” as used herein refers to interchangeably to the expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

In the context of this specification, the term “activity” as it pertains to a protein, polypeptide or polynucleotide means any cellular function, action, effect of influence exerted by the protein, polypeptide or polynucleotide, either by nucleic acid sequence or fragment thereof, or by the protein or polypeptide itself or any fragment thereof.

As used herein, a “reference level” refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a disease, or a biological sample that has not been contacted with a composition, polypeptide, or nucleic acid encoding such polypeptide as disclosed herein).

As used herein, an “appropriate control” refers to an untreated, otherwise identical cell or population (e.g., a biological sample that was not contacted by an agent or composition described herein, or not contacted in the same manner, e.g., for a different duration, as compared to a non-control cell).

The terms “lower”, “reduced”, “reduction” or “decrease” or “inhibit” are all used herein generally to mean a decrease by a statistically significant amount. However, for avoidance of doubt, “lower”, “reduced”, “reduction” or “decrease” or “inhibit” means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms “increased”, “increase” or “enhance” or “higher” are all used herein to generally mean an increase by a statically significant amount; for the avoidance of any doubt, the terms “increased”, “increase” or “enhance” or “higher” means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

By an “increase” in the expression or activity of a gene or protein is meant a positive change in protein or polypeptide or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The term “statistically significant” or “significantly” refers to statistical significance and generally means a two standard deviation (2 SD) below normal, or lower, concentration of the marker. The term refers to statistical evidence that there is a difference. It is defined as the probability of making a decision to reject the null hypothesis when the null hypothesis is actually true. The decision is often made using the p-value.

The term “standard deviation” is a measure of the dispersion of a set of data from its mean. The more spread apart the data, the higher the deviation. Standard deviation is calculated as the square root of variance and can be calculated by one of ordinary skill in the art.

As used herein, the terms “administering,” and “introducing” are used interchangeably, and refer to the placement of a population of airway epithelial cells, or transplant compositions thereof as disclosed herein into a subject by a method or route which results in at least partial localization of the population of airway basal cells, transplant compositions, or traceospheres at a desired site, such as, e.g. the lung or airways. A population of airway epithelial cells, and/or transplant compositions as of the present disclosure can be administered by any appropriate route which results in an effective treatment in the subject.

The term “transplantation” as used herein refers to introduction of new cells (e.g. a population of airway basal cells as described herein), tissues (such as, e.g., transplant compositions produced from the airway basal cells), or organs into a host (i.e. transplant recipient or transplant subject).

The term “transduction” as used herein refers to the use of viral particles to introduce new genetic material into a cell The term “transfection” as used herein refers the use of chemical methods, most often lipid containing vesicles, to introduce new genetic material into a cell The term “transformation” as used herein refers to when a cell becomes functionally abnormal in the process of malignancy, often obtaining a new capacity to multiply indefinitely or under new circumstances.

As used herein, a “reference level” refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a respiratory disease, or a biological sample that has not been contacted with a composition disclosed herein).

As used herein, an "appropriate control" refers to an untreated, otherwise identical cell or population (e.g., a biological sample that was not contacted by a composition described herein, or not contacted in the same manner, e.g., for a different duration, as compared to a non-control cell).

As used herein the term "comprising" or "comprises" is used in reference to compositions, methods, and respective component(s) thereof, that are essential to the disclosure, yet open to the inclusion of unspecified elements, whether essential or not. Accordingly, compositions or methods "comprising" one or more recited elements may include other elements not specifically recited. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Thus, the use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean ±1%. The present disclosure is further explained in detail by the following, including the Examples, but the scope of the disclosure should not be limited thereto.

Although any known methods, devices, and materials may be used in the practice or testing of the invention, the methods, devices, and materials in this regard are disclosed herein.

In some embodiments, the present application may be defined in any of the following paragraphs:

1. A method comprising:

(a) culturing a population of $Nkx2\text{-}1^+$ lung progenitor cells in a first culture medium, wherein the first culture medium comprises, or the $Nkx2\text{-}1^+$ lung progenitor cells are contacted with, one or more of: at least one Wnt agonist; at least one retinoic acid or a derivative thereof; and at least one bone morphogenic protein (BMP) agonist;

(b) re-suspending the $Nkx2\text{-}1^+$ lung progenitor cells in a hydrogel to form epithelial spheres;

(c) culturing the epithelial spheres in a second culture medium, wherein the second culture medium comprises, or the epithelial spheres are contacted with one or more of: at least one fibroblast growth factor (FGF) agonist; at least one steroid; 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells; and (d) passaging and re-suspending the airway progenitor cells in the second culture medium, thereby expanding the airway progenitor cells.

2. The method of paragraph 1, further comprising, culturing the airway progenitor cells from step (d) in a third culture medium, wherein the third culture medium comprises, or the airway progenitor cells from step (d) are contacted with one or more of: at least one inhibitor of SMAD; at least one inhibitor of transforming growth factor β (TGF-β); at least one bone morphogenetic protein (BMP) inhibitor; and at least one ROCK inhibitor; thereby differentiating the airway progenitor cells into airway basal cells (BCs).

3. The method of paragraph 1, wherein the $Nkx2\text{-}1^+$ lung progenitor cells are generated by a method comprising:

(a) culturing a population of stem cells in a serum-free medium;

(b) culturing the population of stem cells in a culture medium wherein the culture medium comprises or the stem cells are contacted with, a Wnt agonist or a Wnt polypeptide;

(c) culturing the population of stem cells in a culture medium wherein the culture medium comprises or the stem cells are contacted with, a bone morphogenic protein (BMP) and a Wnt agonist, thereby inducing the differentiation of the stem cells into a population of lung progenitor cells; and (d) sorting and/or isolating a population of $Nkx2\text{-}1^+$ lung progenitor cells from the population of lung progenitor cells generated in (c).

4. The method of paragraph 1, wherein the airway basal cells (BCs) generated in step (d) express one or more markers selected from the group consisting of: Nkx2-1; tumor protein 63 (TP63); cytoskeletal protein keratin 5 (KRT5); and nerve growth factor receptor (NGFR).

5. The method of any one of paragraphs 1-4, wherein the $Nkx2\text{-}1^+$ lung progenitor cells are genetically modified.

6. The method of any one of paragraphs 1-5, further comprising a step of sorting and/or isolating airway BCs that express one or more markers selected from the group consisting of: Nkx2-1; tumor protein 63 (TP63); cytoskeletal protein keratin 5 (KRT5); and nerve growth factor receptor (NGFR).

7. The method of any of paragraphs 1-6, wherein the hydrogel comprises one or more extracellular matrix components.

8. The method of any of paragraphs 1-7, wherein the hydrogel comprises an extracellular matrix composition comprising a gelatinous protein mixture secreted by Engelbreth-Holm-Swarm (EHS) mouse sarcoma cells (MATRIGEL™).

9. The method of any of paragraphs 1-8, wherein the Wnt agonist is an inhibitor of GSK-3.

10. The method of paragraph 9, wherein the Wnt agonist is CHIR 99021.

11. The method of any of paragraphs 1-10, wherein the BMP is BMP4.

12. The method of any of paragraphs 1-11, wherein the fibroblast growth factors are FGF2 and FGF10.

13. The method of any of paragraph 1-12, wherein the ROCK inhibitor is Y-27632 (Y).

14. The method of any of paragraphs 1-13, wherein the first culture medium comprises CHIR99021, retinoic acid, and BMP4, or the cells in the first culture medium are contacted with CHIR99021, retinoic acid, and BMP4.

15. The method of any of paragraphs 1-14, wherein the second culture medium comprises FGF2, FGF10, dexamethasone, IBMX, 3',5'-cyclic monophosphate sodium salt, and Y-27632; or the cells in the second culture medium are contacted with FGF2, FGF10, dexamethasone, IBMX, 3',5'-cyclic monophosphate sodium salt, and Y-27632.

16. The method of any of paragraphs 1, 2, or 4-15, wherein the cells in steps (b) and/or (d) are cultured in a 3-dimensional microenvironment.

17. The method of any of paragraphs 1-16, wherein the airway BCs are differentiated from induced pluripotent stem cells or embryonic stem cells.

18. The method of any of paragraphs 1-17, wherein the airway BCs are differentiated from human induced pluripotent stem cells.

19. The method of any of paragraphs 2-18, wherein the third culture medium comprises A83-01 and DMH1; or the cells in the third culture medium are contacted with A83-01 and DMH1.

20. The method of any of paragraphs 2-19, wherein the third culture medium comprises bronchial epithelial growth medium, A83-01, and DMH1.

21. The method of any of paragraphs 2-20, wherein the inhibitor of SMAD is A83-01.

22. The method of any of paragraphs 2-21, wherein the inhibitor of transforming growth factor β (TGF-β) is selected from the group consisting of: ALK5 inhibitor II, SB431542, LY364947, and A83-01.

23. The method of any of paragraphs 2-21, wherein the inhibitor of BMP is selected from the group consisting of: dorsomorphin or DMH1.

24. The method of any one of paragraphs 1-23, wherein the cells are cultured for a time period of at least 24 hours or more, at least 36 hours or more, at least 48 hours or more, or at least 72 hours or more in the cell culture medium.

25. The method of any of paragraphs 1-24, further comprising, during or following step (d), sorting the population of Nkx2-1+ lung progenitor cells for F3+/EGFR+ lung/airway progenitor cells.

26. The method of any one of paragraphs 1-25, further comprising a step of cryopreserving the airway BCs.

27. The method of any one of paragraphs 1-26, wherein the stem cells are human induced pluripotent stem cells or human embryonic stem cells.

28. The method of any one of paragraphs 1-27, wherein the stem cells are derived from a healthy subject.

29. The method of any one of paragraphs 1-28, wherein the stem cells are derived from a subject with a pulmonary disease.

30. The method of paragraph 29, wherein the pulmonary disease is selected from the group consisting of: asthma, cystic fibrosis, primary ciliary dyskinesia, interstitial lung disease, and genetic lung malformations.

31. The method of any of paragraphs 1-30, wherein the lung epithelial progenitor cells are genetically modified.

32. The method of paragraph 31, wherein the genetically modified lung epithelial progenitor cells comprise a nucleic acid encoding at least one airway BC marker operably linked to a promoter.

33. The method of paragraph 32, wherein the BC marker is one or more of the BC markers selected from the group consisting of: Nkx2-1; TP63; KRT5; and/or NGFR.

34. The method of any of paragraphs 32-33, wherein the nucleic acid further comprises a reporter gene.

35. An airway basal cell line generated by the method of any one of paragraphs 1-34.

36. The airway basal cell line of paragraph 35, wherein the airway basal cell line is cryopreserved.

37. A nucleic acid comprising:

(a) a promoter;

(b) one or more basal cell markers selected from Nkx2-1; TP63; KRT5; and NGFR; and (c) at least one reporter gene.

38. The nucleic acid of paragraph 37, wherein the basal cell marker is TP63.

39. The nucleic acid of any of paragraphs 37-38, wherein the reporter gene is green fluorescent protein (GFP) or tdTomato.

40. A cell comprising the nucleic acid of any one of paragraphs 37-39.

41. A disease model comprising the airway basal cell line of paragraph 35.

42. The disease model of paragraph 41, wherein the airway basal cell line is genetically modified.

43. The disease model of paragraph 41, wherein the airway basal cell line is derived from a subject with a pulmonary disease.

44. The disease model of paragraph 43, wherein the pulmonary disease is selected from the group consisting of: asthma, cystic fibrosis, primary ciliary dyskinesia interstitial lung disease, and genetic lung malformations.

45. A transplant composition comprising the airway basal cell line of paragraph 35.

46. The transplant composition of paragraph 45, wherein the composition further comprises a pharmaceutically acceptable carrier.

47. The transplant composition of any of paragraphs 45-46, wherein the composition further comprises a scaffold.

48. A method of treating a subject with a pulmonary disease, the method comprising: administering to the trachea of the subject the transplant composition of any one of paragraphs 45-47.

49. The method of paragraph 48, wherein the pulmonary disease is selected from the group consisting of: asthma, cystic fibrosis, primary ciliary dyskinesia interstitial lung disease, and genetic lung malformations.

50. The method of any of paragraphs 48-49, wherein the transplant composition is an autologous transplant composition.

51. The method of any of paragraphs 48-49, wherein the transplant composition is an allogenic transplant composition.

52. A method of generating a population of engineered airway basal cells (BCs), the method comprising:

(a) culturing a population of Nkx2-1+ lung progenitor cells in a first culture medium, wherein the first culture medium comprises, or the lung progenitor cells are contacted with, one or more of: at least one Wnt agonist; at least oneretinoic acid or a derivative thereof; and at least one bone morphogenic protein (BMP) agonist;

(b) re-suspending the Nkx2-1+ lung progenitor cells in a hydrogel to form epithelial spheres;

(c) culturing the epithelial spheres in a second culture medium, wherein the second culture medium comprises, or the epithelial spheres are contacted with, one or more of: at least one fibroblast growth factor (FGF) polypeptide; at least one steroid; and at least one Rho kinase (ROCK) inhibitor, thereby differentiating the epithelial spheres into airway progenitor cells;

(d) passaging and re-suspending the airway progenitor cells in the second culture medium; and (e) culturing the airway progenitor cells from step (d) in a third culture medium, wherein the third culture medium comprises, or the airway progenitor cells are contacted with, one or more of: at least one inhibitor of SMAD; at least one inhibitor of transforming growth factor β (TGF-β); at least one bone morphogenetic protein (BMP) inhibitor; and at least one ROCK inhibitor thereby differentiating the airway progenitor cells into airway basal cells (BCs).

53. The method of paragraph 52, wherein the inhibitor of SMAD is A83-01.

54. The method of any of paragraphs 52-53, wherein the inhibitor of transforming growth factor β (TGF-β) is selected from the group consisting of: ALK5 inhibitor II, SB431542, LY364947, DMH1, and A83-01.

55. The method of any of paragraphs 52-54, wherein the inhibitor of BMP is selected from the group consisting of: dorsomorphin or DMH1.

In some embodiments, the present application may be defined in any of the following paragraphs:

1. A method comprising:

(a) culturing a population of Nkx2-1$^+$ lung progenitor cells in a first culture medium and contacting the Nkx2-1$^+$ lung progenitor cells with, one or more of: at least one Wnt agonist; at least one retinoic acid or a derivative thereof; and at least one bone morphogenic protein (BMP) agonist;

(b) re-suspending the Nkx2-1$^+$ lung progenitor cells in a hydrogel to form epithelial spheres;

(c) culturing the epithelial spheres in a second culture medium and contacting the epithelial spheres with one or more of: at least one fibroblast growth factor (FGF) agonist; at least one steroid; 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells;

(d) passaging and re-suspending the airway progenitor cells in the second culture medium, thereby expanding the airway progenitor cells; and (e) culturing the airway progenitor cells from step (d) in a third culture medium and contacting the airway progenitor cells from step (d) with one or more of: at least one inhibitor of SMAD; at least one inhibitor of transforming growth factor β (TGF-β); at least one bone morphogenetic protein (BMP) inhibitor; and at least one ROCK inhibitor; thereby differentiating the airway progenitor cells into airway basal cells (BCs).

2. The method of paragraph 1, further comprising a step of sorting and/or isolating airway BCs that express one or more markers selected from the group consisting of: Nkx2-1; tumor protein 63 (TP63); cytoskeletal protein keratin 5 (KRT5); and nerve growth factor receptor (NGFR).

3. The method of paragraph 1, wherein the hydrogel comprises one or more extracellular matrix components.

4. The method of paragraph 1, wherein the Wnt agonist is an inhibitor of GSK-3.

5. The method of paragraph 4, wherein the Wnt agonist is CHIR 99021.

6. The method of paragraph 1, wherein the BMP is BMP4.

7. The method of paragraph 1, wherein the fibroblast growth factors are FGF2 and FGF10.

8. The method of paragraph 1, wherein the ROCK inhibitor is Y-27632 (Y).

9. The method of paragraph 1, wherein the inhibitor of SMAD is A83-01.

10. The method of paragraph 1, wherein the inhibitor of transforming growth factor β (TGF-β) is selected from the group consisting of: ALK5 inhibitor II, SB431542, LY364947, and A83-01.

11. The method of paragraph 1, wherein the inhibitor of BMP is selected from the group consisting of: dorsomorphin or DMH1.

12. The method of paragraph 1, wherein step (a) comprises contacting the cells with CHIR99021, retinoic acid, and BMP4.

13. The method of paragraph 1, wherein step (c) comprises contacting the cells with FGF2, FGF10, dexamethasone, IBMX, 3',5'-cyclic monophosphate sodium salt, and Y-27632.

14. The method of paragraph 1, wherein step (e) comprises contacting the cells with A83-01 and DMH1.

15. The method of paragraph 1, wherein the cells in steps (b) and/or (d) are cultured in a 3-dimensional microenvironment.

16. The method of paragraph 1, wherein the Nkx2-1$^+$ lung progenitor cells are generated by a method comprising:

(a) culturing a population of stem cells in a serum-free medium;

(b) culturing the population of stem cells in a culture medium wherein the culture medium comprises or the stem cells are contacted with, a Wnt agonist or a Wnt polypeptide;

(c) culturing the population of stem cells in a culture medium and contacting the stem cells with a bone morphogenic protein (BMP) and a Wnt agonist, thereby inducing the differentiation of the stem cells into a population of lung progenitor cells; and (d) sorting or isolating a population of Nkx2-1$^+$ lung progenitor cells from the population of lung progenitor cells generated in (c).

17. The method of paragraph 16, wherein the stem cells are induced pluripotent stem cells or embryonic stem cells.

18. The method of paragraph 16, further comprising, during or following step (d), sorting the population of Nkx2-1+ lung progenitor cells for F3+/EGFR+ lung/airway progenitor cells.

19. The method of paragraph 1, further comprising a step of cryopreserving the airway BCs.

20. The method of paragraph 16, wherein the stem cells are derived from a healthy subject.

21. The method of paragraph 16, wherein the stem cells are derived from a subject with a pulmonary disease.

22. The method of paragraph 21, wherein the pulmonary disease is selected from the group consisting of: asthma, cystic fibrosis, primary ciliary dyskinesia, interstitial lung disease, and genetic lung malformations.

23. An airway basal cell generated by the method of paragraph 1.

24. The airway basal cell of paragraph 23, wherein the airway basal cell is cryopreserved.

25. A nucleic acid comprising:

(a) a promoter;

(b) one or more basal cell markers selected from Nkx2-1; TP63; KRT5; and NGFR; and (c) at least one reporter gene.

26. The nucleic acid of paragraph 25, wherein the basal cell marker is TP63.

27. The nucleic acid of paragraph 25, wherein the reporter gene is green fluorescent protein (GFP) or tdTomato.

28. A method of treating a subject with a pulmonary disease, the method comprising: administering to the trachea of the subject an airway basal cell generated by the method of paragraph 1.

29. The method of paragraph 28, wherein the pulmonary disease is selected from the group consisting of: asthma, cystic fibrosis, primary ciliary dyskinesia interstitial lung disease, and genetic lung malformations.

It is understood that the foregoing detailed description and the following examples are illustrative only and are not to be taken as limitations upon the scope of the disclosure. Various changes and modifications to the disclosed embodiments, which will be apparent to those of skill in the art, may be made without departing from the spirit and scope of the present disclosure. Further, all patents, patent applications, and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the disclosure has been particularly shown and described with reference to a number of embodiments, it would be understood by those skilled in the art that changes in the form and details may be made to the various embodiments disclosed herein without departing from the spirit and scope of the disclosure and that the various embodiments disclosed herein are not intended to act as limitations on the scope of the claims. All references cited herein are incorporated in their entirety by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the disclosure. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The disclosure can be understood more fully by reference to the following detailed description and illustrative examples, that are intended to exemplify non-limiting embodiments of the disclosure.

EXAMPLES

Example 1: Derivation of Airway Basal Stem Cells from Human Pluripotent Stem Cells The derivation of tissue-specific stem cells from human induced pluripotent stem cells (iPSCs) has broad reaching implications for regenerative medicine. Reported herein is the directed differentiation of human iPSCs into airway basal cells ("iBCs"), a population resembling the stem cell of the airway epithelium. Using a dual fluorescent reporter system (NKX2-1GFP; TP63tdTomato), these cells are tracked and purified as they first emerge as developmentally immature NKX2-1GFP+ lung progenitors and subsequently augment a TP63 program during proximal airway epithelial patterning. In response to primary basal cell medium, NKX2-1GFP+/TP63tdTomato+ cells display the molecular and functional phenotype of airway basal cells, including the capacity to self-renew or undergo multi-lineage differentiation in vitro and in tracheal xenografts in vivo. iBCs and their differentiated progeny model perturbations that characterize acquired and genetic airway diseases, including the mucus metaplasia of asthma, chloride channel dysfunction of cystic fibrosis, and ciliary defects of primary ciliary dyskinesia.

Basal cells (BCs) of the adult mouse and human airways are capable of self-renewal and multi-lineage differentiation in vivo and after culture expansion ex vivo, thereby fulfilling the definition of a tissue-specific adult stem cell (Rock et al., 2009). An extensive literature has established that BCs can regenerate the airway epithelium by serving as precursors for essential specialized epithelial cell types, including secretory cells (SCs) and multicillieated cells (MCCs) (Montoro et al., 2018; Plasschaert et al., 2018; Rock et al., 2009). These stem cell properties make BCs a highly desirable cell type to generate ex vivo for modeling airway diseases and a leading candidate for cell-based therapies designed to reconstitute the airway epithelium.

In human airways, BCs are highly abundant in the pseudostratified epithelium extending from the trachea to the terminal bronchioles (Rock et al., 2010). Airway BCs can be identified based on their classic anatomic location along the basal lamina and by the expression of several markers, including tumor protein 63 (TP63), cytoskeletal protein keratin 5 (KRT5), and nerve growth factor receptor (NGFR) (Rock et al., 2010). TP63, a member of the p53 family of transcription factors, is essential to the BC program in the airway but also other organs (Yang et al., 1999). Although airway BCs in adult lungs have been extensively studied, only recently has their developmental origin been examined. For example, lineage-tracing experiments in mice (Yang et al., 2018) reveal that a Tp63 program is already present early in lung development at the time of initial lung bud formation (embryonic day 9.5 [E9.5]) within a subset of lung epithelial progenitors expressing the transcriptional regulator that marks all developing lung epithelial cells, NK2 homeobox 1 (Nkx2-1). Early Nkx2-1+/Tp63+ co-expressing cells are not BCs because they lack the BC morphology and molecular program. Rather, these fetal cells function as multipotent progenitors of subsequent alveolar and airway epithelia (Yang et al., 2018). Tp63 expression is then gradually restricted to the developing airways, where it is initially broadly expressed in immature airway progenitors and later restricted to a subset of tracheal cells that localize to the basement membrane and upregulate markers of adult BCs, including Krt5 and Ngfr. The signaling pathways that control BC specification and maturation in the lung are not precisely known; however, in-bred mouse models suggest a temporal role for FGF10/FGFR2b (Volckaert et al., 2013) and recent single-cell RNA sequencing (scRNA-seq) of human fetal airways identified fetal BCs and a role for transient activation of SMAD signaling in BC specification (Miller et al., 2020). Although limited data are available regarding the developmental origins of BCs in humans, a similar pattern to that observed in mice has also been described (Nikolic et al., 2017).

Given the stem cell properties of airway BCs, including their established proliferative capacity, well-established protocols have been developed to expand primary human BCs in vitro (Fulcher and Randell, 2013; Fulcher et al., 2005; Mou et al., 2016; Suprynowicz et al., 2017). These BCs, conventionally referred to as human bronchial epithelial cells (HBECs), differentiate into a pseudostratified airway epithelium in air-liquid interface (ALI) culture that recapitulates aspects of in vivo airway biology. The understanding of acquired and genetic human airway diseases, including the mucus metaplasia of asthma, the chloride transport defects of cystic fibrosis (CF), and the ciliary dysfunction of primary ciliary dyskinesia (PCD), has advanced through this model (Clancy et al., 2019; Horani et al., 2016; Seibold, 2018).

Several recent reports have demonstrated the successful directed differentiation of human induced pluripotent stem cells (iPSCs) into airway epithelial cell types, including those that express the canonical BC marker TP63 (Dye et al., 2015; Hawkins et al., 2017; Konishi et al., 2016; McCauley et al., 2017). These cultures contain cells with some markers found in BCs; however, the successful generation of bona fide BCs with detailed characterization and demonstration of stem cell properties that are comparable to adult BCs has yet to be reported.

Here, the inventors have successfully differentiated iPSCs in vitro into putative BCs that share transcriptional and functional similarities to their in vivo counterparts. The resulting approach recapitulates the sequence of key developmental milestones observed in mouse and human fetal lungs. Initially primordial lung progenitors identified by NKX2-1 expression are produced with only low levels of TP63 expression detectable in a minority of cells. Subsequently, a developing airway program is induced characterized by co-expression of NKX2-1 and TP63, with subsequent maturation into cells expressing the functional and molecular phenotype of BCs. As is observed in mature primary BCs, iPSC-derived BCs ("iBCs") express the cell surface marker NGFR that enables their purification by flow cytometry. The resulting sorted cells display long-term, clonal self-renewal capacity, multi-lineage differentiation in ALI cultures in vitro and in tracheal xenografts. iBCs can be applied for disease-modeling studies, exemplified here by recapitulating essential features of asthma, CF, and PCD. The ability to derive tissue-specific stem cells, such as airway BCs, from iPSCs, including capabilities to purify, expand, cryopreserve, and differentiate these cells, overcomes many of the key hurdles that currently limit the more widespread application of iPSC technology and will accelerate the study of human lung disease.

Results

Figure 1A:
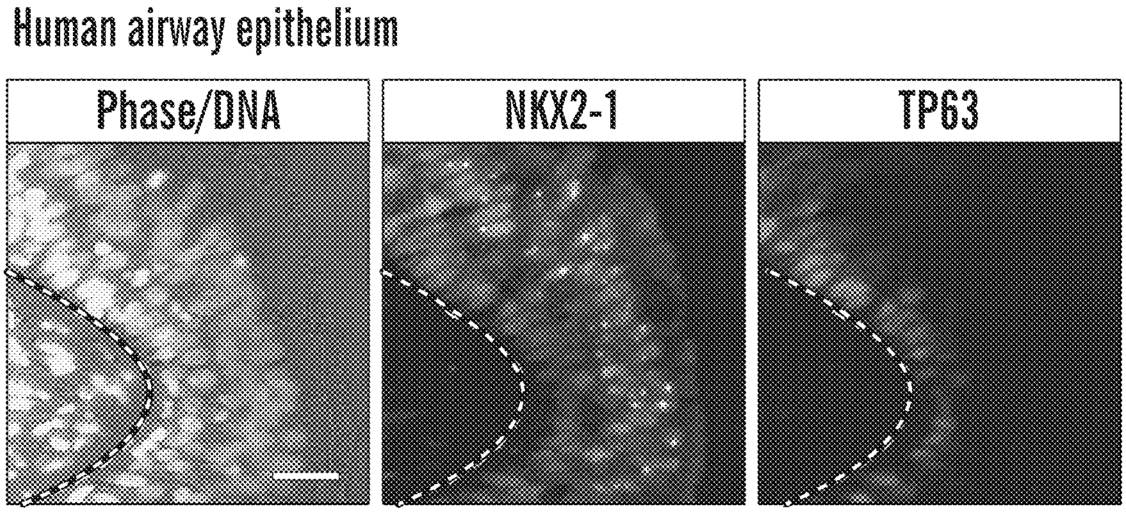
Figure 1B:
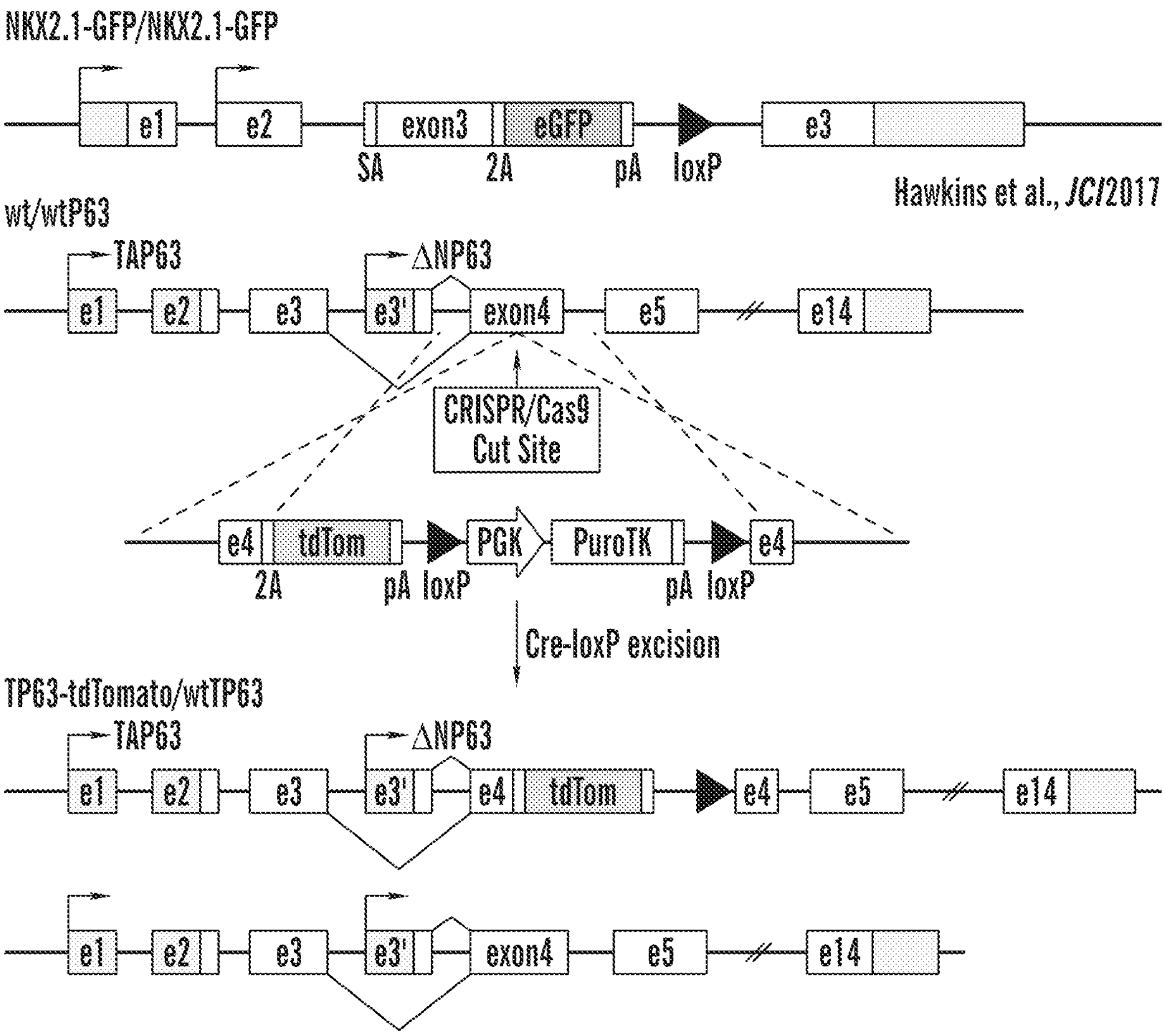

A TP63 Fluorescent Reporter Allows Visualization, Purification, and Interrogation of iPSC-Derived Airway Progenitors Because NKX2-1 is the earliest transcriptional regulator expressed in all developing lung epithelial cells and TP63 is a canonical transcription factor required for expression of the BC program, it was sought to generate a tool that would allow visualization and purification of NKX2-1+/TP63+ putative lung BCs engineered in vitro from iPSCs while excluding any non-lung BCs (NKX2-1−/TP63+; FIGS. 1A and 1B). Using a normal iPSC line (BU3) that carries a GFP reporter targeted to the endogenous NKX2-1 locus (Hawkins et al., 2017), the inventors additionally targeted a tdTomato reporter coding sequence into one allele of the endogenous TP63 locus at exon 4 to ensure reporter expression reflects expression of the predominant known forms of TP63, DeltaN-type, or TA-type at the N terminus while avoiding bias to C-terminal splice forms, such as a-, b-, and g-type (FIG. 1B; Levrero et al., 2000). Karyotypically normal, pluripotent clones with monoallelic targeting of the TP63 locus and biallelic targeting of the NKX2-1 locus were identified (FIGS. 8A-8E), thus establishing a bifluorescent reporter iPSC line, BU3 NKX2-$1^{GFP}$; $P63^{tdTomato}$, hereafter "BU3 NGPT." To test faithfulness and specificity of the reporters, the inventors differentiated this iPSC line into lung epithelium, employing their recently published airway-directed differentiation protocol, in which a population of basal-like cells was identified based on the expression of NKX-2, TP63, and KRT5 (FIG. 1C; McCauley 2017) As expected, NKX2-1GFP+ (hereafter "GFP+") cells, a small fraction of which also expressed tdTomato (hereafter "TOM+"), emerged by day 15 of differentiation, as detected by flow cytometry and fluorescence microscopy (18.1%±19% GFP+; 0.4%±0.8% TOM+; mean±SD). In the experiment shown in FIG. 1E, 45.4% of cells were GFP+ and 2.5% of cells were GFP+/TOM+ (FIGS. 1D and 1E). Almost all TOM+ cells identified at this time point expressed the lung epithelial lineage GFP reporter (FIG. 1E). It was determined that GFP+ cells at this stage of the differentiation are similar to primordial lung progenitors and do not express canonical markers of extra-pulmonary NKX2-1 domains, which include the forebrain and thyroid (Hawkins et al., 2017; Serra et al., 2017).

Figure 1C:
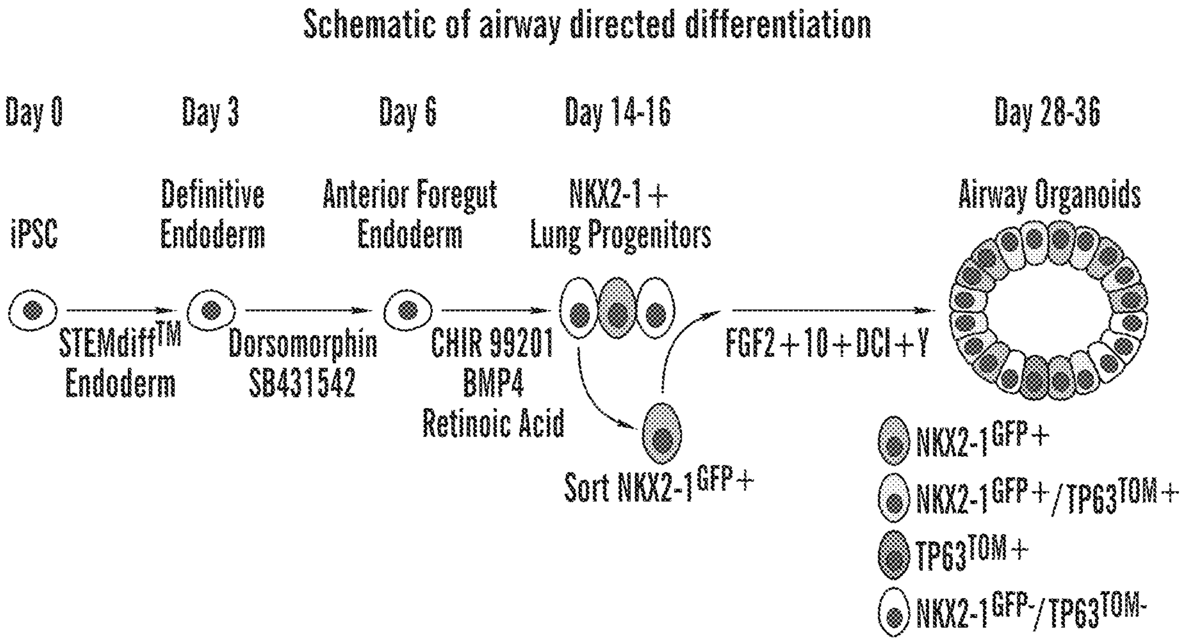
Figure 1D:
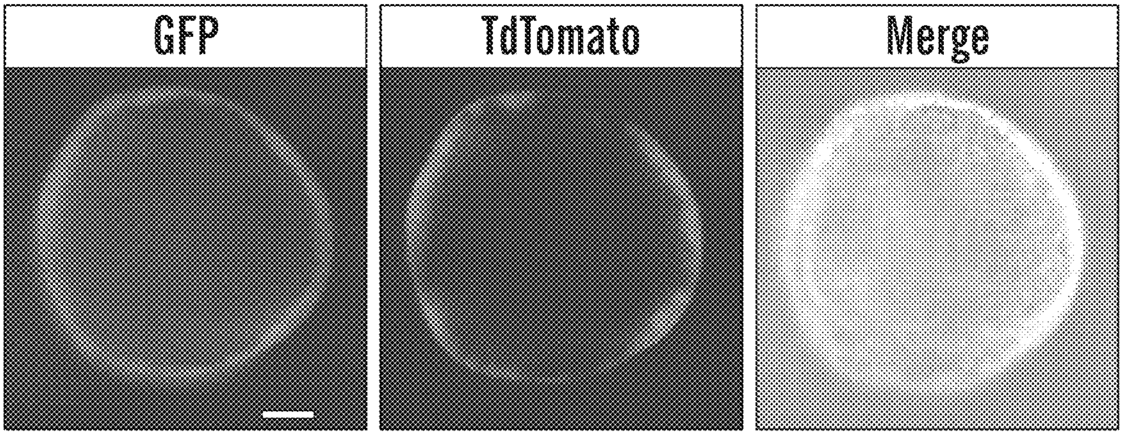
Figure 1E:
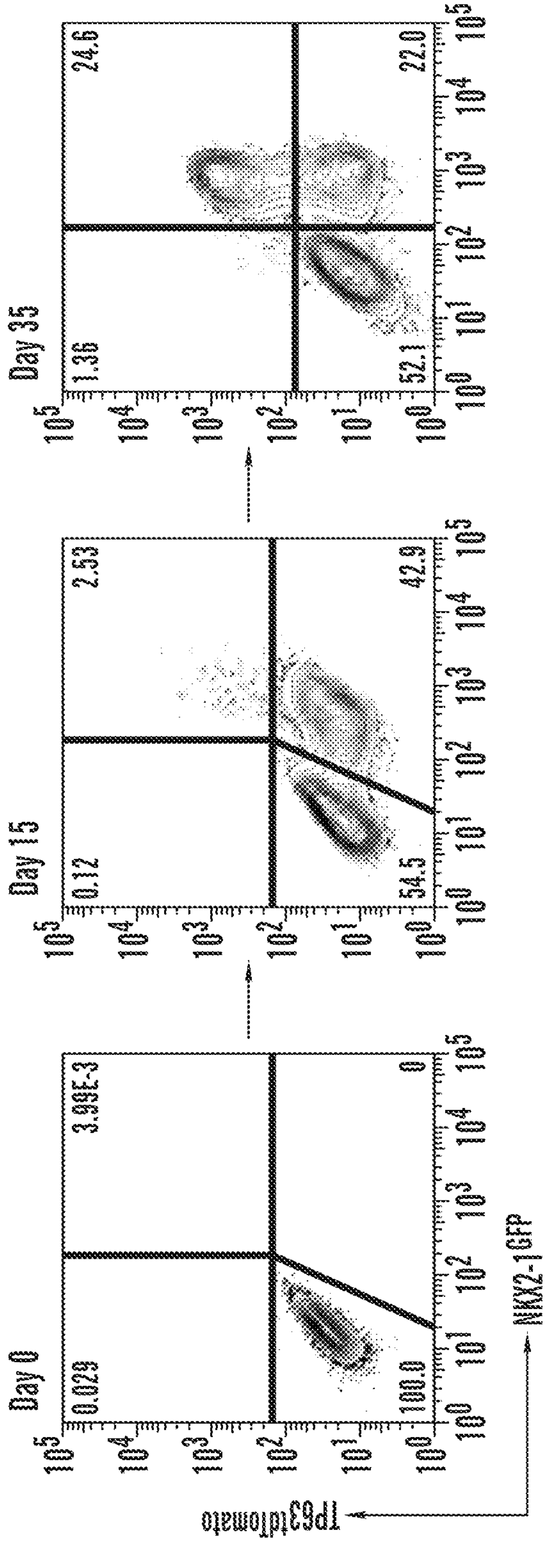
Figure 1F:
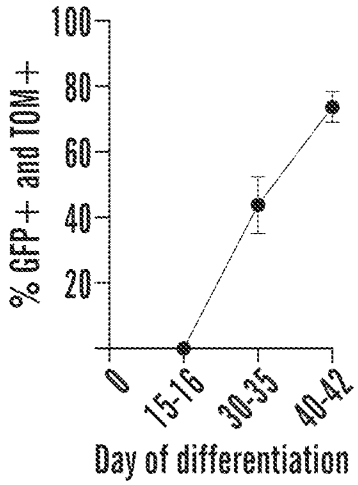

To induce proximal airway differentiation of lung progenitors, GFP+ cells (regardless of TOM expression) were sorted on day 15 of the protocol and suspended in droplets of Matrigel in "airway" serum-free medium, hereafter "FGF2+10+DCI+Y" (FIG. 1C, schematic; McCauley et al., 2017). Between days 28-36, monolayered epithelial spheres emerged and 43.7%±8.6% (mean±SD; 46.6% GFP+, 24.6% GFP+/TOM+ in the experiment shown in FIG. 1E) of cells co-expressed NKX2-1GFP and TP63TOM, hereafter "GFP+/TOM+" (FIGS. 1E and 1F).

Figure 1G:
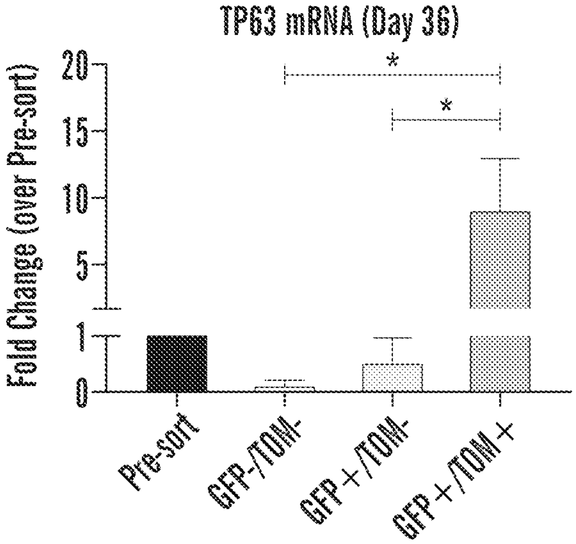
Figure 1H:
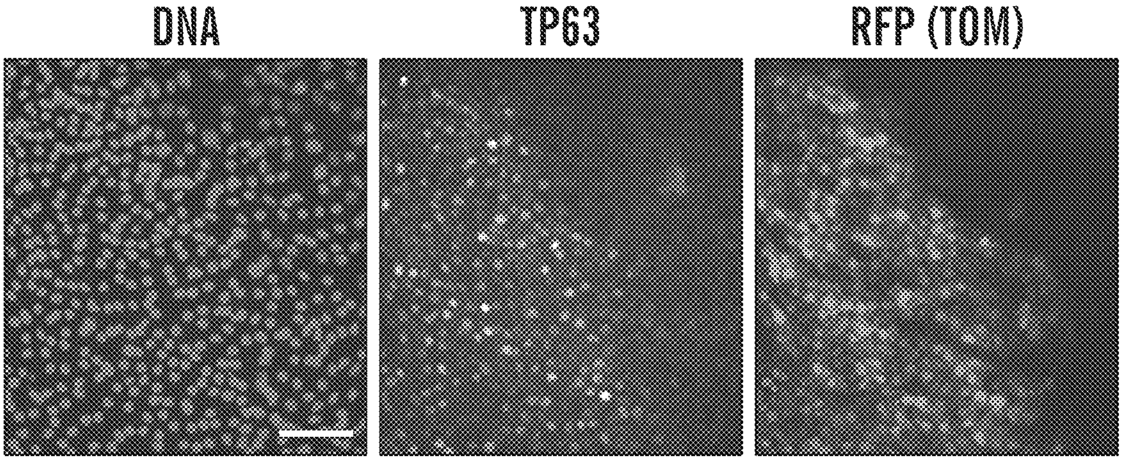
Figure 9B:
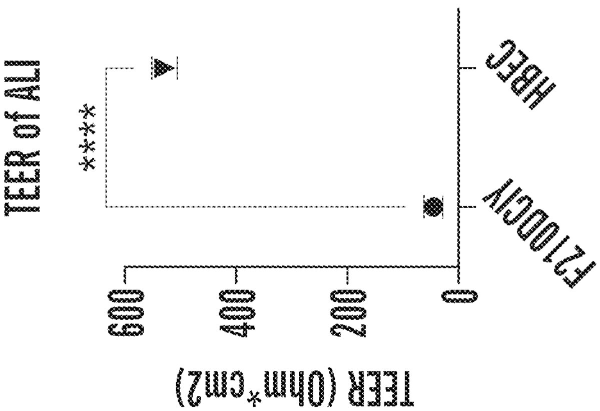
Figure 9A:
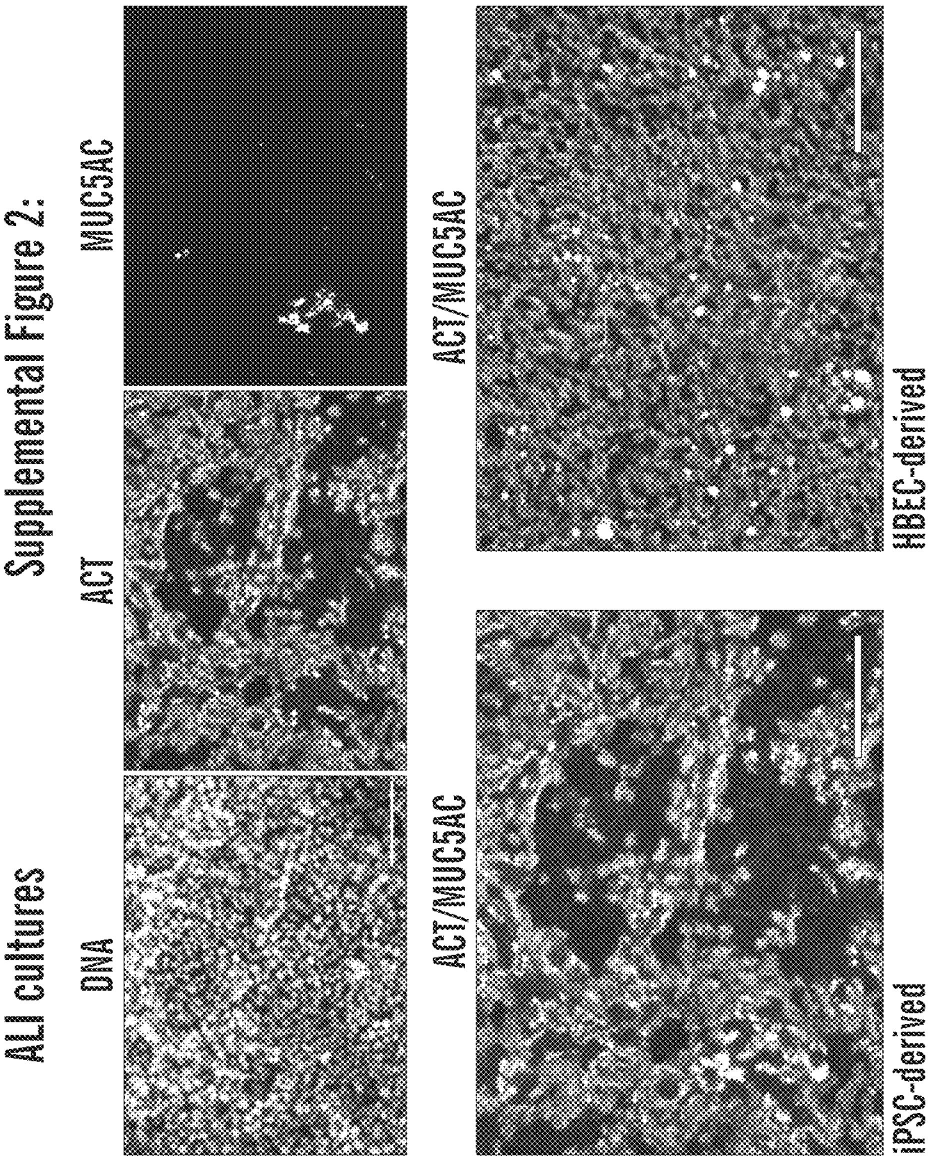
Figure 9C:
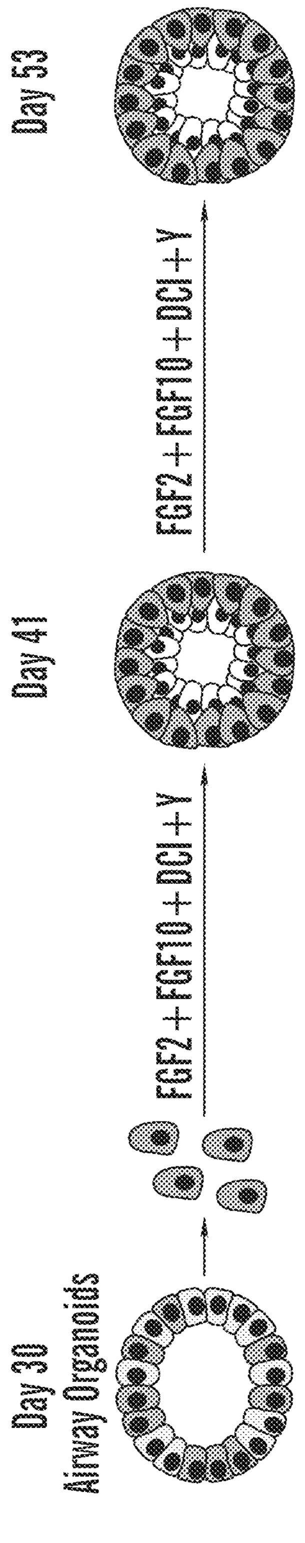
Figure 9D:
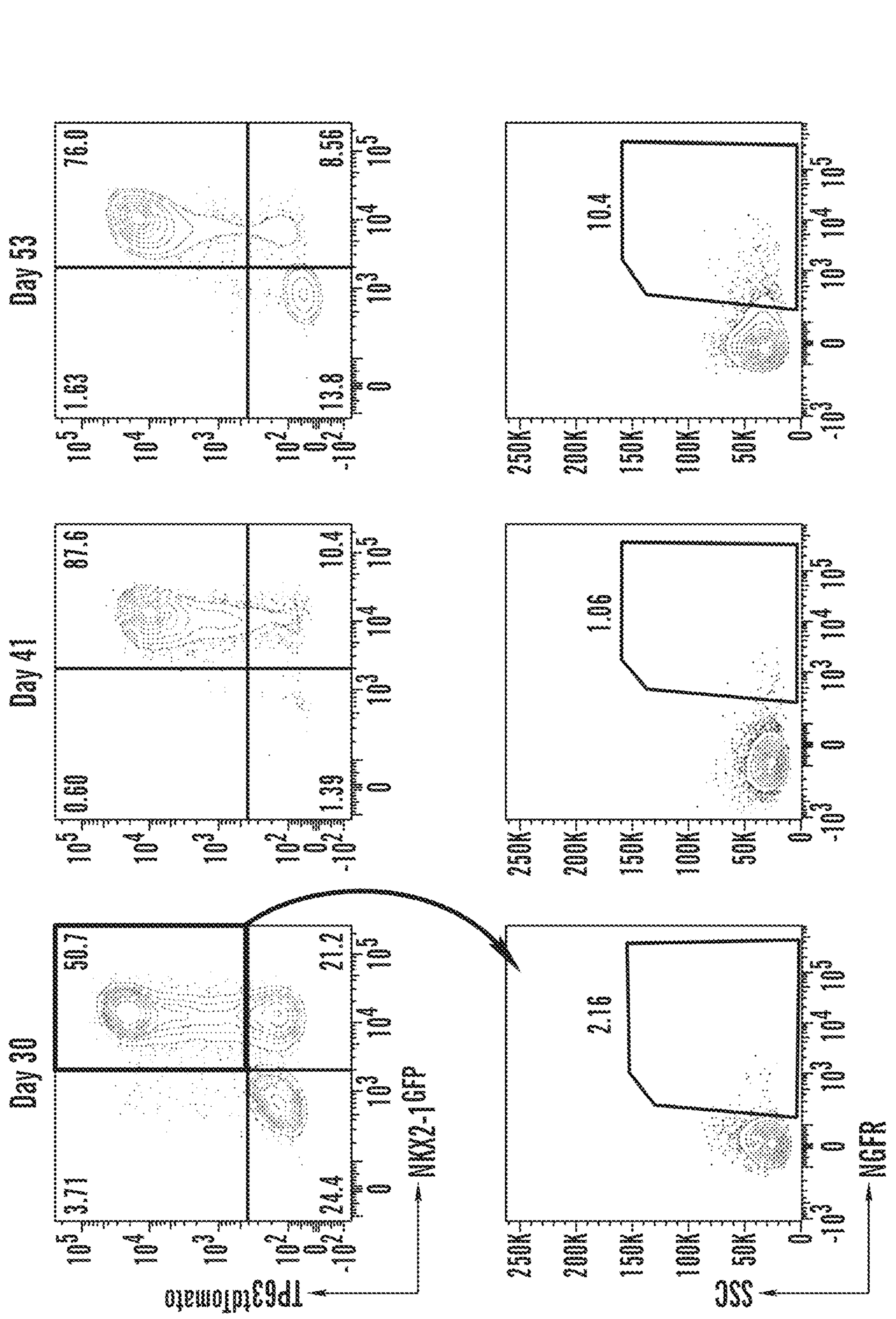
Figure 9E:
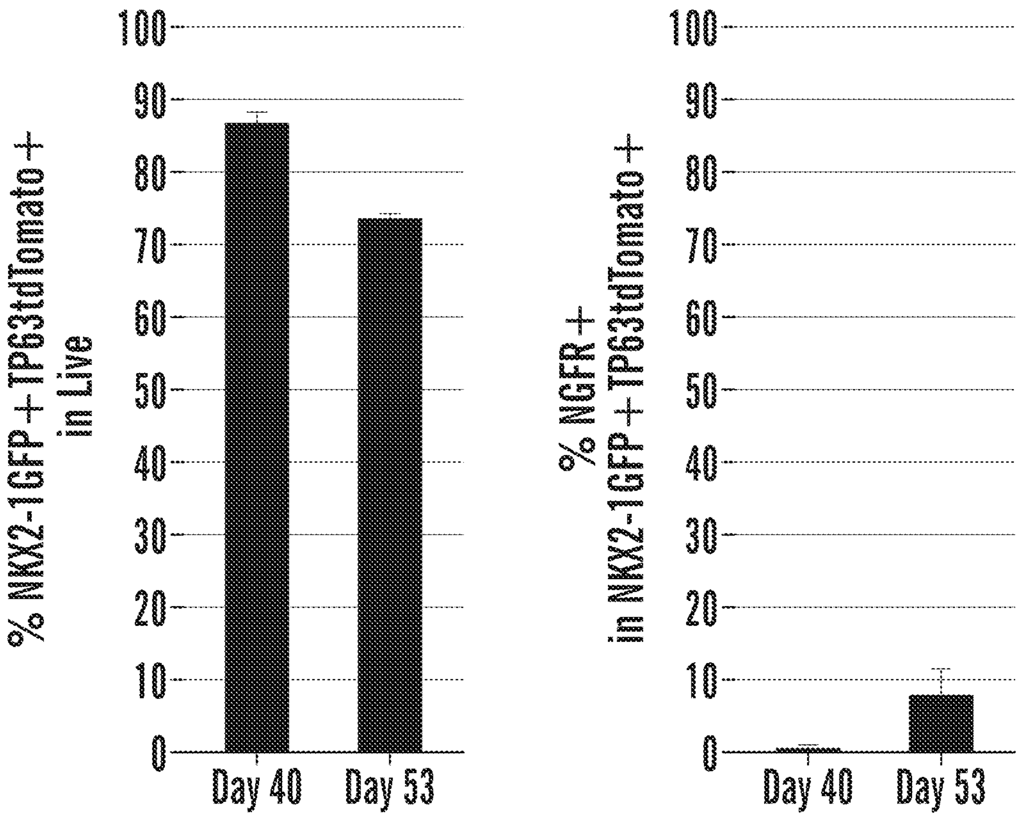
Figure 9F:
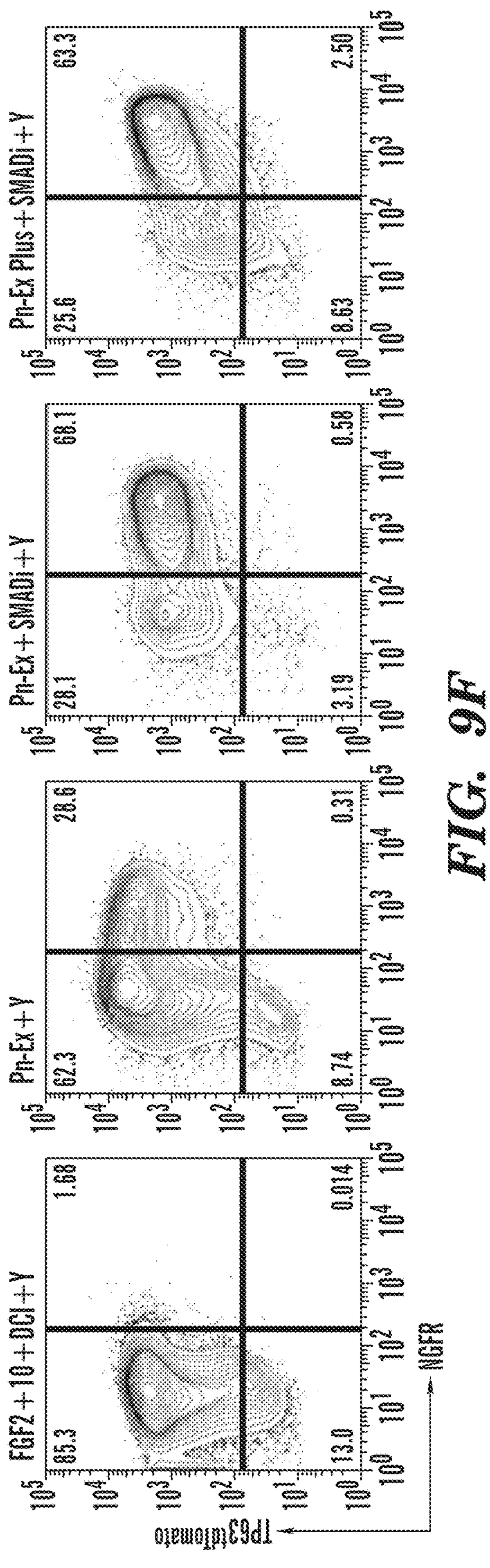
Figure 9G:
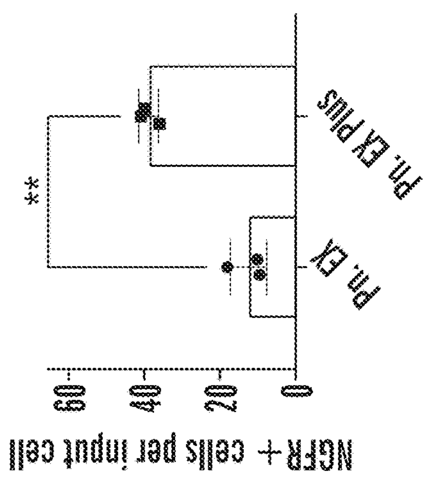

A single-input GFP+ cell on day 15 yielded 15.7±8.25 GFP+/TOM+ cells by days 30-35. After single-cell dissociation of epithelial spheres and expansion in 3D culture conditions, the percentage of cells GFP+/TOM+ increased further to 73.7%±4.7% by day 42 (FIG. 1F). Flow cytometry sorting on day 36 demonstrated enrichment of TP63 mRNA in GFP+/TOM+ cells and depletion in TOM− cells (FIG. 1G). TP63 protein was detected in TOM+ cells; however, TOM− cells lacked TP63 protein (FIGS. 1H and 8F). These findings confirmed the specificity of the tdTomato reporter. In summary, it was determined that NKX2-1GFP+/TP63TOM+ cells emerge and can be expanded in FGF2+10+DCI+Y medium. The early emergence of tdTomato expression in some cells beginning around day 15 is in keeping with prior observations in vitro (Hawkins et al., 2017; McCauley et al., 2017, 2018a) and in vivo (Yang et al., 2018; Nickelic et al., 2017) that Tp63 mRNA and nuclear protein are initially detected at this time point in a subset of early NKX2-1+ primordial lung epithelial progenitors soon after specification of the respiratory lineage, even prior to airway differentiation (see schematic in FIG. 1C).

iPSC-Derived Airway Progenitors Adopt a Molecular Phenotype Similar to Primary Adult Basal Cells Next, NKX2-1GFP+/TP63TOM+ cells produced by the airway differentiation protocol were characterized in terms of capacity for self-renewal, multi-lineage differentiation, and expression of the canonical BC marker NGFR (FIGS. 9A-9E). Day 40-42 iPSC-derived GFP+/TOM+ cells were sorted and placed in ALI 2D cultures for at least 2 weeks, where differentiation into cells expressing markers of MCCs and SCs was observed, although this differentiation appeared to be patchy (FIG. 9A) and cells failed to maintain barrier function based on transepithelial electrical resistance (TEER) measurements (FIGS. 9A and 9B) in contrast to ALI-differentiated primary HBEC controls (FIGS. 9A and 9B). In keeping with these results, NGFR was expressed on only a small fraction, 1.9%±1.8%, of GFP+/TOM+ cells on day 40-42 of differentiation, indicating cells at this time point were unlikely to be mature BCs. Even after 3 additional months of serial sphere passaging of GFP+/TOM+ cells in 3D culture, NGFR expression did not significantly increase, although GFP and TOM co-expression was maintained in the majority of cells (FIGS. 9C-9E), indicating that increased culture time alone would not induce BC maturation of iPSC-derived NKX2-1+/TP63+ cells.

It was contemplated that the low expression of NGFR and inconsistent multi-lineage differentiation of iPSC-derived cells was that GFP+/TOM+ cells were more similar to immature TP63+/NKX2-1+/KRT5− airway progenitors observed in vivo during early airway patterning and were not yet mature BCs (Yang et al., 2018). Thus, it was next sought to identify culture conditions that would further differentiate GFP+/TOM+ cells into a more basal-like state, using NGFR expression as a readout. Recently, inhibition of SMAD and Rho-associated protein kinase (ROCK) signaling was found to induce a proliferative state in primary BCs and significantly increase overall yield from serially passaged cultures while maintaining, to an extent, their differentiation capacity (Mou et al., 2016; Zhang et al., 2018). It was tested whether GFP+/TOM+ iPSC-derived airway progenitors would selectively proliferate and possibly mature in media optimized for primary human BC culture. On days 30-32 of differentiation, GFP+/TOM+ cells were sorted, replated in 3D Matrigel, and exposed to a commercially available BC medium (Pneuma-Cult-Ex Plus) supplemented with small-molecule inhibitors of SMAD signaling (transforming growth factor b [TGF-b] and bone morphogenetic protein (BMP) inhibition with A 83-01 and DMH1, respectively) and Y-27632 (hereafter “BC medium”; FIGS. 2A-2D). In response to BC medium, GFP+/TOM+ spheroids exhibited less distinct lumens (FIG. 2A) with rapid and robust induction of NGFR in GFP+/TOM+ cells within 4 days of exposure to BC medium (FIGS. 2B-2D, 9F, and 9G). For example, between days 1 and 3, NGFR expression increased in frequency from 1% to 35% in response to BC medium. By day 6, 71%±5% (mean±SD) of cells expressed NGFR (FIG. 2B), indicating that the change in medium formulation, rather than selective expansion of rare NGFR+ cells, was inducing NGFR expression in previously NGFR− cells. In contrast, parallel aliquots of cells that continued in FGF2+10+DCI+Y (FIGS. 2B, 2D, and 9F) expressed little to no NGFR.

Figure 2A:
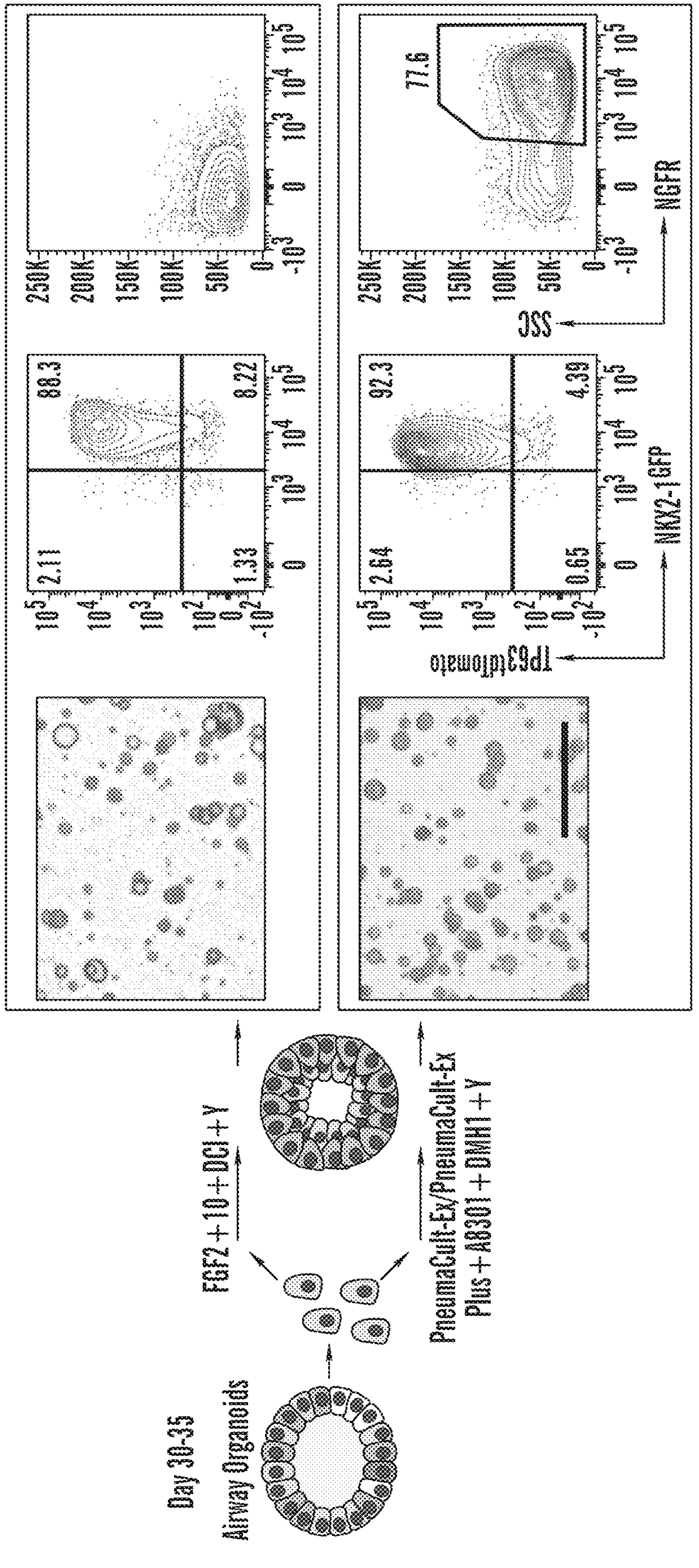
Figure 2B:
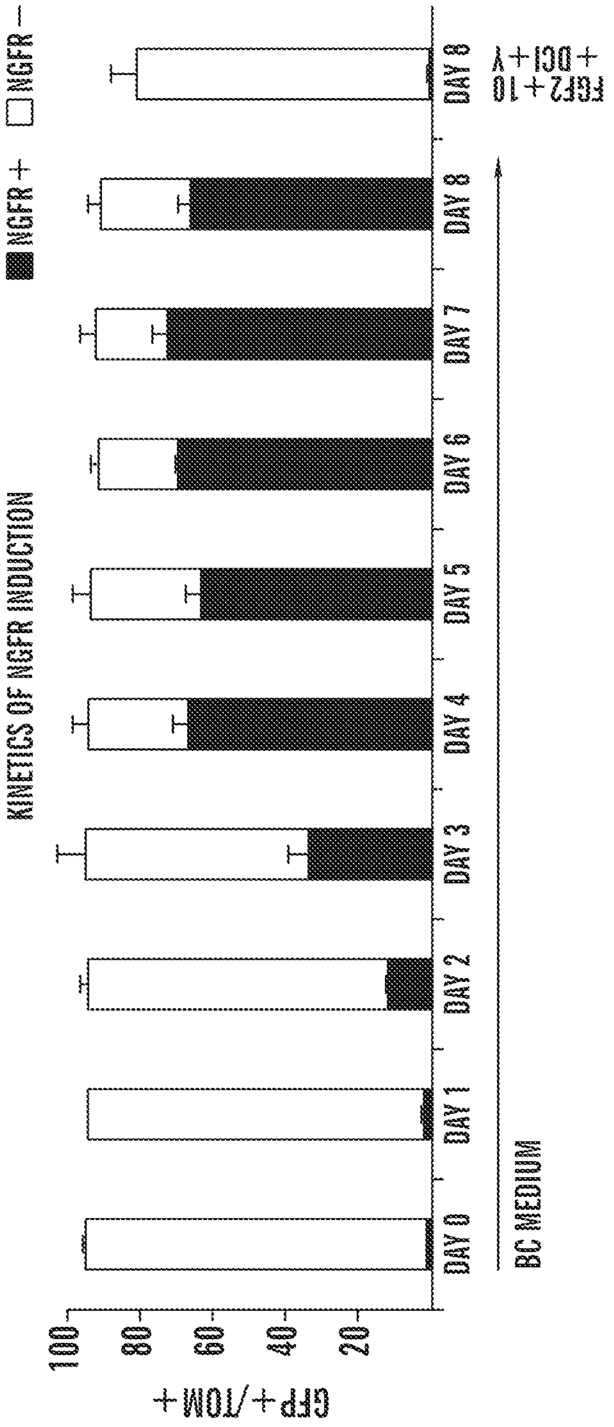
Figure 2C:
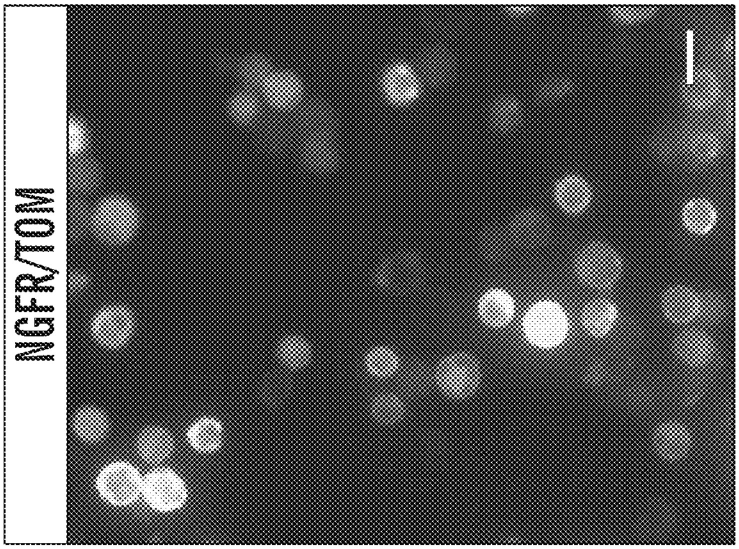
Figure 2D:
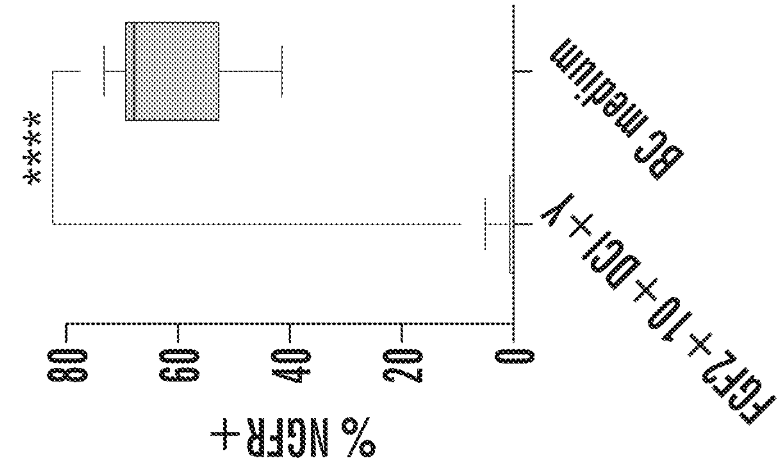
Figure 2E:
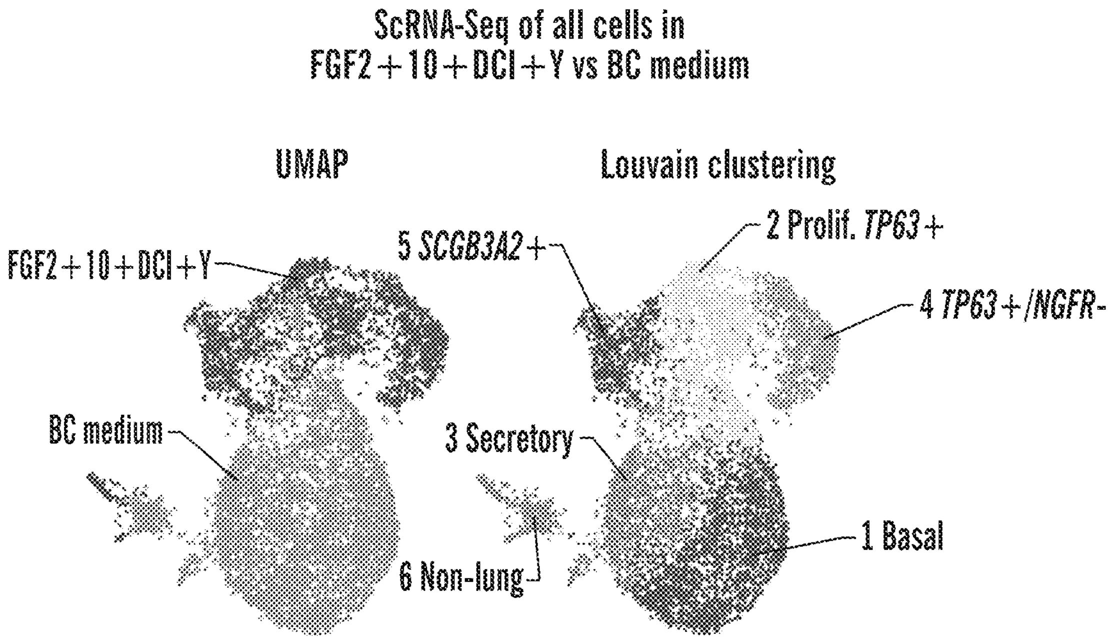
Figure 2F:
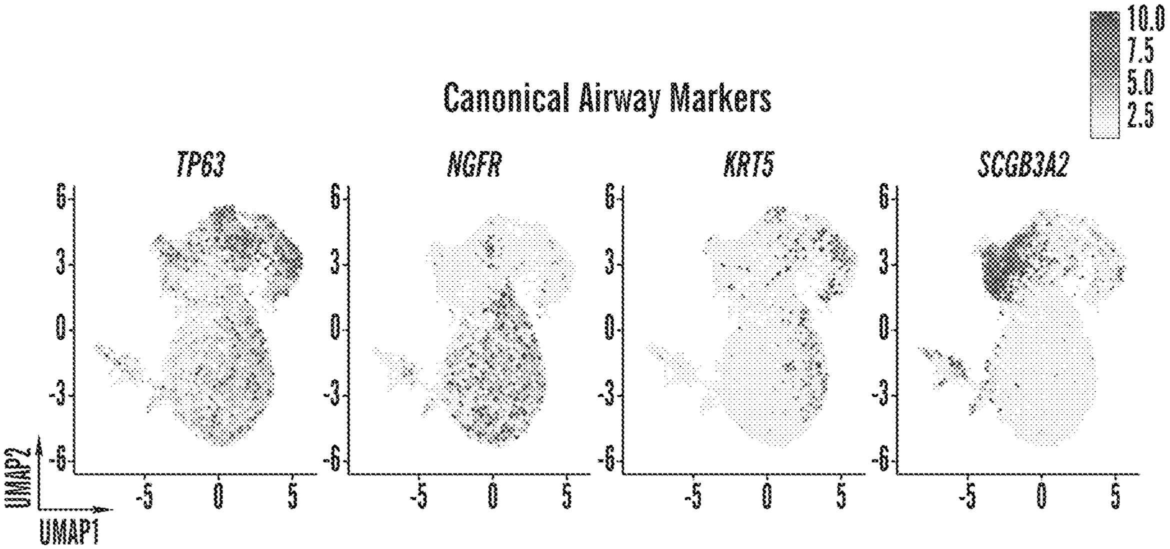
Figure 10A:
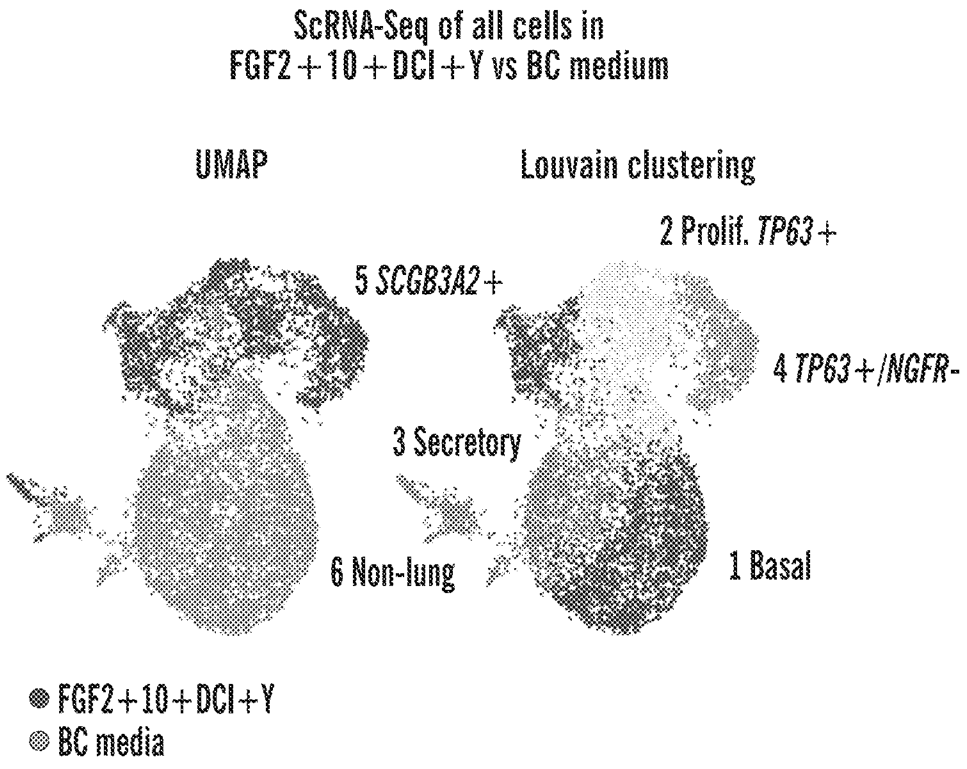
Figure 10B:
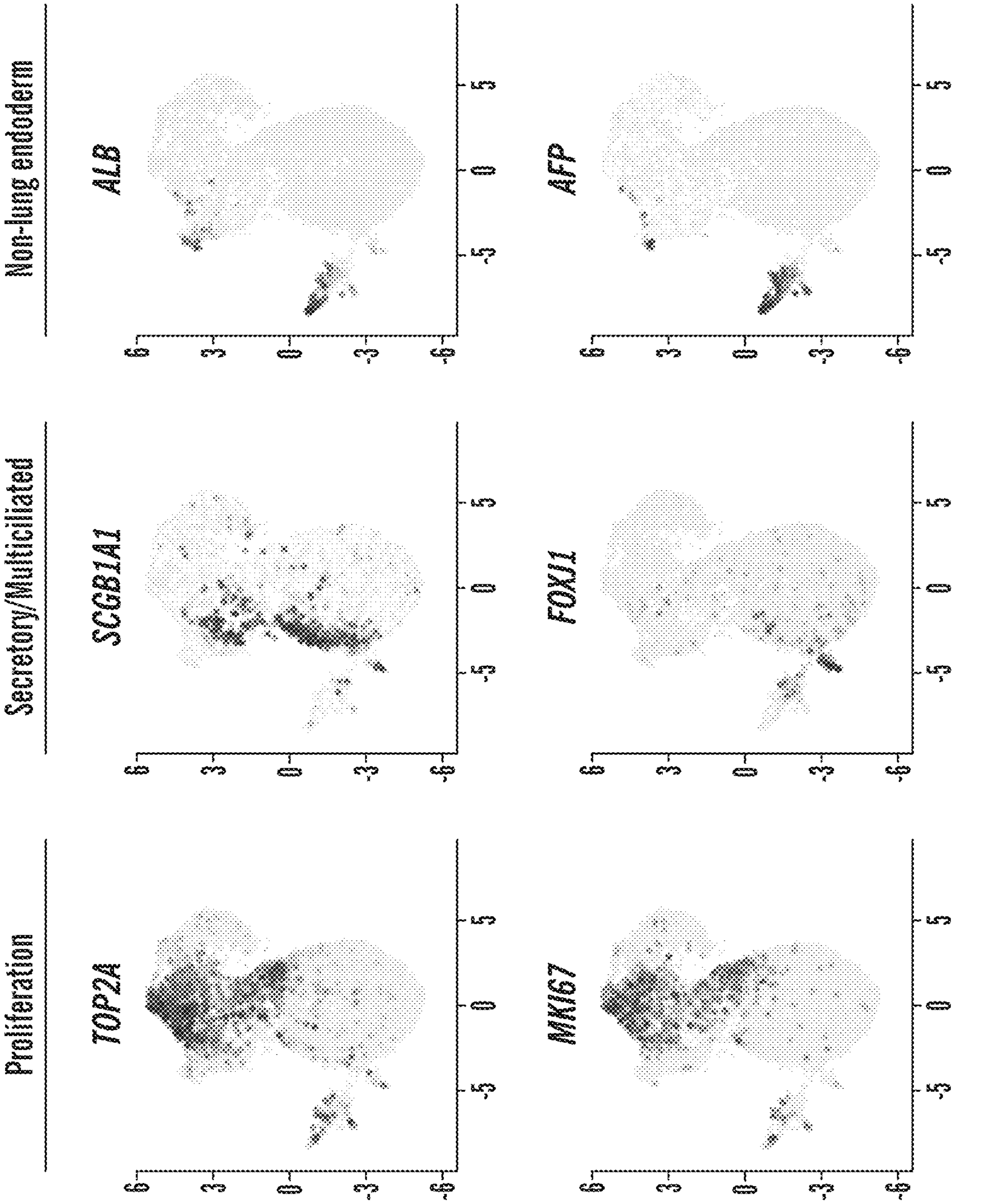
Figure 10C:
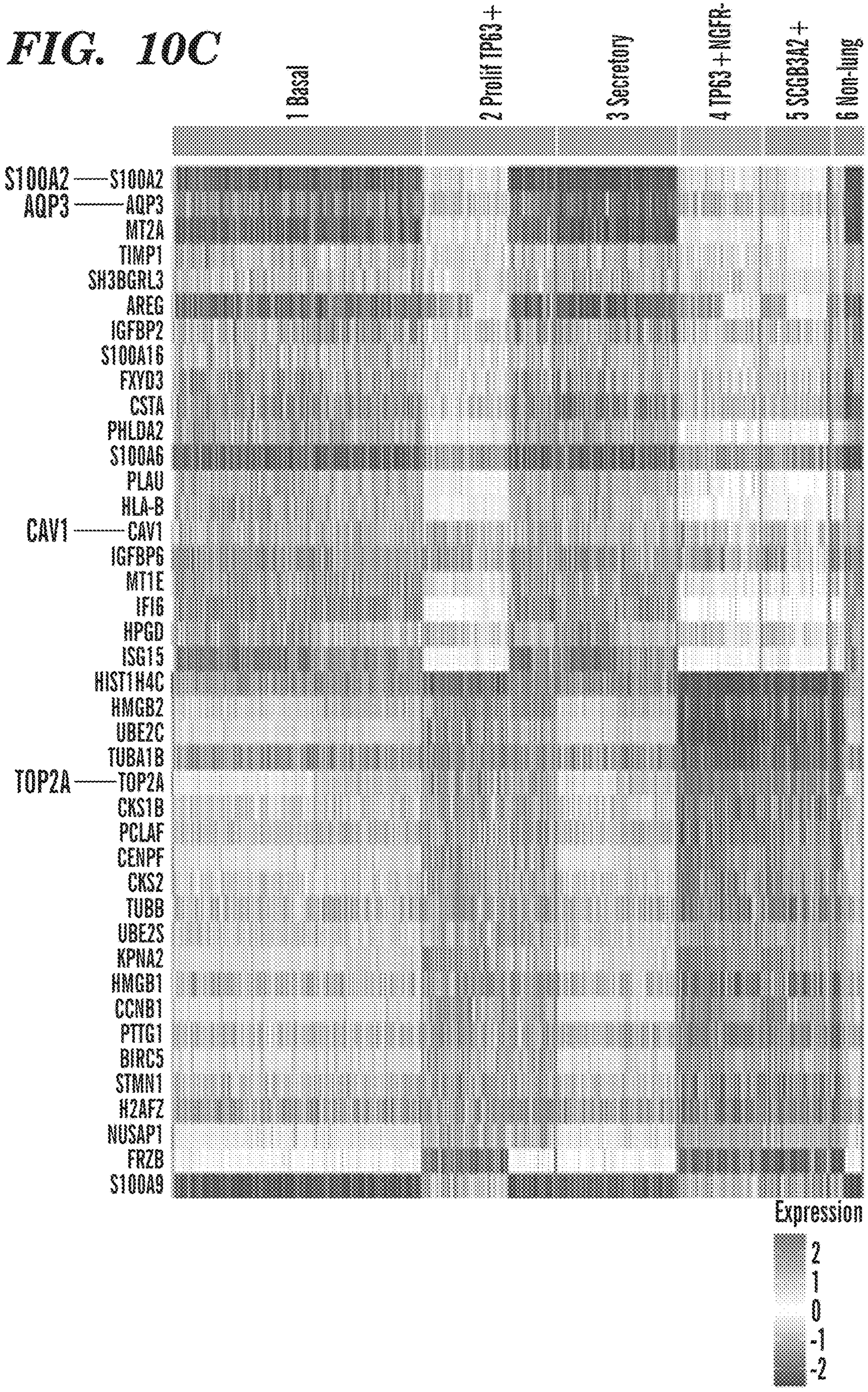
Figure 10C:
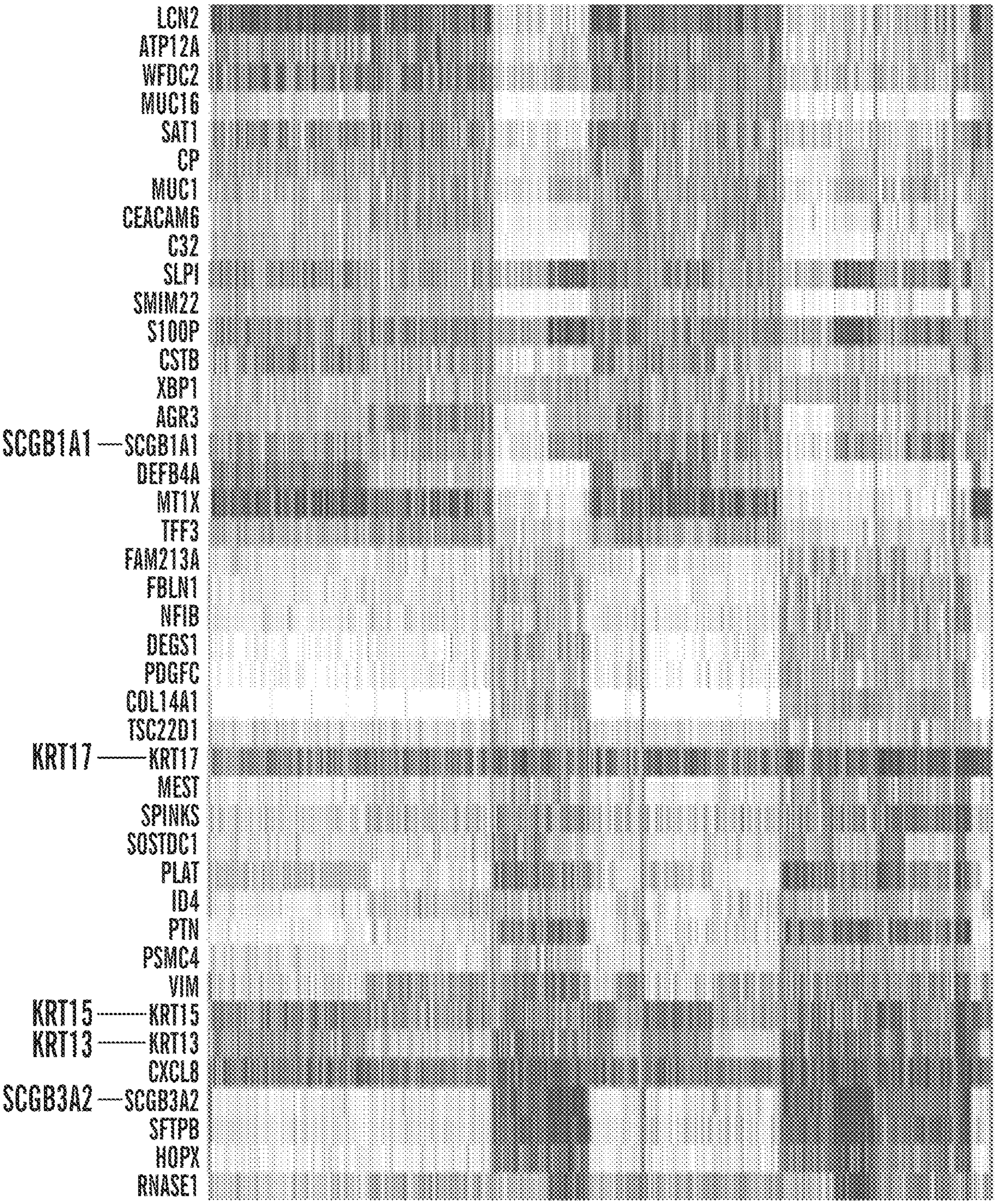
Figure 10C:
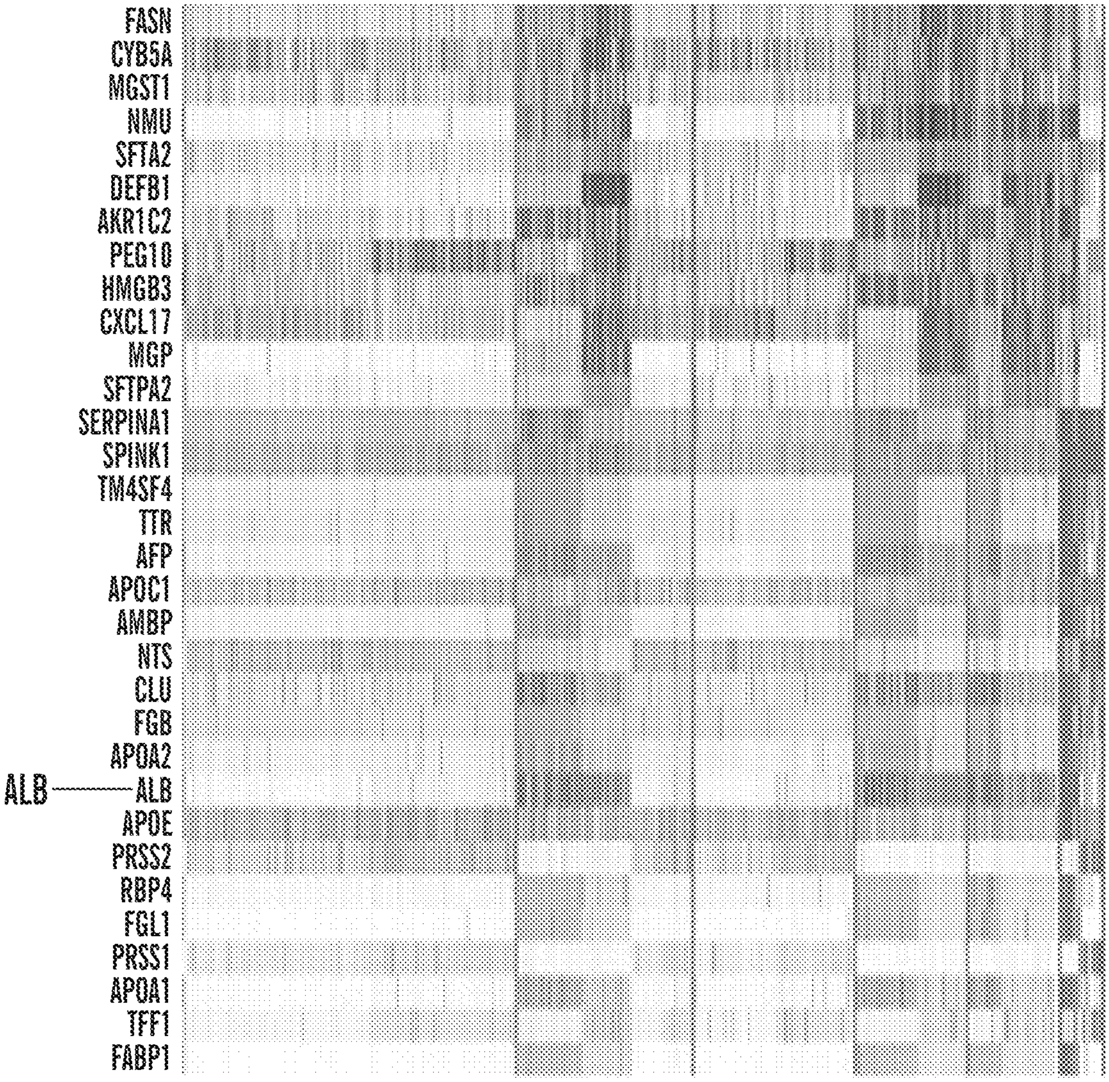

Next, to determine whether the increase in NGFR expression in response to BC medium was coincident with a broader augmentation of a mature BC program, scRNA-seq was performed. BU3 NGPT iPSCs were differentiated in the inventors' protocol (FIG. 2A), purifying GFP+/TOM+ cells on days 30-32 followed by replating for 3D culture in either BC medium versus continuing in FGF2+10+DCI+Y medium until scRNA-seq analysis on day 46. After quality control, a total of 7,331 cells were analyzed (Louvain clustering; FIG. 2E) and six populations were identified based on the expression of canonical markers, cell cycle, and differentially expressed genes (DEGs) (1-6, in descending order of size): (1) “basal”; (2) “proliferative TP63+”; (3) “secretory”; (4) “TP63+/NGFR−”; (5) “SCGB3A2+”; and (6) “non-lung endoderm” (FIGS. 2E, 2F, and 10A-10C). Clusters 1, 2, and 4, with basal-like features, expressed key BC markers as well as TP63 and tdTomato, thus supporting the reporter specificity (FIGS. 10A-10C). As expected, NGFR was only expressed in the basal-like population cultured in BC medium (cluster 1; FIG. 2F). Notably, during lung-directed differentiation, cells can revert to non-lung endodermal lineages (Hurley et al., 2020; McCauley et al., 2018a); however, less than 0.05% of all cells were characterized as non-lung endoderm in this analysis (FIG. 10B).

Figure 2G:
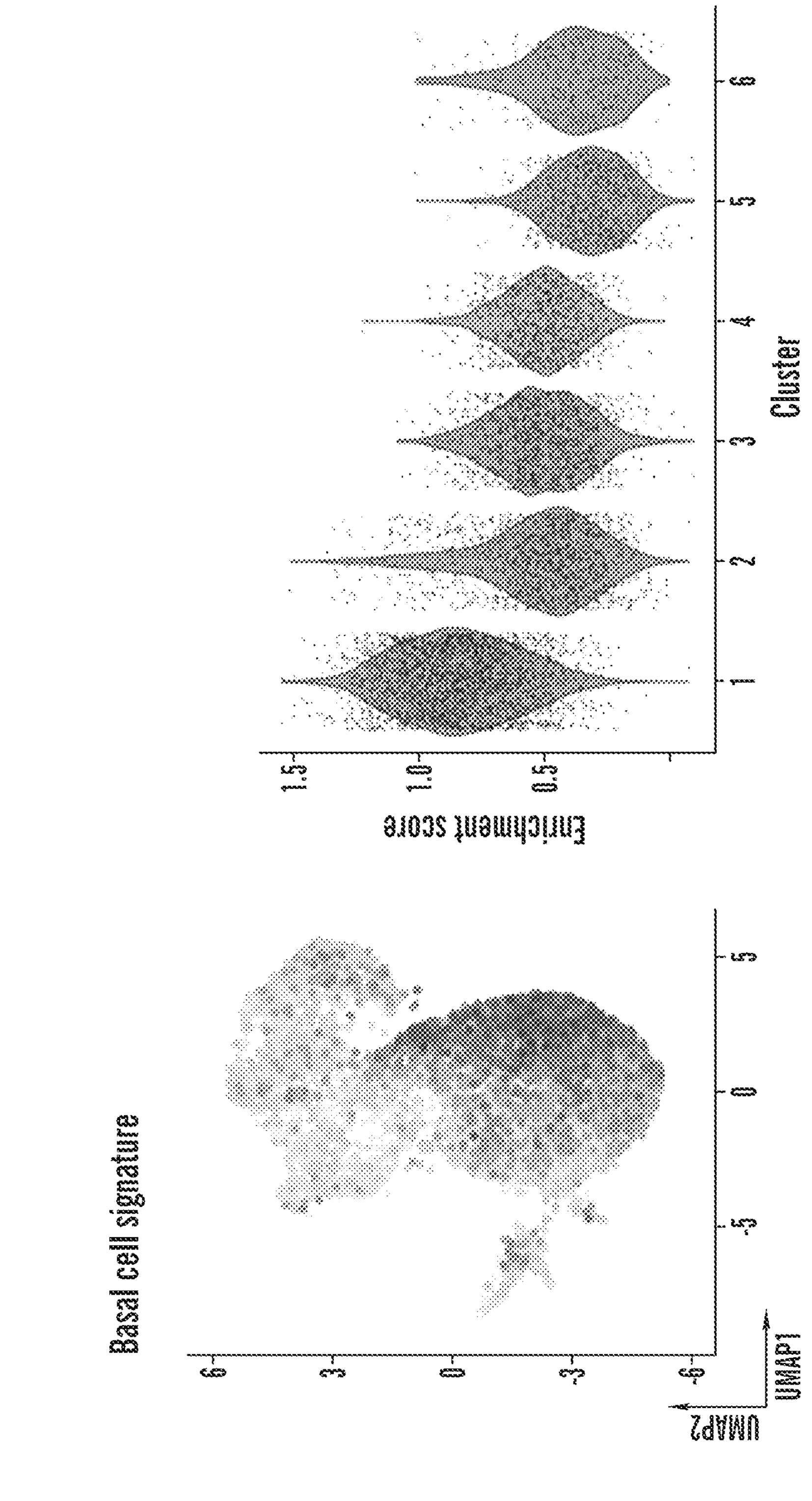
Figure 10D:
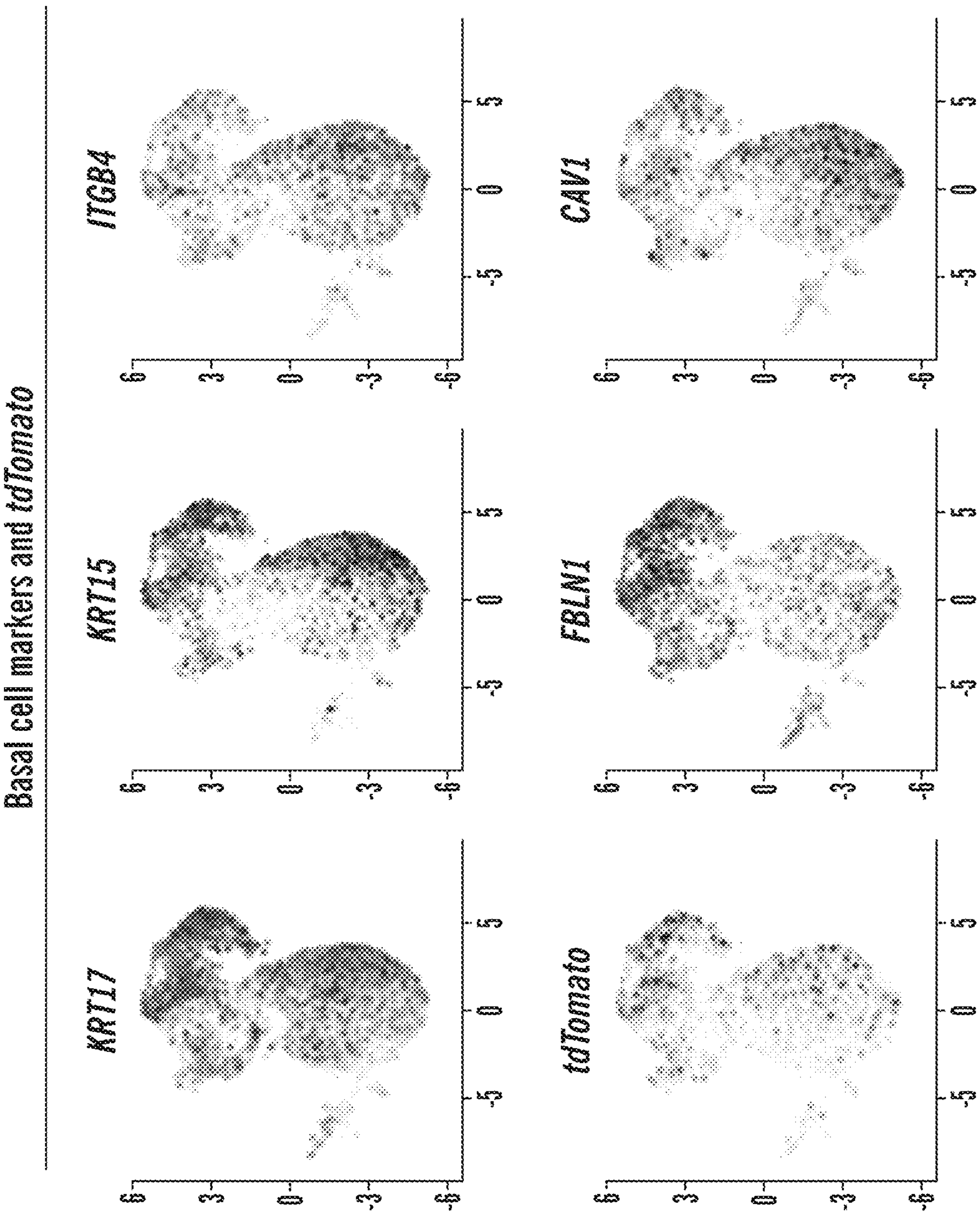

Next, the transcriptomic similarities and differences of these iPSC-derived clusters were quantified and compared to their human airway counterparts. Freshly isolated adult and fetal airway epithelia were used to determine the transcriptomic profile of endogenous airway epithelial cells and also cultured human airway epithelium, the gold standard in vitro platform of airway biology. First, gene signatures composed of the top 30 DEGs in BCs, SCs, and MCCs were generated from scRNA-seq of cultured HBECs (“P0”; minimal culture) before and after ALI differentiation (Fulcher and Randell, 2013; FIG. 15; FIGS. 11A-11D). The validity of these signatures was confirmed by quantifying their expression in freshly isolated human airway epithelium from 6 adult individuals (Carraro et al., 2020; FIG. 10D). The expression of each signature was then visualized on a Uniform Manifold Approximation and Projection (UMAP) of cells from BC medium and FGF2+10+DCI+Y and the enrichment score for BCs, SCs, and MCCs measured in each of clusters 1-6. Cluster 1 (BC medium) had the highest BC enrichment score for the BC signature and expressed canonical BC markers, including S100A2, CAV1, and COL17A1 in addition to TP63, KRT5, KRT17, and ITGB4 (FIGS. 2G and 10C; Rock et al., 2009; Plasschaert et al., 2018).

Figure 2H:
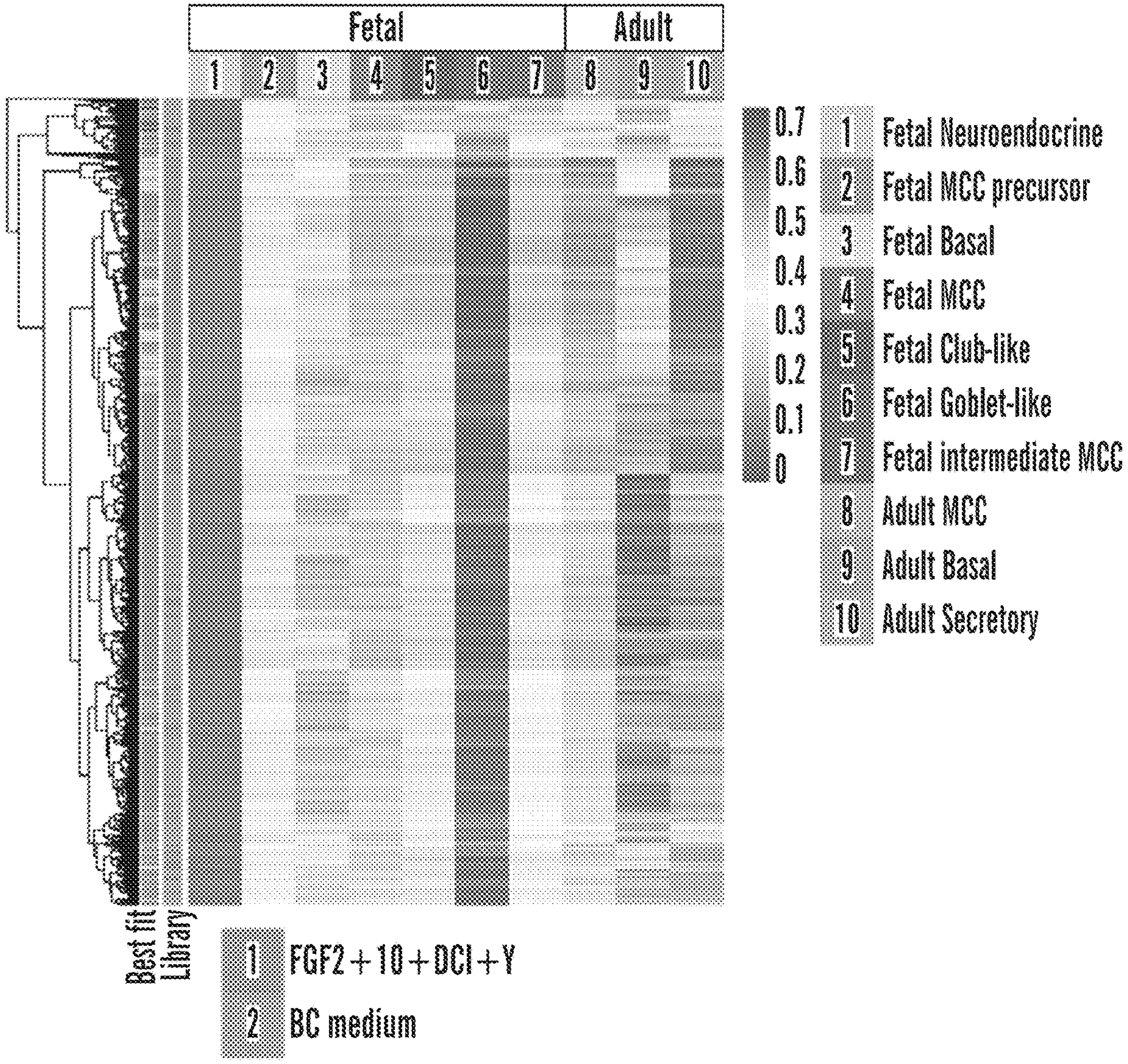
Figure 10E:
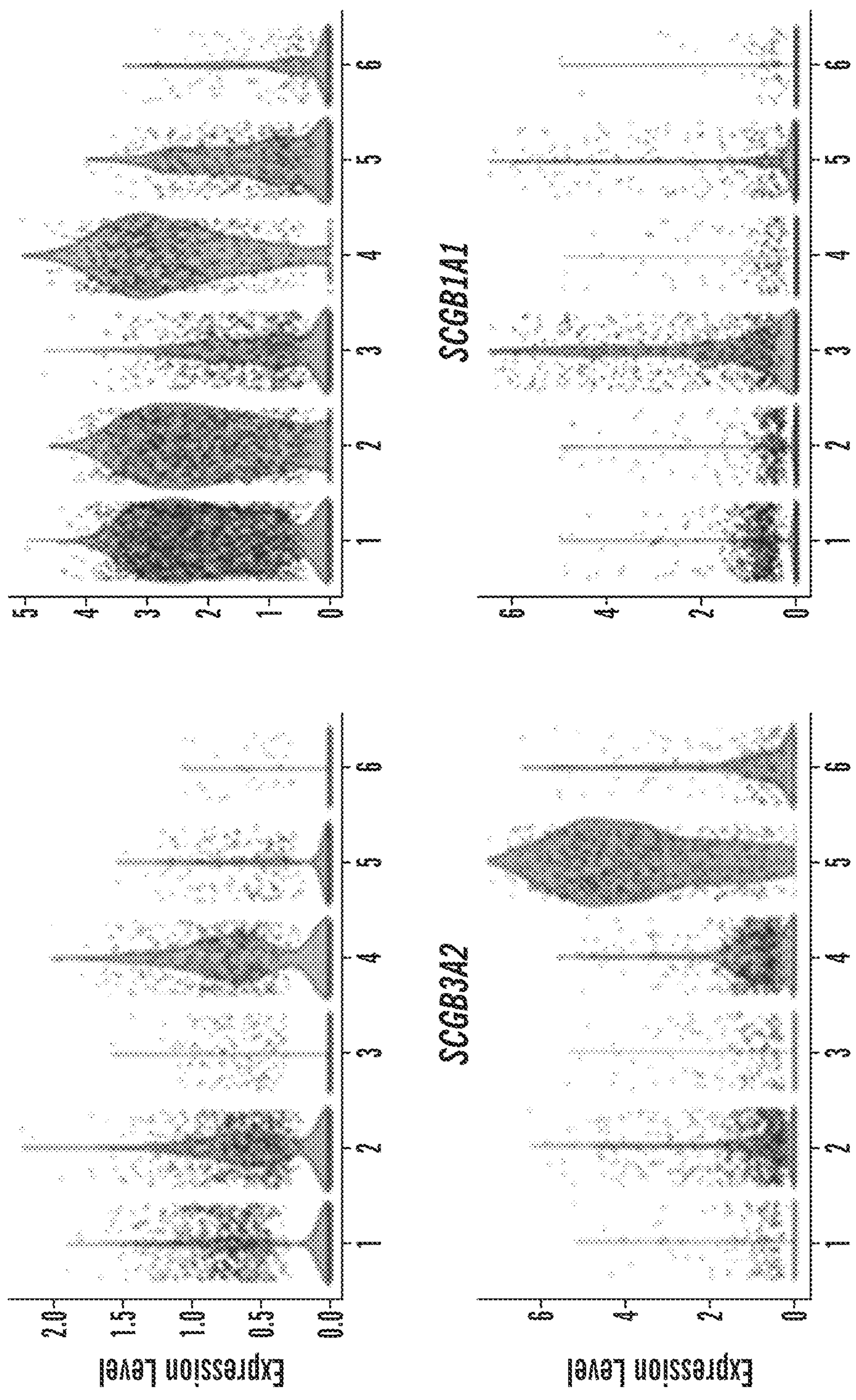
Figure 11B:
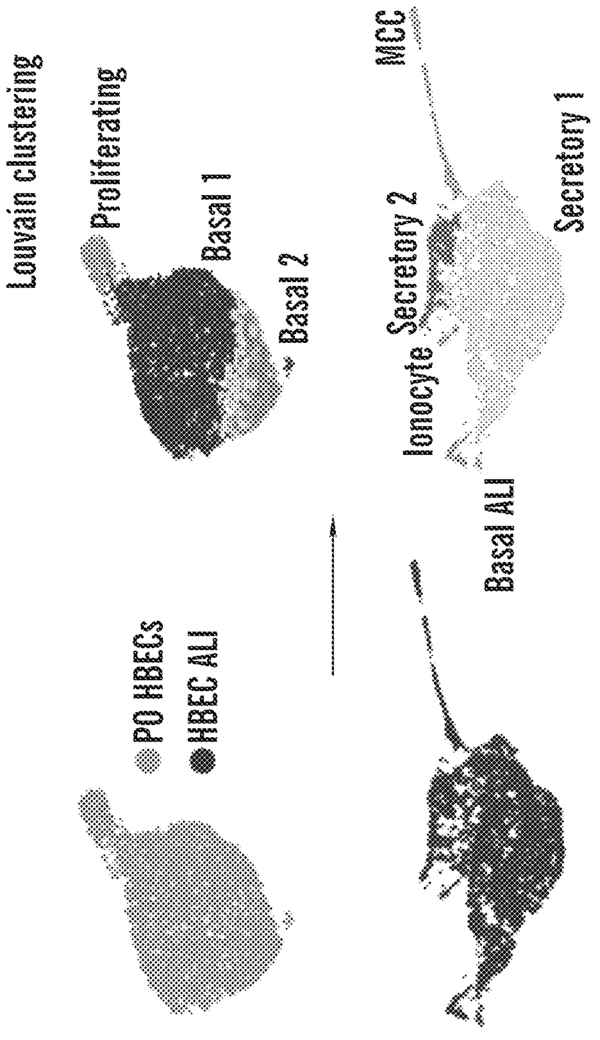
Figure 11A:
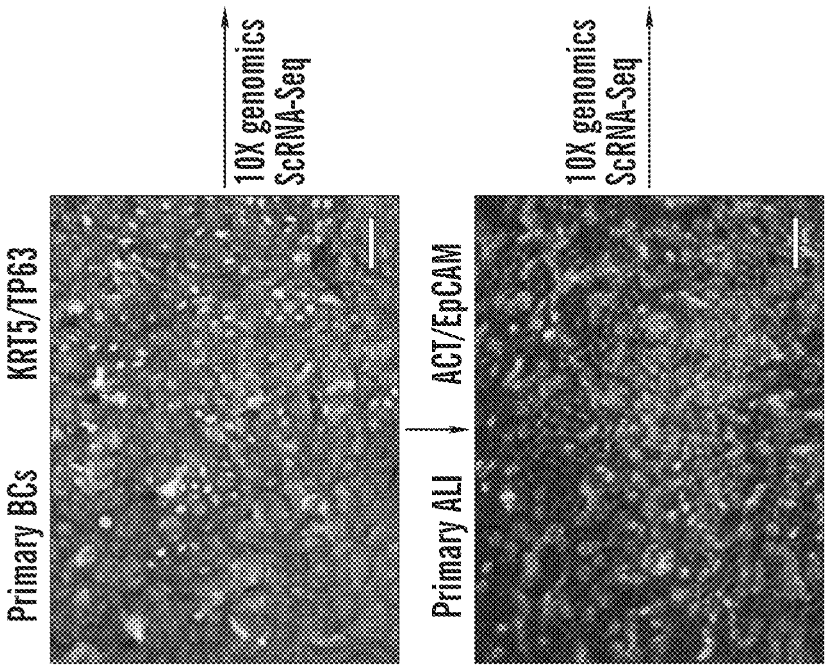
Figure 11C:
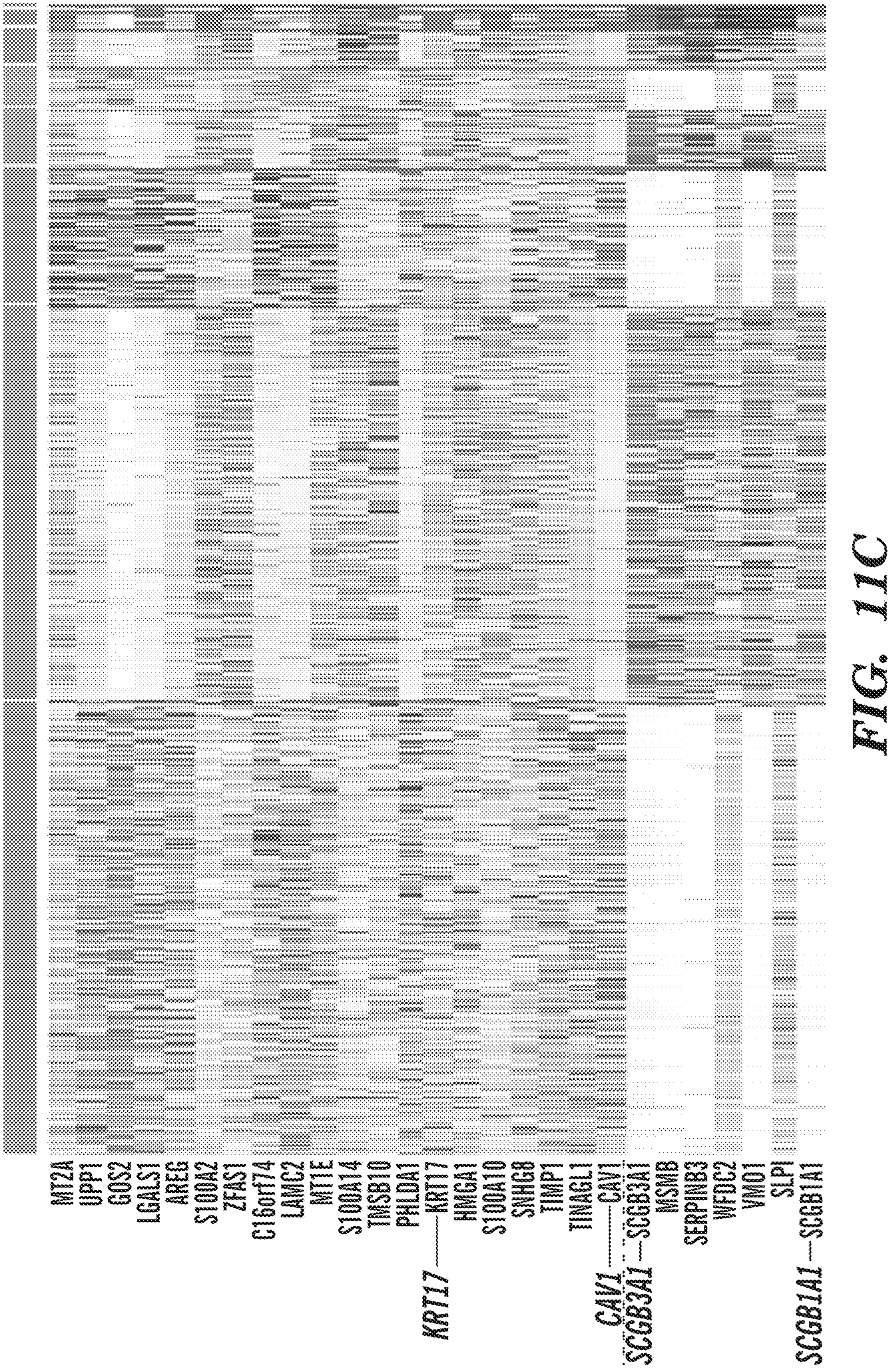
Figure 11C:
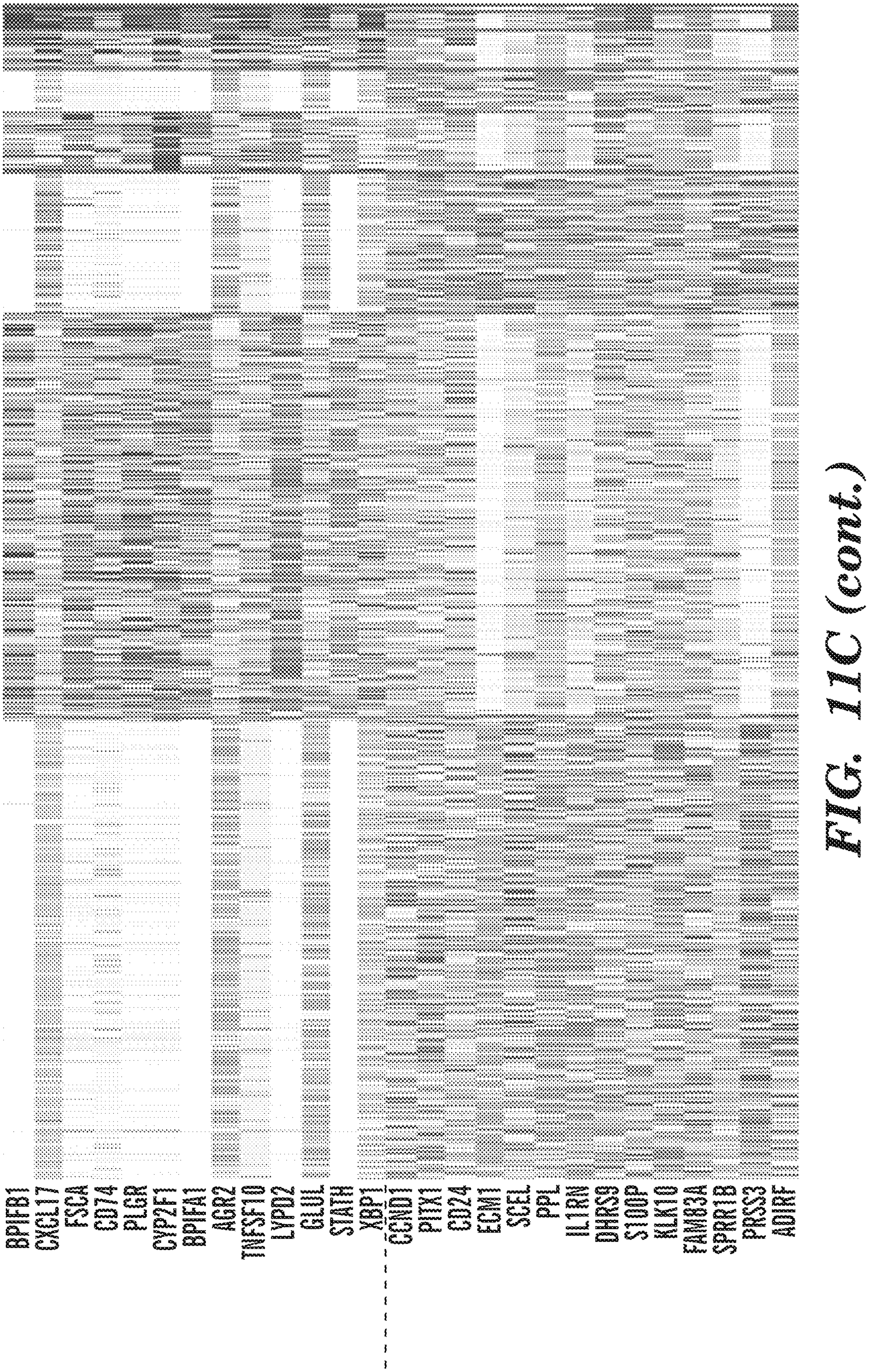
Figure 11C:
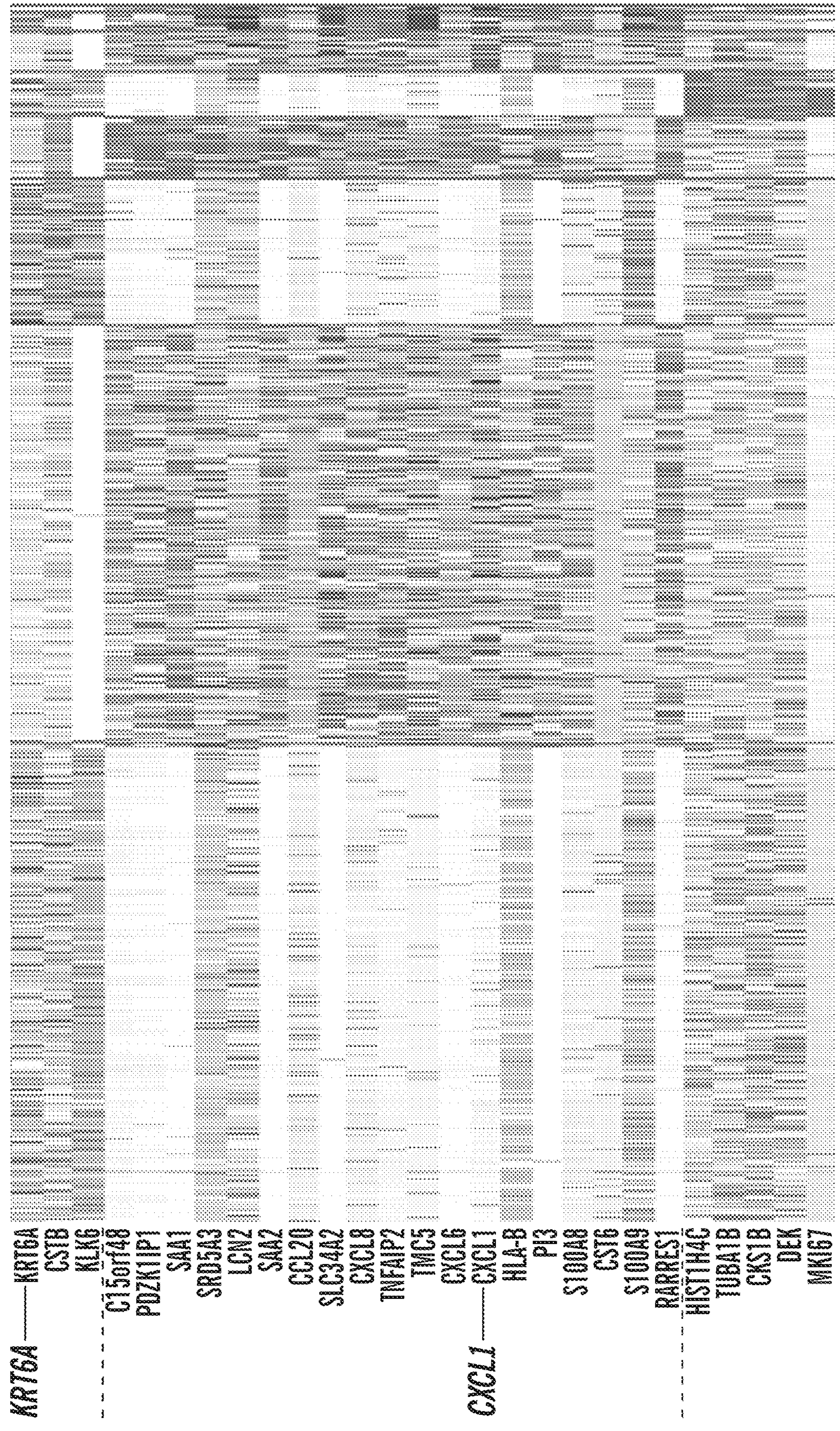
Figure 11C:
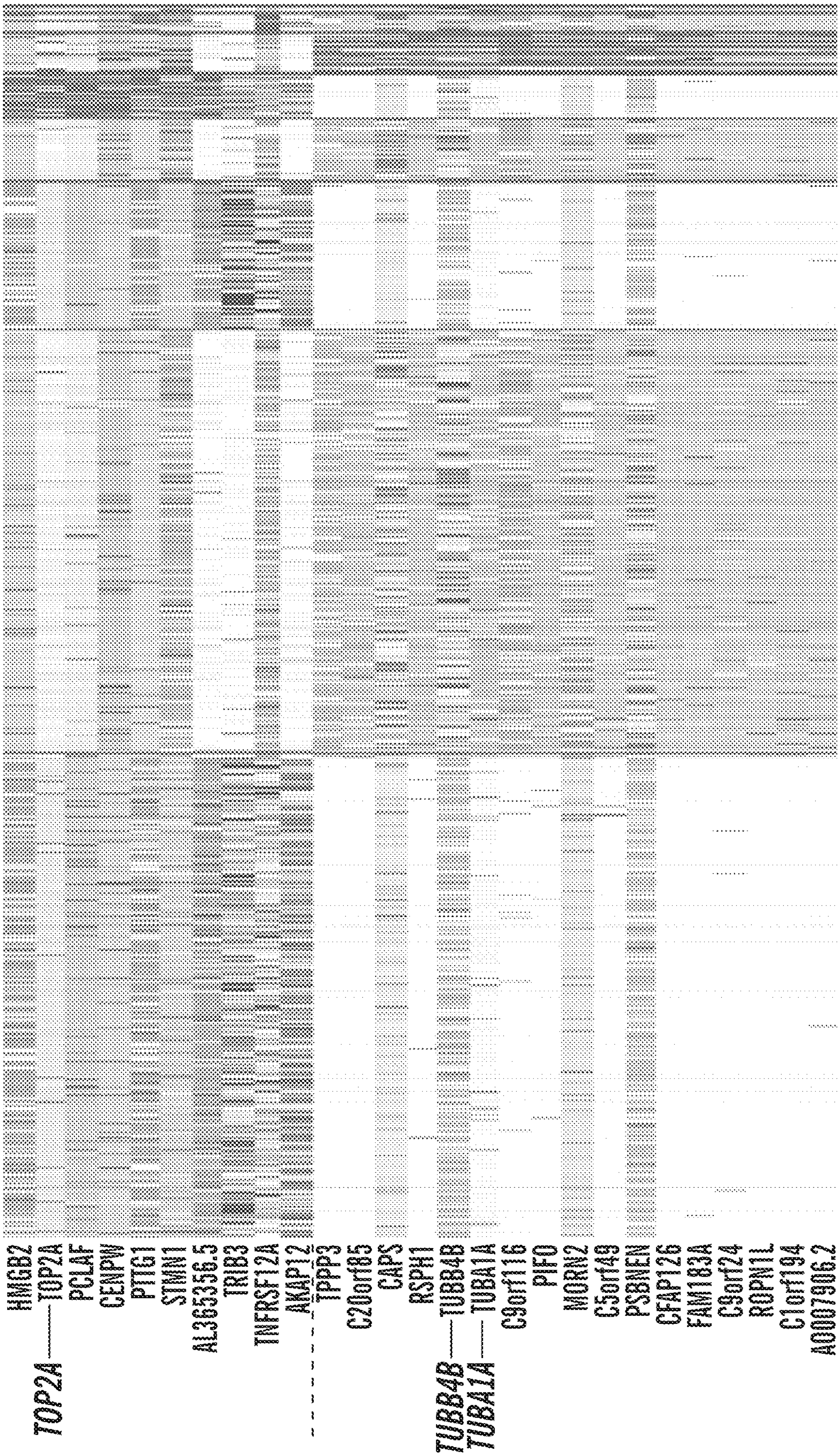
Figure 11C:
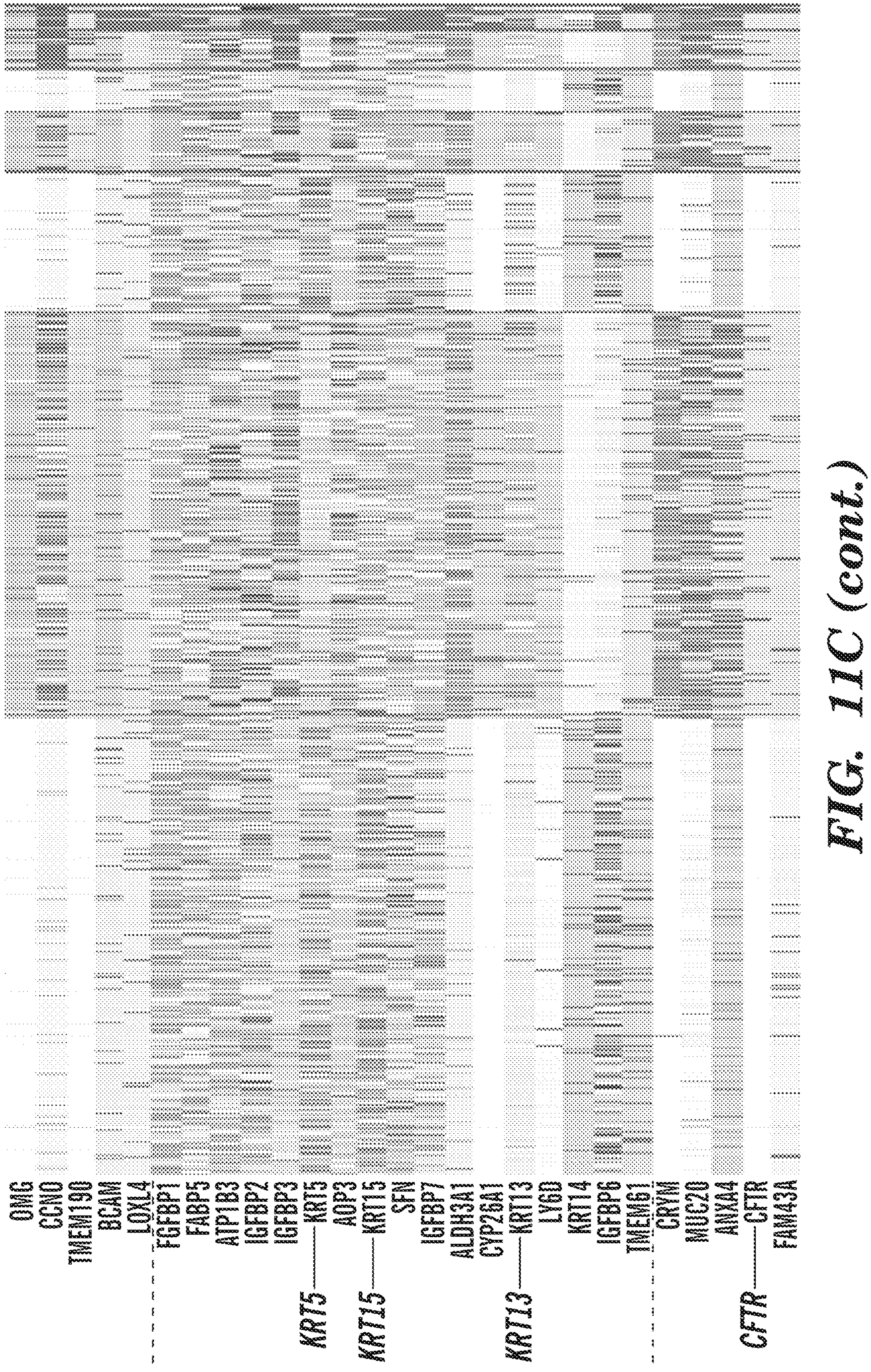
Figure 11C:
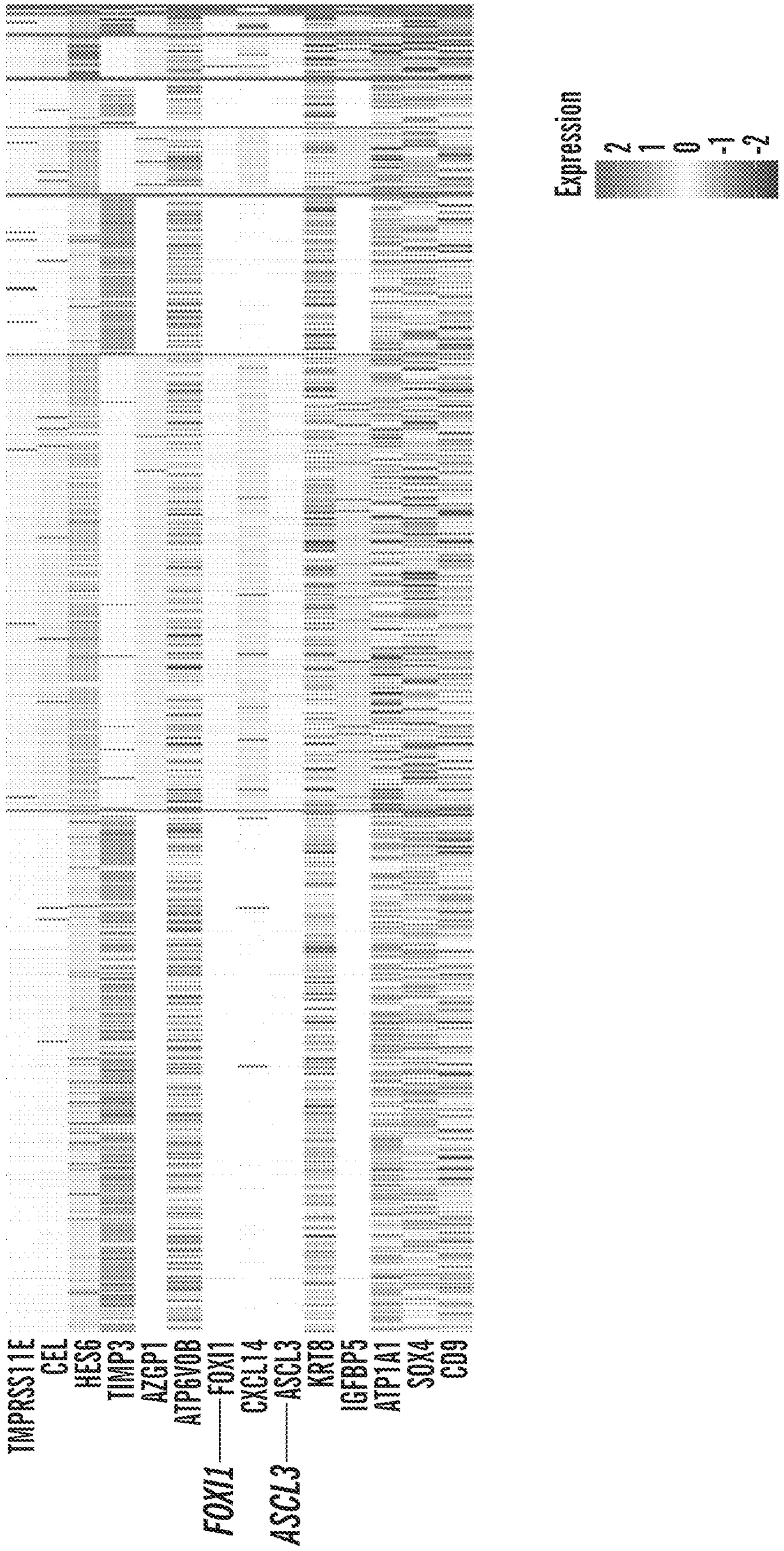
Figure 11D:
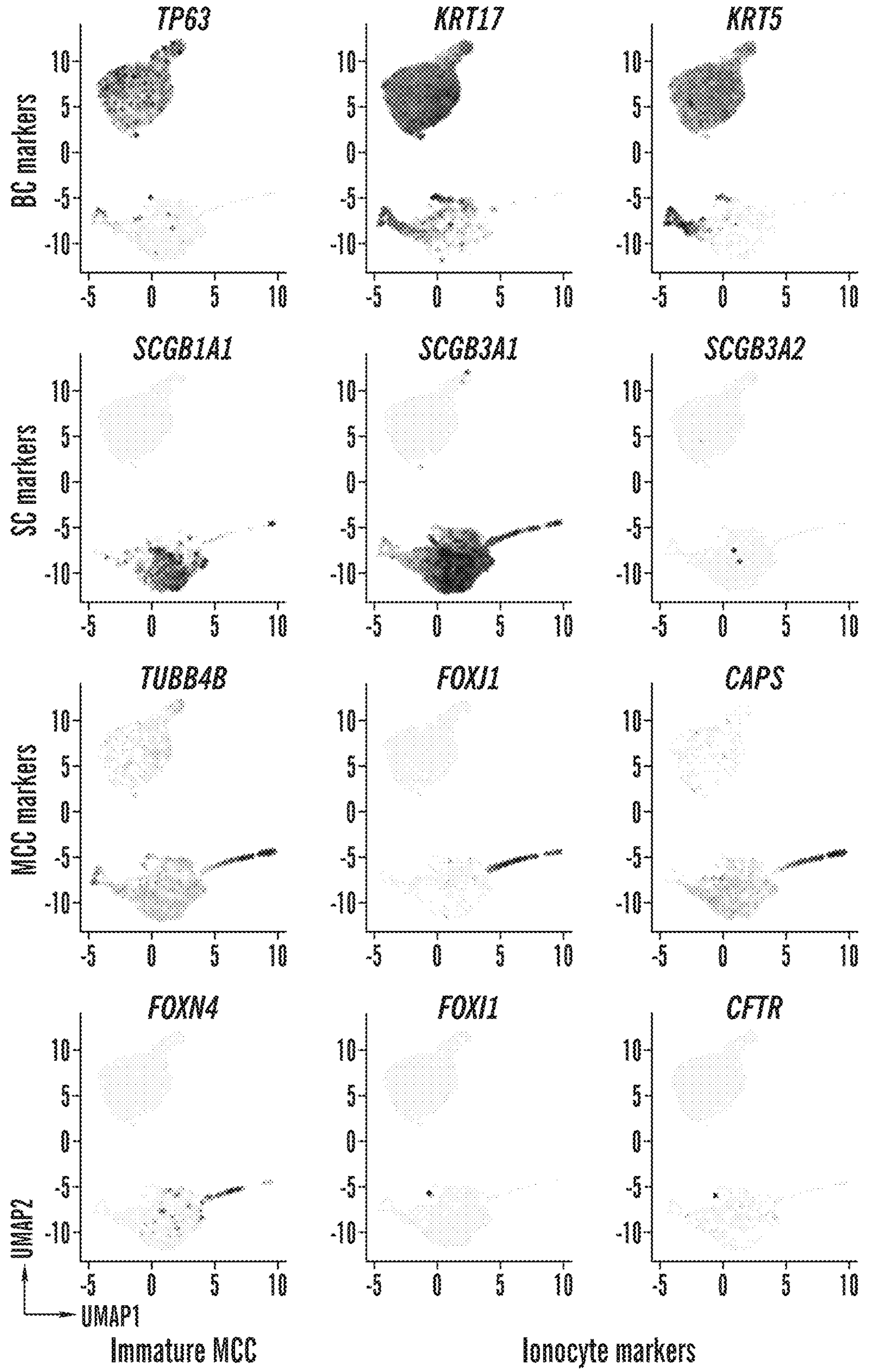

In order to compare iPSC-derived cells with adult and fetal lung cell types and exclude the potential confounding effects of in vitro culture on gene expression, the data-set of freshly isolated adult airway epithelial cells was first integrated with that of fetal airways at different developmental time points (Carraro et al., 2020b; Miller et al., 2020). After identifying DEGs between adult airway cells and their iPSC-derived counterparts (FIG. 15), primary cell comparators were selected consisting of 7 fetal and 3 adult airway cell types and 366 unique markers to quantify the transcriptomic similarities between iPSC-derived cells from FGF2+10+DCI+Y or BC medium and each of these primary cell types using Pearson's correlation coefficients (PCCs) were identified (FIG. 2H; Miller et al., 2020). For each iPSC-derived single cell, the primary epithelial cell type exhibiting the maximum PCC was determined and indicated as “best fit. Cells from FGF2+10+DCI+Y were best fit with either "fetal basal" or "adult basal. On the other hand, the majority of cells in BC medium were most transcriptionally similar to adult basal cells. Consistent with this assignment, NGFR expression was infrequent in fetal BCs (1.4%) compared to adult BCs (40%), indicating it marks more mature BCs. Furthermore, primary HBECs analyzed in the same manner also showed a best fit to adult basal cells, verifying the approach (FIG. 10E). In view of their more basal-like transcriptional profile, GFP+/TOM+ cells in BC medium were designated as iBCs.

Figure 3A:
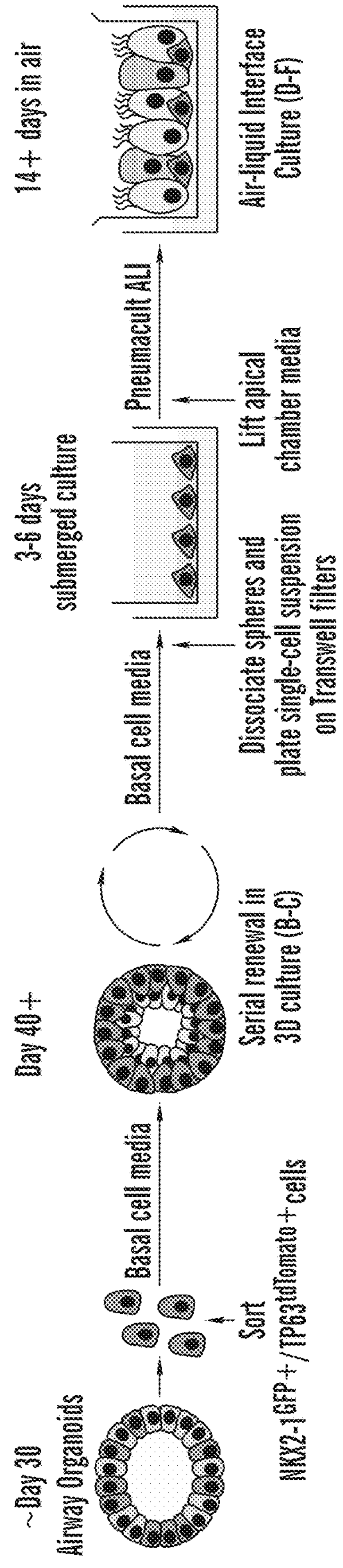
Figure 3B:
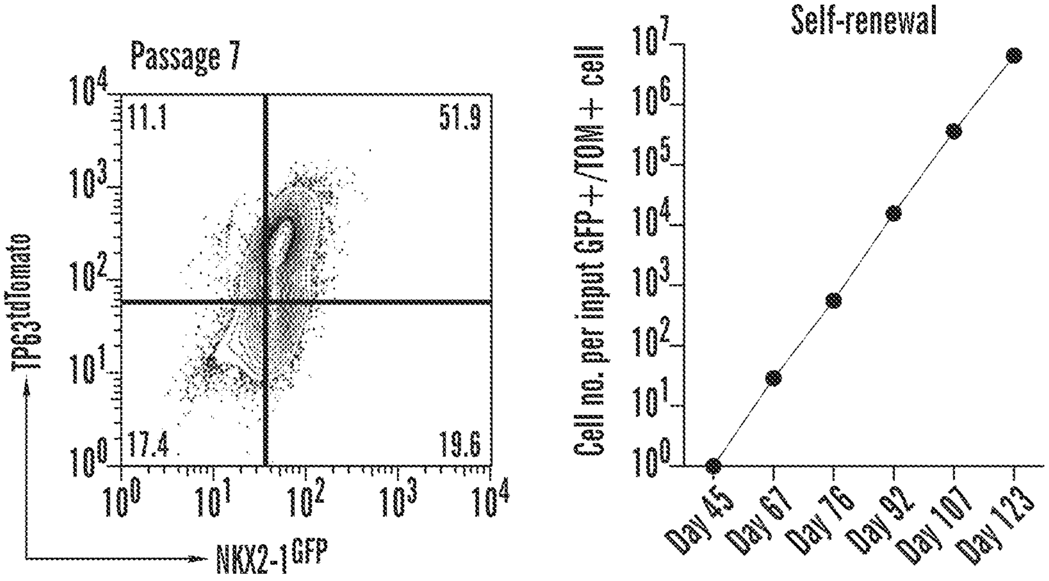
Figure 3C:
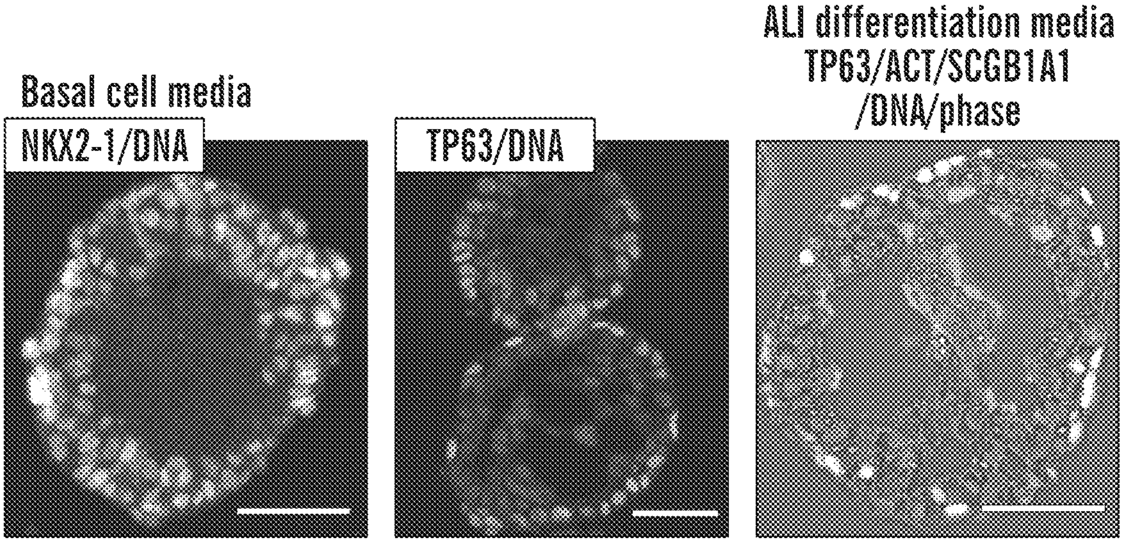
Figure 3D:
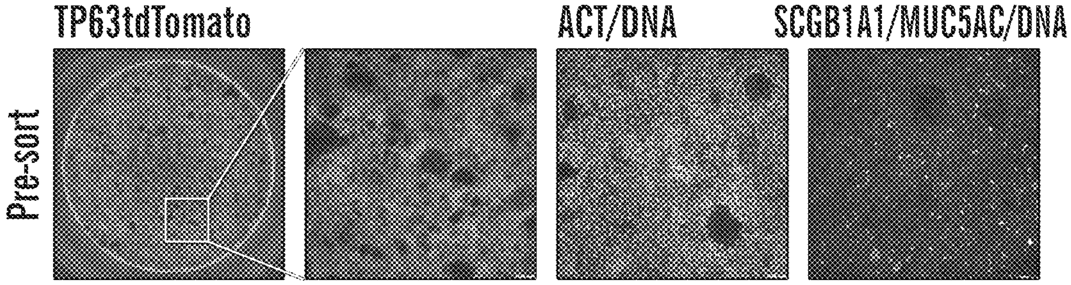
Figure 3E:
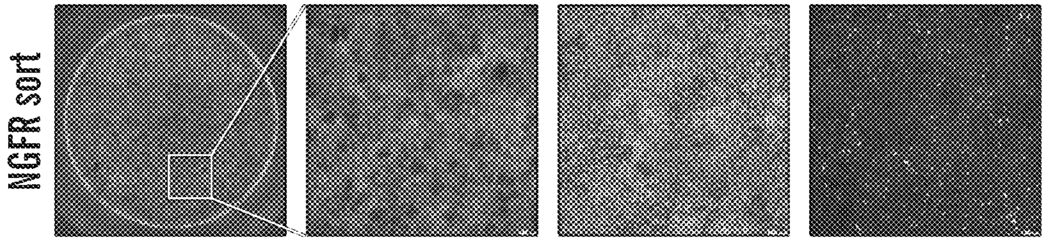
Figure 3F:
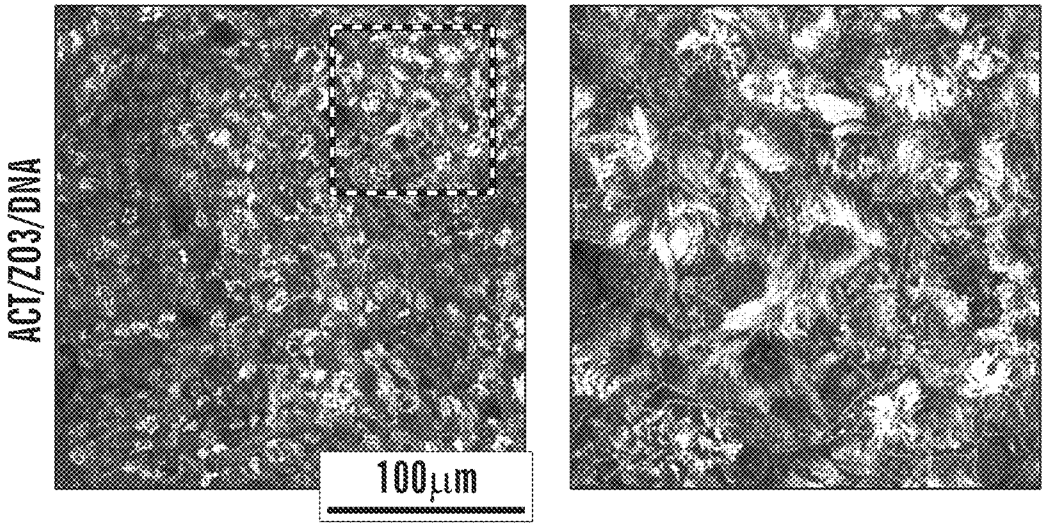
Figure 3G:
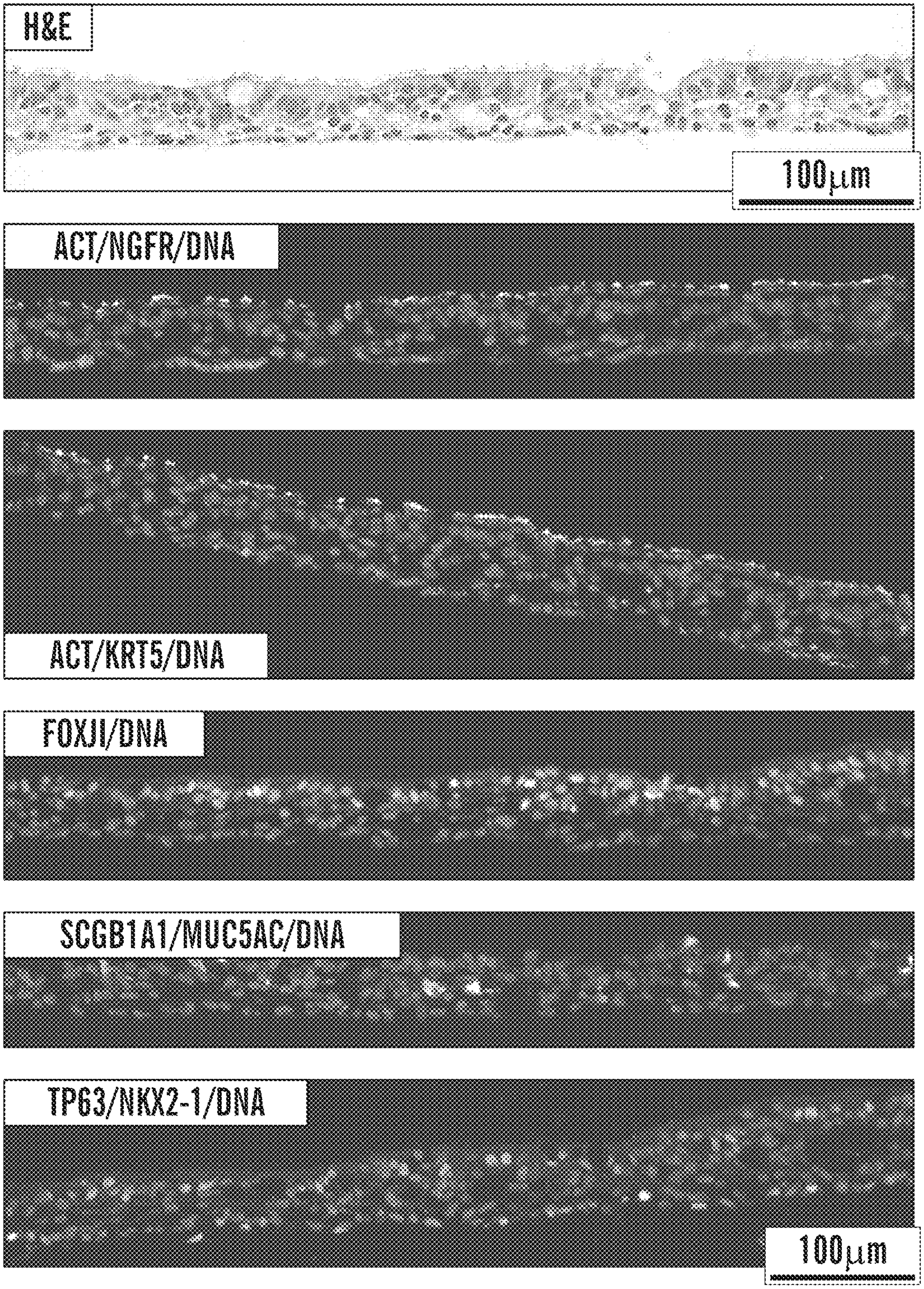
Figure 3H:
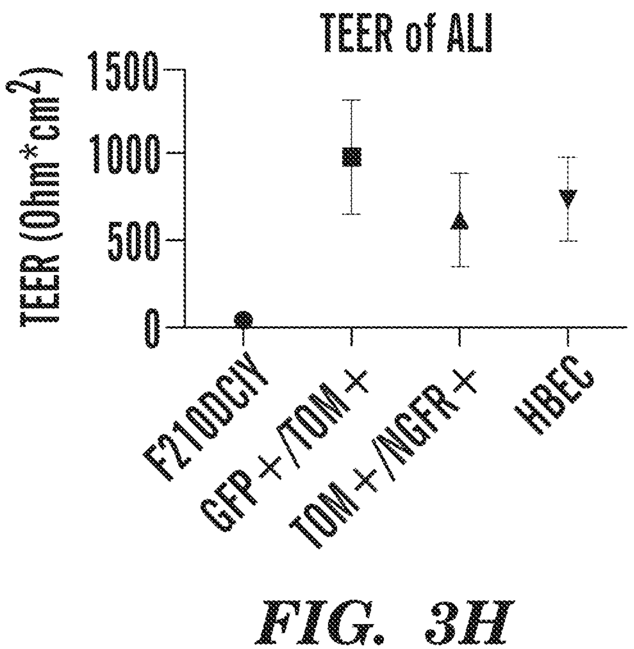
Figure 3I:
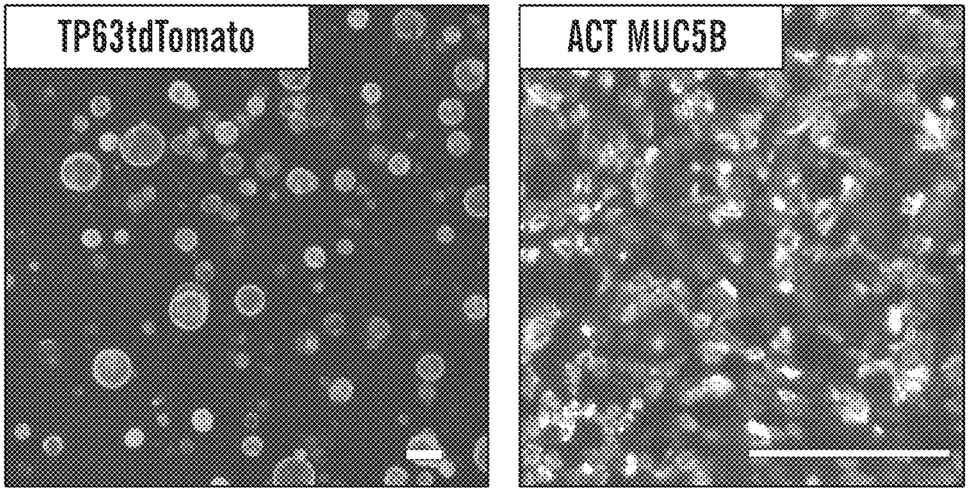
Figure 4A:
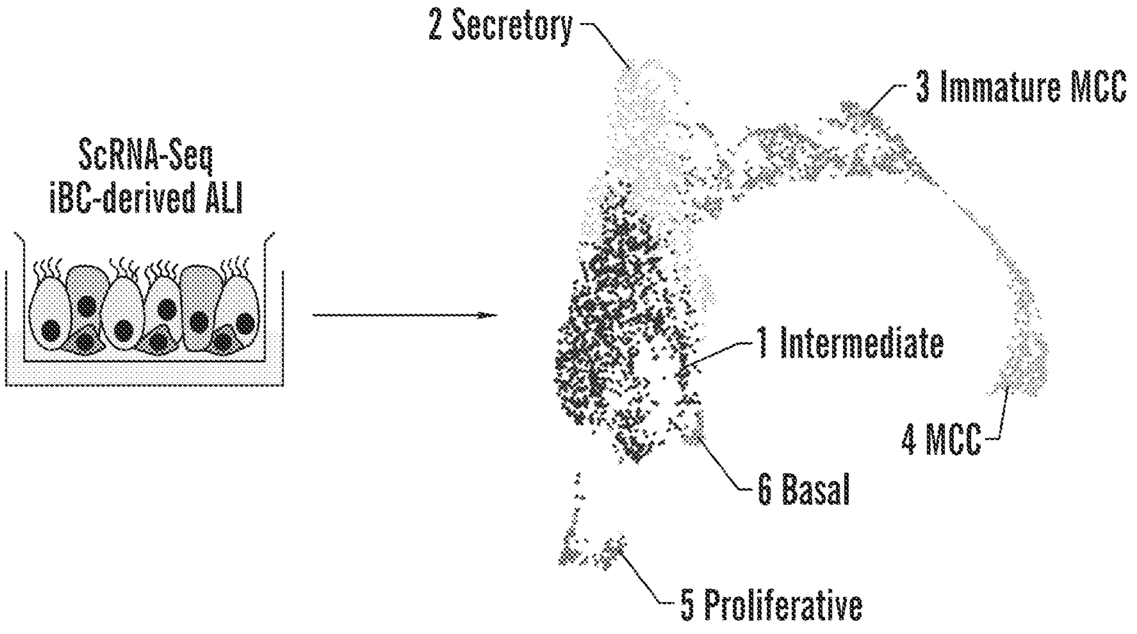
Figure 4B:
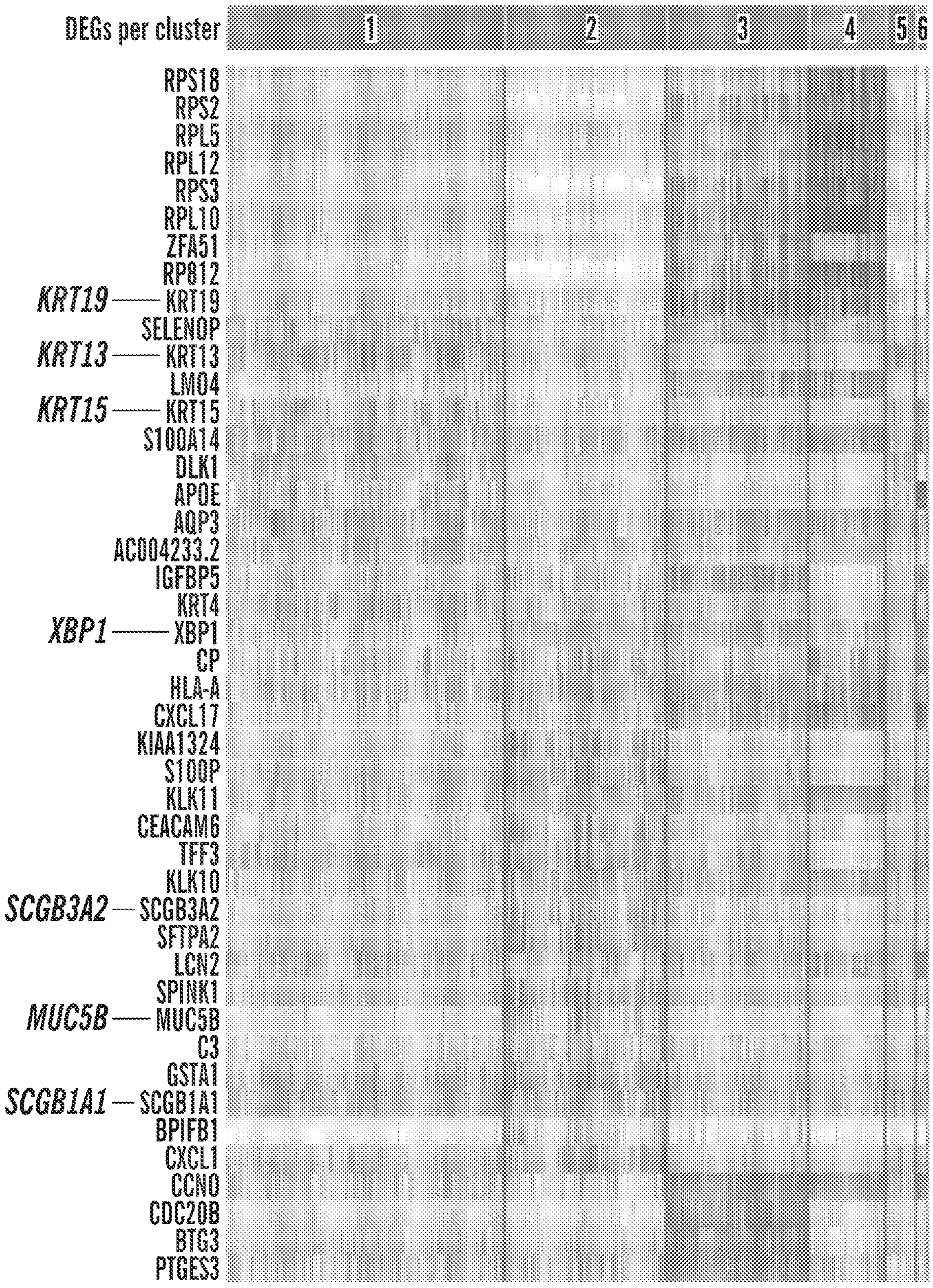
Figure 4B:
Figure 4B:
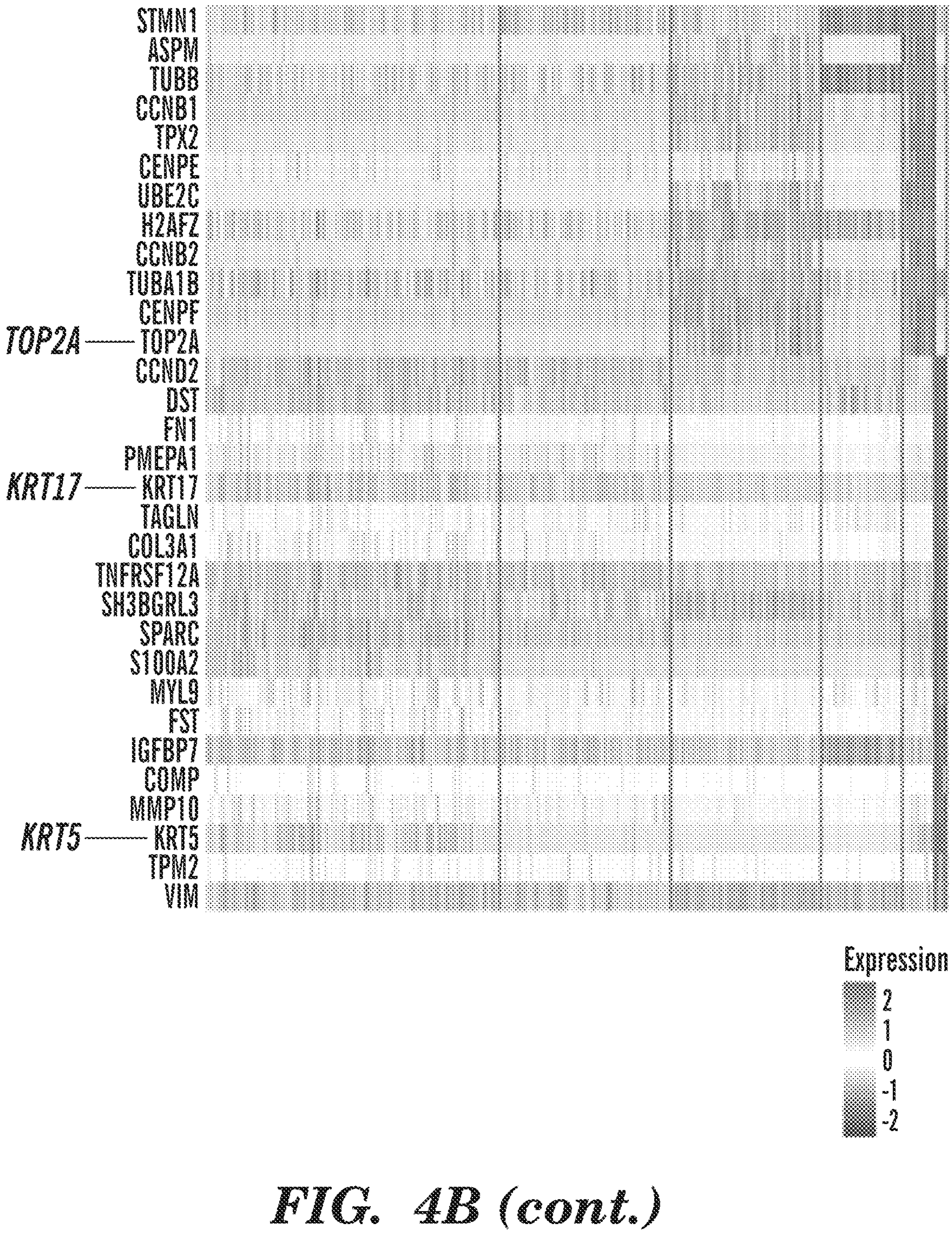
Figure 4C:
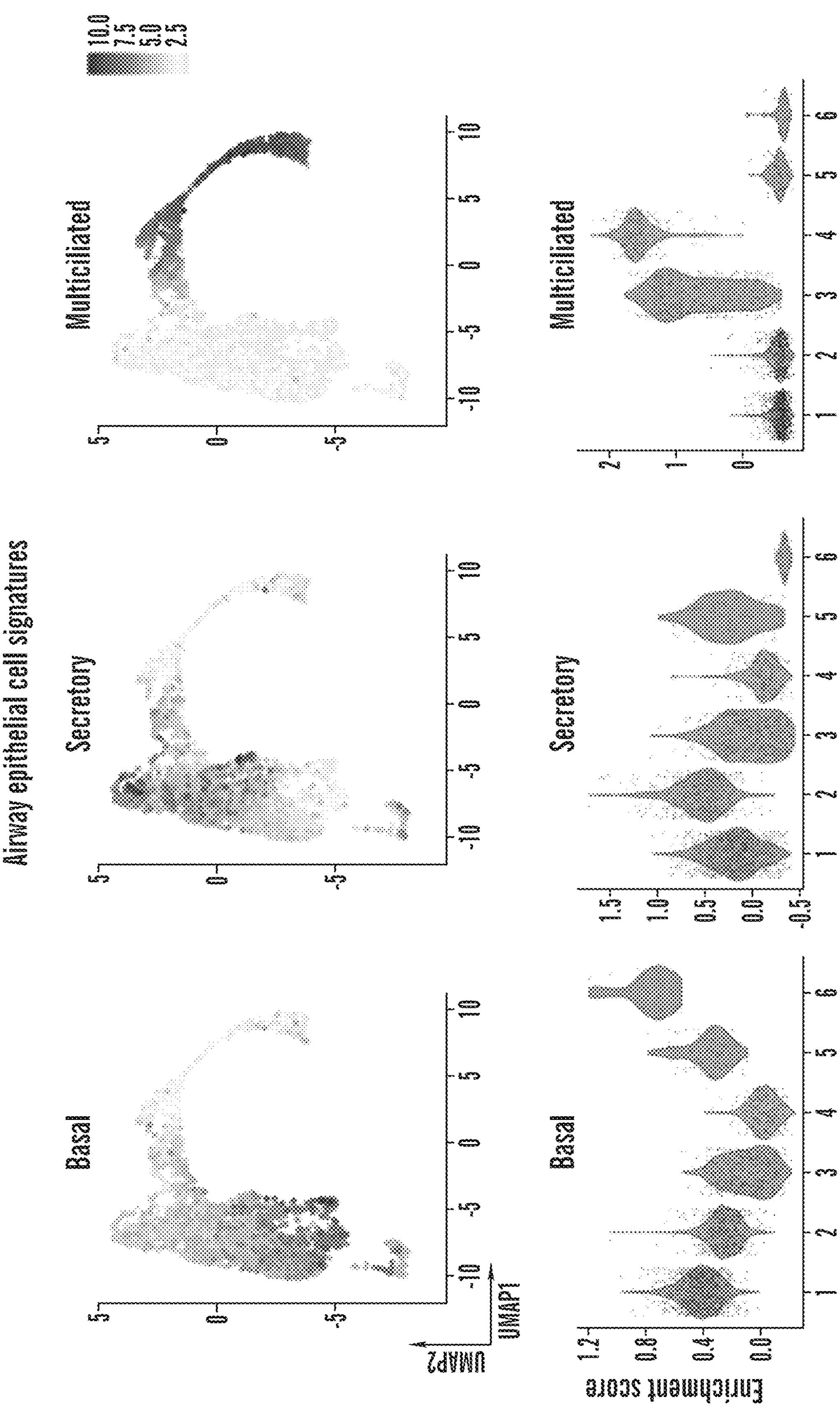
Figure 4D:
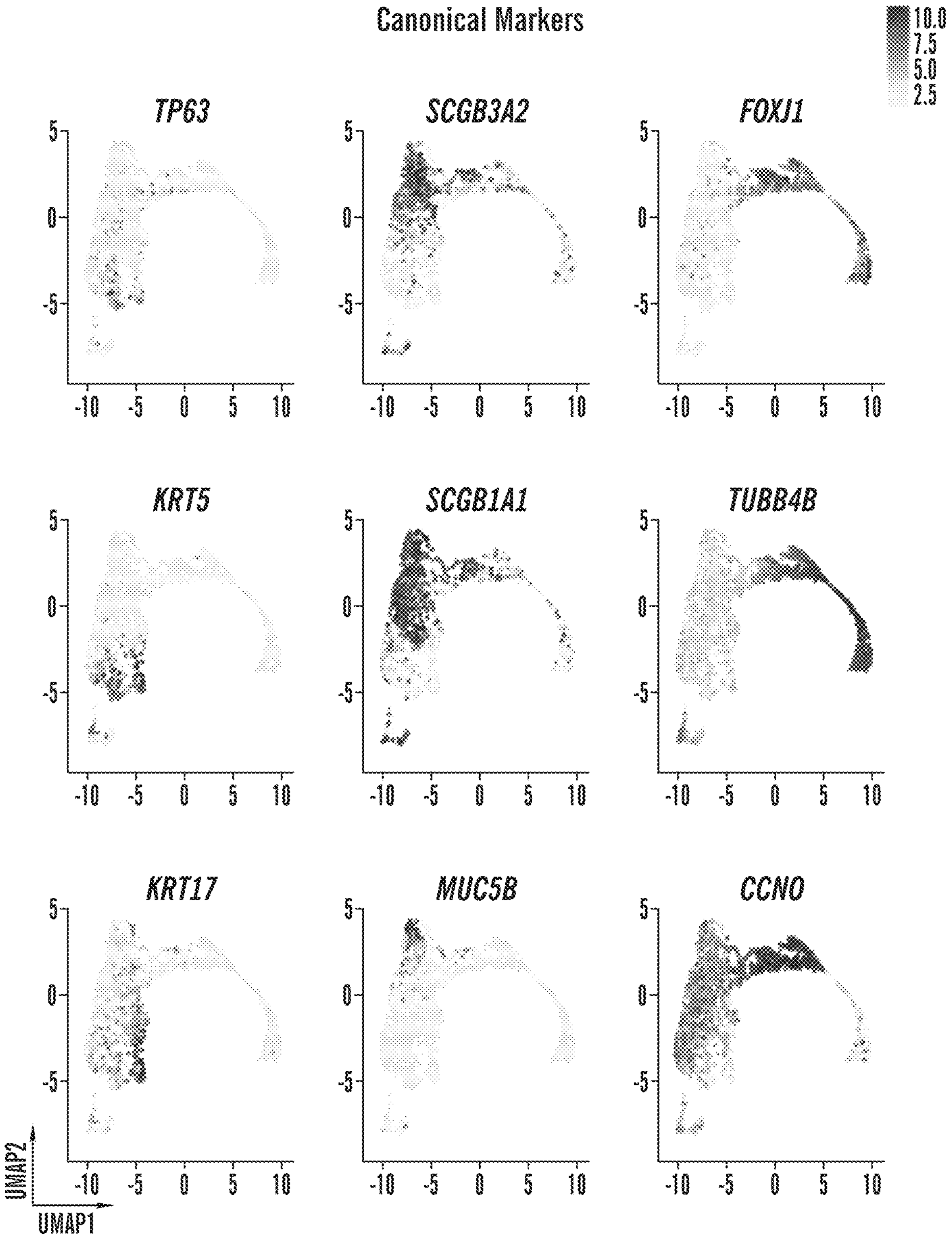
Figure 4E:
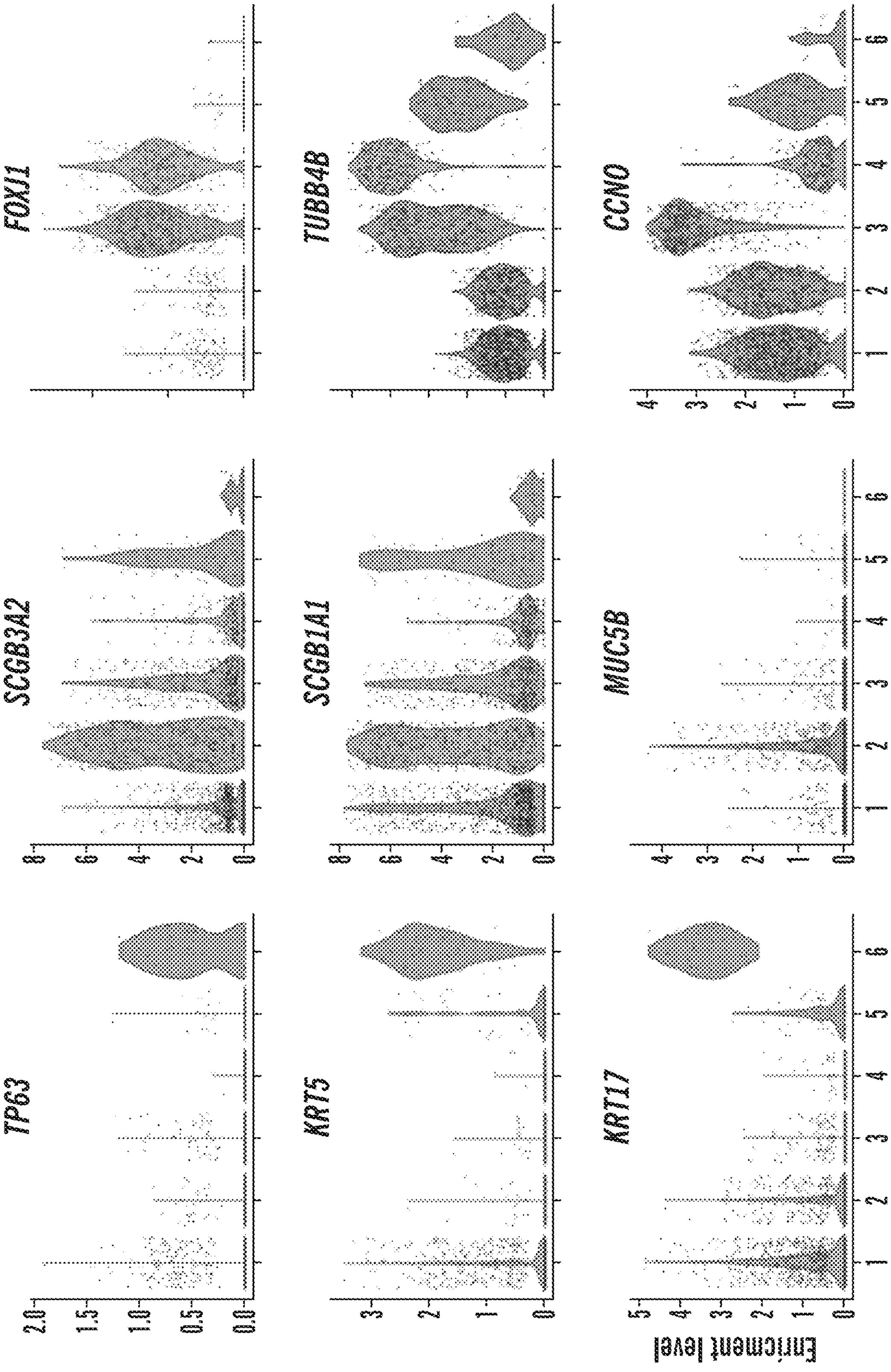
Figure 4F:
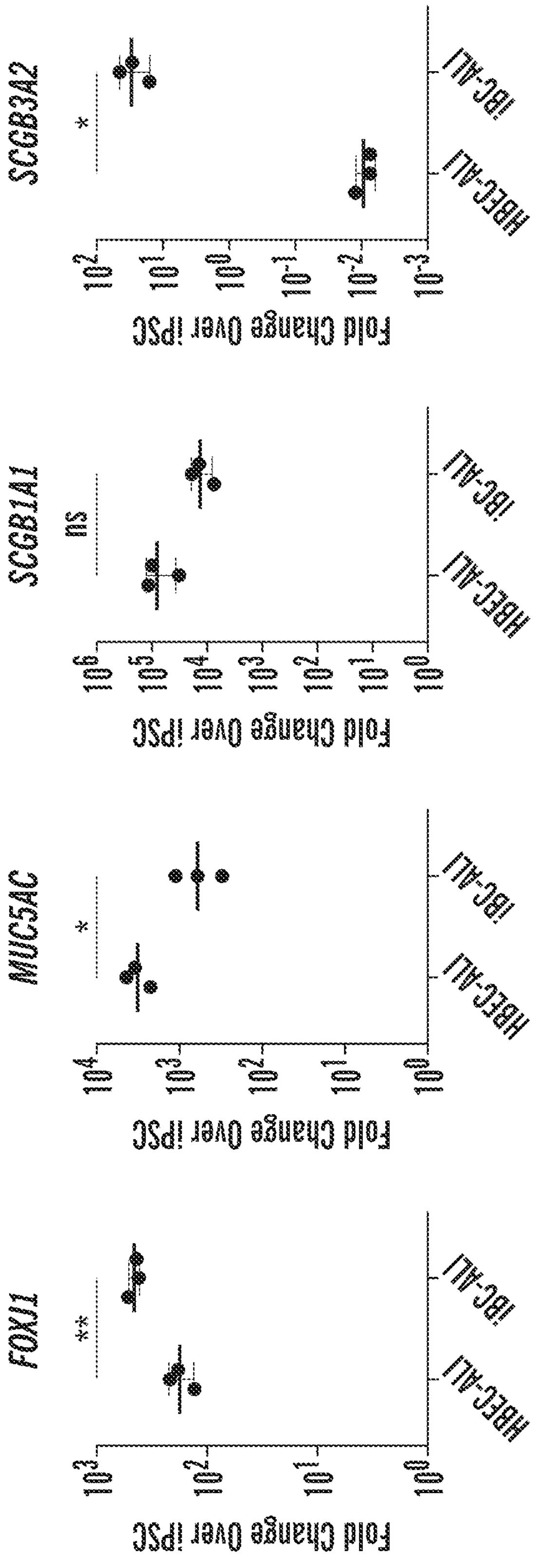
Figure 12A:
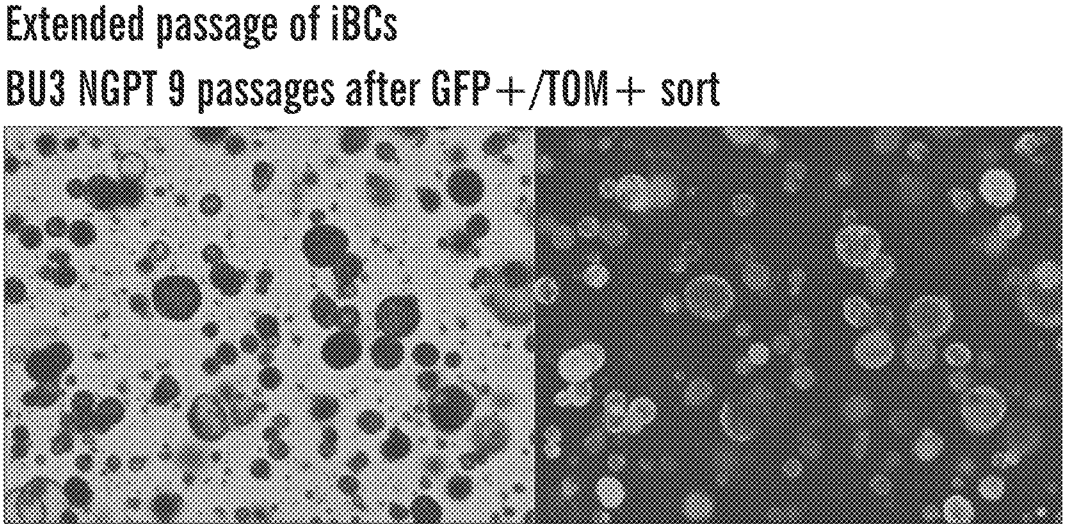
Figure 12B:
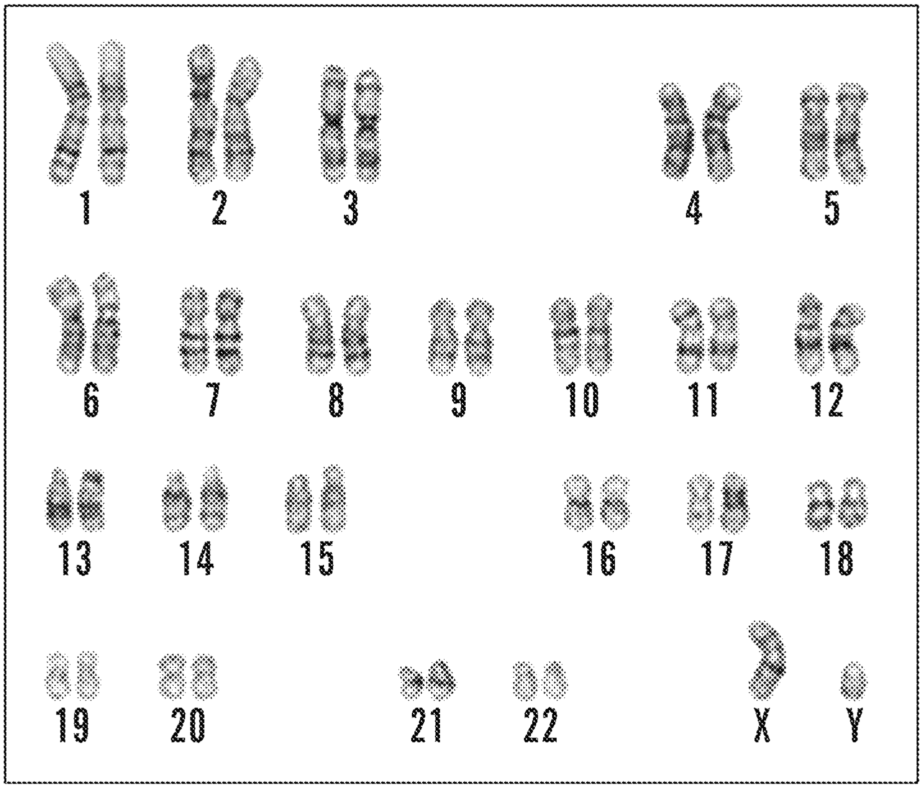
Figures 12C, 12D:
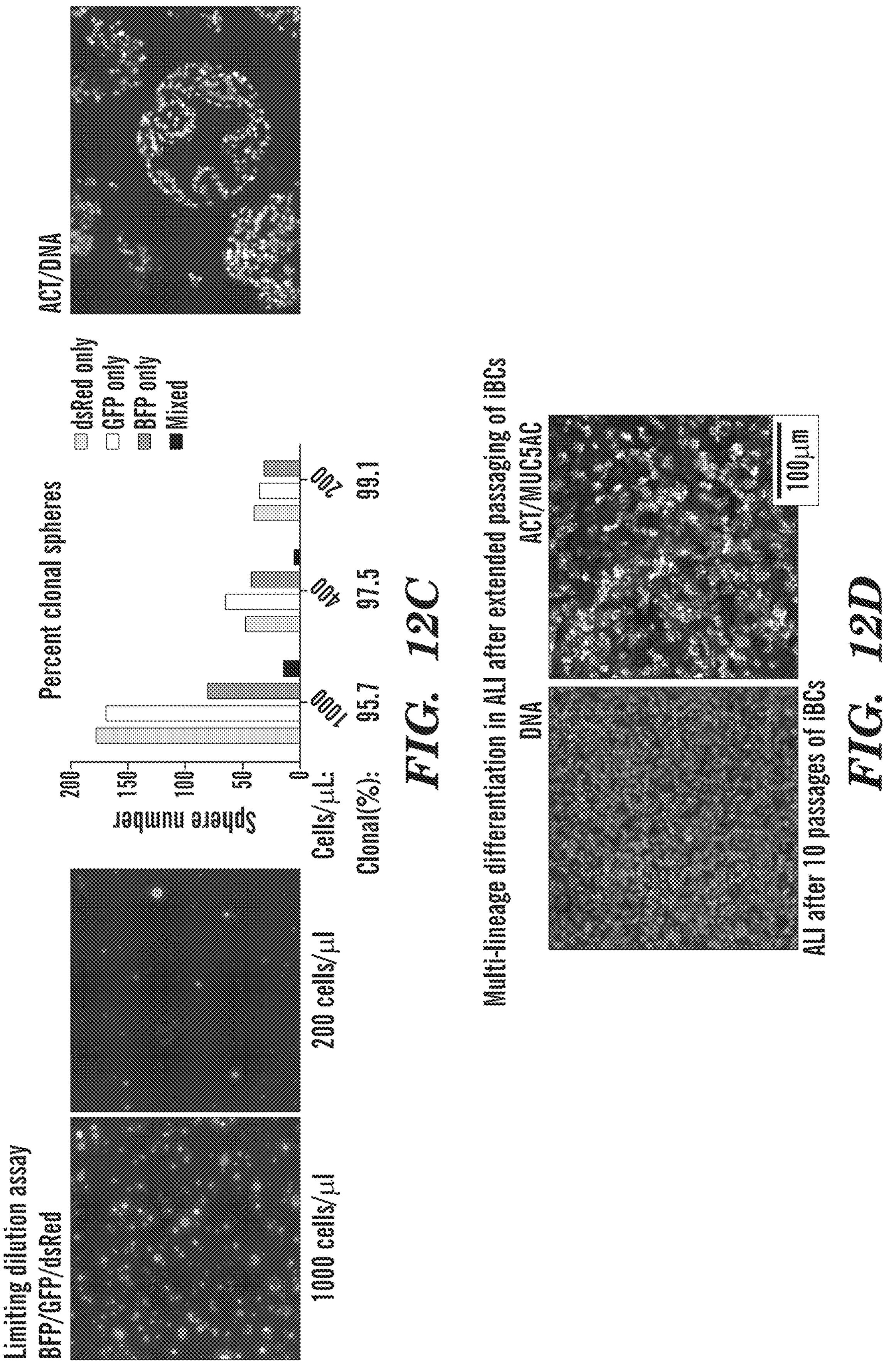
Figure 13A:
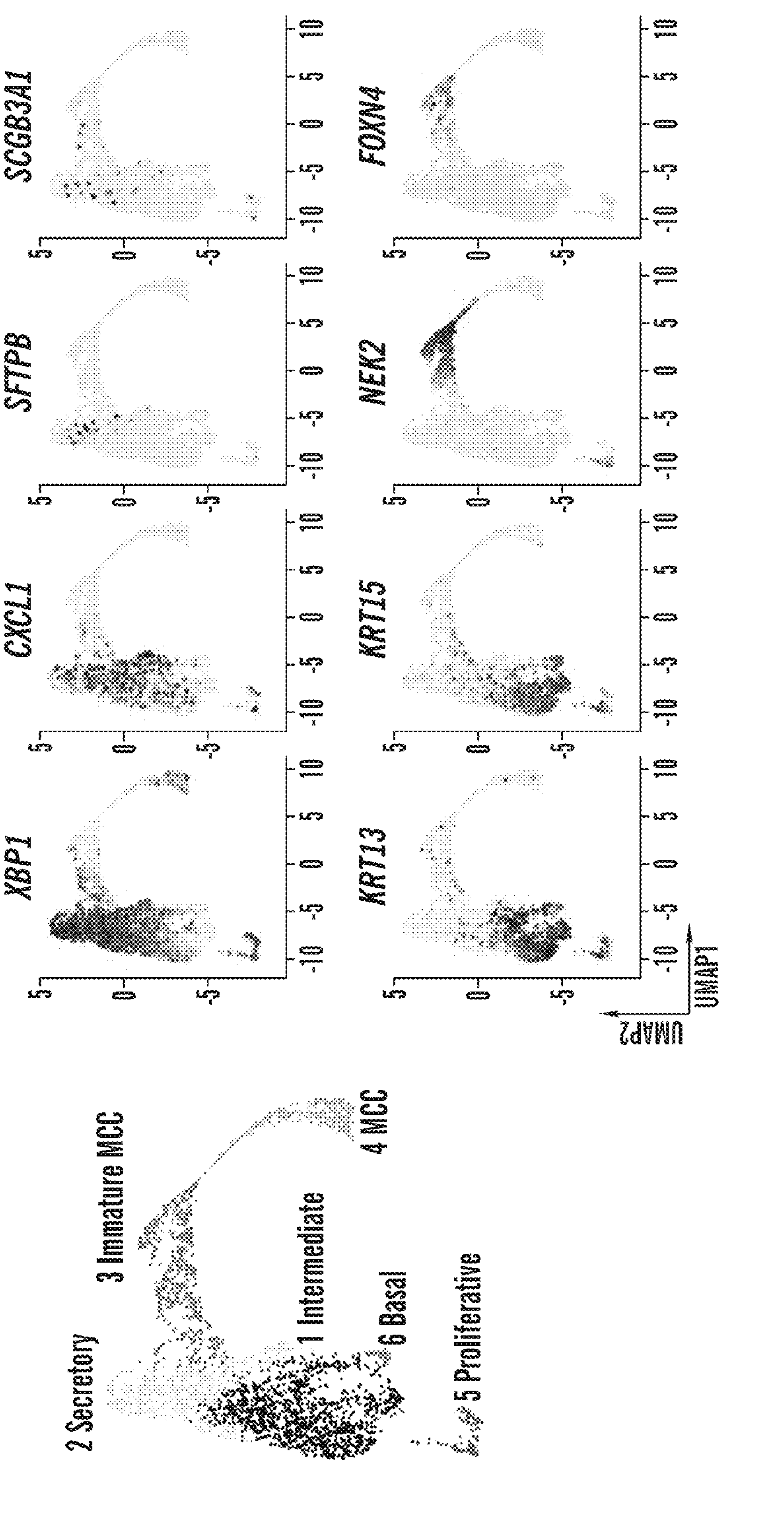
Figure 13B:
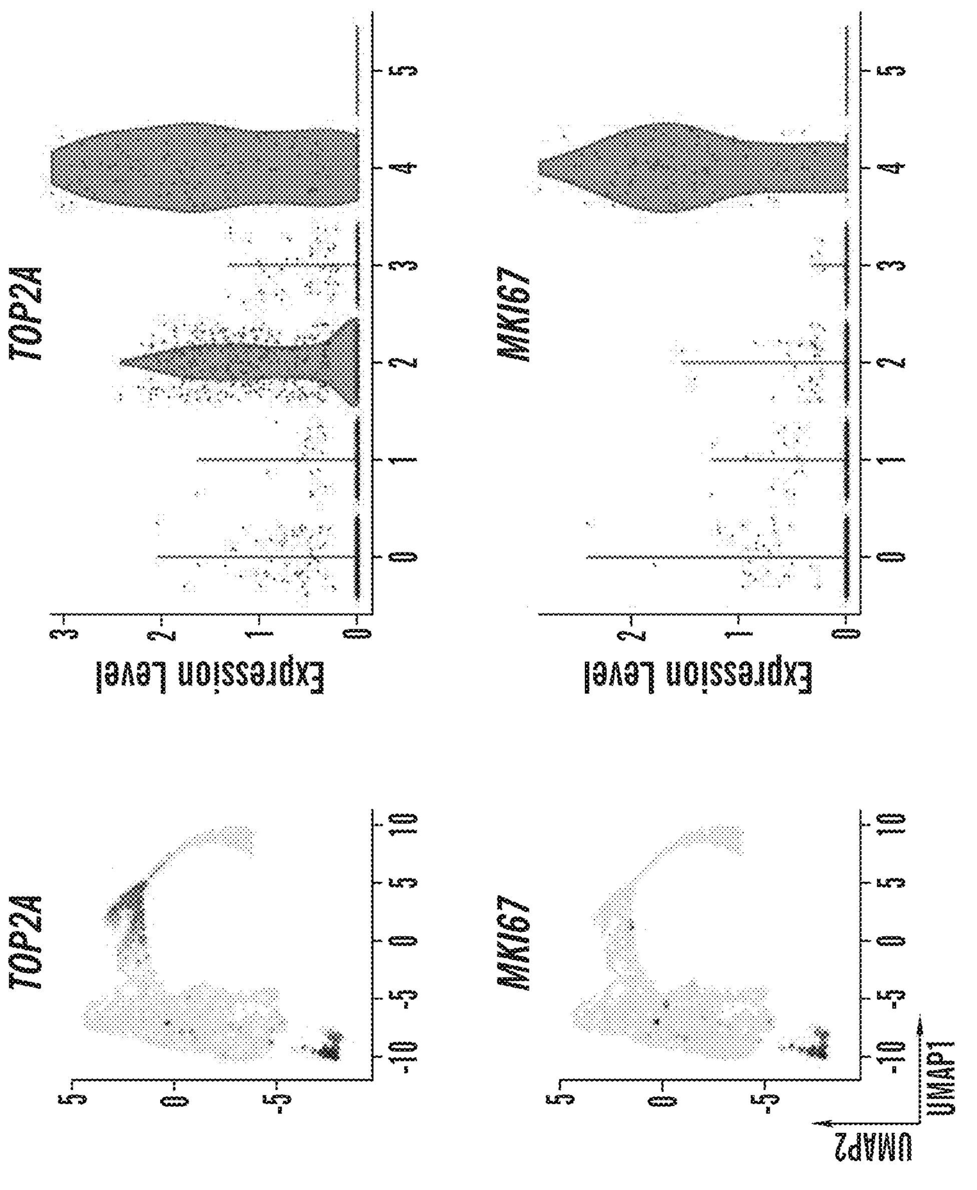
Figure 14A:
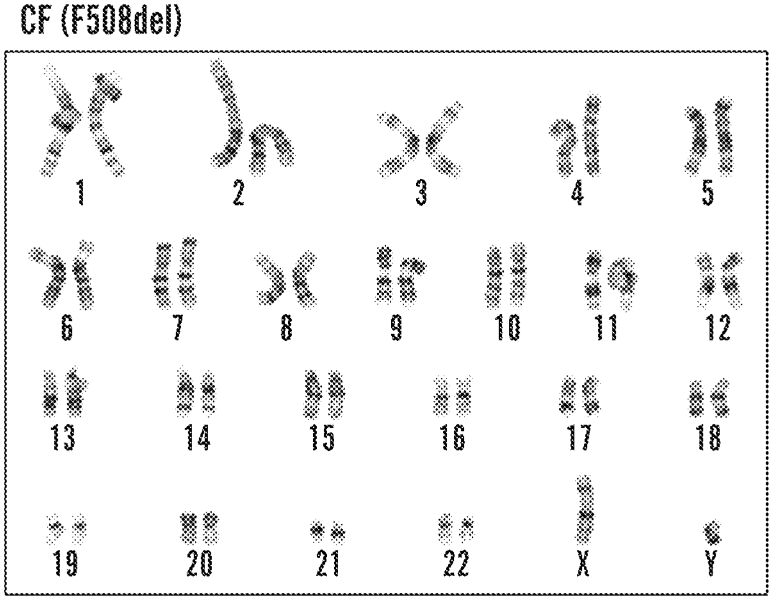
Figure 14B:
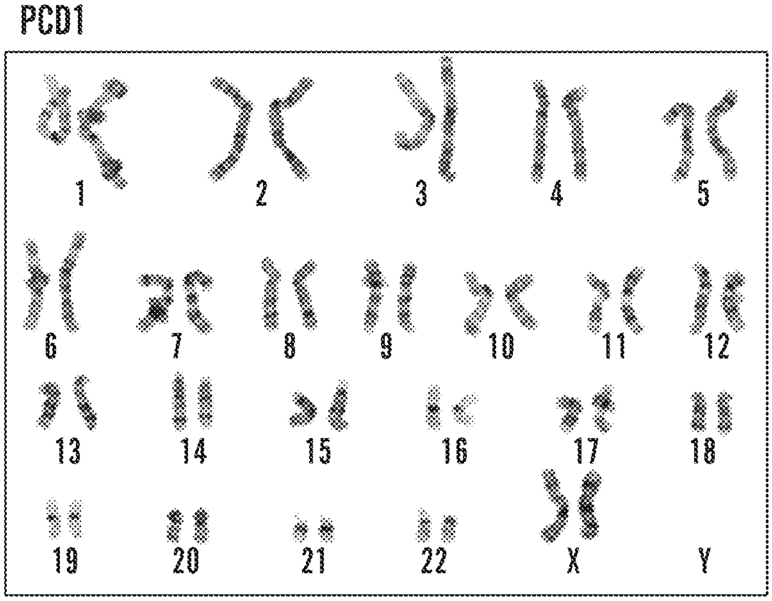
Figure 14C:
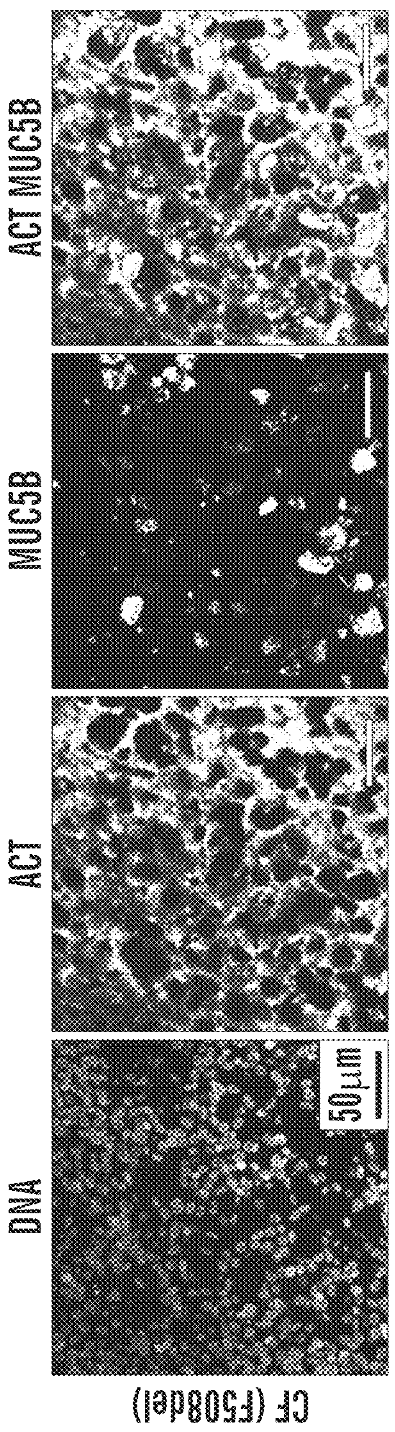
Figure 14D:
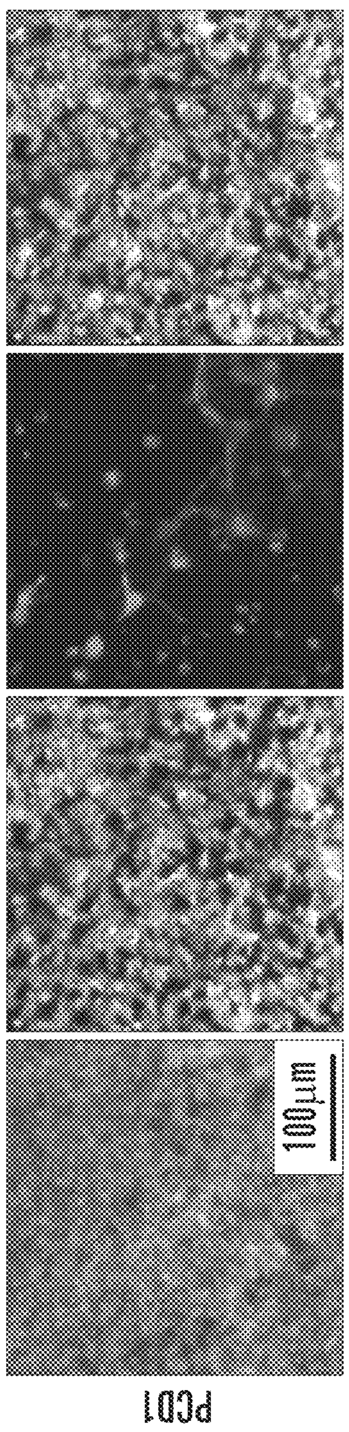
Figure 14E:
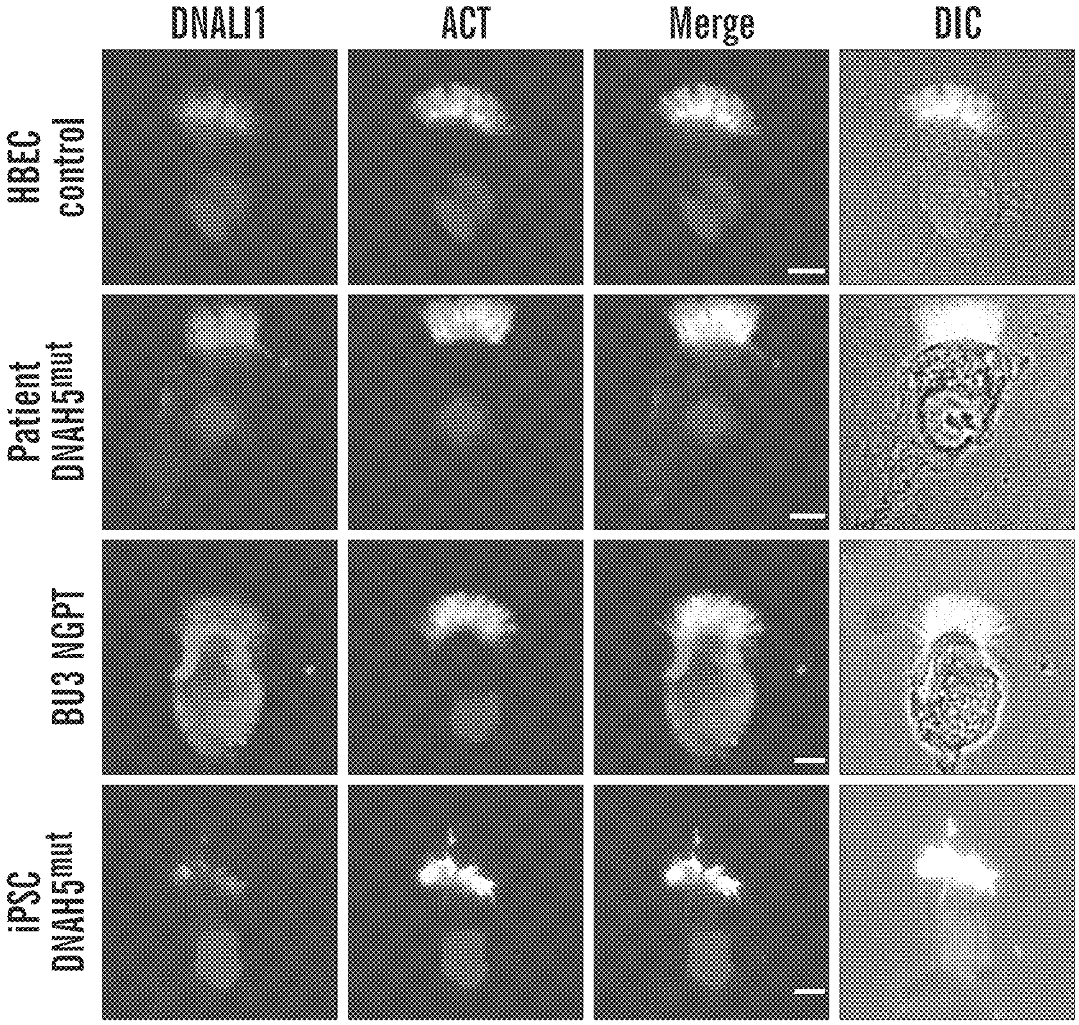

Next, to interrogate possible biological differences between iPSC-derived cells in BC medium and both fetal and adult primary BCs, gene set enrichment analysis (GSEA) (FIG. 10F) was used. Based on the observation that KRAS signaling, known to be downstream of fibroblast growth factor (FGF), was identified in both comparisons and data indicating a role for FGF10 signaling in primary BC development in the airways (Ornitz and Itoh, 2015; Volckaert et al., 2013), FGF signaling was modulated between days 15 and 35 of iPSC differentiation and changes in the yield of GFP+/TOM+ cells per input cell were assessed. GFP+/TOM+ cells were rare in the absence of FGFs, however, increased in a FGF dose-dependent manner, indicating that FGF plays a role in the differentiation of immature lung progenitors into NKX2-1+/TP63+ cells, findings in keeping with the present GSEA results.

iBCs Exhibit Stem Cell Properties: Long-Term Self-Renewal and Multi-lineage Differentiation Next, the inventors asked to what extent iBCs share the key stem cell properties of primary BCs: long-term self-renewal and multi-lineage differentiation (FIGS. 3A-3G). In BC medium, iBCs were propagated for up to 10 passages (170 days) in 3D culture, while retaining GFP/TOM expression (FIGS. 3B and 12A), NGFR expression, and a normal karyotype (FIG. 12B). One input iBC plated on day 45 yielded $6.9\pm1.7\times10^6$ cells (mean±SD) 78 days later with a doubling time of 1.1 days (FIG. 3B). First, to assess the differentiation and self-renewal of individual cells, the 3D tracheosphere assay previously published for primary BCs (Rock et al., 2009) was adapted. A seeding density at which >95% of spheres were clonally derived from a single iBC was established (FIG. 12C). At this clonal density, NGFR+ sorted iBCs were cultured in either BC maintenance or differentiation "ALI" media. In both conditions, spheres formed and were composed of a stratified-appearing layer of predominantly NKX2-1+ cells (FIG. 3C). In BC medium, NKX2-1+/TP63+ cells were readily identified in the outermost cell layer of all spheres. In the differentiation medium, transcriptionally distinct and best fit with "fetal MCC" or "fetal MCC precursor "cell types. The remaining cells were predominantly best fit with fetal basal or "fetal club-like" cell types. The expression levels of key airway epithelial markers in iBC-derived ALI cultures were confirmed using qRT-PCR and directly compared to primary controls cultured in identical conditions (FIG. 4F). In both primary and iPSC-derived samples, there was robust upregulation of FOXJ1, MUC5AC, and SCGB1A1. FOXJ1 expression was significantly higher and MUC5AC expression lower in iPSC-derived ALI cultures (FIG. 4F). SCGB3A2 was expressed in iPSC-derived ALI cultures, but not detected at significant levels in primary HBEC-derived ALI cultures, whereas SCGB1A1 expression was similar between both samples (FIG. 4F). It is noted that iBCs yielded pseudostratified airway epithelium composed of BCs, MCCs, and SCs, irrespective of whether PneumaCult-ALI or UNC-ALI media were utilized in ALI cultures (FIGS. 14D and 14E).

iBCs Form a Differentiated Airway Epithelium in a Tracheal Xenograft

Figure 5A:
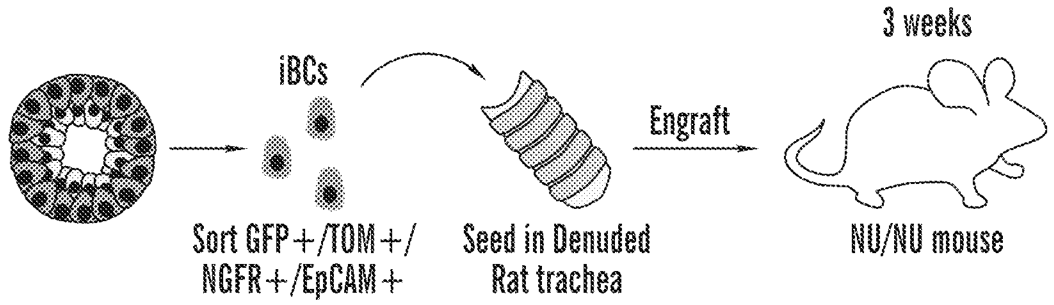
Figure 5B:
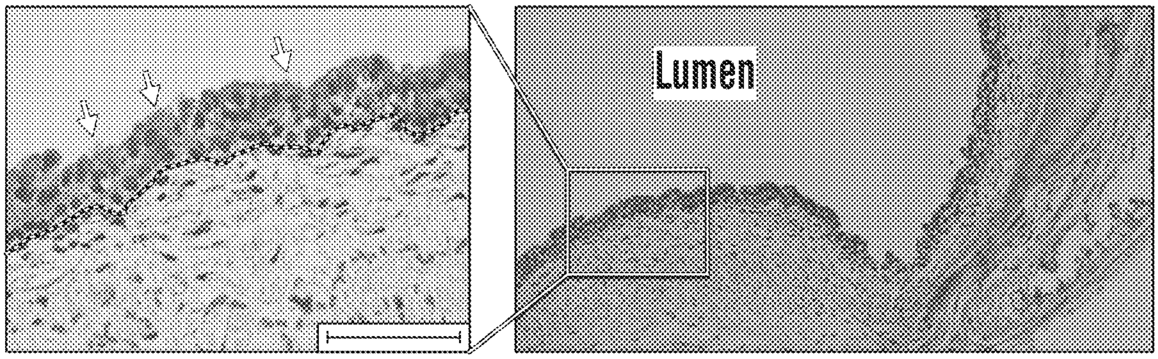
Figure 5C:
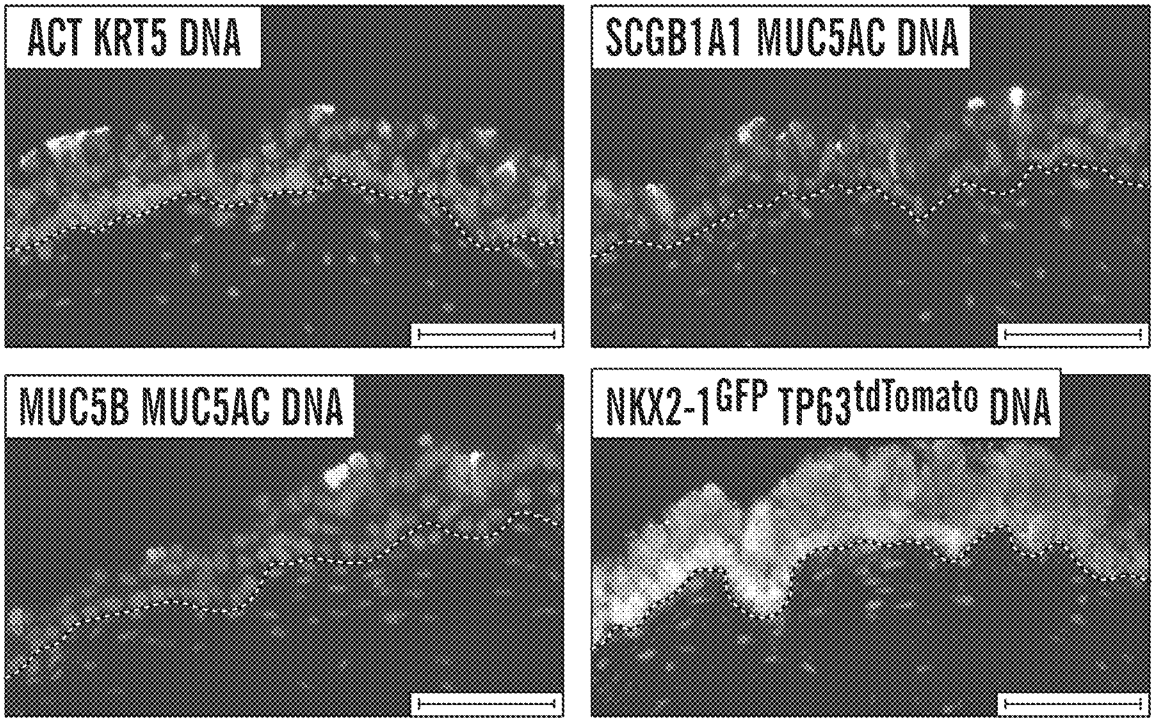

Engraftment and regeneration in vivo after transplantation is a critical measure of stem cell function that has been successfully tested for several non-lung tissues, such as the hematopoietic system, but remains a major challenge for lung epithelia, with only limited success reported to date in the airways (Ghosh et al., 2017; Miller et al., 2018; Nichane et al., 2017). It was sought to determine whether iBCs could establish an airway epithelium in vivo using the tracheal xenograft model (Everitt et al., 1989). Rat tracheas were completely decellularized by repeated freeze thaws, seeded with NGPT-derived iBCs, implanted subcutaneously into the flanks of Foxn1$^{nu}$ immune-compromised mice, and then followed for 3 weeks after transplantation (FIG. 5A). Air exposure through the trachea was maintained in vivo using open-ended tubing. After 3 weeks, a stratified or pseudostratified epithelial layer of cells had formed (FIG. 5B). Using antibodies against canonical markers, we identified BCs (KRT5+) occupying the expected positions along the basement membrane and SCs (SCGB1A1+, MUC5AC+, and MUC5B+) and MCCs (ACT+) oriented toward the air-filled tracheal lumen (FIG. 5C). NKX2-1GFP and TP63$^{tdTomato}$ expression were detected throughout the sections of epithelium analyzed, confirming its origin from transplanted rather than endogenous cells (FIG. 5C). In summary, in the tracheal xenograft model, iBCs form an airway epithelium similar in structure and composition to in vivo airways.

Figure 6A:
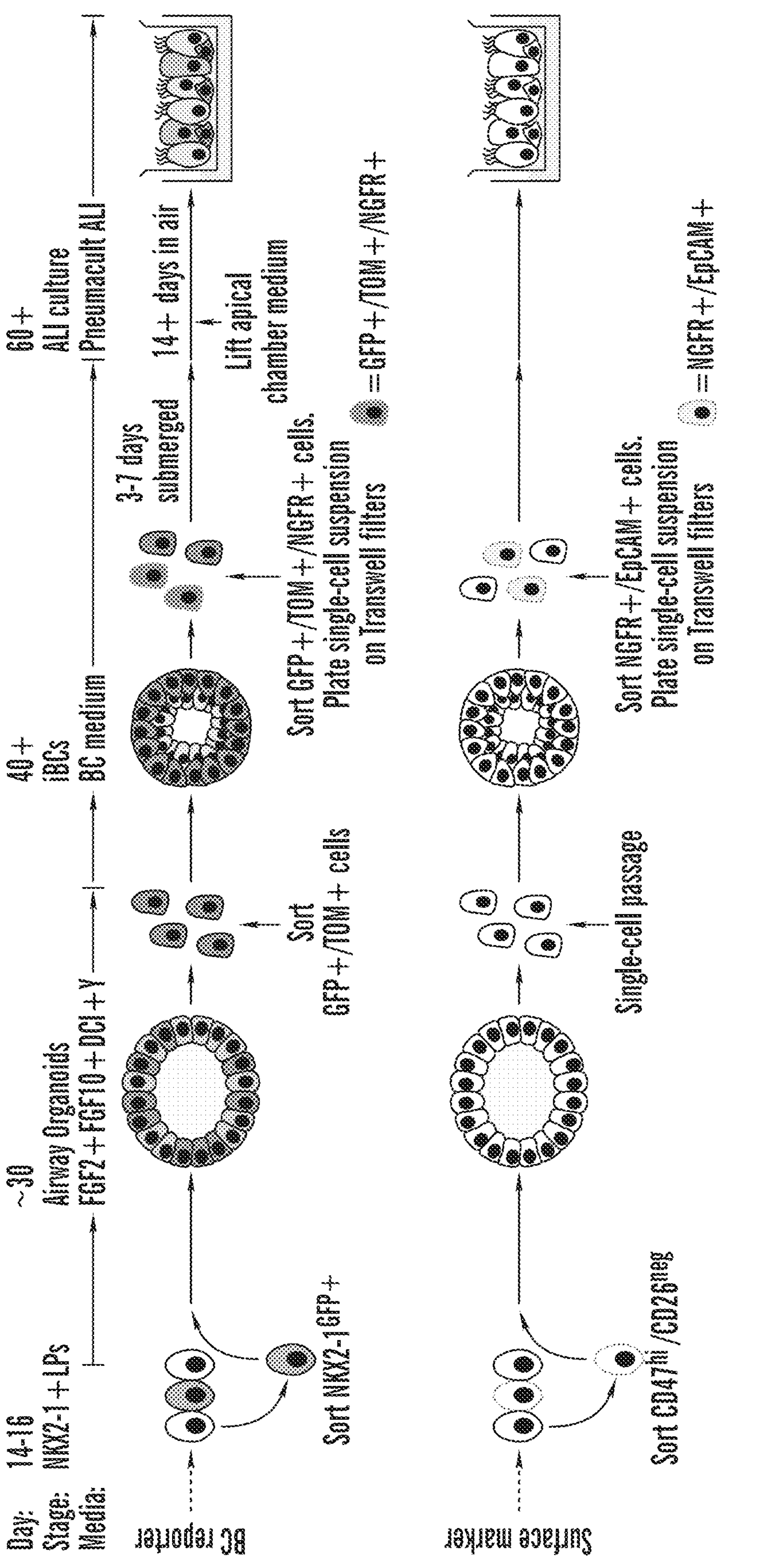
Figure 6B:
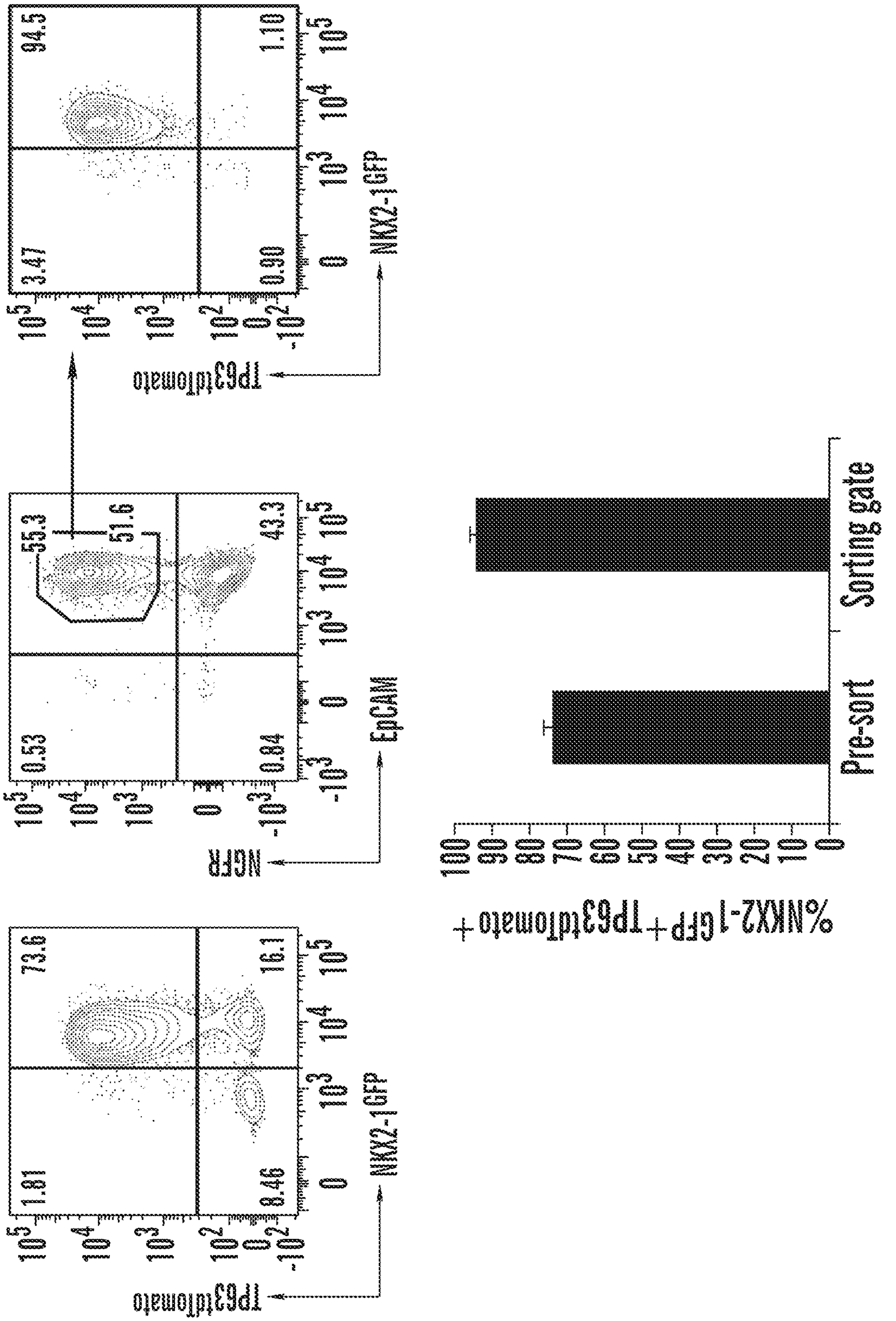
Figure 6C:
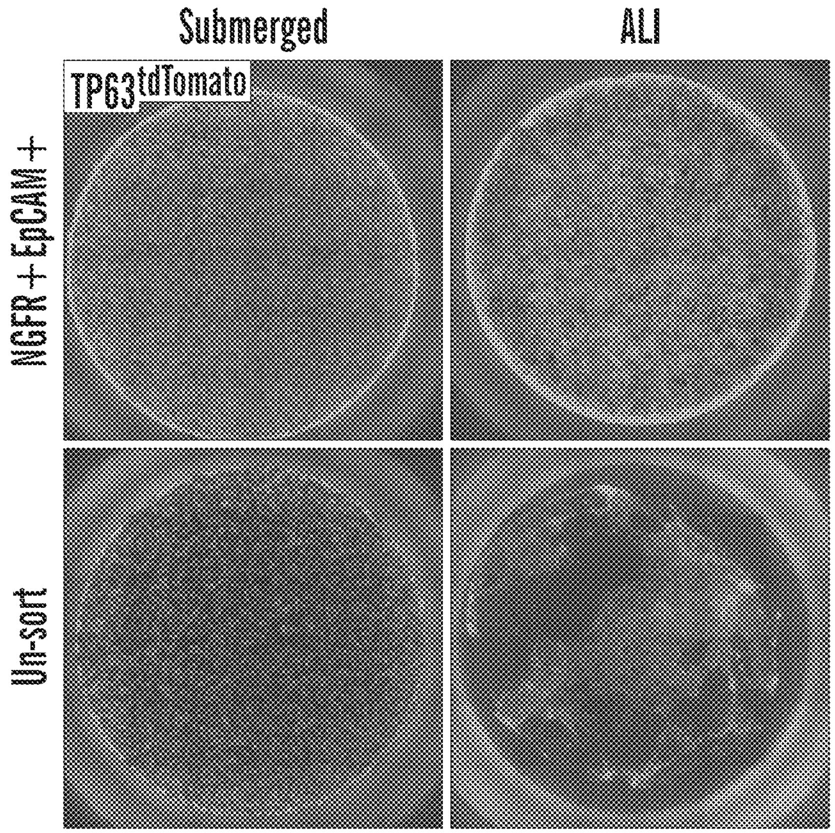
Figure 6D:
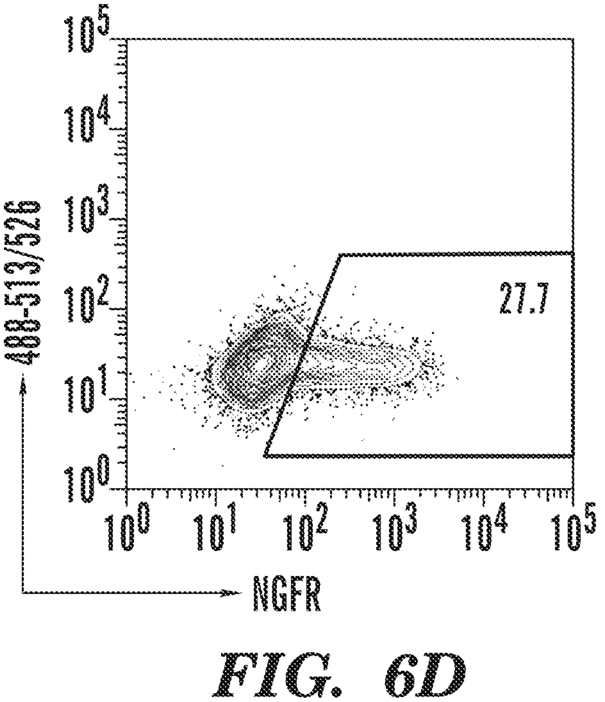
Figure 6E:
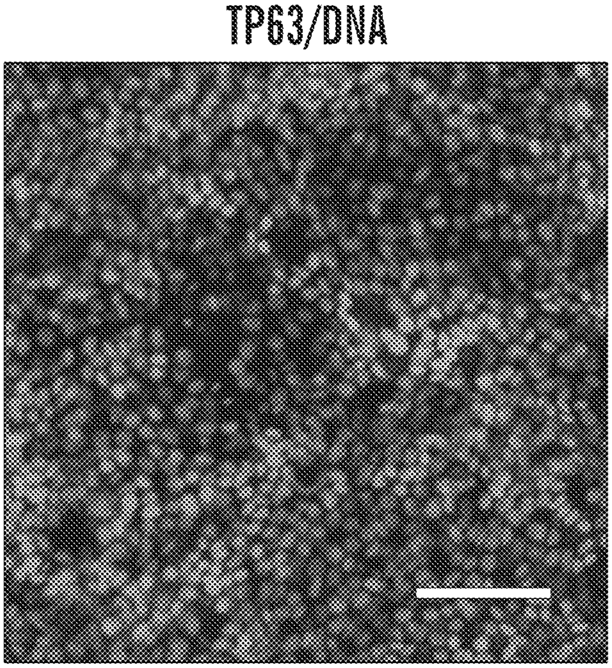
Figure 6F:
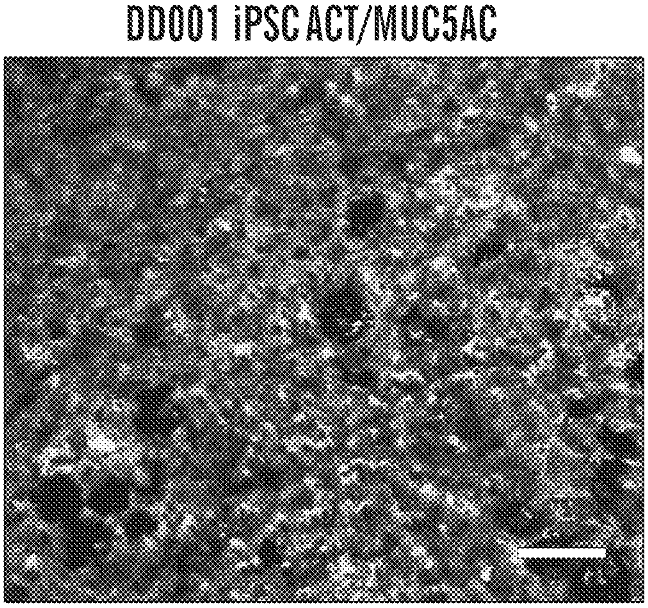
Figure 6G:
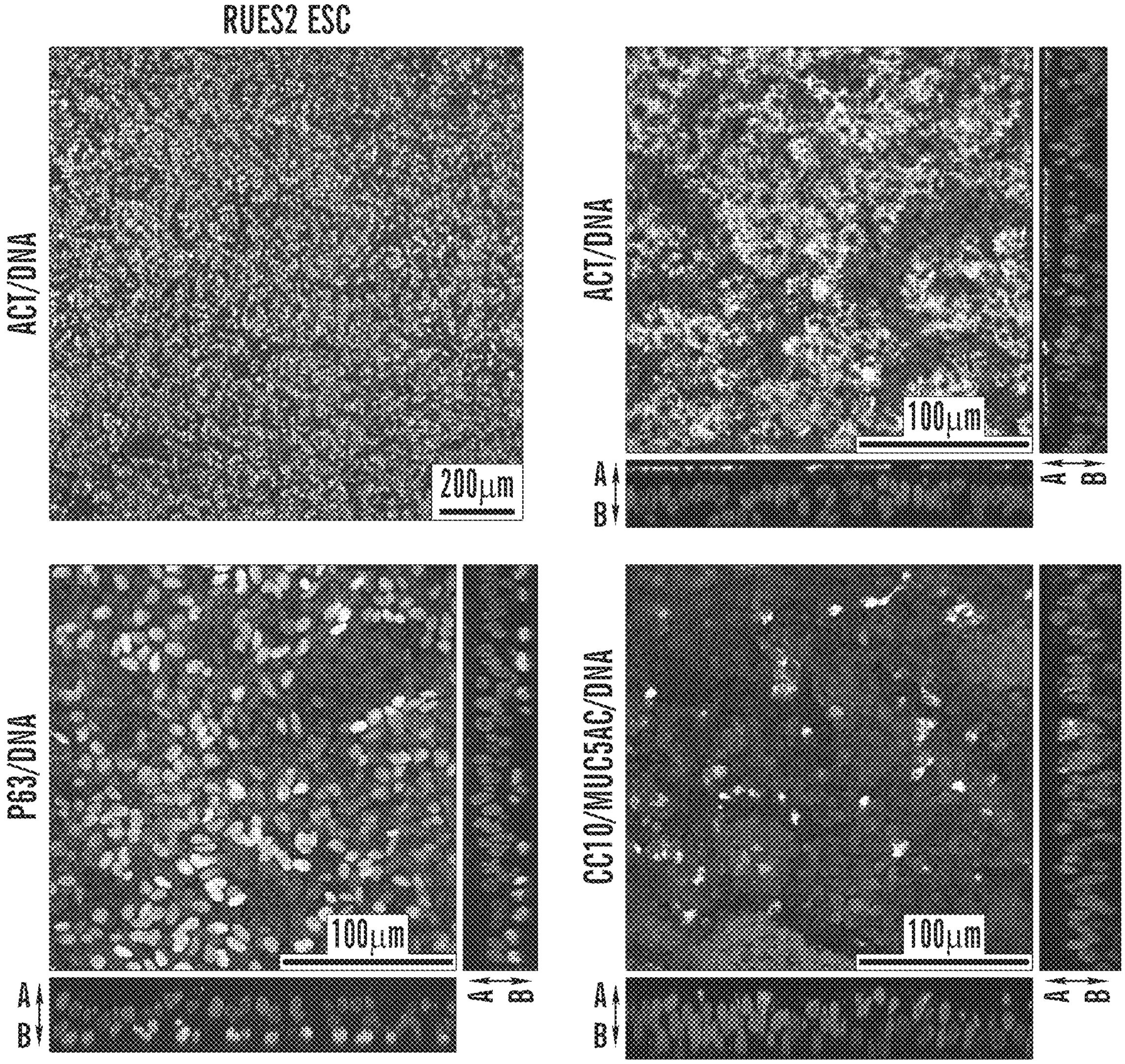

Selection of iBCs from Non-Reporter iPSCs Lines Using Antibodies Directed Against Surface Markers To expand the application of iBCs for disease modeling, it was first sought to adapt the foregoing approach so that a diversity of normal or patient-specific iPSC lines could be differentiated into iBCs without requiring the use of knockin fluorochrome reporters. It was found through repeating the protocol with the BU3 NGPT line, that is was possible to replace GFP+/TOM+ sorting with antibody-based sorting of NGFR+ cells to prospectively isolate putative iBCs (FIG. 6). For example, cells grown until days 40-42 with the protocol (FIGS. 6A-6C) were 73.7%±5.9% (mean±SD) GFP/TOM double positive, and gating on NGFR+/EpCAM+ cells yielded a population of cells highly enriched in GFP/TOM co-expressing cells (94.3%±1.1%; mean±SD; FIG. 6B). A representative experiment is shown in FIG. 6B: 73.6% of cells were GFP+/TOM+; 55.3% were NGFR+/EPCAM+; and 94.5% of sorted NGFR+/EPCAM+ cells were GFP+/TOM+. Sorting solely on NGFR+ or NGFR+/EpCAM+ and replating cells in ALI cultures resulted in successful derivation of a TOM+ pseudostratified airway epithelium, similar to sorting GFP+/TOM+/NGFR+ cells and in contrast to unsorted controls (FIG. 6C). Four additional iPSC lines (DD001m, PCD1, 1566, and 1567) and an embryonic stem cell (ESC) line (RUES2) were also differentiated, recapitulating the BC differentiation protocol while completely replacing the need for fluorescent reporters through the use of CD47$^{hi}$/CD26$^{neg}$ sorting on day 15 to purify NKX2-1+ progenitors as published (Hawkins et al., 2017), followed by NGFR+ sorting after day 40 to purify candidate iBCs (see STAR Methods and schematic in FIG. 6A). NGFR+ cells from all five iPSC/ESC lines differentiated into pseudostratified epithelia composed of MCCs, SCs, and BCs (FIGS. 6D-6G).

iBCs Model Biological Features of the Airway Diseases: Asthma, CF, and PCD

Figure 7A:
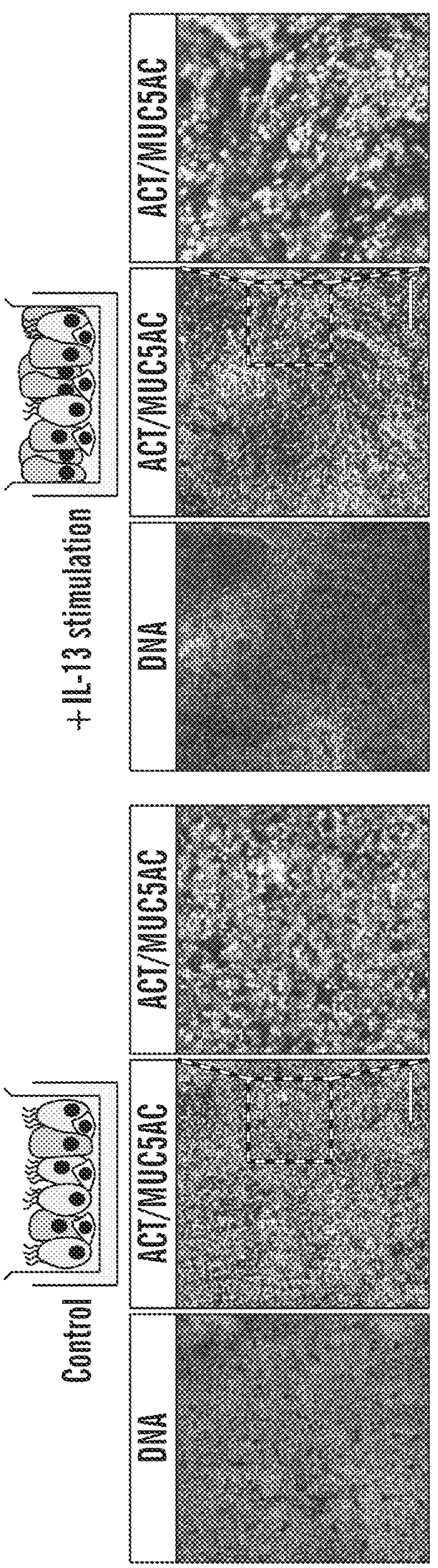
Figure 7B:
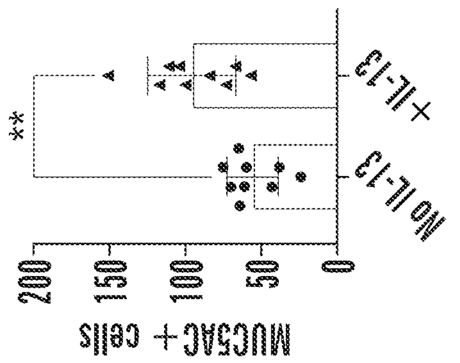
Figure 7C:
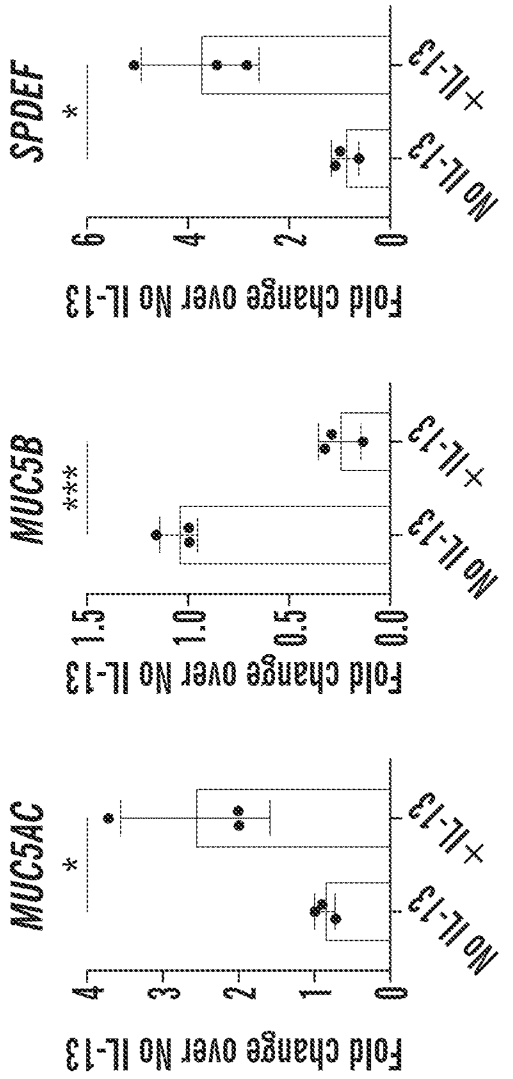

Human airway epithelium has diverse biologic and physiologic roles, some of which are uniquely affected by disease.

it was tested whether iBC-derived ALI cultures could recapitulate features of the three airway disorders with distinct epithelial characteristics: (1) mucus cell metaplasia in asthma; (2) abnormal ion-flux seen in CF; and (3) defective ciliary beating seen in PCD. First, it was tested whether iBC-derived ALI cultures could recapitulate the mucus cell metaplasia seen in asthma. Interleukin-13 (IL-13) is an inflammatory cytokine in asthma and can induce mucus metaplasia. A number of studies, in mice and primary human airway epithelial cell cultures, have found IL-13 leads to increased MUC5AC+ cell numbers via the activation of STAT6 and SPDEF, at the expense of MCCs and MUC5B+ cell frequencies (Kondo et al., 2002; Seibold, 2018; Woodruff et al., 2009). In response to IL-13 added on day 10 of ALI differentiation of iBCs, a significant 1.75-fold increase in numbers of MUC5AC+ cells (p=0.002), increased expression of the goblet cell transcriptional regulator SPDEF, and a decrease in MUC5B expression (FIGS. 7A-7C) was found.

Figure 7D:
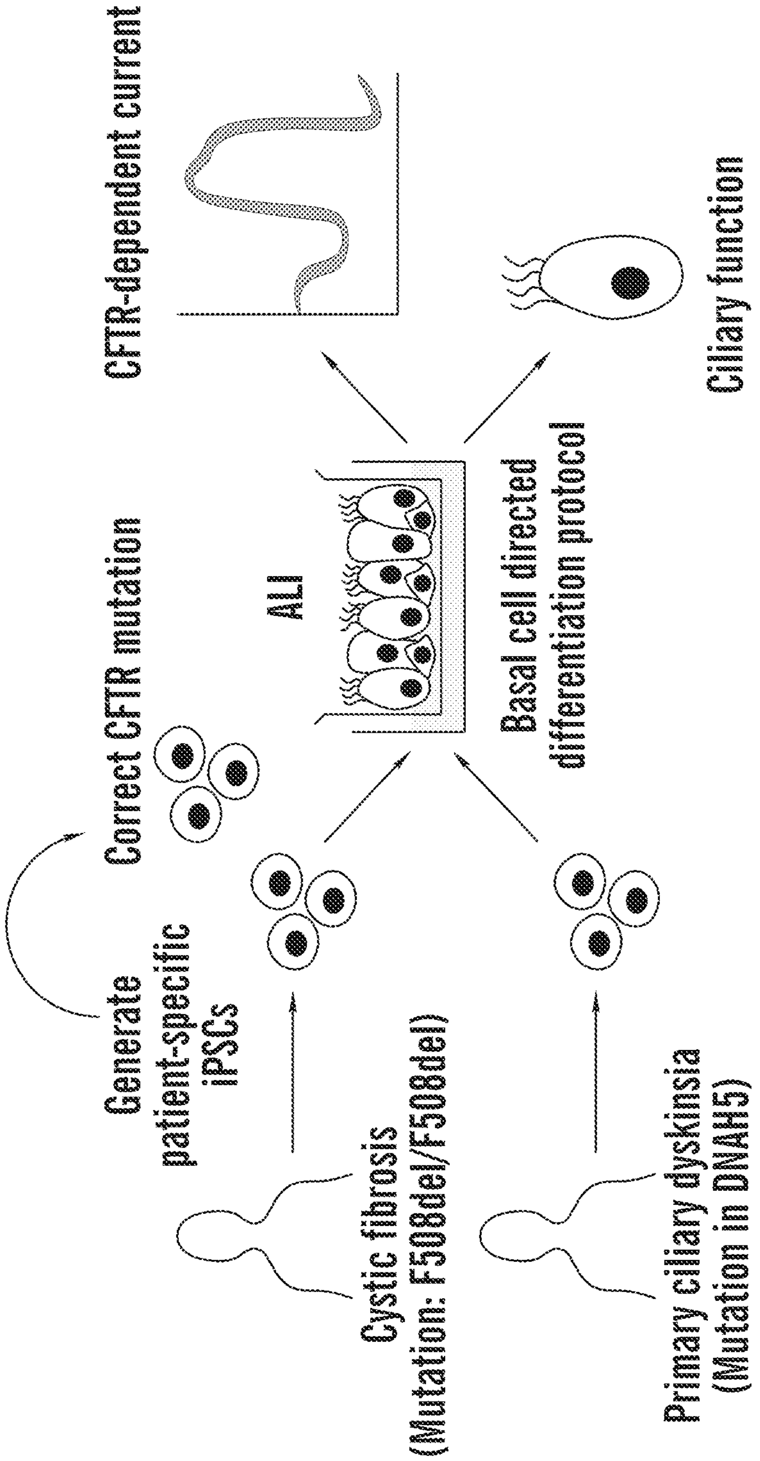
Figure 7F:
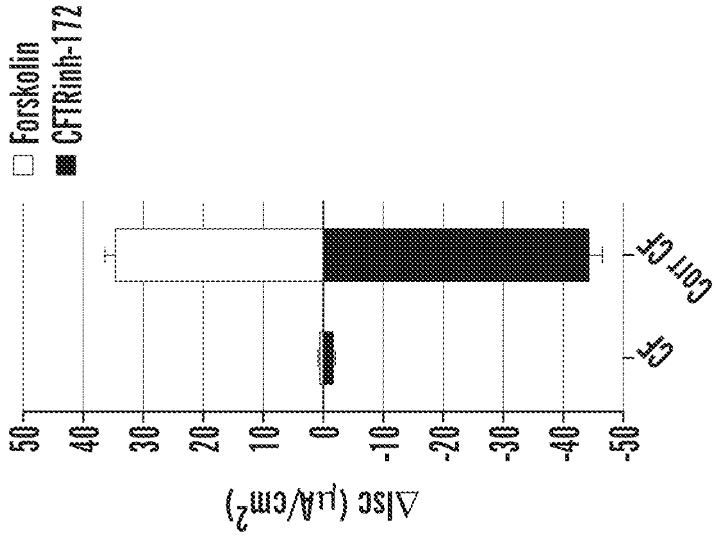
Figure 7E:
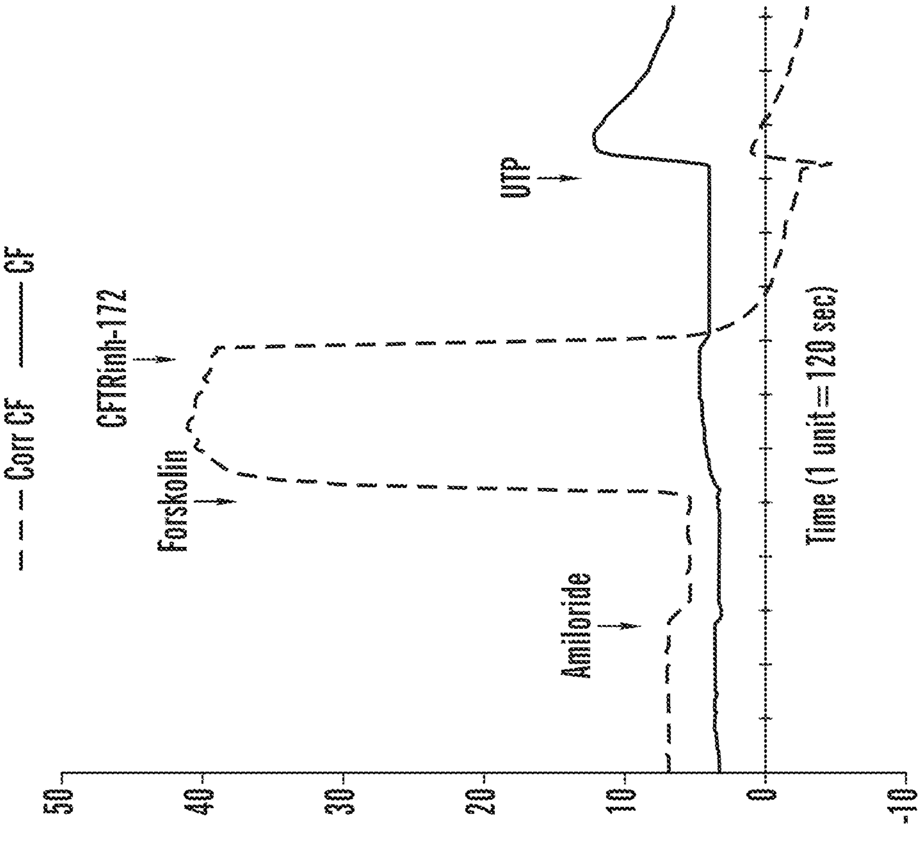

Next, the antibody-based iBC purification protocol was applied for modeling the genetic airway diseases CF and PCD (FIG. 7D). A CF patient homozygous for the most common CFTR mutation (c.1521_1523delCTT, p.Phe508del) and a PCD patient homozygous for one of the most common mutations in DNAH5 (c.12617G>A, p.Trp4206Ter) were identified, and iPSCs generated from these individuals (see STAR Methods and FIG. 8). For CF modeling, gene editing was used to correct the F508del CFTR mutation. Pre- and post-gene corrected paired syngeneic iPSC clones (hereafter CF and Corr CF) were differentiated into iBCs in the present protocol, sorted using the present antibody-based-method and generated ALI cultures composed of BCs, SCs, and MCCs (FIG. 6A). CFTR-dependent current, representing ion flux regulated by apically localized CFTR, was measured using the gold-standard Ussing chamber approach. As expected, Ussing chamber analysis indicated minimal CFTR-dependent current in CF ALI cultures (forskolin AIsc=0.8 pA/cm2; CFTRInh-172 AIsc=−0.8 pA/cm2). In marked contrast, correction of the F508del mutation led to restoration of CFTR-dependent current (forskolin AIsc=35.1±1.8 pA/cm2; CFTRInh-172 AIsc=−43.2±2.5 pA/cm2; FIGS. 7E and 7F). Similar results were obtained from 2 additional CF iPSC lines following CFTR gene correction (data not shown). A limitation of primary HBECs in CF studies is the decrease in CFTR-dependent current with extended passage of primary HBECs (Gentzsch et al., 2017). To address this possibility in iPSC-derived airway epithelium, Ussing chamber analysis was performed on ALI cultures generated from the NGPT line before and after cryopreservation of iBCs and after in vitro expansion of iBCs up to day 87 and found CFTR-dependent current was retained (data not shown).

Figure 7G:
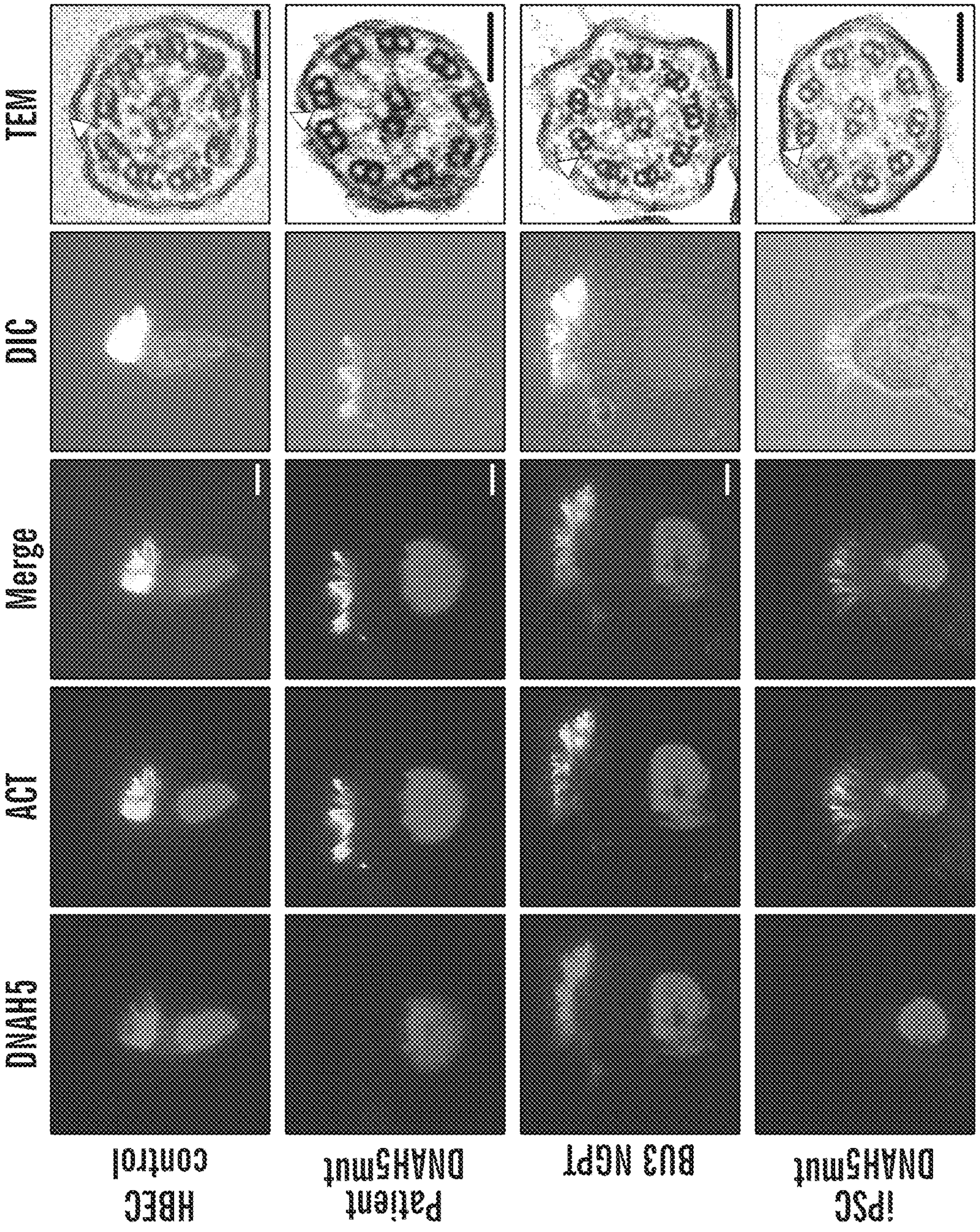
Figure 16:
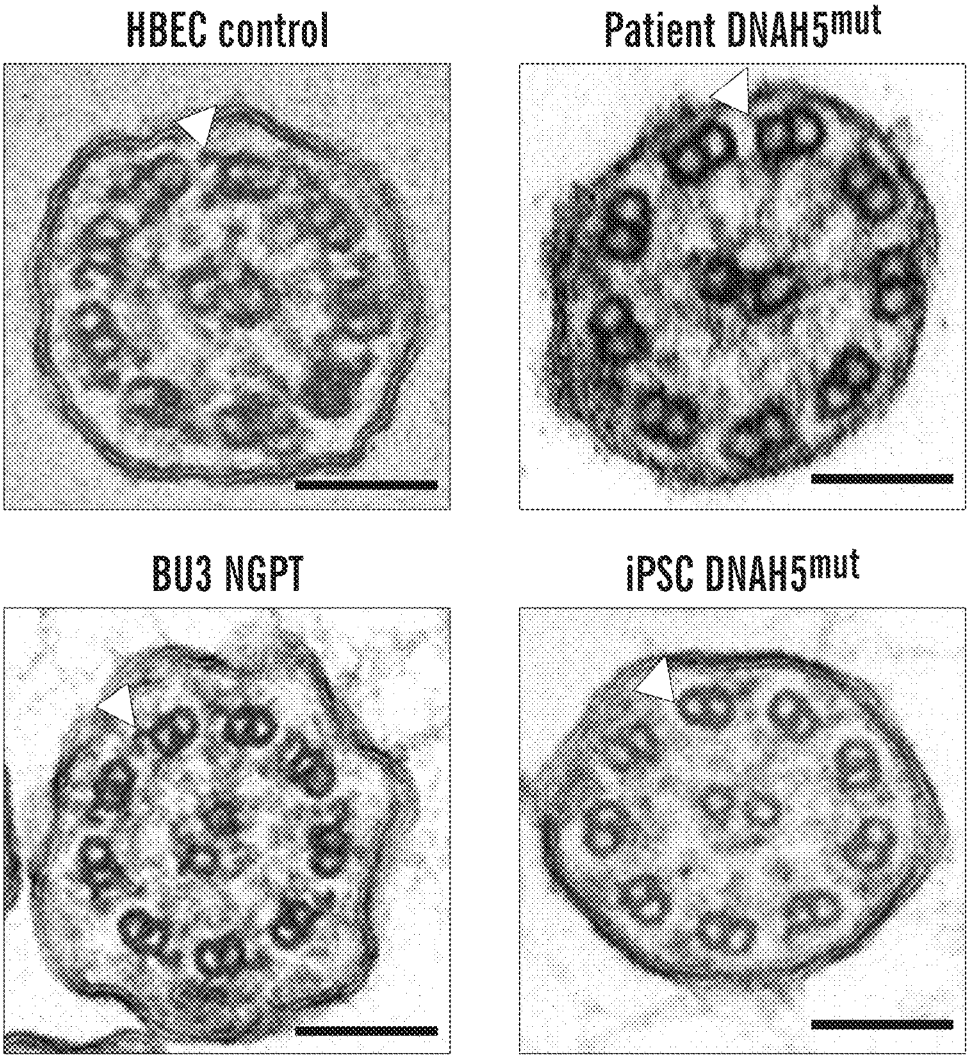
FIG. 16 shows transmission electron microscopy of cilia from samples in FIG. 7I.
Figure 17:
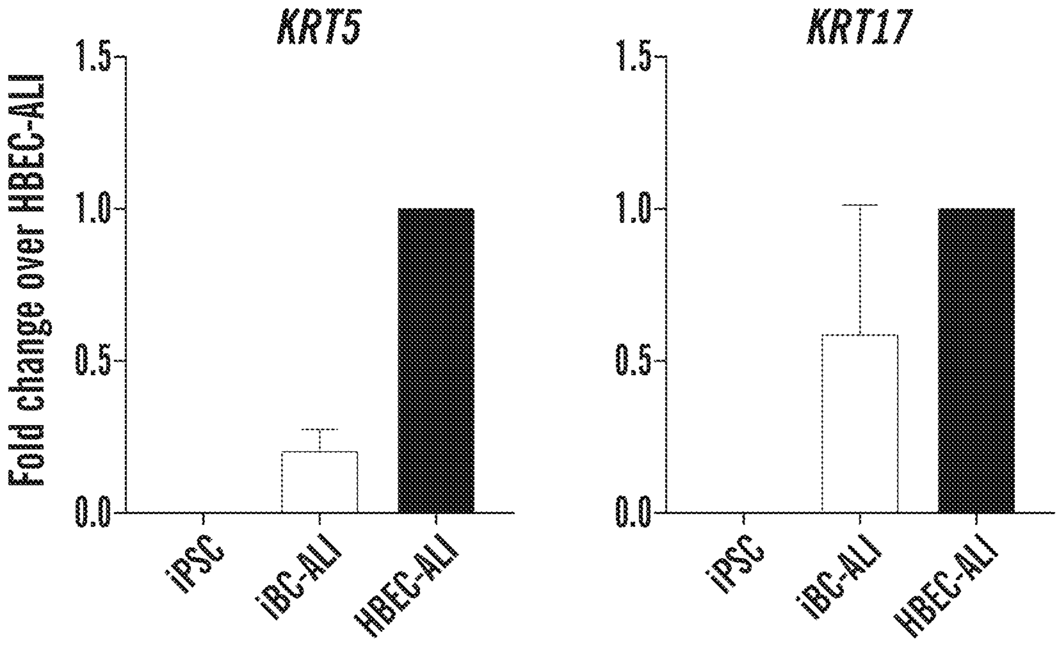
FIG. 17 shows qRT-PCR quantification of mRNA expression levels of KRT5 and KRT17 in iPSCs, iBC-ALI, and HBEC-ALI cells.
Figure 18:
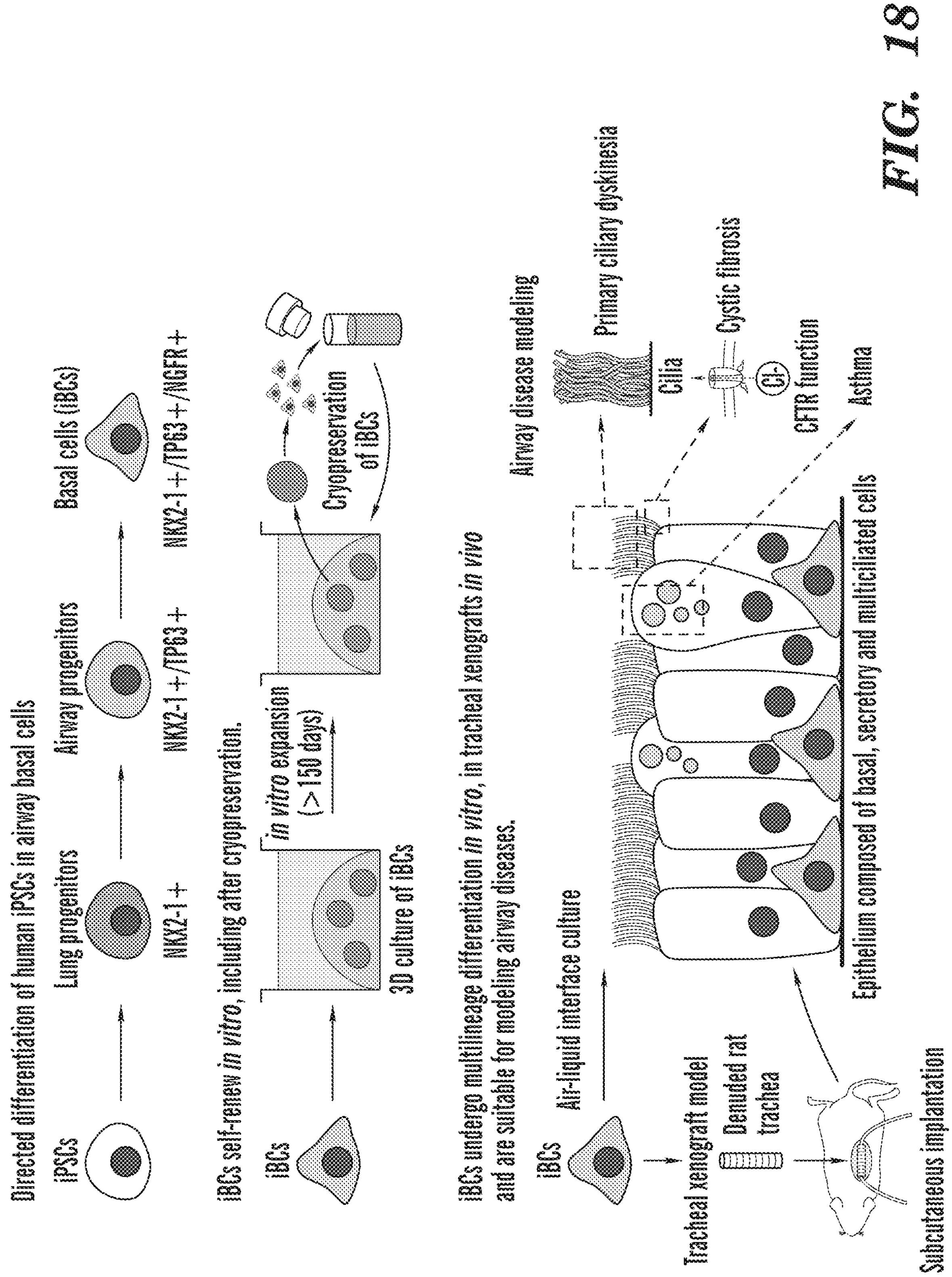
FIG. 18 shows a schematic representation of the human iPSC-derived airway basal cell differentiation, cryopreservation, and airway disease modelling applications provided in the working examples.

To develop a model for PCD, the PCD iPSC line carrying the DNAH5 mutation was differentiated and ALI cultures containing MCCs generated. These cells were compared to control ALI cultures from BU3 NGPT iBCs, primary nasal epithelium from the PCD donor, and normal primary HBECs. Cilia motility was not detected in the MCCs generated from either the DNAH5 mutant iPSC line or from DNAH5 mutant primary cells, in contrast to normal controls (video data not shown). The possibility that DNAH5 mutant iPSCs had failed to produce cilia was excluded by immunofluorescent staining with antibodies against ACT, which confirmed the widespread presence of normal-appearing cilia in all samples (FIG. 7G). In addition, increased tethering of MUC5AC+ mucus strands was observed on the apical surface of the differentiated epithelium generated from the mutant iPSCs (FIG. 16).

Figure 7I:
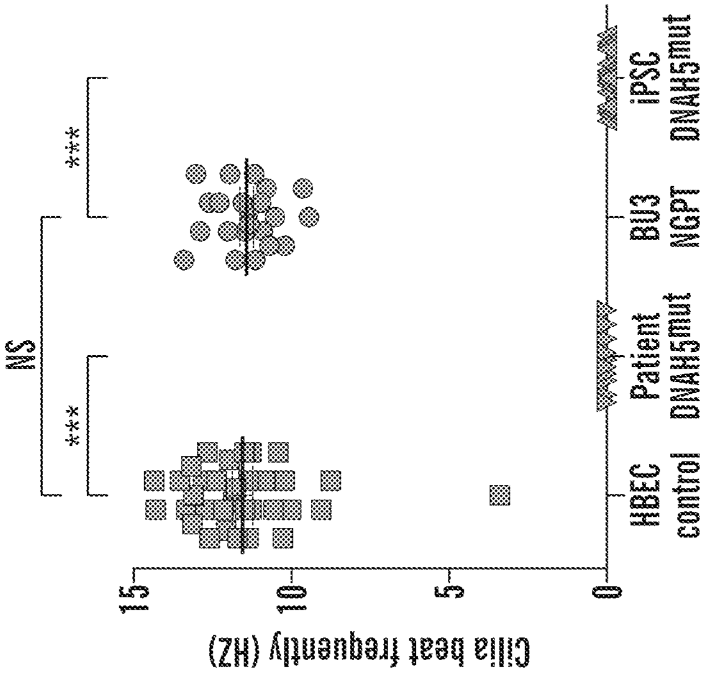
Figure 7H:
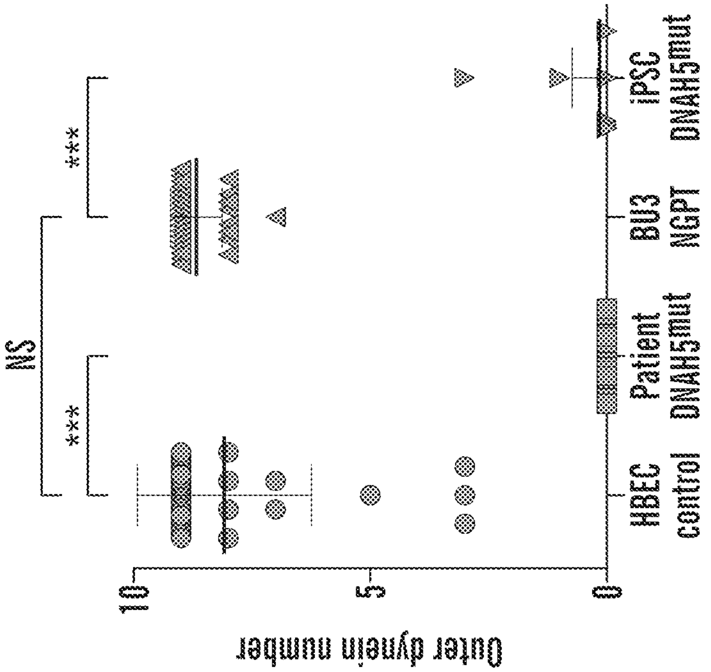
Figure 8A:
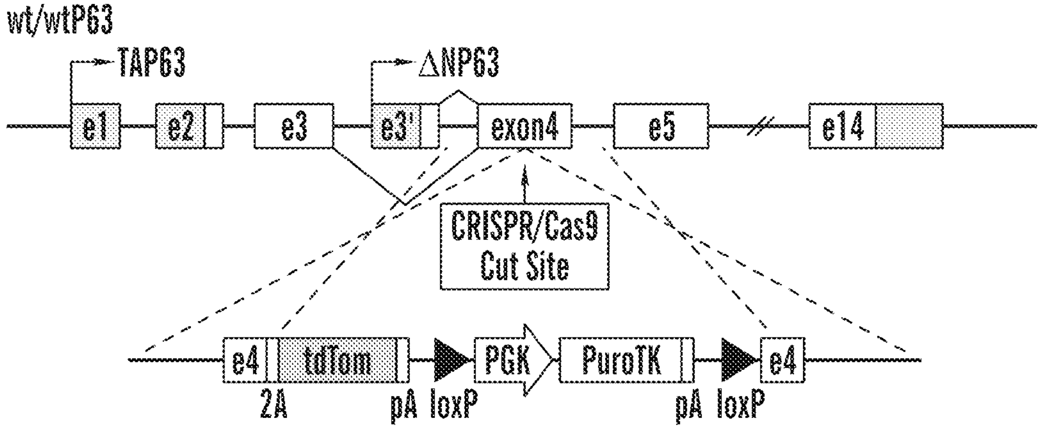
Figure 8B:
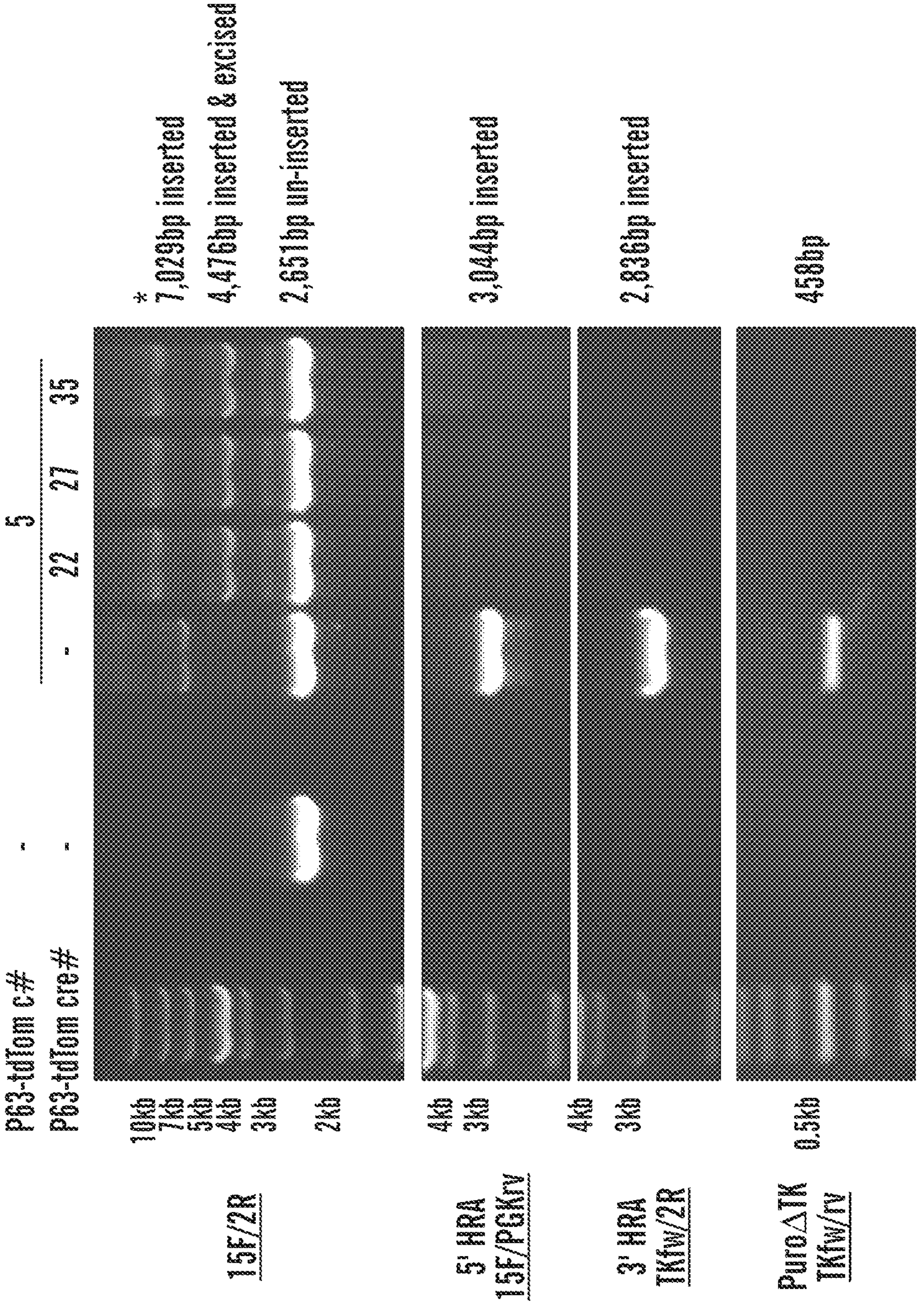
Figure 8C:
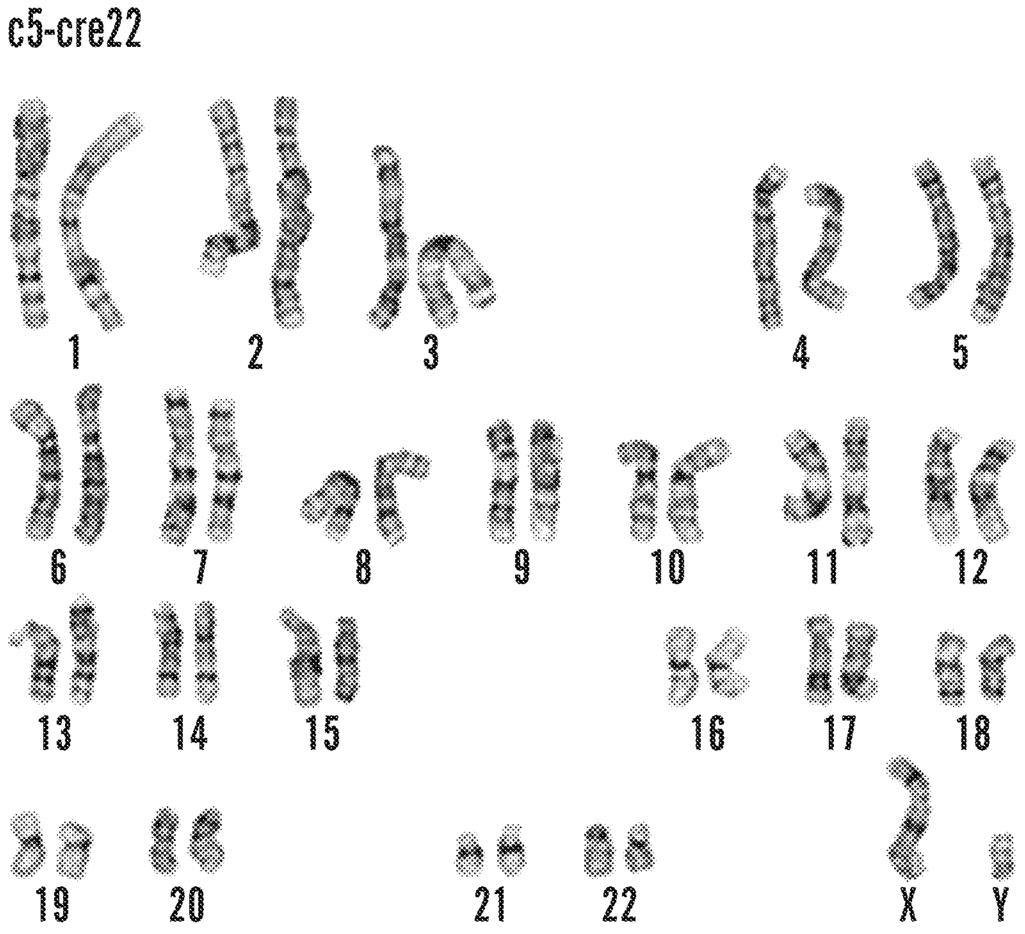
Figure 8D:
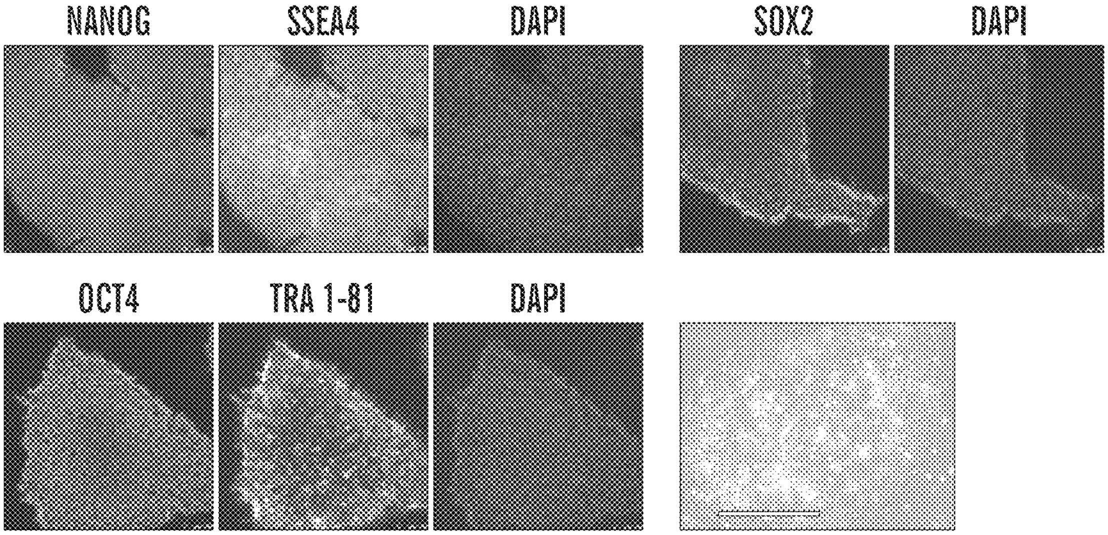
Figure 8E:
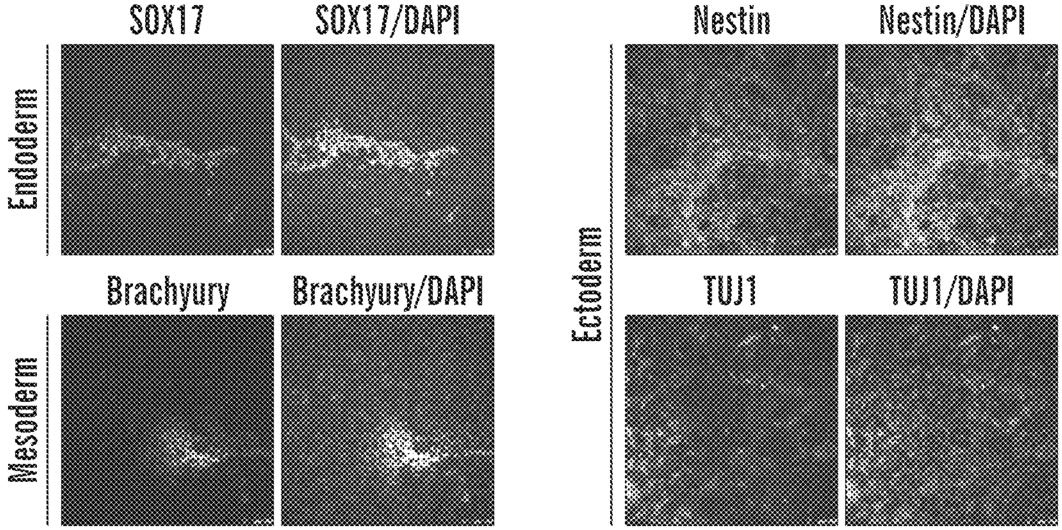

In MCCs generated from normal iPSCs and normal HBECs, DNAH5 protein was present and colocalized with ACT along the length of cilia although DNAH5 protein was not detected in either PCD iPSC-derived or primary nasal-derived MCC cells (FIG. 7G). In contrast, DNALI1, an inner dynein arm (IDA) protein, was detectable by immunostaining, suggesting an intact IDA complex (FIG. 14G). Transmission electron microscopy of DNAH5 mutant iPSC-derived MCCs cells showed lack of the outer dynein arm (ODA), identical to the defect in cilia of nasal cells obtained from the patient and in contrast to MCCs obtained from control iPSC and normal HBEC (FIGS. 7G and 7H). Ciliary beat frequency (CBF) was not detected in DNAH5 mutant MCCs from the patient or from mutant iPSCs, whereas CBF was similar between normal HBECs and BU3 NGPT-derived MCCs (FIG. 7I). Taken together, these results indicate that iPSC-derived airway epithelium shares key physiologic and biologic features with human airway epithelium. In addition, patient-specific iBCs purified without using fluorescent protein reporters can be successfully applied to model a variety of airway epithelial diseases, including CF and PCD.

Discussion

Provided herein is the differentiation of iPSCs into iBCs, cells that are molecularly and functionally similar to the predominant stem cell of human airways, the basal cell. These iBCs can be used to model human development and disease and are demonstrated to have the capacity to regenerate airway epithelium in vivo in a tracheal xenograft model.

The derivation of a tissue-resident stem cell from human iPSCs has considerable implications for regenerative medicine research as it overcomes several important hurdles currently limiting progress in this field. For example, despite significant progress in recent years, directed differentiation protocols are often lengthy, complex, and yield immature and heterogeneous cells (Dye et al., 2015; Firth et al., 2014; Gotoh et al., 2014; Hawkins et al., 2017; Huang et al., 2014; Jacob et al., 2017; McCauley et al., 2017; Miller et al., 2018). Frequently, these issues are due to lack of precise knowledge regarding developmental roadmaps associated with cellular embryonic origin. TP63+ populations have previously been observed stochastically in iPSC-directed differentiation protocols, and their characterization was based only on the expression of a handful of canonical markers, limiting any conclusions as to whether basal-like cells had been produced (Hawkins et al., 2017; McCauley et al., 2017; Chen et al., 2017; Konishi et al., 2016; Dye et al., 2015). Without the ability to purify these cells from the heterogeneous mix of other iPSC-derived lineages, little progress has been made in phenotyping or testing their functional potential.

Described herein are several advances that culminate in the efficient derivation and purification of BCs from iPSCs. Using a dual-fluorescence BC reporter iPSC line, in vitro the milestones of in vivo airway development and BC specification were recapitulated (Yang et al., 2018). First, during the emergence of the earliest detectable lung epithelial program, rare TP63+ cells were detected. Next, in response to the withdrawal of Wnt signaling and in the presence of FGF2 and FGF10, an immature airway program with upregulation of TP63 and SCGB3A2 was evident. In response to primary BC medium and inhibition of SMAD signaling, these TP63+ cells adopted molecular and functional phenotypes similar to adult BCs, including the capacity for extensive self-renewal for over 150 days in culture and multi-lineage airway epithelial differentiation both in vitro and in vivo. It was discovered that the resulting cells fulfill the criteria to be termed iBCs. From a practical perspective, insight and methodologies developed herein should expand the application of iPSC technology. The shared properties of primary BCs and iBCs for expansion and differentiation in ALI culture makes them attractive for a variety of in vitro or in vivo applications. Specifically, the ability to purify iBCs based on the surface marker NGFR, expand the resulting cells in 3D culture, and cryopreserve cells should minimize variability associated with directed differentiation and can potentially offset the cost and time required for these protocols.

In terms of the utility of this platform for disease modeling, diseases were selected with unique research challenges. In asthma, the epithelium plays a sentinel role in pathogenesis, and there is significant interest in understanding epithelial dysfunction and the contribution of genetic variants to asthma susceptibility (Loxham et al., 2014). It is demonstrated herein that a mucus metaplasia phenotype is induced in iPSC-derived airway epithelium in response to stimulation with the Th-2 cytokine IL-13. In CF, where many mutations in one gene necessitate individual models of disease for predicting personalized therapeutics, it was demonstrated that patient-specific iPSCs or their gene-edited progeny can be differentiated into iBCs and give rise to airway epithelia exhibiting quantifiable CFTR-dependent currents of sufficient magnitude for disease modeling using the gold-standard Ussing chamber assay of CFTR function. Although airway ionocytes were not detected in our scRNA-seq profiles of iPSC-derived cells, given the known rarity of this cell type in vivo or in cultured HBEC preparations, further work is required to determine whether ionocytes, which are known to be rich in CFTR (Plasschaert et al., 2018), occur at low frequencies in the present cultures or contribute in any way to the measured. For PCD, where many mutations in many genes controlling ciliogenesis can contribute to the disease, it was determined that iBC-derived MCCs model both the functional and ultrastructural defects observed in DNAH5 mutant primary-donor-derived cells. These experiments indicate that the iPSC platform can be used in determining mechanisms of pathogenicity for genetic airway diseases and serve as a platform to develop novel therapeutics.

Example 2: Star Methods

Human Subjects

The Institutional Review Board of Boston University approved the generation and differentiation of human iPSCs with documented informed consent obtained from participants. The generation of CF iPSCs was approved by Boston Children's Hospital Institutional Review Board. Human airway tissue and primary HBECs were received from the CF Center Tissue Procurement and Cell Culture Core (Dr. Scott Randell) at the University of North Carolina. Human lung tissue was procured under the University of North Carolina Office of Research Ethics Biomedical Institutional Review Board Protocol No. 03-1396. For PCD studies, human protocols were approved by the institutional review board at Washington University in St. Louis. Subjects with known mutations causative of PCD were recruited from the PCD and Rare Airway Disease clinic at St. Louis Children's Hospital and Washington University. Informed consent was obtained from individuals (or their legal guardians). All human samples were de-identified. Details of procurement and isolation of airway epithelial cells from fetal and adult human lungs were previously described (Miller et al., 2020).

Human iPSC Reprogramming and iPSC/ESC Maintenance

All iPSC and ESC lines were maintained in feeder-free conditions on hESC-qualified Matrigel (Corning) in StemFlex Medium (Thermo Fisher Scientific, Waltham, Mass.) or mTeSR1 medium (StemCell Technologies, Inc., Vancouver, Canada) and passaged with Gentle Cell Dissociation Reagent (StemCell Technologies, Inc.) or ReLeSR (StemCell Technologies, Inc.). All human ESC/iPSC lines used were characterized for pluripotency and were found to be karyotypically normal. The reprogramming and gene-editing methods to derive BU3 iPSCs and target the NKX2-1 locus to generate BU3 NKX2-1GFP iPSCs were previously described (Hawkins et al., 2017). PCD1 iPSC line (DNAH5 mutation) was generated by reprogramming peripheral blood mononuclear cells with the human EF1a-STEMCCA-loxp lentiviral vector followed by Cre-mediated vector excision, according to our detailed protocol (Sommer et al., 2012). DD001m iPSCs were generated from "DD001m" P0 primary HBECs by modifying a Sendai virus based reprogramming F508del (p.Phe508del) iPSCs were generated from peripheral blood mononuclear cells at Boston Children's Hospital Stem Cell Program by Sendai virus using the Cytotune 2 kit (Thermo Fisher), yielding clones 791 and 792 ("CF"). Clone 792 was selected for correction of the p.Phe508del deletion and the experiments in FIG. 7. Standard immunolabeling for pluripotency markers and G-band karyo-typing was performed to ensure pluripotency and normal karyotype in clones selected for these experiments (as shown in FIG. 8). For BU3 NGPT iPSCs spontaneous differentiation into mesoderm, endoderm and ectodermal lineages was demonstrated by generating embryoid bodies with iPSC medium in ultra-low attachment plate (Corning) and then replacing with base medium supplemented with 10% fetal bovine serum in adherent culture. The cell types from each lineage were identified with standard immunolabeling (as shown in FIG. 8) using anti-bodies listed in Table 3. Primocin (Invivogen, San Diego, Calif.) was routinely added to prevent mycoplasma contamination and all iPSC and ESC lines screened negative for mycoplasma contamination and were routinely tested and remained negative.

Basal Cell Reporter iPSC

The dual reporter, NKX2-1GFP and P63tdTomato, iPSC lines (BU3 NGPT) were derived from the published single reporter, NKX2-1GFP, iPSC line (BU3 NG), a normal donor iPSC carrying homozygous NKX2-1GFP reporters (Hawkins et al., 2017). The BU3 NG line was targeted and integrated with a P63tdTomato fluorescent reporter using CRISPR/Cas9 technology. A gRNA was designed to target exon 4 of the endogenous TP63 (target sequence TGCGCGTGGTCTGTGTTATA (SEQ ID NO: 62)) and a donor template was constructed to contain the tdTomato sequence and removable antibiotic selection cassette via Cre recombination flanked by arms of homology. In this report the clone BU3 NGPT c5-cre22 was used, where P63tdTomato fluorescent reporter-integrated clone 5 was further cre-excised to remove selection cassette (sub-clone 22).

Gene Corrected CF-iPSCs

Monoallelic correction of homozygous F508del CF iPSC, clone 792, was performed by nucleofecting 1M TrypLE-Select dissociated cells with 5 mg Cas9-GFP plasmid (Addgene, 44719), 5 mg of a U6 promoter driven sgRNA plasmid (target sequence ACCATTAAA-GAAAATATCAT (SEQ ID NO: 63)), 10 mg of a plasmid containing a 1.4 kb piece of the WT CFTR that includes the exon encoding F508. Repaired clones were identified by ddPCR and Sanger sequencing of long-range PCR products. Clones 1566

(CFTR WT/F508del) and 1567 (CFTR F508del/F508del) were confirmed by DNA STR fingerprint (match with donor) and karyotype analysis (no abnormalities).

Primary HBECs and Human Airway Tissue

De-identified, cryopreserved human bronchial epithelial cells (HBECs) were received from the CF Center Tissue Procurement and Cell Culture Core, Marsico Lung Institute, University of North Carolina where they were harvested and cultured as previously described in detail. Paraffin-embedded sections of de-identified human airway tissue were also received. These samples are exempt from regulation by HHS regulation 45 CFR Part 46. Freshly isolated P0 HBECs were expanded in culture on collagen type I/III-coated tissue culture plates in non-proprietary bronchial epithelial growth medium (BEGM). At 70%-90% confluence HBECs were dissociated with Accutase (Sigma), counted and transferred to human placental type IV collagen-coated membranes (Transwell, Corning Inc., Corning, N.Y.) at a density of 100,000-150,000 cells per 6.5 mm insert and differentiated using air-liquid interface conditions in either a non-proprietary medium, "UNC-ALI" medium, or PneumaCult-ALI for 2-3 weeks or longer before analysis. Frequency of each epithelial cell-type was assessed 14 days after establishing ALI culture for both iBC and HBEC samples previously expanded in Basal Cell medium described below. FIG. 4F analysis was performed 21 days after establishing ALI culture for both iBC and HBEC samples. FIG. 14D analysis was performed 30 days after establishing ALI culture.

Animals

All animal procedures were performed at an AAALAC accredited facility and in accordance with National Institutes of Health's Guide for the Care and Use of Laboratory Animals and were approved by the University of Texas Health Science Center at Houston (UTHealth) Institutional Animal Care and Use Committee.

Adult mice (Foxn1nu, The Jackson Laboratory) and rats (NIH-Foxn1rnu, Charles River) used for these experiments were housed in the barrier facility of the Brown Institute of Molecular Medicine at the UTHealth. Animals were group housed in autoclaved, individually ventilated cages (IVC), and provided irradiated corncob bedding with cotton square nestlets for enrichment. Animals were fed adlibitum a commercially available, irradiated, balanced mouse diet (no. 5058, LabDiet, St Louis, Mo.) and had free access to acidified water. A mouse received xenografts was single housed. Rooms were maintained at 21-23° C. and under a 12:12-h light:dark cycle. All animals were maintained specific pathogen free (the list of tested pathogens is available upon a request).

Method Details

This protocol is based on previously described approaches to derive airway organoid from hPSCs (Hawkins et al., 2017; McCauley et al., 2017) including a detailed step-by-step protocol prior to basal cell medium (McCauley et al., 2018b). NKX2-1+ lung progenitors were generated from hPSCs first by inducing definitive endoderm with STEMdiff Definitive Endoderm Kit (StemCell Technologies, Inc.) for 60-72 hours. Endoderm-stage cells were dissociated and passaged in small clumps to hES-qualified MATRIGEL-coated (Corning) tissue culture plates (Corning) in a complete serum free differentiation medium (cSFDM) consisting of a base medium of IMDM (Thermo Fisher, Waltham, Mass.) and Ham's F12 (Thermo Fisher) with B27 Supplement with retinoic acid (Invitrogen, Waltham, Mass.), N2 Supplement (Invitrogen), 0.1% bovine serum albumin Fraction V (Invitrogen), monothioglycerol (Sigma, St. Louis, Mo.), Glutamax (Thermo Fisher), ascorbic acid (Sigma), and antibiotics. To pattern endoderm into anterior foregut the cSFMD base medium was supplemented with 10 μM SB431542 (Tocris, Bristol, United Kingdom) and 2 μM Dorsomorphin (Stemgent, Lexington, Mass.) for 72 hours (Green et al., 2011). Cells were then cultured for 9-11 additional days (typically, 144 hr—day 15) in cSFDM containing 3 μM CHIR99021 (Tocris), 10 ng/mL recombinant human BMP4 (rhBMP4, R&D Systems), and 50-100 nM retinoid acid (Millipore-Sigma) to induce NKX2-1 primordial lung progenitors (Serra et al., 2017). NKX2-1+ lung progenitors were sorted by NKX2-1GFP expression for BU3 NGPT or enriched based on the expression of cell surface markers CD47hi/CD26− for non-reporter iPSC (see below) and then were resuspended in three-dimensional growth factor reduced Matrigel (Corning) at a density of 400 cells per μl and pipetted in 25-50 μL droplets onto the base of tissue culture plates (Hawkins et al., 2017). After 10-15 minutes at 37° C. to allow gelling of Matrigel™ airway medium composed of cSFDM containing 250 ng/ml FGF2 (rhFGFbasic; R&D Systems), 100 ng/ml FGF10, 50 nM dexamethasone, 100 nM 8-Bromoadenosine 3',5'-cyclic monophosphate sodium salt (cAMP; Millipore-Sigma), 100 μM 3-Isobutyl-1-methyloxan-thine (IBMX; Millipore-Sigma), and 10 μM Y-27632 (Y; Tocris) (FGF2+10+DCI+Y) was added.

Sorting of PSC-derived Lung and Airway Progenitors

To facilitate directed differentiation from hPSCs, NKX2-1+ lung progenitors and airway progenitors of iBCs were purified by cell sorting. This sorting protocol is further detailed in previous publications (Hawkins et al., 2017; McCauley et al., 2018b). On day 15, cells were harvested by incubation with 0.05% Trypsin-EDTA for 15-20 min at 37° C. Trypsin was neutralized and cells were washed with medium containing 10% fetal bovine serum (FBS, Thermo Fisher). Harvested cells were spun at 300 RCF for 5 min and resuspended in the buffer containing Hank's Balanced Salt Solution (Thermo Fisher), 2% FBS, 25 mM HEPES 2 mM EDTA (FACS buffer) supplemented with 10 μM Y-27632 and stained with propidium iodide (PI, ThermoFisher) or calcein blue AM (Thermo Fisher) for live cell selection during flow cytometry. Live cells were sorted based on NKX2-1GFP expression for BU3 NGPT or by staining for CD47 (Bio-legend) and CD26 (Biolegend) for non-reporter PSCs and gating for CD47hi/CD26−. Airway progenitors were sorted on day 30 of directed differentiation. Organoids cultured in 3D Matrigel were harvested by incubation with 1 U/mL Dispase (Stemcell technologies) or 2 mg/ml Dispase (Thermo Fisher) for −60 min at 37 C. until Matrigel™ was fully dissolved. Dissociated organoids were collected with a 1000 μL pipette, transferred to a 15 ml conical and centrifuged at 200 RCF for 3 min. The cells were resuspended and incubated in 0.05% trypsin at 37° C. for approximately 10 min until a single cell suspension was achieved. Trypsin was inactivated by adding 10% fetal bovine serum (Hyclone) in DMEM (GIBCO). Cells were then centrifuged at 300 RCF for 5 min at 4° C., counted and resuspended in FACS buffer. 10 μM of the cell viability dye Calcein blue (ThermoFisher) was added and Calcein Blue+/NKX2-1GFP+/TP63tdTomato+ or PI−/NKX2.1GFP+/TP63tdTomato+ cells were sorted and replated at 400 cells per μl of density in Matrigel (Corning) and cultured in FGF2+10+DCI+Y medium.

Generation, Purification and Maintenance of iBCs

The iPSC-derived basal cells (iBCs) were generated from airway organoids in FGF2+10+DCI+Y described above. For BU3 NGPT, one day after (unless indicated) sorting and replating NKX2-1GFP+/TP63td Tomato+ on day 30 of directed differentiation, culture medium was switched to Pneumacult ExPlus™ (StemCell Technologies, Inc.) supplemented with 1 μM A83-01 (Tocris), 1 μM DMH1 (Tocris), and 10 μM Y-27632 (Basal cell medium). In some cases, Pneumacult Ex™ (Stemcell technologies) supplemented with 1 μM A83-01, 1 μM DMH1, and 10 μM Y-27632 was used as indicated in figures. For non-reporter iPSCs, single cells dissociated from airway organoids in FGF2+10+DCI+Y were replated without a sorting step and changed to basal cell medium as above. Viable iBCs at –Day 40 of directed differentiation or later were sorted based by dissociating organoids to a single-cell suspensions as above and flow sorting based NKX2-1GFP+/TP63tdTomato+/NGFR+ cells for BU3 NGPT, or by labeling with mouse monoclonal anti-NGFR (Cat. #345108, Biolegend) and mouse monoclonal anti-EpCAM (Cat. #24234, Bio-legend) with isotype controls (mouse monoclonal IgG1k APC-conjugated, Cat. #400122, Biolegend). Both anti-NGFR and anti-EpCAM antibodies were used at a dilution of 1:100 in a suspension of $1\times10^6$ cells per 50 or 100 μL on ice for 30 min. For these sorting experiments a MoFlo Astrios™ Cell sorter (Beckman Coulter, Indianapolis, Ind.) was used at Boston University Medical Center Flow Cytometry Core Facility or BD FACSMelody™ (BD biosciences) was used at the UTHealth Flow Cytometry Service Center. Sorted iBCs were either replated in ALI culture (see below) or resuspended in Matrigel (Corning) droplets at 400 cells/ul, plated and cultured in basal cell medium as above for expansion of iBCs. iBCs in 3D Matrigel droplets were fed with basal cell medium every 2-3 days and required passaging every-10-14 days. iBCs were cryopreserved by first dissociating organoids to single-cells as above and resuspending in basal cell medium supplemented with 10% dimethylsulfoxide (ThermoFisher) and transferred to cryovials. Cryovials were placed in cryostorage containers in a –80° C. freezer to cool at –1° C./min for 24 hours and then transferred to –150° C. freezer or into liquid nitrogen the following day for long-term storage. iBCs were thawed by warming to 37° C. in a water or bead bath, diluting in 5-10 ml of basal cell medium (37° C.) added dropwise and centrifuged at 300 RCF for 5 min. The cell pellet was then resuspended in Matrigel at 1000 cells/μl, plated in tissue culture plates and after 10-15 min at 37° C. basal medium was added to the well. Expanded or cryopreserved cells-derived organoids in 3D Matrigel™ were dissociated and sorted for iBC makers prior to replating in ALI culture.

ALI Culture of iBCs or Other iPSCs-Derived AECs

To differentiate iBCs in Air Liquid Interface (ALI) culture existing, detailed protocols for primary HBECs were adapted (Fulcher and Randell, 2013). iPSCs-derived airway epithelial cells (AECs) including iBCs were seeded on 6.5 mm Transwells with 0.4 mm pore polyester membrane inserts (Corning Inc., Corning, N.Y.), coated with Matrigel™ diluted in DMEM/F12 (GIBCO) according to the recommended dilution factor from the lot-specific certificate of analysis, at 150,000-200,000 cells per insert with a medium used to culture each cell culture (e.g., iBCs cultured in Basal cell medium were plated on Transwells and cultured in Basal cell medium) for 3 to 7 days. Once visual inspection confirmed the Transwell membranes were covered by a confluent sheet of cells the culture medium was switched to PneumaCult-ALI medium (StemCell Technologies, Inc.) or non-proprietary "UNC-ALI medium (Fulcher and Randell, 2013) in both apical and basal chambers. The following day, the medium from top chamber was removed and the cells were further differentiated in air-liquid interface conditions for 2-3 weeks or longer before analysis. ScRNA-Seq (FIGS. 4A-4E), qRT-PCR (FIGS. 4F and 14E) were analyzed 21 days after establishing ALI culture.

Flow Cytometry Analysis

Flow cytometry analysis was performed as described above. NKX2-1GFP, TP63tdTomato expression or fluorochrome-conjugated primary antibodies (listed in Table 3) were detected using a FACS Calibur (BD Biosciences), Stratedigm S1000 EXi (Stratedigm Inc, San Jose, Calif.) or MoFlo Astrios™ (Beckman Coulter) at Boston University Medical Center or with BD FACSMelody™ and BD FACSChorus™ software (BD Biosciences) at the UTHealth Flow Cytometry Service Center. Calcein blue or PI was used to identify viable cells depending on the flow cytometer used. FlowJo™ software (BD biosciences) was used for further analysis.

Histological Analysis

Organoids in 3D Matrigel were harvested by incubation in Dispase as described above, and then fixed in 4% paraformaldehyde (PFA) (ThermoFisher or Electron Microscopy Sciences, Hatfield, Pa.) for four hours at room temperature, paraffin-embedded and immuno-stained as previously described (McCauley et al., 2017, McCauley et al., 2018b). ALI cultures were fixed by placing Transwell filters in 4% PFA at 4° C. overnight. Either whole mount immunostaining of Transwell filters or paraffin-embedding was performed. Tracheal xenografts were also fixed with 4% PFA at 4° C. overnight and embedded in the paraffin. For paraffin sections, fixed samples were dehydrated with a series of increasing concentrations of ethanol, cleared with xylene and infiltrated with paraffin before embedding in wax. Sections of 5 mm thickness were transversely cut using an HM 325 Rotary Microtome (Thermo Fisher Scientific). Sectioned samples were stained with hematoxylin and eosin. For immunofluorescence analysis, antigen retrieval was performed on sectioned samples using Antigen retrieval reagent-Basic (R&D Systems) or Antigen Unmasking Solution, Citric Acid Based (Vector Labs, Burlingame Calif.) following manufacturer's instructions. Whole inserts and sectioned samples were stained with primary and secondary antibodies (antibody information and sources are detailed in the Table 3). Briefly, samples were permeabilized with 0.1% or 0.3% Triton X-100 (Sigma) in PBS for 15-30 min and blocked with 2% bovine serum albumin (BSA) with or without 4% Normal Donkey Serum and 0.1% Triton X-100 or 0.1% Tween20 for 1 hour at room temperature. Samples were then incubated with primary antibodies overnight at 4° C., followed by the incubation with the respective secondary antibodies at room temperature for one to two hours. Prolong Gold Antifade Mountant with DAPI (Thermo Fisher Scientific) was added to counter-stain and coverslipped. Images were acquired using a Leica DMi8 microscope (Leica Microsystems, Wetzlar, Germany) and Leica Application Suite Software (Leica Microsystems) or a Nikon Eclipse Ni-E microscope (Melville, N.Y.). In order to generate an image of whole transwell or of large field with AECs in Xenograft model, the automated tile-scanning and stitching functions were used through Leica Application Suite Software. Confocal microscopy was performed for whole mount staining samples stained with antibodies as described above and counter-stained with DRAQ5 (Cell Signaling Technology, Beverely, Mass.) using Leica Application Suite Software. Quantification of each epithelial cell-type was performed manually by counting the number of cells stained for specific markers in transverse sections. Three inserts for each condition were independently prepared and approximately 1,000 cells in random 40× magnification fields were analyzed for each insert. The frequency of each cell-type was calculated relative to the total number of cells as determined by DAPI-stained nuclei.

To characterize the ciliary defect in DNAH5 mutant cells (FIG. 7), airway cells were fixed and immunostained as previously described (Pan et al., 2007; You et al., 2002). Primary and secondary antibodies used to detect dynein arms included anti-DNAH5 (1:100, HPA037470, Millipore-Sigma, St. Louis, Mo.), ACT (1:4000, clone 6-11-B1, Millipore-Sigma), DNALI1 (1:100, HPA028305, Millipore-Sigma). Primary antibodies were detected using fluorescently labeled secondary antibodies (Alexa Fluor, Life Technologies, Grand Island, N.Y., USA). Nuclei were stained using DAPI (Vector Laboratories, Burlingame, Calif., USA). Images were acquired using an epiflourescent microscope interfaced with imaging software (LAS X™, Leica, Buffalo Grove, Ill.) and adjusted globally for brightness and contrast using Affinity Photo™ (Serif Ltd, Nottingham, UK).

Single-Cell RNA-Sequencing

Cells were prepared for sc-RNA-Seq by dissociating organoids or ALI cultures using the methods described above. Live cells were sorted on a MoFlo Astrios™ Cell sorter (Beckman Coulter, Indianapolis, Ind.) at Boston University Medical Center Flow Cytometry Core and scRNA-Seq was performed using the Chromium Single Cell 30 system (10× Genomics) at the Single Cell Sequencing Core at Boston University Medical Center according to the manufacturer's instructions (10× Genomics). Single cell reads were aligned to the reference genome GRCh38 to obtain a gene-to-cell count matrix with Cell Ranger version 3.0.2 (10× Genomics). The average sample had a mean of 40,154 reads per cell (ranging from 18,415 to 50,219 depending of the library). The median number of genes detected per cell on the average sample was 3,303 genes. This matrix was pre-processed using Seurat version 3.1.0 (Butler et al., 2018), and filtered to remove stressed or dead cells (those with a high percentage of reads mapping to mitochondrial genes, that is beyond 10%-20%, depending on the shape of the distribution of mitochondrial reads per cell) and potential doublets (where the number of genes detected is above a percentile set as threshold based on the expected proportion of doublets at any given cell density (100−(number of cells/1000)/100). After normalizing, scaling and regressing out unwanted sources of variation (like cell degradation), highly variable genes were identified and used for linear dimensionality reduction (PCA). The first 20 principal components were then used for clustering based on the Louvain method for community detection at different resolutions (from 0.25 to 1.5 at intervals of 0.25). Further non-linear dimensionality reduction was performed using Uniform Manifold Approximation and Projection (UMAP) for visualization purposes. Clusters identified with the Louvain method were annotated based on their differentially expressed genes (computed using hurdle models for sparse single cell data from the MAST package) (Finak et al., 2015). Gene set enrichment analysis for molecular signatures was done using the method described by Tirosh et al. (2016), as implemented in Seurat. In order to obtain a molecular signature of airway epithelial cell types that could be used to characterize iPSC-derived lung cells, a combination of two datasets of primary airway epithelial cells was first analyzed: (1) P0 HBECs in BEGM medium and (2) ALI cultures subsequently derived from these cells. The single cell pipeline above was used with one variation during the preprocessing: in addition to regressing the mitochondrial content, the "library" batch effect was also regressed out. Once ad annotated (based on the expression of known markers of basal, secretory and ciliated cells) the clusters obtained by the Louvain method (FIG. 11B), each cell type was compared against all others. In the cases where the cell type of interest was represented in more than one cluster, such clusters were combined before performing the comparison to ensure the purity of both query and background populations. This rationale is to ensure that the fold changes were not diluted by the presence of the same cell type in both the query and the background of each comparison, for example, when basal cell populations that were originally in different clusters belonging to HBEC samples and ALI samples were grouped, and to avoid noise by excluding clusters with poorly characterized or intermediate phenotypes. All single cell visualizations were made with Seurat™ (heatmaps, UMAPs, violin plots).

Quantification of the Similarity Between AECs

In order to quantify the similarity between the iPSC-derived airway epithelial cells and the freshly isolated primary airway epithelial cells of both fetal and adult tissues, a similar procedure as Miller et al. (2020) was used. As a positive control, correlations between primary cultured HBECs and HBECs differentiated in ALI were included. Briefly this assessment consists of two steps: first, selecting a list of informative markers whose profile can discriminate between cell types and developmental stages; and second, calculating the correlation between cells in the in-vitro organoid cultures and the primary fresh cell types using the markers selected. For the first step (marker selection), the single-cell primary fetal airway (Miller et al., 2020) and the single-cell primary adult airway (Carraro et al., 2020) were analyzed separately. Each dataset was normalized using regularized-negative binomial transformation (Hafemeister and Satija, 2019), and its percentage of mitochondrial reads was regressed out. Then differential expression test was performed (Finak et al., 2015) and the top 50 markers for each cell type selected. This resulted in 353 unique markers for fetal cell types and 149 unique markers for adult cell types. These two lists were combined into one and confounding genes (cell cycle markers) were excluded, resulting in a total of 419 unique markers. From this list, those that were not expressed in any of the in-vitro samples were filtered out, resulting in a total of 366 unique markers. For the second step (computing the correlations), the normalized expression for each cell type was averaged (for both adult and fetal cell types), and then the Pearson correlation of the features selected in the previous step between in-vitro cells (normalized with the same method) and the in-vivo averaged cell types was iteratively computed. A heatmap with the resulting coefficients for the epithelial cell types was generated (FIG. 2H), with each cell being annotated with the epithelial cell type to which it had the highest correlation.

The data discussed herein have been deposited in NCBI's Gene Expression Omnibus (Edgar et al., 2002) and are accessible through GEO Series accession number: GSE142246 available on the world wide web at ncbi.nlm.nih.gov/geo/query/acc.cgi?acc=GSE142246.

Tracheal Xenografts

The tracheal xenograft model was utilized to assay the ability of iBCs to establish well-differentiated airway epithelium in an in vivo setting. Open-ended xenografts were prepared as previously described (Filali et al., 2002). Briefly, following multiple freeze and thaw cycles to decellularize rat tracheas, tubing was attached, and xenografts were seeded with 106 iBCs (NKX2-1GFP±/TP63tdTomato±/NGFR±/EpCAM±) per trachea. Tracheas (two per mouse) were then implanted subcutaneously into the flanks of immune-compromised Nu/Nu mice, maintaining air exposure through the open-ended tubing. Three weeks after transplantation, tracheas were removed and examined via H&E staining and immunostaining for the establishment of pseudostratified, well-differentiated airway epithelium.

Epithelial Cell Electrophysiological Analysis

Barrier function of the Air Liquid Interface Cultures (ALI) was measured using the Millicell ERS-2 Volt-ohm Meter (Millipore cat #MERS00002). The transepithelial electrical resistance (TEER) was measured at varying time points after the medium was removed from the apical chambers. All Transwells, including blanks (no cells), received 0.6 ml of fresh PneumaCult-ALI medium in the baso-lateral chamber and 0.2 ml in the apical chamber. Ohms (U) were measured by inserting the longer portion of the electrode into the lower chamber of the Transwell while the shorter end was kept in the apical chamber, and after readings were stabilized for at least six seconds. All measurements were performed in triplicate. The resistance across each cell layer (Rtissue) was obtained by calculating the average resistance of the blank wells (Rblank) and subtracting them from the average of an individual Transwell's 3 readings (Rtotal): (Rtissue=Rtotal−Rblank). TEER (U. cm2)=(Rtissue)*surface area (cm2) of the Transwell.

Ussing chamber experiments were performed on Easy-Mount Ussing Chamber Systems at voltage clamp mode, and Acquiciliare™ & Analyze software (Physiologic Instruments) was employed to record and analyze data. Briefly, Transwell inserts were mounted into chambers and bathed in low chloride Ringer's solution (1.2 mM NaCl, 140 mM Na-gluconate, 25 mM NaHCO3, 3.33 mM KH2PO4, 0.83 mM K2HPO4, 1.2 mM CaCl2, 1.2 mM MgCl2, 10 mM glucose) at apical and Ringer's solution (120 mM NaCl, 25 mM NaHCO3, 3.33 mM KH2PO4, 0.83 mM K2HPO4, 1.2 mM CaCl2, 1.2 mM MgCl2, 10 mM glucose) at basolateral side of monolayer. After base line is stabilized, 100 pM amiloride (Sigma) applied to both sides of the chamber to carry out complete inhibition of ENaC (Epithelial sodium channel). Subsequently, 10 pM forskolin (Sigma) were administered to stimulate chloride current. At the end of experiments, 10 pM CFTR inhibitor-172 (Sigma) employed at the apical side to specifically inhibit CFTR function followed by 100 pM UTP at the apical side to assess the integrity of developed epithelium. For BU3 NGPT derived ALI, 5 pM VX-770, CFTR modulator, was treated subsequent to forskolin. The resulting change in short circuit current was calculated as DIsc. The data were expressed in mean±SD.

Ussing chamber analysis was also used to measure TEER at the beginning of each recording, prior to compound administration, in some cases. Briefly, a blank insert was mounted into the Ussing chamber and each side was incubated with Ringer solution as above, followed by compensation for voltage electrode asymmetry and fluid resistance. The blank insert was now replaced with the insert with cells, which was then voltage clamped and monitored for short-circuit current to calculate TEER based on Ohm's law.

Limiting Dilution and Tracheosphere Assays

On day 10 of directed differentiation, cells were treated with 5 pg/ml polybrene and then separate wells were infected with pHAGE-EF1alphaL-eGFP-W, pHAGE-Ef1alphaL-TagBFP-W, or pHAGE-CMV-DsRED-W at an MOI=1 for 24 hr. On Day 20 of differentiation, cells were dissociated and GFP+, BFP+ and DsRed+ cells were sorted according to the same protocol described above. Equal numbers of GFP+, BFP+ and dsRED+ cells were combined and plated at 1000 cell/pL, 400 cells/pL and 200 cells/pL in 50 ul droplets of 3D Matrigel in triplicate. On day 34, the Matrigel™ droplets were imaged and the number of GFP, BFP, dsRed or mixed colonies were manually counted. For the tracheosphere assay GFP+/TOM+/NGFR+BU3 NGPT cells were sorted as above and plated at a density of 200 cells/pL in basal cell medium. Once organoids had formed, 10 days, triplicate wells were either continued in basal cell medium or changed to PneumaCult-ALI for an additional 10 days. For the scRNA-Seq experiment in FIG. 12E, GFP+/TOM+/NGFR+BU3 NGPT cells were sorted as above and plated at a density of 400 cells/pL in basal cell medium and cultured for 29 days.

Mucus Cell Metaplasia Model

BU3 NGPT iBSC-derived ALI culture was prepared as described above. Ten days after air-lifted, cells were treated with 10 ng/ml IL-13 and cultured for 10 days prior to the assessments. Mucus cell metaplasia was assessed by immunofluorescence staining for the increment of MUC5AC expressing cells or gene expression changes via qRT-PCR. Quantification of MUC5AC+ cells was performed using ImageJ™ software by manually counting MUC5AC+ cells in 3 randomly selected fields per well (n=3 wells per condition).

Quantitative RT-PCR

RNA was extracted by first lysing cells in QIAzol (QIAGEN) and subsequently using the RNeasy Mini kit (QIAGEN). Taqman Fast Universal PCR mastermix (Applied Biosystems) were used to reverse transcribe RNA into cDNA and analyzed during 40 cycles of real time PCR using Taqman probes (Applied Biosystems). Relative gene expression, normalized to 18S control, was calculated as fold change in 18S-normalized gene expression, over baseline, using the 2(-DDCT) method. Baseline, defined as fold change=1, was set to undifferentiated iPSCs. If undetected, a cycle number of 40 was assigned to allow fold change calculations.

Transmission Electron Microscopy

Electron microscopy was performed as previously described (Horani et al., 2012, 2013). In short, cultured airway epithelial cells collected from subjects with PCD, or iPSC derived cells were fixed using 2.5% glutaraldehyde+2% paraformaldehyde in 0.15M ca-codylate buffer at 37° C. Secondary fixation was performed in 1% OsO4/1.5% potassium ferrocyanide, and then in 2% uranyl acetate. Post-staining with 0.1% lead citrate and 0.2% tannic acid was done for additional contrast enhancement. At least 10 cilia cross sections were evaluated per group.

High Speed Video-microscopy

Cilia beat frequency was analyzed live in at least 5 fields obtained from each preparation, using a high-speed video camera and processed with the Sisson-Ammons Video Analysis system (Amons Engineering, Mt Morris, Mich.) as described (Horani et al., 2012; Sisson et al., 2003).

Quantification and Statistical Analysis

Statistical methods relevant to each figure are outlined in the accompanying figure legend or described in Results section. Unless otherwise indicated unpaired, two-tailed Student's t tests were applied to two groups of n=3 or more samples, where each replicate ("n") represents either entirely separate differentiations from the pluripotent stem cell stage or replicates differentiated simultaneously and sorted into separate wells. A p value <0.05 was considered to indicate a significant difference between groups.

TABLE 1

| TaqMan Gene Expression Assay Information. | |
|---|---|
| Gene | TaqMan Probe Number |
| FOXJ1 | HS00230964 |
| KRT5 | HS00361185 m1 |
| KRT17 | HS00356958 m1 |
| MUC5AC | HS00873651 |
| MUC5B | HS00861595 m1 |
| NGFR | HS00609976 m1 |
| SCGB3A2 | HS0036978 m1 |
| SCGB1A1 | HS0036978 m1 |
| TP63 | HS00978340 m1 |
| SPEDF | HS0017942 m1 |

TABLE 2

| Primers used for characterization of the integrated reporter. | |
|---|---|
| Name | 5' to 3' |
| P63-15F | gttagcggatgctagggcaaatg (SEQ ID NO: 4) |
| P63-5F | gtggcttcagcggctaata (SEQ ID NO: 5) |
| P63-2R | agtgagagggaagcagaaatgaa (SEQ ID NO: 6) |
| PGKrv | ccggtggatgtggaatgtgt (SEQ ID NO: 7) |
| TKfw | tccgagacaatcgcgaacat (SEQ ID NO: 8) |
| TKrv | accgtattggcaagtagccc (SEQ ID NO: 9) |

TABLE 3

| Key Resources- Commercially Available Agents | | |
|---|---|---|
| Reagent, Resource, Antibody | Source | Identifier |
| Mouse monoclonal anti-FOXJ1 (2A5) | INVITROGEN ® | Cat. # 14996580; RRID: AB_1548836 |
| Mouse monoclonal anti-Acetylated Tubulin (ACT) (6-11B-1) | MILLIPORE-SIGMA ® | Cat. # T7451; RRID: AB_609894 |
| Rabbit monoclonal anti-Acetyl-a-Tubulin (Lys40) (D20G3) | CELL SIGNALING TECHNOLOGIES ® | Cat. # 5335S: RRID: AB_10544694 |
| Mouse monoclonal anti-TP63 (4A4) | BIOCARE ® | Cat. # CM163A: RRID: AB_10582730 |
| Rabbit monoclonal anti-MUC5AC (E309I) | CELL SIGNALING TECHNOLOGIES ® | Cat. # 61193: RRID: AB_2799603 |
| Mouse monoclonal anti-MUC5AC (45M1) | INVITROGEN ® | Cat. # MA5-12178: RRID: AB_10978001 |
| Mouse monoclonal anti-MUC5B (A-3) | SANTA CRUZ ® | Cat. # Sc-393952: |
| Rabbit monoclonal anti-KRT5 (D4U8Q) | CELL SIGNALING TECHNOLOGIES ® | Cat. # 25807: RRID: AB_2798912 |
| Chicken polyclonal anti-KRT5 (Poly9059) | BIOLEGEND ® | Cat. # 905901: RRID: AB_2565054 |
| Mouse monoclonal anti-NGFR (NGFR5) | INVITROGEN ® | Cat. # MA5-13314: RRID: AB_10982037 |
| Rabbit monoclonal anti-p75NTR/NGFR (D4B3) | CELL SIGNALING TECHNOLOGIES ® | Cat. # 8238: RRID: AB_10839265 |
| Mouse monoclonal anti-CC10 (E-11) | SANTA CRUZ ® | Cat. # Sc-365992; RRID: AB_10915481 |
| Rabbit polyclonal anti-RFP | ROCKLAND IMMUNOCHEMICALS ® | Cat. # 600-401-379; RRID: AB_2209751 |
| Chicken polyclonal anti-GFP | INVITROGEN ® | Cat. # A10262; RRID: AB_2534023 |
| Rabbit monoclonal anti-NKX2-1 (EP1584Y) | ABCAM ® | Cat. # ab76013; RRID: AB_1310784 |
| Rabbit monoclonal anti-ZO-3 (D57G7) | CELL SIGNALING TECHNOLOGIES ® | Cat. # 3704S; RRID: AB_2203606 |
| APC-mouse monoclonal anti-CD47 (CC2C6) | BIOLEGEND ® | Cat. # 323123; RRID: AB_2716202 |
| PE-mouse monoclonal anti-CD26 (BA5b) | BIOLEGEND ® | Cat. # 302705; RRID: AB_314289 |
| APC/Fire750-mouse monoclonal anti-EpCAM (9C4) | BIOLEGEND ® | Cat. # 324234: RRID: AB_2629703 |
| APC-mouse monoclonal anti-human CD271/NGFR (ME20.4) | BIOLEGEND ® | Cat. # 345108; RRID: AB_10645515 |
| Mouse monoclonal anti-EpCAM (AUA1) | ABCAM ® | Cat. #ab20160: RRID: AB_445379 |
| Goat polyclonal anti-SOX17 | R&D SYSTEM ® | Cat. # AF1924; RRID: AB_355060 |
| Mouse monoclonal anti-NESTIN (Clone 25) | BD ® | Cat. # 611658; RRID: AB_399176 |
| Mouse monoclonal anti- Tubulin b3 (TUJ1) | BIOLEGEND ® | Cat. # 801201; RRID: AB_2313773 |

TABLE 3-continued

| Key Resources- Commercially Available Agents | | |
|---|---|---|
| Reagent, Resource, Antibody | Source | Identifier |
| Goat polyclonal anti-Brachyury | R&D SYSTEM ® | Cat. # AF2085; RRID: AB_2200235 |
| Mouse IgG1kappa isotype control, APC-conjugated | BIOLEGEND ® | Cat. # 400122; RRID: AB_326443 |
| Mouse IgG1 isotype control, PE-conjugated | BIOLEGEND ® | Cat. # 400113; RRID: AB_326435 |
| Mouse IgG1 isotype control, PerCP/Cy5.5-conjugated | BIOLEGEND ® | Cat. # 400149; RRID: AB_893680 |
| Rabbit anti-DNAH5 | MILLIPORE-SIGMA ® | Cat. #HPA037470; RRID: AB_10672348 |
| Rabbit anti-DNALI1 | MILLIPORE-SIGMA ® | Cat. # HPA028305; RRID: AB_10601807 |
| pHAGE-EF1alphaL-eGFP-W | ADDGENE ® | Plasmid# 126686; RRID: RRID: Addgene_126686 |
| pHAGE-EF1alphaL-TagBFP-W | ADDGENE ® | Plasmid# 126687; RRID: RRID: Addgene_126687 |
| pHAGE-CMV-DsRED-W | N/A | N/A |
| SB431542 | TOCRIS ® | Cat. # 1614 |
| Dorsomorphin | STEMGENT ® | Cat. # 04-0024 |
| CHIR99021 | TOCRIS ® | Cat. # 4423 |
| Recombinant human BMP4 | R&D SYSTEMS ® | Cat. # 314-BP |
| Retinoic acid | SIGMA ® | Cat. # R2625 |
| Y-27632 dihydrochloride | TOCRIS ® | Cat. # 1254 |
| Recombinant human FGF10 | R&D SYSTEMS ® | Cat. # 345-FG-025 |
| Recombinant human FGF2 | R&D SYSTEMS ® | Cat. # 233-FB |
| Dexamethasone | SIGMA ® | Cat. # D4902 |
| 8-bromoadenosine 30,50-cyclic monophosphate sodium salt (cAMP) | SIGMA ® | Cat. # B7880 |
| 3-Isobutyl-1-methylxanthine (IBMX) | SIGMA ® | Cat. # I5879 |
| A83-01 | THERMOFISHER SCIENTIFIC ® | Cat. # 293910 |
| DMH1 | THERMOFISHER SCIENTIFIC ® | Cat. # 412610 |

Figure 19:
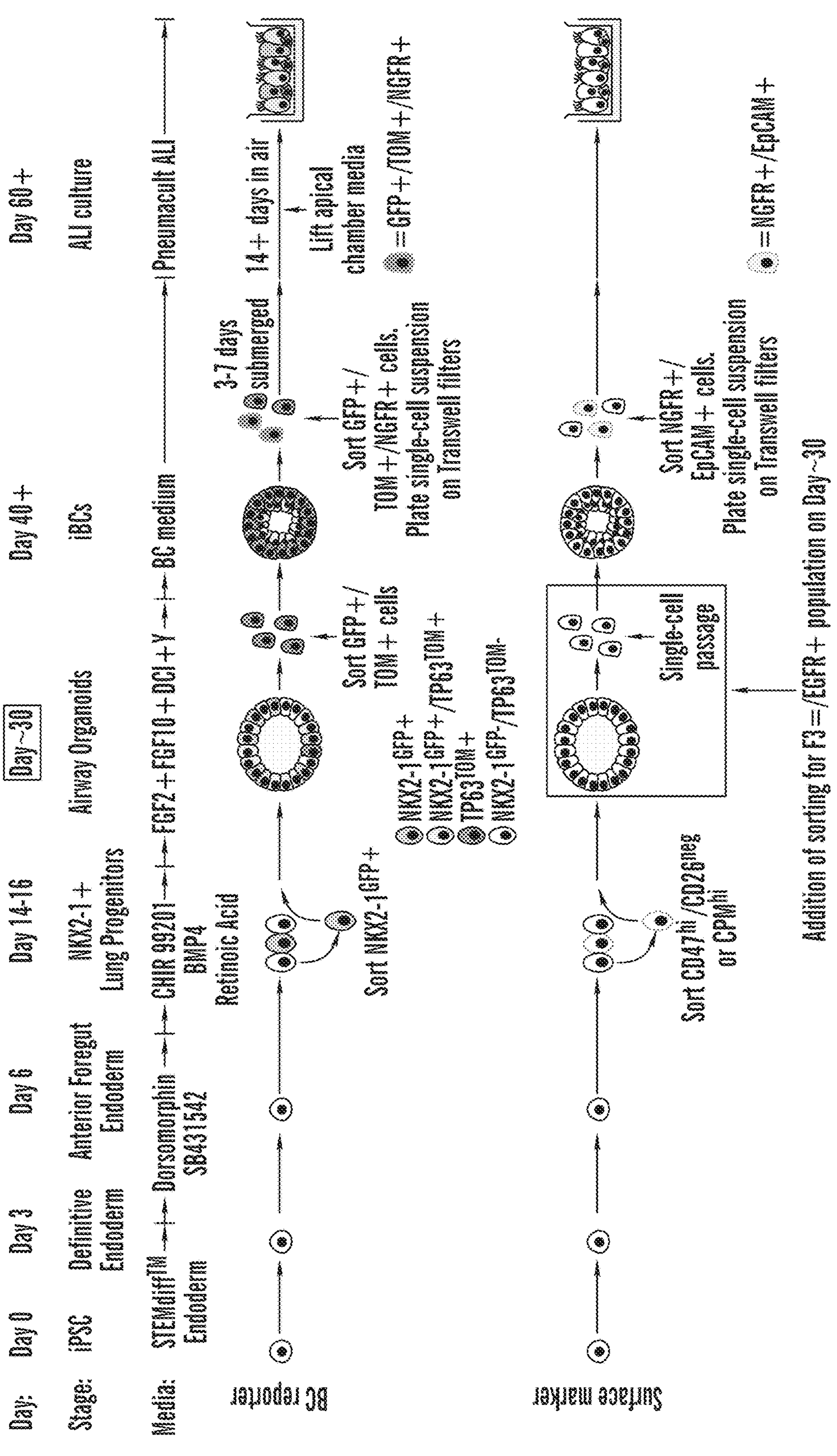
FIG. 19 shows and highlights a cell sorting step for F3+/EGFR+ airway cells to enrich for lung progenitor populations—NKX2-1 expressing lung/airway linage cells, and airway progenitors co-expressing NKX2-1 and TP63.

Example 3: Enriching Lung/Airway Progenitor Cells in Airway Epithelial Organoid Derived from Human Pluripotent Stem Cells (HPSCS) Through the Cell-Surface Marker Strategy Isolation of lung/airway Progenitor Cells in hPSC-derived Airway Epithelial Organoids When performing the directed differentiation protocol to obtain induced basal cells (iBCs) from hPSCs (Hawkins and Suzuki et al., 2020), there was some degree of difficulty with some non-reporter iPSC lines (second row in FIG. 19). It was contemplated that this was likely due to a predominating non-lung population (NKX2-1 negative) present in culture on ~Day 30, that was carried to later stages by the passaging step on ~Day 30. This modification to the protocol has the objective of enriching lung/airway progenitor cells in the airway epithelial organoids from ~Day 30, thus minimizing the carry forward of the undesired non-lung cell population to the downstream further steps of differentiation. On approximately Day 30 of directed differentiation, cells that had been cultured in 3D MATRIGEL™ containing FGF2+FGF10+DCI+Y were harvested by incubation with 1 U/mL Dispase (Stemcell technologies) for ~60 min at 37 C. and subsequent incubation with 0.05% trypsin at 37 C. until a single cell suspension was achieved. Single cells were prepared for sorting by immunolabeling for Coagulation factor III (F3) and Epidermal growth factor receptor (EGFR) in FACS buffer.

After sorting for F3+/EGFR+ cells (FIG. 20A), the sorted cells are highly enriched (80% or higher) with lung/airway progenitor populations: both NKX2-1 expressing lung/airway linage cells, and airway progenitors co-expressing NKX2-1 and TP63 (FIG. 20B). The sorted cells can be subsequently differentiated into iBCs expressing both EpCAM and Nerve growth factor receptor (NGFR): difficult-to-differentiate iPSC lines typically show ~10% of population or less in the culture without the F3/EGFR sorting step (shown in FIG. 20C, top panel, 10.1%) while F3/EGFR-sorted cells generate iBC at levels of 30 to 50% in the culture (shown in FIG. 20C, bottom panel, 34.5%). The key advance of this modification to the protocol is allowing one to overcome PSC line to line variability, often claimed as an issue in the hPSC field, to yield the target cell population (in this case iBCs) in both purity and quantity. This modification has further enhanced the utility of patient-specific PSC for airway disease modeling, drug screening and other applications.

It is noted that there is flexibility in the timing for when this cell surface marker strategy can be applied as lung/airway progenitor cells in FGF2+FGF10+DCI+Y medium can be expanded and cultured for up to several months.

REFERENCES FOR EXAMPLES 1-3

Berical, A., Lee, R. E., Randell, S. H., and Hawkins, F. (2019). Challenges facing airway epithelial cell-based therapy for cystic fibrosis. Front. Pharmacol. 10, 74.

Butler, A., Hoffman, P., Smibert, P., Papalexi, E., and Satija, R. (2018). Integrating single-cell transcriptomic data across different conditions, technol¬ogies, and species. Nat. Biotechnol. 36, 411-420.

Carraro, G., Mulay, A., Yao, C., Mizuno, T., Konda, B., Petrov, M., Lafkas, D., Arron, J. R., Hogaboam, C. M., Chen, P., et al. (2020b). Single cell reconstruc¬tion of human basal cell diversity in normal and IPF lung. Am. J. Respir. Crit. Care Med. Published online Jul. 21, 2020. https://doi.org/10.1164/rccm. 201904-07920C.

Chen, Y.-W., Huang, S. X., de Carvalho, A. L. R. T., Ho, S.-H., Islam, M. N., Volpi, S., Notarangelo, L. D., Ciancanelli, M., Casanova, J.-L., Bhattacharya, J., et al. (2017). A three-dimensional model of human lung development and disease from pluripotent stem cells. Nat. Cell Biol. 19, 542-549.

Clancy, J. P., Cotton, C. U., Donaldson, S. H., Solomon, G. M., VanDevanter, D. R., Boyle, M. P., Gentzsch, M., Nick, J. A., Illek, B., Wallenburg, J. C., et al. (2019). CFTR modulator theratyping: current status, gaps and future direc¬tions. J. Cyst. Fibros. 18, 22-34.

Dye, B. R., Hill, D. R., Ferguson, M. A. H., Tsai, Y.-H., Nagy, M. S., Dyal, R., Wells, J. M., Mayhew, C. N., Nattiv, R., Klein, O. D., et al. (2015). In vitro generation of human pluripotent stem cell derived lung organoids. eLife 4, 1999.

Edgar, R., Domrachev, M., and Lash, A. E. (2002). Gene Expression Omnibus: NCBI gene expression and hybridization array data repository. Nucleic Acids Res. 30, 207-210.

Everitt, J. I., Boreiko, C. J., Mangum, J. B., Martin, J. T., Iglehart, J. D., and Hesterberg, T. W. (1989). Development of a tracheal implant xenograft model to expose human bronchial epithelial cells to toxic gases. Toxicol. Pathol. 17, 465-473.

Filali, M., Zhang, Y., Ritchie, T. C., and Engelhardt, J. F. (2002). Xenograft model of the CF airway. Methods Mol. Med. 70, 537-550.

Finak, G., McDavid, A., Yajima, M., Deng, J., Gersuk, V., Shalek, A. K., Slichter, C. K., Miller, H. W., McElrath, M. J., Prlic, M., et al. (2015). MAST: a flexible sta¬tistical framework for assessing transcriptional changes and characterizing heterogeneity in single-cell RNA sequencing data. Genome Biol. 16, 278.

Firth, A. L., Dargitz, C. T., Qualls, S. J., Menon, T., Wright, R., Singer, O., Gage, F. H., Khanna, A., and Verma, I. M. (2014). Generation of multiciliated cells in functional airway epithelia from human induced pluripotent stem cells. Proc. Natl. Acad. Sci. USA 111, E1723-E1730.

Fulcher, M. L., and Randell, S. H. (2013). Human nasal and tracheo-bronchial respiratory epithelial cell culture. Methods Mol. Biol. 945, 109-121.

Fulcher, M. L., Gabriel, S., Burns, K. A., Yankaskas, J. R., and Randell, S. H. (2005). Well-differentiated human airway epithelial cell cultures. Methods Mol. Med. 107, 183-206.

Gentzsch, M., Boyles, S. E., Cheluvaraju, C., Chaudhry, I. G., Quinney, N. L., Cho, C., Dang, H., Liu, X., Schlegel, R., and Randell, S. H. (2017). Pharmacological rescue of conditionally reprogrammed cystic fibrosis bron¬chial epithelial cells. Am. J. Respir. Cell Mol. Biol. 56, 568-574.

Ghosh, M., Ahmad, S., White, C. W., and Reynolds, S. D. (2017). Transplantation of airway epithelial stem/progenitor cells: a future for cell-based therapy. Am. J. Respir. Cell Mol. Biol. 56, 1-10.

Gotoh, S., Ito, I., Nagasaki, T., Yamamoto, Y., Konishi, S., Korogi, Y., Matsumoto, H., Muro, S., Hirai, T., Funato, M., et al. (2014). Generation of alve¬olar epithelial spheroids via isolated progenitor cells from human pluripotent stem cells. Stem Cell Reports 3, 394-403.

Green, M. D., Chen, A., Nostro, M.-C., d'Souza, S. L., Schaniel, C., Lemischka, I. R., Gouon-Evans, V., Keller, G., and Snoeck, H.-W. (2011). Generation of anterior foregut endoderm from human embryonic and induced pluripotent stem cells. Nat. Biotechnol. 29, 267-272.

Hafemeister, C., and Satija, R. (2019). Normalization and variance stabilization of single-cell RNA-seq data using regularized negative binomial regression. Genome Biol. 20, 296.

Hawkins, F., Kramer, P., Jacob, A., Driver, I., Thomas, D. C., McCauley, K. B., Skvir, N., Crane, A. M., Kurmann, A. A., Hollenberg, A. N., et al. (2017). Prospective isolation of NKX2-1-expressing human lung progenitors derived from pluripotent stem cells. J. Clin. Invest. 127, 2277-2294.

Horani, A., Druley, T. E., Zariwala, M. A., Patel, A. C., Levinson, B. T., Van Arendonk, L. G., Thornton, K. C., Giacalone, J. C., Albee, A. J., Wilson, K. S., et al. (2012). Whole-exome capture and sequencing identifies HEATR2 muta¬tion as a cause of primary ciliary dyskinesia. Am. J. Hum. Genet. 91, 685-693.

Horani, A., Ferkol, T. W., Shoseyov, D., Wasserman, M. G., Oren, Y. S., Kerem, B., Amirav, I., Cohen-Cymberknoh, M., Dutcher, S. K., Brody, S. L., et al. (2013). LRRC6 mutation causes primary ciliary dyskinesia with dynein arm defects. PLoS ONE 8, e59436.

Horani, A., Ferkol, T. W., Dutcher, S. K., and Brody, S. L. (2016). Genetics and biology of primary ciliary dyskinesia. Paediatr. Respir. Rev. 18,18-24.

Huang, S. X. L., Islam, M. N., O'Neill, J., Hu, Z., Yang, Y.-G., Chen, Y.-W., Mumau, M., Green, M. D., Vunjak-Novakovic, G., Bhattacharya, J., and Snoeck, H. W. (2014). Efficient generation of lung and airway epithelial cells from human pluripotent stem cells. Nat. Biotechnol. 32,84-91.

Hurley, K., Ding, J., Villacorta-Martin, C., Herriges, M. J., Jacob, A., Vedaie, M., Alysandratos, K. D., Sun, Y. L., Lin, C., Werder, R. B., et al. (2020). Reconstructed single-cell fate trajectories define lineage plasticity windows during differentiation of human PSC-derived distal lung progenitors. Cell Stem Cell 26, 593-608.e8.

Jacob, A., Morley, M., Hawkins, F., McCauley, K. B., Jean, J. C., Heins, H., Na, C.-L., Weaver, T. E., Vedaie, M., Hurley, K., et al. (2017). Differentiation of hu¬man pluripotent stem cells into functional lung alveolar epithelial cells. Cell Stem Cell 21, 472-488.e10.

Kondo, M., Tamaoki, J., Takeyama, K., Nakata, J., and Nagai, A. (2002). Interleukin-13 induces goblet cell differentiation in primary cell culture from Guinea pig tracheal epithelium. Am. J. Respir. Cell Mol. Biol. 27,536-541.

Konishi, S., Gotoh, S., Tateishi, K., Yamamoto, Y., Korogi, Y., Nagasaki, T., Matsumoto, H., Muro, S., Hirai, T., Ito, I., et al. (2016). Directed induction of functional multiciliated cells in proximal airway epithelial spheroids from hu¬man pluripotent stem cells. Stem Cell Reports 6,18-25.

Levrero, M., De Laurenzi, V., Costanzo, A., Gong, J., Wang, J. Y., and Melino, G. (2000). The p53/p63/p73 family of transcription factors: overlapping and distinct functions. J. Cell Sci. 113,1661-1670.

Loxham, M., Davies, D. E., and Blume, C. (2014). Epithelial function and dysfunction in asthma. Clin. Exp. Allergy 44,1299-1313.

McCauley, K. B., Hawkins, F., Serra, M., Thomas, D. C., Jacob, A., and Kotton, D. N. (2017). Efficient derivation of functional human airway epithelium from pluripotent stem cells via temporal regulation of Wnt signaling Cell Stem Cell 20, 844-857.e6.

McCauley, K. B., Alysandratos, K.-D., Jacob, A., Hawkins, F., Caballero, I. S., Vedaie, M., Yang, W., Slovik, K. J., Morley, M., Carraro, G., et al. (2018a). Single-cell transcriptomic profiling of pluripotent stem cell-derived SCGB3A2+ airway epithelium. Stem Cell Reports 10,1579-1595.

McCauley, K. B., Hawkins, F., and Kotton, D. N. (2018b). Derivation of epithe¬lial-only airway organoids from human pluripotent stem cells. Curr. Protoc. Stem Cell Biol. 45, e51.

Miller, A. J., Hill, D. R., Nagy, M. S., Aoki, Y., Dye, B. R., Chin, A. M., Huang, S., Zhu, F., White, E. S., Lama, V., and Spence, J. R. (2018). In vitro induction and in vivo engraftment of lung bud tip progenitor cells derived from human pluripotent stem cells. Stem Cell Reports 10, 101-119.

Miller, A. J., Yu, Q., Czerwinski, M., Tsai, Y.-H., Conway, R. F., Wu, A., Holloway, E. M., Walker, T., Glass, I. A., Treutlein, B., et al. (2020). In vitro and in vivo development of the human airway at single-cell resolution. Dev. Cell 53, 117-128.e6.

Montoro, D. T., Haber, A. L., Biton, M., Vinarsky, V., Lin, B., Birket, S. E., Yuan, F., Chen, S., Leung, H. M., Villoria, J., et al. (2018). A revised airway epithelial hierarchy includes CFTR-expressing ionocytes. Nature 560, 319-324.

Mou, H., Vinarsky, V., Tata, P. R., Brazauskas, K., Choi, S. H., Crooke, A. K., Zhang, B., Solomon, G. M., Turner, B., Bihler, H., et al. (2016). Dual SMAD signaling inhibition enables long-term expansion of diverse epithelial basal cells. Cell Stem Cell 19, 217-231.

Nichane, M., Javed, A., Sivakamasundari, V., Ganesan, M., Ang, L. T., Kraus, P., Lufkin, T., Loh, K. M., and Lim, B. (2017). Isolation and 3D expansion of mul-tipotent Sox9+ mouse lung progenitors. Nat. Methods 14, 1205-1212.

Nikolic, M. Z., Caritg, O., Jeng, Q., Johnson, J.-A., Sun, D., Howell, K. J., Brady, J. L., Laresgoiti, U., Allen, G., Butler, R., et al. (2017). Human embryonic lung epithelial tips are multipotent progenitors that can be expanded in vitro as long-term self-renewing organoids. eLife 6, 4139.

Ornitz, D. M., and Itoh, N. (2015). The fibroblast growth factor signaling pathway. Wiley Interdiscip. Rev. Dev. Biol. 4, 215-266.

Pan, J., You, Y., Huang, T., and Brody, S. L. (2007). RhoA-mediated apical actin enrichment is required for ciliogenesis and promoted by Foxj 1. J. Cell Sci. 120, 1868-1876.

Park, S., and Mostoslaysky, G. (2018). Generation of human induced pluripo-tent stem cells using a defined, feeder-free reprogramming system. Curr. Protoc. Stem Cell Biol. 45, e48.

Plasschaert, L. W., Zilionis, R., Choo-Wing, R., Savova, V., Knehr, J., Roma, G., Klein, A. M., and Jaffe, A. B. (2018). A single-cell atlas of the airway epithelium reveals the CFTR-rich pulmonary ionocyte. Nature 560, 377-381.

Reynolds, S. D., Reynolds, P. R., Pryhuber, G. S., Finder, J. D., and Stripp, B. R. (2002). Secretoglobins SCGB3A1 and SCGB3A2 define secretory cell subsets in mouse and human airways. Am. J. Respir. Crit. Care Med. 166, 1498-1509.

Rock, J. R., Onaitis, M. W., Rawlins, E. L., Lu, Y., Clark, C. P., Xue, Y., Randell, S. H., and Hogan, B. L. M. (2009). Basal cells as stem cells of the mouse trachea and human airway epithelium. Proc. Natl. Acad. Sci. USA 106, 12771-12775.

Rock, J. R., Randell, S. H., and Hogan, B. L. M. (2010). Airway basal stem cells: a perspective on their roles in epithelial homeostasis and remodeling. Dis. Model. Mech. 3, 545-556.

Seibold, M. A. (2018). Interleukin-13 stimulation reveals the cellular and func¬tional plasticity of the airway epithelium. Ann. Am. Thorac. Soc. 15 (Suppl 2), S98-S102.

Serra, M., Alysandratos, K.-D., Hawkins, F., McCauley, K. B., Jacob, A., Choi, J., Caballero, I. S., Vedaie, M., Kurmann, A. A., Ikonomou, L., et al. (2017). Pluripotent stem cell differentiation reveals distinct developmental pathways regulating lung-versus thyroid-lineage specification. Development 144, 3879-3893.

Sisson, J. H., Stoner, J. A., Ammons, B. A., and Wyatt, T. A. (2003). All-digital im¬age capture and whole-field analysis of ciliary beat frequency. J. Microsc. 211, 103-111.

Sommer, A. G., Rozelle, S. S., Sullivan, S., Mills, J. A., Park, S.-M., Smith, B. W., Iyer, A. M., French, D. L., Kotton, D. N., Gadue, P., et al. (2012). Generation of human induced pluripotent stem cells from peripheral blood using the STEMCCA lentiviral vector. J. Vis. Exp. 4327.

Studer, L., Vera, E., and Cornacchia, D. (2015). Programming and reprogram¬ming cellular age in the era of induced pluripotency. Cell Stem Cell 16, 591-600.

Suprynowicz, F. A., Kamonjoh, C. M., Krawczyk, E., Agarwal, S., Wellstein, A., Agboke, F. A., Choudhury, S., Liu, X., and Schlegel, R. (2017). Conditional cell reprogramming involves non-canonical b-catenin activation and mTOR-medi-ated inactivation of Akt. PLoS ONE 12, e0180897.

Tirosh, I., Izar, B., Prakadan, S. M., Wadsworth, M. H., 2nd, Treacy, D., Trombetta, J. J., Rotem, A., Rodman, C., Lian, C., Murphy, G., et al. (2016). Dissecting the multicellular ecosystem of metastatic melanoma by single-cell RNA-seq. Science 352, 189-196.

Volckaert, T., Campbell, A., Dill, E., Li, C., Minoo, P., and De Langhe, S. (2013). Localized Fgf10 expression is not required for lung branching morphogenesis but prevents differentiation of epithelial progenitors. Development 140, 3731-3742.

Woodruff, P. G., Modrek, B., Choy, D. F., Jia, G., Abbas, A. R., Ellwanger, A., Koth, L. L., Anon, J. R., and Fahy, J. V. (2009). T-helper type 2-driven inflamma¬tion defines major subphenotypes of asthma. Am. J. Respir. Crit. Care Med. 180, 388-395.

Yang, A., Schweitzer, R., Sun, D., Kaghad, M., Walker, N., Bronson, R. T., Tabin, C., Sharpe, A., Caput, D., Crum, C., and McKeon, F. (1999). p63 is essential for regenerative proliferation in limb, craniofacial and epithelial devel¬opment. Nature 398, 714-718.

Yang, Y., Riccio, P., Schotsaert, M., Mori, M., Lu€, J., Lee, D.-K., García-Sastre, A., Xu, J., and Cardoso, W. V. (2018). Spatial temporal lineage restrictions of embryonic p63+ progenitors establish distinct stem cell pools in adult airways. Dev. Cell 44, 752-761.e4.

You, Y., Richer, E. J., Huang, T., and Brody, S. L. (2002). Growth and differen¬tiation of mouse tracheal epithelial cells: selection of a proliferative population. Am. J. Physiol. Lung Cell. Mol. Physiol. 283, L1315-L1321.

Zhang, C., Lee, H. J., Shrivastava, A., Wang, R., McQuiston, T. J., Challberg, S. S., Pollok, B. A., and Wang, T. (2018). Long-term in vitro expansion of epithe¬lial stem cells enabled by pharmacological inhibition of PAK1-ROCK-myosin II and TGF-b signaling. Cell Rep. 25, 598-610.e5.

What is claimed herein is:

1. A method comprising:

(a) culturing a population of Nkx2-1$^+$ lung progenitor cells in a first culture medium and contacting the Nkx2-1$^+$ lung progenitor cells with, one or more of: at least one Wnt agonist; at least one retinoic acid or a derivative thereof; and at least one bone morphogenic protein (BMP) agonist;

(b) re-suspending the Nkx2-1$^+$ lung progenitor cells in a hydrogel to form epithelial spheres;

(c) culturing the epithelial spheres in a second culture medium and contacting the epithelial spheres with one or more of: at least one fibroblast growth factor (FGF) agonist; at least one steroid; 3',5'-cyclic monophosphate sodium salt; 3-isobutyl-1-methyxanthine (IBMX); and at least one Rho kinase (ROCK) inhibitor, thereby differentiating the epithelial spheres into airway progenitor cells;

(d) passaging and re-suspending the airway progenitor cells in the second culture medium, thereby expanding the airway progenitor cells; and (e) culturing the airway progenitor cells from step (d) in a third culture medium and contacting the airway progenitor cells from step (d) with at least one inhibitor of SMAD; at least one inhibitor of transforming growth factor β (TGF-β); at least one bone morphogenetic protein (BMP) inhibitor; and at least one ROCK inhibitor; thereby differentiating the airway progenitor cells into airway basal cells (BCs).

2. The method of claim 1, further comprising a step of sorting and/or isolating airway BCs that express one or more markers selected from the group consisting of: Nkx2-1; tumor protein 63 (TP63); cytoskeletal protein keratin 5 (KRT5); and nerve growth factor receptor (NGFR).

3. The method of claim 1, wherein the hydrogel comprises one or more extracellular matrix components.

4. The method of claim 1, wherein the Wnt agonist is an inhibitor of GSK-3.

5. The method of claim 4, wherein the Wnt agonist is CHIR99021.

6. The method of claim 1, wherein the BMP agonist is BMP4.

7. The method of claim 1, wherein the fibroblast growth factors are FGF2 and FGF10.

8. The method of claim 1, wherein the ROCK inhibitor is Y-27632.

9. The method of claim 1, wherein the inhibitor of SMAD is A83-01.

10. The method of claim 1, wherein the inhibitor of transforming growth factor β (TGF-β) is selected from the group consisting of: ALK5 inhibitor II, SB431542, LY364947, and A83-01.

11. The method of claim 1, wherein the inhibitor of BMP is selected from the group consisting of: dorsomorphin and DMH1.

12. The method of claim 1, wherein step (a) comprises contacting the cells with CHIR99021, retinoic acid, and BMP4.

13. The method of claim 1, wherein step (c) comprises contacting the cells with FGF2, FGF10, dexamethasone, IBMX, 3',5'-cyclic monophosphate sodium salt, and Y-27632.

14. The method of claim 1, wherein step (e) comprises contacting the cells with A83-01 and DMH1.

15. The method of claim 1, wherein the cells in steps (b) and/or (d) are cultured in a 3-dimensional microenvironment.

16. The method of claim 1, wherein the Nkx2-1$^+$ lung progenitor cells are generated by a method comprising:

(a) culturing a population of pluripotent stem cells in a serum-free medium;

(b) culturing the population of pluripotent stem cells in a culture medium wherein the culture medium comprises or the stem cells are contacted with a Wnt agonist or a Wnt polypeptide;

(c) culturing the population of pluripotent stem cells in a culture medium and contacting the pluripotent stem cells with a bone morphogenic protein (BMP) and a Wnt agonist, thereby inducing the differentiation of the pluripotent stem cells into a population of lung progenitor cells; and (d) sorting or isolating a population of Nkx2-1$^+$ lung progenitor cells from the population of lung progenitor cells generated in (c).

17. The method of claim 16, wherein the pluripotent stem cells are induced pluripotent stem cells or embryonic stem cells.

18. The method of claim 16, further comprising, during or following step (d), sorting the population of Nkx2-1+ lung progenitor cells for F3+/EGFR+ lung/airway progenitor cells.

19. The method of claim 1, further comprising a step of cryopreserving the airway BCs.

20. The method of claim 16, wherein the pluripotent stem cells are derived from a healthy subject.

21. The method of claim 16, wherein the pluripotent stem cells are derived from a subject with a pulmonary disease.

22. The method of claim 21, wherein the pulmonary disease is selected from the group consisting of: asthma, cystic fibrosis, primary ciliary dyskinesia, interstitial lung disease, and genetic lung malformations.

23. The method of claim 1, further comprising administering the airway basal cells to the trachea of a subject with a pulmonary disease.

24. The method of claim 23, wherein the pulmonary disease is selected from the group consisting of: asthma, cystic fibrosis, primary ciliary dyskinesia interstitial lung disease, and genetic lung malformations.

25. The method of claim 1, wherein the airway basal cell expresses NKX2-1, TP63; KRT5; and NGFR.

26. The method of claim 2, the one or more markers is nerve growth factor receptor (NGFR).

* * * * *